US010254274B2

(12) United States Patent
Miklas et al.

(10) Patent No.: US 10,254,274 B2
(45) Date of Patent: Apr. 9, 2019

(54) COMPOSITIONS AND METHODS FOR MAKING AND USING THREE-DIMENSIONAL TISSUE SYSTEMS

(71) Applicants: Jason Miklas, Thornhill (CA); Milica Radisic, Toronto (CA); Nimalan Thavandiran, Toronto (CA); Sara Vasconcelos, Toronto (CA); Yun Xiao, Toronto (CA); Boyang Zhang, Toronto (CA); Yimu Zhao, Mississauga (CA)

(72) Inventors: Jason Miklas, Thornhill (CA); Milica Radisic, Toronto (CA); Nimalan Thavandiran, Toronto (CA); Sara Vasconcelos, Toronto (CA); Yun Xiao, Toronto (CA); Boyang Zhang, Toronto (CA); Yimu Zhao, Mississauga (CA)

(73) Assignee: Milica RADISIC, Toronto, ON (CA)

( * ) Notice: Subject to any disclaimer, the term of this patent is extended or adjusted under 35 U.S.C. 154(b) by 0 days.

(21) Appl. No.: 15/033,542

(22) PCT Filed: Oct. 30, 2014

(86) PCT No.: PCT/CA2014/051046
§ 371 (c)(1),
(2) Date: Apr. 29, 2016

(87) PCT Pub. No.: WO2015/061907
PCT Pub. Date: May 7, 2015

(65) Prior Publication Data
US 2016/0282338 A1 Sep. 29, 2016

Related U.S. Application Data

(60) Provisional application No. 61/897,276, filed on Oct. 30, 2013.

(51) Int. Cl.
*G01N 33/50* (2006.01)
*C12M 1/34* (2006.01)
*C12M 3/00* (2006.01)
*C12M 1/32* (2006.01)
*C12M 3/06* (2006.01)
*C12M 1/12* (2006.01)
*C12M 1/42* (2006.01)

(52) U.S. Cl.
CPC ........ *G01N 33/5082* (2013.01); *C12M 21/08* (2013.01); *C12M 23/12* (2013.01); *C12M 23/16* (2013.01); *C12M 25/14* (2013.01); *C12M 35/02* (2013.01); *C12M 41/46* (2013.01); *G01N 33/502* (2013.01); *G01N 33/5061* (2013.01)

(58) Field of Classification Search
None
See application file for complete search history.

(56) References Cited

U.S. PATENT DOCUMENTS

| 7,338,517 | B2 | 3/2008 | Yost et al. |
| 7,363,091 | B1 | 4/2008 | Chen et al. |
| 7,410,665 | B2 | 8/2008 | Ragheb et al. |
| 7,449,306 | B2 | 11/2008 | Elson et al. |
| 7,846,202 | B2 | 12/2010 | Bates et al. |
| 2003/0064358 | A1 | 4/2003 | Elson et al. |
| 2006/0258004 | A1 | 11/2006 | Kosnik et al. |
| 2011/0091926 | A1* | 4/2011 | Frerich ................. C12M 21/08 435/29 |

FOREIGN PATENT DOCUMENTS

| EP | 2 498 796 B1 | 9/2012 | |
| WO | WO2012170490 A2 * | 12/2012 | ............ C12N 5/071 |
| WO | WO-2013056019 A1 | 4/2013 | |

OTHER PUBLICATIONS

Venugopal, J. R. et al., "Biomaterial strategies for alleviation of myocardial infarction", J. R. Soc. Interface, 2012, vol. 9, pp. 1-19.
Corin, K. A. and Gibson L. J., "Cell contraction forces in scaffolds with varying pore size and cell density", Biomaterials, Jun. 2010 (Jun. 2010), vol. 31(18) pp. 4835-4845.
Jeon, H et al., "Measurement of contractile forces generated by individual fibroblasts on self-standing fiber scaffolds". Biomed Microdevices, Feb. 2011 (Feb. 2011), vol. 13(1), pp. 107-115.
Cheng K., "Three dimensional polymer scaffolds for high throughput cell-based assay systems". University of Georgia, 2008, pp. 1-208, [online] [retrieved on Dec. 16, 2014 (Dec. 16, 2014)]. Retrieved from the Internet: <https://getd.libs.uga.edu/pdfs/cheng_ke_200808_phd.pdf> see abstract, pp. 5, 25, 35, 73, 75, 85, 91 and 175.
International Search Report from corresponding International Application No. PCT/CA2014/051046, dated Feb. 5, 2015.
International Preliminary Report on Patentability issued in corresponding International Application No. PCT/CA2014/051046 dated May 12, 2016.
International Preliminary Report on Patentability for PCT/CA2014/051046, dated May 3, 2016.
Extended European Search Report from corresponding European Application No. EP14857966.7 dated Jun. 20, 2017.
Thomas Boudou et al: "A Microfabricated Platform to Measure and Manipulate the Mechanics of Engineered Cardiac Microtissues", Tissue Engineering Part A, vol. 18, No. 9-10, May 1, 2012 (May 1, 2012) pp. 910 (1)-919 (9).
W. R. Legant et al: "Microfabricated tissue gauges to measure and manipulate forces from 3D microtissues", Proceedings of the National Academy of Sciences, vol. 106, No. 25, Jun. 23, 2009 (Jun. 23, 2009), pp. 10097-10102.

(Continued)

Primary Examiner — Michelle F. Paguio Frising
(74) Attorney, Agent, or Firm — Cooley LLP; William Christiansen; Chun L. Yu

(57) ABSTRACT

The present disclosure provides methods, compositions, and devices for making and using three-dimensional biological tissues that accurately mimic native physiology, architecture, and other properties of native tissues for use in, among other applications, drug testing, tissue repair and/or treatment, and regenerative medicine.

26 Claims, 116 Drawing Sheets

(56) References Cited

OTHER PUBLICATIONS

Deepak Choudhury et al: "Exploitation of physical and chemical constraints for three-dimensional microtissue construction in microfluidics", Biomicrofluidics, vol. 5, No. 2, Jan. 1, 2011 (Jan. 1, 2011), p. 022203.
Abilez, O. J. et al. (2017). "Passive Stretch Induces Structural and Functional Maturation of Engineered Heart Muscle as Predicted by Computational Modeling." Stem Cells. Feb. 2018; 36(2): 265-277.
ACEA Biosciences, HESI Stem Cell Working Group, "Assessment of Inotropic Compounds in Functional Enhanced iPSC Derived Cardiomyocytes." Apr. 19, 2017, 7 pages.
Agarwal, A. et al. (2013). "Microfluidic heart on a chip for higher throughput pharmacological studies." Lab Chip 13: 3599-3608.
Antos, C. L. et al. (2002). "Activated glycogen synthase-3 β suppresses cardiac hypertrophy in vivo." Proceedings of the National Academy of Sciences of the United States of America 99(2): 907-12.
Baharvand, H. et al. (2005). "The effect of extracellular matrix on embryonic stem cell-derived cardiomyocytes." J Mol Cell Cardiol 38: 495-503; doi:S0022-2828(04)00409-2 10.1016/j.yjmcc.2004.12. 011.
Bakooshli, M. A. et al. (2018). "A 3D model of human skeletal muscle innervated with stem cell-derived motor neurons enables epsilon-subunit targeted myasthenic syndrome studies". bioRxiv; doi: https://doi.org/10.1101/275545, 63 pages.
Barker, D. J. (1997). "The fetal origins of coronary heart disease." BMJ, vol. 311, Jul. 15, 1995: 171-174.
Barker, D. J. et al. (2002). "Fetal origins of adult disease: strength of effects and biological basis." International Journal of Epidemiology 31(6): 1235-9.
Berger, H. J. et al. (1994). "Continual electric field stimulation preserves contractile function of adult ventricular myocytes in primary culture." Am J Physiol 266: H341-349.
Bhute, V. J. et al. (2017). "Metabolomics Identifies Metabolic Markers of Maturation in Human Pluripotent Stem Cell-Derived Cardiomyocytes." Theranostics. May 26, 2017; 7(7): 2078-2091.
Bird, S. D. et al. (2003). "The human adult cardiomyocyte phenotype." Cardiovasc Res 58: 423-434; doi:S0008636303002530.
Biswas, S. et al. (2018). "LncRNAs: Proverbial Genomic "Junk" or Key Epigenetic Regulators During Cardiac Fibrosis in Diabetes?" Front Cardiovasc Med 5(28): 1-13.
Blazeski, A. et al. (2012). "Electrophysiological and contractile function of cardiomyocytes derived from human embryonic stem cells." Prog Biophys Mol Biol 110: 178-195; doi:S0079-6107(12)00065-X10.1016/j.pbiomolbio.2012.07.012.
Borg, T. K. et al. (2000). "Specialization at the Z line of cardiac myocytes." Cardiovasc Res 46: 277-285; doi:S0008-6363(99)00433-2.
Boyle, P. M. et al. (2018). "Cardiac Optogenetics: 2018." JACC: Clinical Electrophysiology 4(2): 155-167.
Carvajal-Vergara, X. et al. (2010). "Patient-specific induced pluripotent stem-cell-derived models of Leopard syndrome." Nature 465: 808-812; doi:nature09005 [pii] 10.1038/nature09005.
Caspi, O. et al. (2007). "Tissue engineering of vascularized cardiac muscle from human embryonic stem cells." Circ Res 100: 263-272; doi:01.RES.0000257776.05673.ff 10.1161/01.RES.0000257776. 05673.ff.
Caspi, O. et al. (2009). "In vitro electrophysiological drug testing using human embryonic stem cell derived cardiomyocytes." Stem Cells Dev 18: 161-172; doi:10.1089/scd.2007.0280.
Chattergoon, N. N. et al. (2012). "Thyroid hormone drives fetal cardiomyocyte maturation." FASEB J 26: 397-408; doi:fj.10-179895 10.1096/fj.10-179895.
Cheng, C. S. et al. (2016). "Cell Density and Joint microRNA-133a and microRNA-696 Inhibition Enhance Differentiation and Contractile Function of Engineered Human Skeletal Muscle Tissues." Tissue Eng Part A. Apr. 2016;22(7-8): 573-83.
Chien, K. R. et al. (1991). "Regulation of cardiac gene expression during myocardial growth and hypertrophy: molecular studies of an adaptive physiologic response." FASEB J 5: 3037-304.
Conant, G. et al. (2017). "Kinase inhibitor screening using artificial neural networks and engineered cardiac biowires." Sci Rep. Sep. 18, 2017; 7(1): 11807, 12 pages.
Davis, R. P. et al. (2011). "Pluripotent stem cell models of cardiac disease and their implication for drug discovery and development." Trends in Molecular Medicine 17(9): 475-84.
De Weer et al. (1988). "Voltage dependence of the Na—K pump." Annu Rev Physiol 50: 225-241; doi:10.1146/annurev.ph.50.030188. 001301.
Derby, B. (2012). "Printing and Prototyping of Tissues and Scaffolds." Science 338: 921-926; doi:10.1126/science.1226340.
Dixon, T. A. et al., (2018). "Bioinspired 3D Human Neuromuscular Junction Development in Suspended Hydrogel Arrays." Tissue Eng Part C Methods. May 9, 2018; DOI:10.1089/TEN.tec.2018.0062, 44 pages.
Dolnikov, K. et al. (2006). "Functional properties of human embryonic stem cell-derived cardiomyocytes: intracellular Ca2+ handling and the role of sarcoplasmic reticulum in the contraction." Stem Cells 24: 236-245; doi:2005-0036 10.1634/stemcells.2005-0036.
Doss, M. X. et al. (2012). "Maximum diastolic potential of human induced pluripotent stem cell-derived cardiomyocytes depends critically on I(Kr)." PLoS One 7: e40288; doi:10.1371/journal.pone. 0040288 PONE-D-12-03570, 17 pages.
Dubois, N. C. et al. (2011). "SIRPA is a specific cell-surface marker for isolating cardiomyocytes derived from human pluripotent stem cells." Nat Biotechnol 29: 1011-1018; doi:nbt.2005 10.1038/nbt. 2005.
Eder, A. et al. (2012). "Multi-Well Engineered Heart Tissue for Drug Screening and Predictive Toxicology and Drug Testing." InTech Europe (Ed. Prof. Bill Acree) Ch. 4: 71-89, Toxicity and Drug Testing.
Engelmayr, G. C. et al. (2008). "Accordion-like honeycombs for tissue engineering of cardiac anisotropy." Nature Materials 7: 1003-1010; doi:10.1038/nmat2316.
Eschenhagen, T. et al. (2015). "Modelling sarcomeric cardiomyopathies in the dish: from human heart samples to iPSC cardiomyocytes," Cardiovascular Research 105: 424-438.
Feiner, R. et al. (2016). "Engineered hybrid cardiac patches with multifunctional electronics for online monitoring and regulation of tissue function." Nat Mater 15(6): 679-685.
Feng, J. et al. (1996). "Properties of sodium and potassium currents of cultured adult human atrial myocytes." The American Journal of Physiology 270: H1676-1686.
Feric, N. T. and Radisic, M. (2016). "Towards Adult-Like Human Engineered Cardiac Tissue: Maturing human pluripotent stem cell-derived cardiomyocytes in human engineered cardiac tissues." Adv Drug Deliv Rev. Jan. 15, 2016; 96: 110-134.
Fleisch, J. H. & Titus, E. (1972). "The prevention of isoproterenol desensitization and isoproterenol reversal." J Pharmacol Exp Ther 181: 425-433.
Fleischer, S. et al. (2017). "Modular assembly of thick multifunctionalcardiac patches." Proc Natl Acad Sci U S A. Feb. 21, 2017; 114(8): 1898-1903.
Frank, D. et al. (2008). "Gene expression pattern in biomechanically stretched cardiomyocytes: evidence for a stretch-specific gene program." Hypertension 51: 309-318; doi:HYPERTENSIONAHA.107. 098046 10.1161/HYPERTENSIONAHA.107.098046.
Frey, N. & Olson, E. N. (2003). "Cardiac hypertrophy: the good, the bad, and the ugly." Annu Rev Physiol 65: 45-79; doi:10.1146/annurev.physiol.65.092101.142243 092101.142243.
Goldberg, L. et al. (1960). "The direct effects of norepinephrine, epinephrine, and methoxamine on myocardial contractile force in man." Circulation 22: 1125-1132.
Gray, M. O. et al. (1998). "Angiotensin II stimulates cardiac myocyte hypertrophy via paracrine release of TGF-beta 1 and endothelin-1 from fibroblasts." Cardiovascular Research 40(2): 352-63.
Grosberg, A. et al. (2012). "Muscle on a chip: in vitro contractility assays for smooth and striated muscle." J Pharmacol Toxicol Methods 65: 126-135; doi:S1056-8719(12)00041-X 10.1016/j.vascn. 2012.04.001.
Grzelkowska-Kowalczyk, K. (2016). "The Importance of Extracellular Matrix in Skeletal Muscle Development and Function." Intech;

(56) References Cited

OTHER PUBLICATIONS http://www.intechopen.com/books/composition-and-functino-of-the-extracellular-matrix-in-the-human-body, 23 pages.
Hadley, R. W. and Lederer, W. J. (1995). "Nifedipine inhibits movement of cardiac calcium channels through late, but not early, gating transitions." Am J Physiol. Nov. 1995; 269(5 Pt 2): H1784-90.
Hansen, A. et al. (2010). "Development of a drug screening platform based on engineered heart tissue." Circ Res 107: 35-44; doi:CIRCRESAHA.109.211458 10.1161/CIRCRESAHA.109.211458.
Hazeltine, L. B. et al. (2012). "Effects of substrate mechanics on contractility of cardiomyocytes generated from human pluripotent stem cells." Int J Cell Biol 2012, 508294; doi:10.1155/2012/508294, 13 pages.
Henderson, D. J. & Chaudhry, B. (2011). "Getting to the heart of planar cell polarity signaling." Birth Defects Res A Clin Mol Teratol 91: 460-467; doi:10.1002/bdra.20792.
Hinson, J. T. et al. (2016). "Integrative Analysis of PRKAG2 Cardiomyopathy iPS and Microtissue Models Identifies AMPK as a Regulator of Metabolism, Survival, and Fibrosis." Cell Rep. 17: 3292-3304.
Horvath, A. et al. (2018). "Low Resting Membrane Potential and Low Inward Rectifier Potassium Currents Are Not Inherent Features of hiPSC-Derived Cardiomyocytes." Stem Cell Reports 10: 1-12.
Hoshi, R. A. (2009). "Nanoporous Biodegradable Elastomers." Advanced Materials 21: 188-192.
Ionescu-Zanetti, C. et al. (2005). "Mammalian electrophysiology on a microfluidic platform." Proc Natl Acad Sci U S A 102: 9112-9117; doi:0503418102 10.1073/pnas.0503418102.
Ito, A. et al. (2014). "Induction of functional tissue-engineered skeletal muscle constructs by defined electrical stimulation." Sci Rep 4: 4781, 7 pages.
Itzhaki, I. et al. (2011). "Modelling the long QT syndrome with induced pluripotent stem cells." Nature 471(7337): 225-9.
Iwanaga, Y. et al. (1998). "Cardiac endothelin-1 plays a critical role in the functional deterioration of left ventricles during the transition from compensatory hypertrophy to congestive heart failure in salt-sensitive hypertensive rats." Circulation 98(19): 2065-73.
Jia G. et al. (2018). "Diabetic Cardiomyopathy." Circulation Research 122(4): 624-638.
Karagueuzian, H. S. et al. (2017). "Enhanced Late Na and Ca Currents as Effective Antiarrhythmic Drug Targets." Front Pharmacol 8: 36, 17 pages.
Kattman, S. J. et al. (2011). "Stage-specific optimization of activin/nodal and BMP signaling promotes cardiac differentiation of mouse and human pluripotent stem cell lines." Cell Stem Cell 8: 228-240; doi:S1934-5909(10)00703-4 10.1016/j.stem.2010.12.008.
Kehat, I. et al. (2001). "Human embryonic stem cells can differentiate into myocytes with structural and functional properties of cardiomyocytes." J Clin Invest 108: 407-414; doi:10.1172/JCI12131.
Kerscher, P. et al. (2016). "Direct hydrogel encapsulation of pluripotent stem cells enables ontomimetic differentiation and growth of engineered human heart tissues." Biomaterials 2016; 83: 383-395.
Kolanowski, T. J. et al. (2017). "Making human cardiomyocytes up to date: Derivation, maturation state and perspectives." Int J Cardiol. Aug. 15, 2017; 241: 379-386.
Kriegel, A. J., et al. (2017). "Molecular Approaches in HFpEF: MicroRNAs and iPSC-Derived Cardiomyocytes." J Cardiovasc Transl Res 10(3): 295-304.
Kuwahara, K. et al. (2003). "NRSF regulates the fetal cardiac gene program and maintains normal cardiac structure and function." EMBO J 22: 6310-6321; doi:10.1093/emboj/cdg601.
Laflamme, M. A. & Murry, C. E. (2011). "Heart regeneration." Nature 473: 326-335; doi:nature10147 10.1038/nature10147.
Lambernd S. et al. (2012). "Contractile activity of human skeletal muscle cells prevents insulin resistance by inhibiting pro-inflammatory signalling pathways." Diabetologia. 4: 1128-39.

Lee, P. et al. (2012). Simultaneous voltage and calcium mapping of genetically purified human induced pluripotent stem cell-derived cardiac myocyte monolayers. Circ Res. Jun. 8, 2012; 110(12): 1556-63.
Lemoine, M. D. et al. (2017). "Human iPSC-derived cardiomyocytes cultured in 3D engineered heart tissue show physiological upstroke velocity and sodium current density." Sci Rep. Jul. 14, 2017; 7(1): 5464; doi:10.1038/s41598-017-05600-w, 11 pages.
Lian, X. (2012). "Robust cardiomyocyte differentiation from human pluripotent stem cells via temporal modulation of canonical Wnt signaling." Proceedings of the National Academy of Sciences of the United States of America 109: E1848-1857; doi:10.1073/pnas.1200250109.
Liang, P. et al. (2013). "Drug screening using a library of human induced pluripotent stem cell-derived cardiomyocytes reveals disease-specific patterns of cardiotoxicity." Circulation 127(16): 1677-91.
Liau, B. et al. (2012). "Functional cardiac tissue engineering," Regen Med. 7(2): 187-206.
Lieu, D. K. et al. (2009). "Absence of transverse tubules contributes to non-uniform Ca(2+) wavefronts in mouse and human embryonic stem cell-derived cardiomyocytes." Stem Cells Dev 18: 1493-1500; doi:10.1089/scd.2009.0052.
Liu, J. et al. (2007). "Functional sarcoplasmic reticulum for calcium handling of human embryonic stem cell-derived cardiomyocytes: insights for driven maturation." Stem Cells 25: 3038-3044; doi:2007-0549 10.1634/stemcells.2007-0549.
Loyer, X. et al. (2018). "Intra-Cardiac Release of Extracellular Vesicles Shapes Inflammation Following Myocardial Infarction," Circ Res; 123:100-106; doi: 10.1161/CIRCRESAHA.117.311326.
Lundy, S. D. et al. (2013). "Structural and Functional Maturation of Cardiomyocytes Derived From Human Pluripotent Stem Cells." Stem Cells Dev 22(14): 1991-2002; doi:10.1089/scd.2012.0490.
Luo, Z. C. et al. (2006). "Tracing the origins of "fetal origins" of adult diseases: programming by oxidative stress?" Medical Hypotheses 66(1): 38-44.
Ma, J. et al. (2011). "High purity human-induced pluripotent stem cell-derived cardiomyocytes: electrophysiological properties of action potentials and ionic currents." Am J Physiol Heart Circ Physiol. Nov. 2011; 301(5): H2006-H2017.
Madden, L. et al. (2015). "Bioengineered human myobundles mimic clinical responses of skeletal muscle to drugs." Elife 4: e04885, 14 pages.
Maffioletti, S. A. et al. (2018). "Three-Dimensional Human iPSC-Derived Artificial Skeletal Muscles Model Muscular Dystrophies and Enable Multilineage Tissue Engineering." Cell Rep. 23(3): 899-908.
Mannhardt, I. et al. (2016). "Human engineered heart tissue: analysis of contractile force." Stem Cell Reports. Jul. 12, 2016; 7: 1-14.
Mannhardt, I. et al. (2017). "Blinded Contractility Analysis in hiPSC-Cardiomyocytesin Engineered Heart Tissue Format: Comparison With Human Atrial Trabeculae." Toxicol Sci. Jul. 1, 2017; 158(1): 164-175.
Marotta, M. et al. 2004). "Design and performance of an electrical stimulator for long-term contraction of cultured muscle cells." BioTechniques 36: 68-73.
Maruyama, S. et al. (2018). "Relaxin Family Member Insulin-Like Peptide 6 Ameliorates Cardiac Fibrosis and Prevents Cardiac Remodeling in Murine Heart Failure," J Am Heart Assoc. 7: e008441; doi:10.1161/JAHA.117.008441, 24 pages.
McDevitt, T. C. et al. (2005). "Proliferation of cardiomyocytes derived from human embryonic stem cells is mediated via the IGF/PI 3-kinase/Akt signaling pathway." J Mol Cell Cardiol 39: 865-873; doi:S0022-2828(05)00287-7 [pii]10.1016/j.yjmcc.2005.09.007.
McMullen, J. R. et al. (2004). "The insulin-like growth factor 1 receptor induces physiological heart growth via the phosphoinositide 3-kinase(p110alpha) pathway." J Biol Chem 279: 4782-4793; doi:10.1074/jbc.M310405200 M310405200.
Miklas, J. W. et al. (2013). "Engineering Cardiac Tissues from Pluripotent Stem Cells for Drug Screening and Studies of Cell Maturation," Israel Journal of Chemistry, 53(9-10): 680-694.

(56) References Cited

OTHER PUBLICATIONS

Miklas, J. W. et al. (2014). "Bioreactor for modulation of cardiac microtissue phenotype by combined static stretch and electrical stimulation." Biofabrication 6(2): 024113, 27 pages.

Miller, J. S. et al. (2012). "Rapid casting of patterned vascular networks for perfusable engineered three-dimensional tissues." Nature Materials 11: 768-774; doi:10.1038/nmat3357).

Moretti, A. et al. (2010). "Patient-specific induced pluripotent stem-cell models for long-QT syndrome." The New England Journal of Medicine 363(15): 1397-409.

Morgan, P. et al. (2018). "Impact of a five-dimensional framework on R&D productivity at AstraZeneca." Nat Rev Drug Discov 17: 167-181.

Mosqueira, D. et al. (2018). "CRISPR/Cas9 editing in human pluripotent stem cell-cardiomyocytes highlights arrhythmias, hypocontractility, and energy depletion as potential therapeutic targets for hypertrophic cardiomyopathy." Eur Heart J. 1-16.

Mummery, C. et al. (2003). Differentiation of human embryonic stem cells to cardiomyocytes: role of coculture with visceral endoderm-like cells. Circulation 107, 2733-2740; doi:10.1161/01.CIR.0000068356. 38592.68 01.CIR.0000068356.38592.68.

Nag, S. et al. (2017). "The myosin mesa and the basis of hypercontractility caused by hypertrophic cardiomyopathy mutations." Nat Struct Mol Biol 24(6): 525-533.

Nanthakumar, K. et al. (2007). "Optical mapping of Langendorff-perfused human hearts: establishing a model for the study of ventricular fibrillation in humans." Am J Physiol Heart Circ Physiol 293: H875-880; doi:01415.2006 10.1152/ajpheart.01415.2006.

Navarrete, E. G. et al. (2013). "Screening adverse drug-induced arrhythmia events using human induced pluripotent stem cell-derived cardiomyocytes and low-impedance microelectrode arrays." Circulation 128(11 Suppl 1): pp. S3-13.

Nawroth, J. C. et al. (2017). "Automated fabrication of photopatterned gelatin hydrogels for organ-on-chips applications." Biofabrication Jan. 16, 2018; 10(2): 025004, 16 pages.

Nuccitelli, R. (1992). "Endogenous ionic currents and DC electric fields in multicellular animal tissues." Bioelectromagnetics Suppl 1: 147-204.

Nunes, S. S. et al. (2011). "Stem cell-based cardiac tissue engineering." J Cardiovasc Transl Res 4: 592-602; doi:10.1007/s12265-011-9307-x.

Nunes, S. S. et al. (2013). "Biowire: a new platform for maturation of human pluripotent stem cell-derived cardiomyocytes." Nature Methods 10(8): 781-7.

Ofstad, A. P. et al. (2018). "The heart failure burden of type 2 diabetes mellitus—a review of pathophysiology and interventions." Heart Fail Rev; https://doi.org/10.1007/s10741-018-9685-0, 21 pages.

Owens, J. et al. (2013)."Characterization of primary human skeletal muscle cells from multiple commercial sources." In Vitro Cell Dev Biol Anim. Oct. 2013; 49(9): 695-705.

Parsa, H. et al. (2017). "A microfluidic platform for the high-throughput study of pathological cardiac hypertrophy." Lab Chip. Sep. 26, 2017; 17(19): 3264-3271.

Patterson, M. et al. (2012). "Defining the nature of human pluripotent stem cell progeny." Cell Res 22: 178-193; doi:cr2011133 10.1038/cr.2011.133.

Piccini, J. P. et al. (2009). "Current challenges in the evaluation of cardiac safety during drug development: translational medicine meets the Critical Path Initiative." Am Heart J 158: 317-326; doi:S0002-8703(09)00449-9 10.1016/j.ahj.2009.06.007.

Polak, S. & Fijorek, K. (2012). "Inter-individual variability in the pre-clinical drug cardiotoxic safety assessment—analysis of the age-cardiomyocytes electric capacitance dependence." Journal of Cardiovascular Translational Research 5: 321-332; doi:10.1007/s12265-012-9357-8.

Puppala, D. et al. (2013). "Comparative gene expression profiling in human-induced pluripotent stem cell—derived cardiocytes and human and cynomolgus heart tissue." Toxicol Sci. Jan. 2013; 131(1): 292-301.

Radisic, M. et al. (2004). "Functional assembly of engineered myocardium by electrical stimulation of cardiac myocytes cultured on scaffolds." Proc Natl Acad Sci U S A 101: 18129-18134; doi:0407817101 10.1073/pnas.0407817101.

Rajamohan, D. et al. (2013). "Current status of drug screening and disease modelling in human pluripotent stem cells," BioEssays : News and Reviews in Molecular, Cellular and Developmental Biology. 35(3): 281-98.

Rao, L. et al. (2018). "Engineering human pluripotent stem cells into a functional skeletal muscle tissue." Nat Commun 9(1): 126; doi: 10.1038/s41467-017-02636-4, 12 pages.

Rao, L. et al. (2018). "Engineering human pluripotent stem cells into a functional skeletal muscle tissue." Nat Commun 9(1): 126; doi: 10.1038/s41467-017-02636-4; Supplemental Materials, 17 pages.

Rodriguez, A. G. et al. (2011). "Substrate stiffness increases twitch power of neonatal cardiomyocytes in correlation with changes in myofibril structure and intracellular calcium." Biophys J 101: 2455-2464; doi:S0006-3495(11)01193-3 10.1016/j.bpj.2011.09. 057.

Ronaldson-Bouchard, K. et al. (2018). "Advanced maturation of human cardiac tissue grown from pluripotent stem cells." Nature; https://doi.org/10.1038/s41586-018-0016-3, 23 pages.

Rupert, C. E. et al. (2017). IGF1 and NRG1 Enhance Proliferation, Metabolic Maturity, and the Force-Frequency Response in hESC-Derived Engineered Cardiac Tissues. Stem Cells Int. 2017; 2017: 7648409, 13 pages.

Sadeghi, A. H. et al. (2017). "Engineered 3D Cardiac Fibrotic Tissue to Study Fibrotic Remodeling." Adv Health Mater. Jun. 2017; 6(11); doi: 10.1002/adhm.201601434, 14 pages.

Sadeghian, R. et al. (2017). "Electrical stimulation of microengineered skeletal muscle tissue: Effect of stimulus parameters on myotube contractility and maturation." J Tissue Eng Regen Med. 1-11.

Sage, D. et al. (2005). "Automatic tracking of individual fluorescence particles: Application to the study of chromosome dynamics." IEEE Transactions on Image Processing 14(9): 1372-1383.

Sakai, R. et al. (1996). "Sodium-potassium pump current in rabbit sino-atrial node cNa cells." J Physiol 490 (Pt 1): 51-62.

Sanchez-Freire, V. et al. (2016). "Use of engineered cardiac tissue constructs (ETCs) as a model for studying human cardiac diseases." ISSCR Poster, 1 page.

Satin, J. et al. (2004). "Mechanism of spontaneous excitability in human embryonic stem cell derived cardiomyocytes." J Physiol 559: 479-496; doi:10.1113/jphysiol.2004.068213.

Satin, J. et al. (2008). "Calcium handling in human embryonic stem cell-derived cardiomyocytes." Stem Cells 26: 1961-1972; doi:2007-0591 10.1634/stemcells.2007-0591.

Schaaf, S. (2011). "Human engineered heart tissue as a versatile tool in basic research and preclinical toxicology." PLoS One 6: e26397; doi:10.1371/journal.pone.0026397 PONE-D-11-08333, 11 pages.

Schroer, A. K. et al. (2017). "I-Wire Heart-on-a-Chip II: Biomechanical analysis of contractile three-dimensional cardiomyocyte tissue constructs." Acta Biomater. Jan. 15, 2017; 48: 79-87.

Seif-Naraghi, S. B. et al. (2013). "Safety and efficacy of an injectable extracellular matrix hydrogel for treating myocardial infarction." Science Translational Medicine 5(173); doi:10.1126/scitranslmed.3005503, 20 pages.

Serrao, G. W. (2012). "Myocyte-depleted engineered cardiac tissues support therapeutic potential of mesenchymal stem cells." Tissue Eng Part A 18: 1322-1333; doi:10.1089/ten.TEA.2011.0278.

Shadrin, Y. et al. (2017). "Cardiopatch platform enables maturation andscale-up of human pluripotent stem cell-derivedengineered heart tissues." Nat Commun. Nov. 28, 2017; 8(1): 1825; doi: 10.1038/s41467-017-01946x, 15 pages.

Shah, S. J. (2017). "Precision Medicine for Heart Failure with Preserved Ejection Fraction: An Overview." J Cardiovasc Transl Res 10(3): 233-244.

Shah, S. J. et al. (2015). "Phenomapping for novel classification of heart failure with preserved ejection fraction." Circulation 131(3): 269-279.

Sidorov, V. Y. et al. (2017). "I-Wire Heart-on-a-Chip I: Three-dimensional cardiac tissue constructs for physiology and pharmacology." Acta Biomater. Jan. 15, 2017; 48: 68-78.

(56) References Cited

OTHER PUBLICATIONS

Simmons, A. et al. (2008). "Biostability and biological performance of a PDMS-based polyurethane for controlled drug release." Biomaterials 29: 2987-2995.
Snir, M. et al. (2003). "Assessment of the ultrastructural and proliferative properties of human embryonic stem cell-derived cardiomyocytes." Am J Physiol Heart Circ Physiol 285: H2355-2363; doi:10.1152/ajpheart.00020.2003 285/6/H2355.
Snyders, D. J. & Chaudhary, A. (1996). "High affinity open channel block by dofetilide of HERG expressed in a human cell line." Mol Pharmacol 49: 949-955.
Sun, N. et al. (2012). "Patient-specific induced pluripotent stem cells as a model for familial dilated cardiomyopathy." Sci Transl Med 4(130): p. 130ra47, 20 pages.
Tandon, N. et al. (2009). "Electrical stimulation systems for cardiac tissue engineering." Nat Protoc. 2009; 4(2): 155-73.
Tandon, N. et al. (2011). "Optimization of Electrical Stimulation Parameters for Cardiac Tissue Engineering." J Tissue Eng Regen Med. Jun. 2011; 5(6): e115-25.
Thavandiran, N. et al., (2013) "Design and formulation of functional pluripotent stem cell-derived cardiac microtissues." Proc Natl Acad Sci USA Dec. 3, 2013; 110(49): E4698-707.
Tiburcy, M. et al. (2017). "Defined Engineered Human Myocardium with Advanced Maturation for Applications in Heart Failure Modelling and Repair." Circulation. May 9, 2017; 135(19): 1832-1847.
Tran, R. et al. (2010) "Synthesis and characterization of a biodegradable elastomer featuring a dual crosslinking mechanism." Soft Matter. Jan. 1, 2010; 6(11): 2449-2461.
Tulloch, N. L. et al. (2011). "Growth of engineered human myocardium with mechanical loading and vascular coculture." Circ Res 109: 47-59.
Turner, N. A. (2018). "Strength in Numbers: Cardiac Fibroblast Clustering and Myocardial Remodeling." Circ Res. 2018; 123: 12-14.
Uezumi, A. et al. (2011). "Fibrosis and adipogenesis originate from a common mesenchymal progenitor in skeletal muscle." Cell Sci. 24(Pt 21): 3654-64.
Vandenburgh, H. et al. (2008). "Drug-screening platform based on the contractility of tissue-engineered muscle." Muscle Nerve 37: 438-447; doi:10.1002/mus.20931.
Wang, J. et al. (2011). "Review on regulation of inwardly rectifying potassium channels." Crit Rev Eukaryot Gene Expr 21: 303-311.
Wang, L. et al. (2018). "Arrhythmogenic cardiomyopathy: Identification of desmosomal gene variations and desmosomal protein expression in variation carriers." Exp Ther Med 15(3): 2255-2262.
Weinberger, F. et al. (2016) "Cardiac repair in guinea pigs with human engineered heart tissue from induced pluripotent stem cells." Sci Transl Med. Nov. 2, 2016; 8:363ra148, 12 pages.
Weiss, J. N. et al. (2010). "Early afterdepolarizations and cardiac arrhythmias." Heart Rhythm 7(12): 1891-1899.
Wiedeman, M. P. (1963). "Dimensions of blood vessels from distributing artery to collecting vein." Circ Res 12: 375-378.
Wu, Z. et al. (2007). "Effects of surface coating on the controlled release of vitamin B1 from mesoporous silica tablets." J Control Release 119: 215-221; doi:S0168-3659(07)00126-5 10.1016/j.jconrel.2007.03.001.
Xu, C. et al. (2001). "Feeder-free growth of undifferentiated human embryonic stem cells." Nature Biotechnology 19: 971-974; doi:10.1038/nbt1001-971.
Yang, L. et al. (2008). "Human cardiovascular progenitor cells develop from a KDR+ embryonic-stem-cell-derived population." Nature 453(7194): 524-8.
Yang, P. C. (2018). "Induced Pluripotent Stem Cell (iPSC)—Derived Exosomes for Precision Medicine in Heart Failure." Circulation Research 122(5): 661-663.
Yang, Y. et al. (2018). "Improved calcium sensor GCaMP-X overcomes the calcium channel perturbations induced by the calmodulin in GCaMP." Nat Commun 9(1): 1504;18 pages.
Yazawa, M. et al. (2011). "Using induced pluripotent stem cells to investigate cardiac phenotypes in Timothy syndrome." Nature 471(7337): 230-4.
Ye, X. et al. (2013). "A biodegradable microvessel scaffold as a framework to enable vascular support of engineered tissues." Biomaterials 34(38): 10007-10015; doi:10.1016/j.biomaterials.2013.09.039.
Zhang, B. et al. (2016). "Biodegradable scaffold with built-in vasculature for organ-on-a-chip engineering and direct surgical anastamosis." Nat Matr. Jun. 2016; 15(6): 669-678.
Zhang, J. et al. (2009). "Functional cardiomyocytes derived from human induced pluripotent stem cells." Circ Res 104(4): e30-41.
Zhang, Y. S. et al. (2015). "From Cardiac Tissue Engineering to Heart-on-a-Chip: Beating Challenges." Biomed Mater. Jun. 11, 2015; 10(3): 034006, 21 pages.
Zhao, M. et al. (1999). "A small, physiological electric field orients cell division." Proceedings of the National Academy of Sciences of the United States of America 96: 4942-4948.
Zhu, W. Z. et al. (2009). "Local control of excitation-contraction coupling in human embryonic stem cell-derived cardiomyocytes." PloS One 4: e5407; doi:10.1371/journal.pone.0005407, 11 pages.
Zimmermann, W. H. et al. (2006). "Engineered heart tissue grafts improve systolic and diastolic function in infarcted rat hearts." Nat Med 12: 452-458; doi:nm1394 10.1038/nm1394.
Nunes, S. S. et al. (2013). "Biowire: a new platform for maturation of human pluripotent stem cell-derived cardiomyocytes." Nature Methods 10(8): 781-7, Online Methods, Supplemental Figures, 25 pages.

* cited by examiner

|  | EBd34 | Non-stimulated control | 3 Hz | 6 Hz |
|---|---|---|---|---|
| Round | 195 ± 31 | 248 ± 94 | 279 ± 93 | 208 ± 115 |
| Rod-like | 562 ± 79 | 857 ± 187* | 977 ± 246* | 917 ± 171* |

Table 1

FIG. 26

| | Non-stimulated control (n=18) | 3 Hz (n=11) | 6 Hz (n=19) | P value (control vs. 6 Hz) |
|---|---|---|---|---|
| Amplitude (F/F0) | 2.50 ± 0.13 | 2.64 ± 0.18 | 2.93 ± 0.12* | 0.017 |
| Rising slope (F/F0/s) | 5.29 ± 0.55 | 5.55 ± 0.66 | 7.36 ± 0.64* | 0.025 |
| Time to peak (s) | 0.511 ± 0.046 | 0.496 ± 0.044 | 0.403 ± 0.037* | 0.049 |
| τ-decay (s) | 0.591 ± 0.058 | 0.521 ± 0.057 | 0.419 ± 0.043* | 0.022 |
| Time to base (s) | 1.461 ± 0.137 | 1.310 ± 0.147 | 1.142 ± 0.091* | 0.035 |

Table 2

FIG. 27

| Gene | Forward 5'-3' | Reverse 3'-5' |
|---|---|---|
| RYR2 | AGAACTTACACACGCGACCTG | CATCTCTAACCGGACCATACTGC |
| NPPA | GAACCAGAGGGGAGAGACAGAG | CCCTCAGCTTGCTTTTTAGGAG |
| NPPB | TTCCTGGGAGGTCGTTCCCAC | CATCTTCCTCCCAAAGCAGCC |
| TNNT | TTCACCAAAGATCTGCTCCTCGCT | TTATTACTGGTGTGGAGTGGGTGTG |
| Cx43 | GGCTTTTAGCGTGAGGAAAGTACCA | TCCCCAGCAGCAGGATTCGG |
| GAPDH | GAGTCAACGGATTTGGTCGT | GACAAGCTTCCCGTTCTCAG |
| TBP | TGAGTTGCTCATACCGTGCTGCTA | CCCTCAAACCAACTTGTCAACAGC |
| MYH6 | TCAGCTGGAGGCCAAAGTAAAGGA | TTCTTGAGCTCTGAGCACTCGTCT |
| MYH7 | TCGTGCCTGATGACAAACAGGAGT | ATACTCGGTCTCGGCAGTGACTTT |
| KCNJ2 | TGGTGTGTGTGTCTTCACCGAACA | GACTCCAGTGCTTCTGCTTTGGAA |

FIG. 28 a b
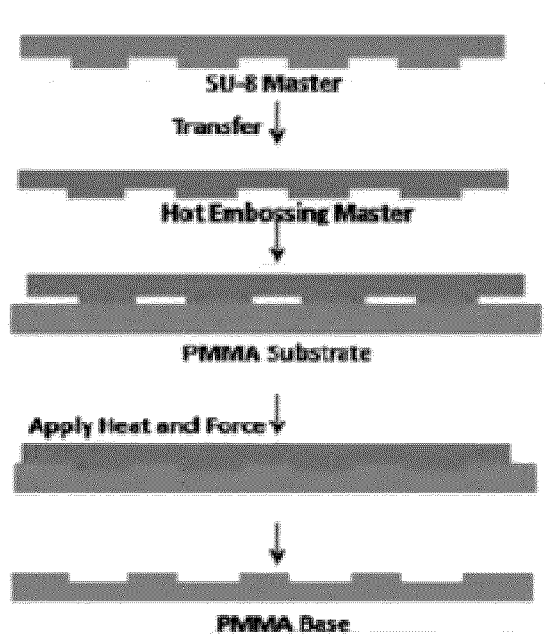
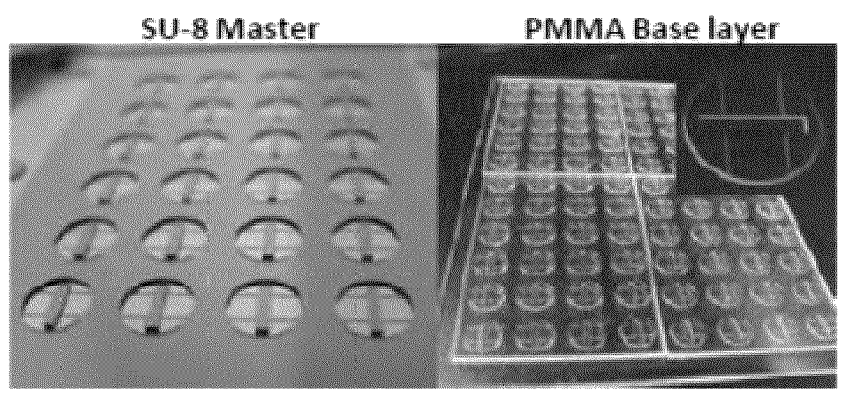
FIG. 37 Cont.)

c d
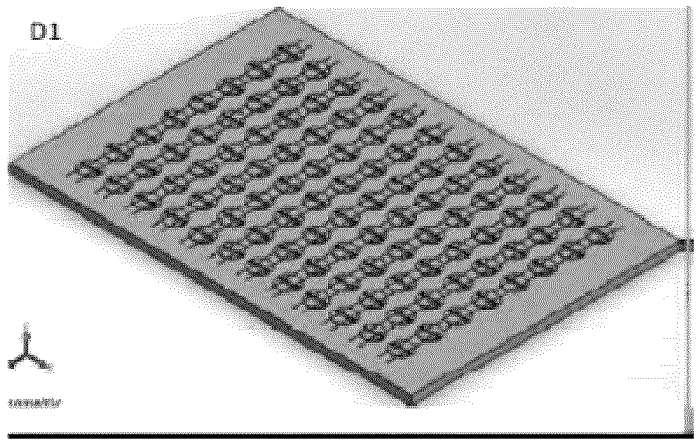
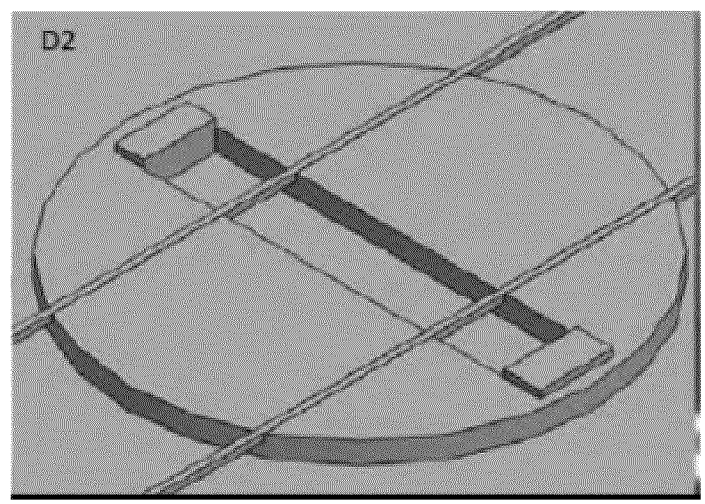
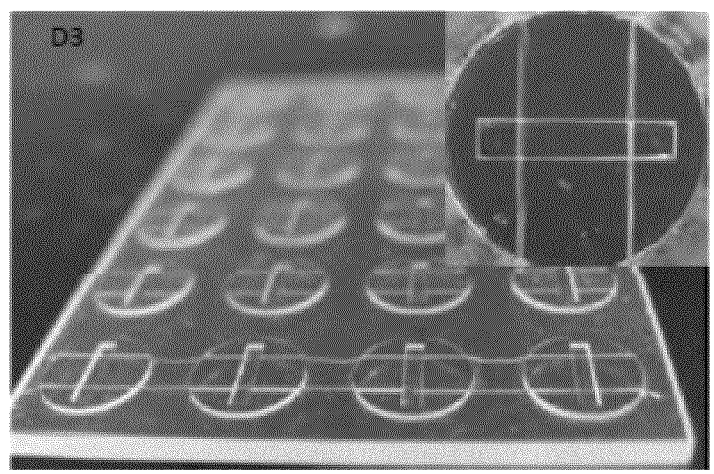
FIG. 37 Cont.)

$$y = \frac{W_o}{24EI}\left(\frac{L^4}{16} - La^3 + a^4\right)$$

$$W_o = \frac{24yEI}{\frac{L^4}{16} - La^3 + a^4}$$

$$F = W_o(L - 2a)$$

$$\frac{Load}{Cross-section} = \frac{F}{A}$$

$E$ = Young's Modulus
$I$ = Moment of Inertia
$W_o$ = Load /length
$y$ = Deflection
$L$ = Length of Beam
$a$ = Distance between fixed end to loading session
$F$ = Total force generated
$A$ = Cross-section Area of tissue In situ IHC Staining and Imaging

E

| Parameter | AngioChip Scaffold | | | Rat Myocardium (n=4) |
|---|---|---|---|---|
| | Design A (n=3) | Design B (n=3) | Design C (n=3) | |
| $E_{LD}$ (kPa) | 89±22# | 60±10* | 22±6*# | 43±9* |
| $E_{SD}$ (kPa) | 53±10# | 31±4# | 18±7 | 12±5 |
| $E_{LD}/E_{SD}$ | 1.7±0.8# | 2±0.6 | 1.4±0.6# | 3.9±1.2 |
| $UTS_{LD}$ (kPa) | 56±17 | 39±8 | 25±14 | |
| $UTS_{SD}$ (kPa) | 22±8 | 15±3 | 8±4 | |
| $εfL_D$ | 0.7±0.2 | 0.7±0.2 | 1.0±0.4 | |
| $εf_{SD}$ | 0.5±0.2 | 0.6±0.2 | 0.5±0.05 | |

\* Significantly different from corresponding sample tested in the short-edge direction.
Significantly different from adult rat myocardium.

FIG. 62

FIG. 68
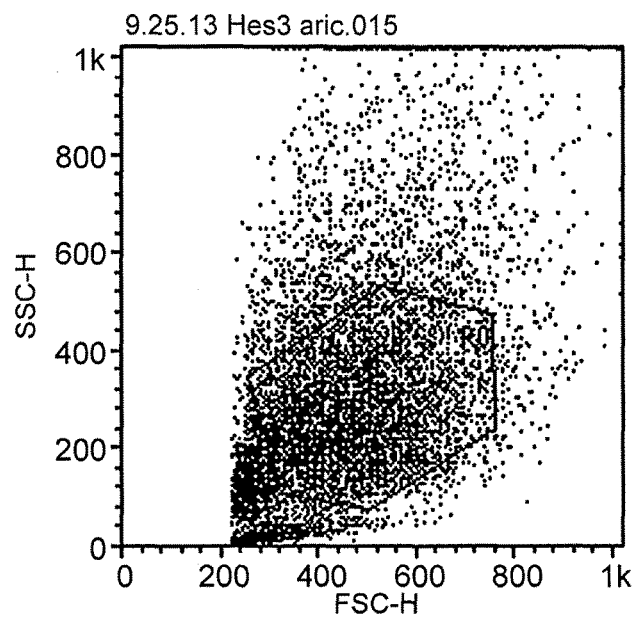
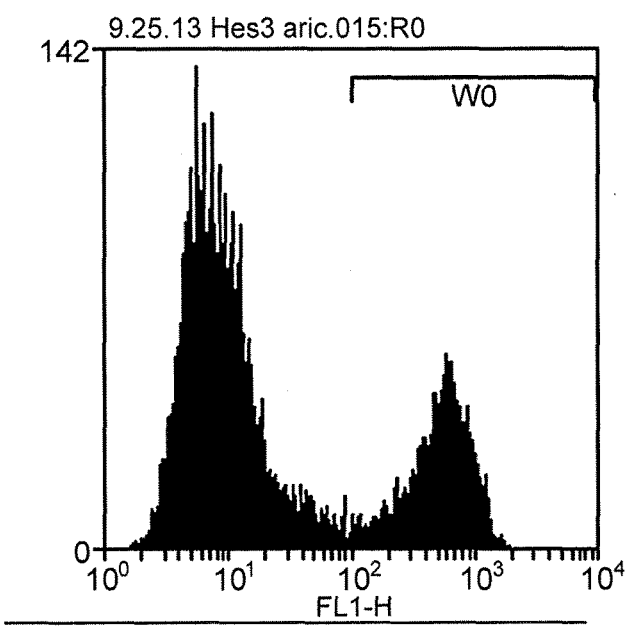
File: 9.25.13 Hes3 aric.015   Gate:
...   Region Stats: Overlay 0   ....
Region:           %Gated
0: R0             100
...   Window Stats: Overlay 0   ....
Window:           %Gated
0: W0             28.19

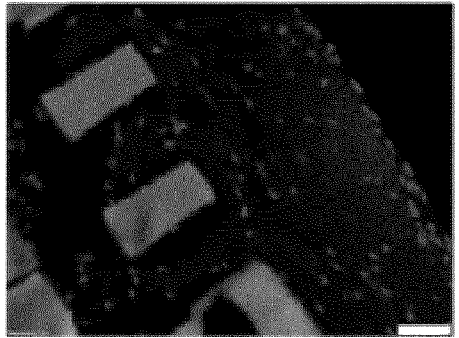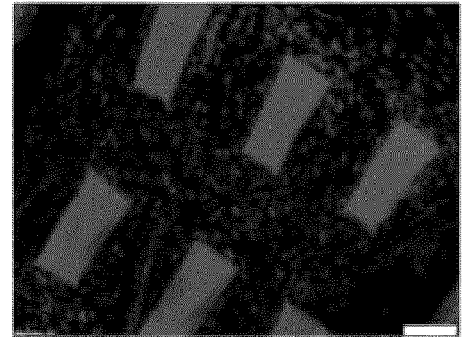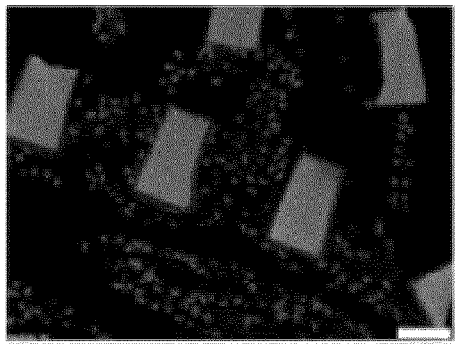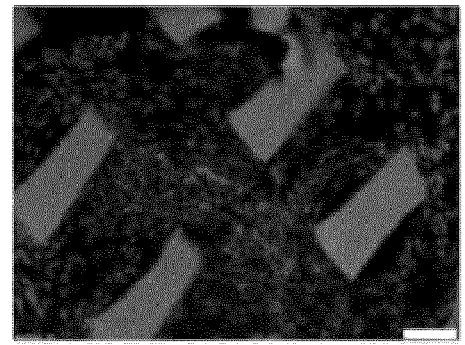
FIG. 73

|  | Area (μm$^2$) |
|---|---|
| Control | 260.0 ±46 |
| ISO | 351.9 ±47 |
| AngII | 359.9 ±90 |
| Et-1 | 531.8 ±33 |

FIG. 85

COMPOSITIONS AND METHODS FOR MAKING AND USING THREE-DIMENSIONAL TISSUE SYSTEMS

CROSS-REFERENCE TO RELATED APPLICATIONS

This application is a national stage application filed pursuant 35 U.S.C. 371 based on International Application No. PCT/CA2014/051046, which claims priority to U.S. Provisional Patent Application Ser. No. 61/897,276, filed Oct. 30, 2013, which is incorporated herein by reference in its entirety for all purposes.

FIELD OF THE INVENTION

The present disclosure relates to methods, compositions, and devices for making and using three-dimensional biological tissues, as well as tissue scaffolds, which accurately mimic native conditions and structures, such as, but not limited to, native physiology, tissue architecture, vasculature, and other properties of native tissues. The synthetic or engineered tissues may include, but are not limited to, cardiac, hepatic, neural, vascular, kidney, and muscle tissues. The methods, composition, and devices may be used in a variety of applications that include drug testing, tissue repair, tissue replacement, treatment, regenerative medicine or combinations thereof.

BACKGROUND

Tissue engineering is the use of a combination of cells, engineering, materials and methods, as well as suitable biochemical (e.g., growth factors) and physico-chemical factors (e.g., chemically-modified extracellular matrices) to improve, replace or mimic biological structures and/or functions. Tissue engineering is widely accepted as an interdisciplinary field that applies the principles of engineering and life sciences toward the development of biological substitutes that restore, maintain, or improve tissue function or a whole organ. Engineered tissue systems not only have significant potential in the area of regenerative medicine to restore and/or repair damage or diseased tissues (e.g., myocardial infarct), but have also been proposed for use in drug discovery and development as providing access to more accurate and physiologically relevant model systems for predicting and/or testing the pharmacokinetic and pharmacodynamic responses associated with pharmacologic agents.

Among the major challenges facing tissue engineering is the need for more complex and physiologically relevant engineered tissues that better mimic the structure, physiology, and function, of native tissues. This is particularly important and challenging when attempting to use engineered tissues to screen, test, and/or evaluate therapeutic agents.

Drug discovery and development consists of an arduous testing process, beginning with the demonstration of pharmacological effects in experimental cell and animal models and ending with drug safety and efficacy studies in patients. It is estimated that only 1 out of 5,000 screened compounds receives FDA approval as a safe and effective new medicine. Approximately 25% of compounds are eliminated in pre-clinical toxicological studies. Thus, a significant number of drug candidates in pre-clinical development fail to progress out of this stage due to unacceptable levels of toxicity in test systems.

Typically, multiple pharmacologic parameters are considered when evaluating a drug candidate. Knowledge of the absorption, distribution, metabolism and excretion (ADME) profile of a drug and its metabolites in humans (and animals used in toxicology assessments) is crucial to understanding differences in effects among individuals in a population and for optimizing dosing aspects. Absorption and bioavailability are standard measures of the amount of biologically active material distributed to the systemic circulation or local site of action. Duration of drug action is often dependent on how rapidly the body eliminates the active molecules, either through metabolism, which involves chemical modification by drug-metabolizing enzymes, or by excretion, which involves binding and transport away from biologically active sites in the body. Thus, typical pre-clinical studies involve monitoring permeation across epithelial membranes (e.g., gastrointestinal mucosa), studies of drug metabolism, identification of plasma protein binding and evaluation of transport into and out of tissues, especially organs that eliminate drug products, such as the kidney and liver.

Current pre-clinical toxicity and pharmacology studies typically utilize in vitro assays involving cultured cells or subcellular organelles, as well as in vivo animal models to investigate drug metabolism, toxicity and possible efficacy. While technological advances in cell, molecular, and biochemical assays have made significant strides, a number of significant problems still exist. First, in vitro assays using purified or recombinant enzymes and cell cultures provide the first step in determining pharmacologic and toxicologic parameters to be used thereafter in animal models, but are often too simplistic to account for the myriad events that occur during drug metabolism in a native human tissue or system. Second, data obtained in animal models can be difficult to extrapolate to human systems. Third, many drugs used to treat chronic diseases such as HIV infection or Alzheimer's disease necessitate dosing regimens that are applied over long periods of time, and in some cases, over the lifetime of an individual. Currently, development of chronic toxicity is most practically observed during long-term patient use.

Given the high failure rate of drug candidates and the high costs and other hinderances associated with such failures, there is a great need for more effective pre-clinical models and assay systems that can reliably understand and predict the various aspects of how a drug may interact with a human subject, including toxicity, effectiveness, and overall pharmacodynamics and/or pharmacokinetic properties associated with the drug. Tissue engineering may be a solution for providing three-dimensional biological tissues that accurately mimic native physiology, architecture, and other properties of native tissues, such as cardiac, neural, vascular, kidney, and muscle tissues, that can be used to effectively, reliably, and accurately evaluate the interaction and effects of pharmacologic agents on a subject. However, given the many significant complexities in developing suitable engineered tissue systems that may be reliably used to assess drug effects, the use of engineered tissues in drug testing and development has limited utility and value presently.

This is particularly the case of drug screening with engineered cardiovascular tissue models. Cardiovascular diseases are important targets for pharmacological therapy because they are typically associated with high morbidity and mortality rates. In vitro engineered models may serve as cost-effective alternatives to animal models due to improved system control and higher throughput. In recent years, tissue engineering methods have been significantly advanced to generate functional three-dimensional (3D) cardiac tissues in vitro, which better recapitulate the complexity and electromechanical function of native myocardium. However, the current systems fail to recapitulate closely enough the architectural complexity of native cardiac tissue and therefore are insufficiently relevant to the physiological aspects of actual native cardiac tissue.

Improved engineered tissue model systems would provide better opportunities to obtain meaningful pre-clinical information on drug safety and efficacy. Such systems would improve the arduous drug development and discovery process. Such a need exists in the art. The present disclosure provides various solutions to these art-recognized problems by providing methods, compositions, and devices for making three-dimensional biological tissues that accurately mimic native physiology, architecture, and other properties of native tissues, such as, e.g., cardiac, neural, vascular, and muscle tissues, for use in, among other applications, drug testing, tissue repair, transplantation, disease treatment, regenerative medicine or combinations thereof.

SUMMARY

The present disclosure provides methods, compositions, and devices for making and using biological tissues, preferably, three-dimensional tissues, that accurately mimic native physiology, architecture, and other properties of native tissues for use in, among other applications, drug testing, tissue repair, transplantation, disease treatment, regenerative medicine or combinations thereof.

In one aspect, the present disclosure provides various tissue culture or tissue engineering bioreactor systems for cultivating, growing, and/or testing engineered tissue constructs, and preferably, three-dimensional tissue constructs.

In another aspect, the present disclosure relates to the engineered tissue constructs, e.g., the three-dimensional tissue constructs, grown or prepared from the various tissue culture systems of the invention.

In still another aspect, the present disclosure relates to both the tissue culture systems described herein and the tissue constructs grown therein.

In yet another aspect, the present disclosure relates to methods of using the three-dimensional tissue constructs, the devices, and/or the systems of the invention in various applications, including, but not limited to, (a) the testing of the efficacy and safety (including toxicity) of experimental pharmacologic agents (including, but not limited to, small molecule drugs, biologics, nucleic acid-based agents), (b) the defining of pharmacokinetics and/or pharmacodynamics of pharmacologic agents (including, but not limited to, small molecule drugs, biologics, nucleic acid-based agents), (c) characterizing the properties and therapeutic effects of pharmacologic agents (including, but not limited to, small molecule drugs, biologics, nucleic acid-based agents) on a subject, (d) screening of new pharmacologic agents, (e) providing implantable engineered tissues for use in regenerative medicine for treating damaged and/or diseased tissues, (e.g., use of the tissue constructs, devices, and/or systems of the disclosure to study cardiac disease states, including patients with electrical conduction defects (iPSC-CM)), and (f) personalized medicine.

In various other aspects, the present disclosure provides devices and methods for cultivating tissue, and in certain embodiments, three-dimensional tissues.

In still further aspects, the present disclosure also provides methods for fabrication of the devices and systems of the invention.

In various forms, the various tissue systems of the disclosure are comprised of cardiac tissue, liver tissue, kidney tissue, cartilage tissue, skin, bone marrow tissue, or combinations of such tissues. In particular embodiments, the three-dimensional tissue system comprises cardiac tissue. In other particular embodiments, the tissue systems are comprised of kidney tissue. In certain embodiments, the tissues formed in the systems described herein are three-dimensional tissues.

In a first aspect, the disclosure relates to a bioreactor system comprising a bioreactor having a well or channel, a longitudinal scaffold, suture, or otherwise cell growth element supported or suspended across the well or channel. The well or channel is configured to receive cells seeded therein, as well as growth media and/or nutrient and/or factors. The cells, once seeded, cultivate to form a tissue culture, and preferable in certain embodiments, a three-dimensional tissue strand contained on, around, over, and/or integrated with the longitudinal scaffold, stuture, or otherwise cell growth element.

In a second aspect, the disclosure relates to a bioreactor system for growing a tissue culture, e.g., a three dimensional tissue strand. The bioreactor system includes a well or channel suitable for seeding cells and a perfusable scaffold with one or more lumens and which is supported or suspended over the well or channel, e.g., along the longitudinal axis of the well or channel. Once cells are seeded into the well or channel, along with optional suitable growth media, growth factors, and other nutrients suitable for the culture of the cells, the cells grow to form a tissue strand that surrounds and/or integrates with the perfusable scaffold. In use, nutrients and growth factors, as well as test agents (e.g., drugs, proteins, toxins etc.) may be delivered to the tissue strand via the perfusable lumen which is integrated with a means for delivering such materials (e.g., a reservoir element connected to the luman via a tube or vessel). In addition, the bioreactor system may also include in various embodiments a passage that exits from the perfusable lumen, e.g., a drain or otherwise terminal reservoir that allows waste and otherwise metabolic products to diffuse from the tissue strand into the perfusable lumen and out through to the terminal reservoir. In various embodiments involving cardiac cells (or other electrically-stimulated cells), the bioreactor can be further configured to include electrodes configured to generate an electric field across the channel of the bioreactor. The direction of the electric field can be in any direction, but preferably in a direction that is parallel or perpendicular to the longitudinal axis of the tissue strand that forms along the length of the perfusuable luminal element.

In a third aspect, the invention relates to a bioreactor system for growing a tissue culture, e.g., a three-dimensional tissue strand, that is suitable for measuring contractile forces. This aspect of the invention can comprise a bioreactor having a well or channel and at least one set of opposing scaffold elements (which can be formed from a single scaffold or separate scaffolds) that are disposed within the well or chamber and function to form at least two anchor points for a three-dimensional tissue strand formed therebetween. Preferably, the at least one set of opposing scaffold elements are reversibly affixed to the walls of the well or channel but suspended thereover such that there is a gap between the bottom of the well or chamber and the elements. The bioreactor of the third aspect is not limited to having two such elements, but may include more than two, such as, three, four, five, six, seven, eight, nine, or ten, or more such elements. Any number of elements per channel may be provided so long as there is the ability to form a three dimensional tissue strand that forms around each of the opposing elements and becomes joined therebetween such that the tissue strand becomes disposed between the opposing set or sets of scaffold elements and is suspended above the channel or well.

The scaffold elements are preferably deflectable, deformable, bendable, or the like, which are further configured to allow the measurement of contractile forces exerted by the tissue strand on the scaffold elements.

In a preferred embodiment of the third aspect, each of the well or channels is configured with a set (two) or opposing scaffold elements, and preferably whereby a single scaffold element is disposed at or near the opposing ends of the longitudinal axis of the well or channel.

In certain embodiments of the third aspect, the scaffold elements are elevated off of the bottom surface of the well or channel.

In a fourth aspect, the invention relates to a bioreactor system for growing a three-dimensional tissue comprising a three-dimensional branched tissue scaffold or matrix having one or more luminal passageways (e.g., mimicking a vascularized three-dimensional tissue structure) integrated therein. The three-dimensional scaffold or matrix may contain a first portion or region for growing seeded cells and a second portion or region for providing interconnected channels that pass through or are integrated with the first portion. Preferably, the interconnected channels are perfusable with respect to the first portion and may be configured to mimic a biological vasculature. The first portion can contain one or more open regions or chambers, thereby providing an open network of chambers for growing cells and/or tissues. The three-dimensional scaffold or matrix may also contain pores or open connections between all of the components. For example, open pores or connections can be positioned between the open network of chambers for growing cells. In addition, open pores or connections can be positioned or integrated with the one or more luminal passageways. The open pores or connections facilitate movement of cells, media, growth factors, nutrients, and waste through the bioreactor system. The bioreactor can be further configured to include electrodes configured to generate an electric field across the bioreactor system. The direction of the electric field can be in any direction, but preferably in a direction that is generally perpendicular or parallel to the scaffold or matrix.

In a fifth aspect, the disclosure relates to a bioreactor system for growing a tissue culture, e.g., a three dimensional perfusable tissue strand, that is suitable for measuring contractile forces. The bioreactor system includes a well or channel suitable for seeding cells and a perfusable scaffold with one or more lumens and which is supported or suspended over the well or channel, e.g., along the longitudinal axis of the well or channel. In addition, the perfusable scaffold is configured with one set or more of opposing scaffold elements (which can be formed from a single scaffold or separate scaffolds) that are disposed within the well or chamber along the longitudinal axis of the perfusable scaffold and function to form at least two anchor points for a three-dimensional tissue strand formed therebetween and which are capable of deforming or bending in response to the contractile state of the tissue strand. The bioreactor of the fifth aspect is not limited to having two such deformable elements, but may include more than two, such as, three, four, five, six, seven, eight, nine, or ten, or more such elements. Any number of elements per channel may be provided so long as there is the ability to form a three dimensional tissue strand that forms around each of the opposing elements and along the longitudinal length of the perfusable element and becomes joined therebetween such that the tissue strand becomes disposed between the opposing set or sets of scaffold elements and is suspended above the channel or well.

The scaffold elements are preferably deflectable, deformable, bendable, or the like, which are further configured to allow the measurement of contractile forces exerted by the tissue strand on the scaffold elements.

In a preferred embodiment of the fifth aspect, each of the wells or channels is configured with a set (two) or opposing scaffold elements, and preferably whereby a single scaffold element is disposed at or near the opposing ends of the longitudinal axis of a given well or channel.

Once cells are seeded into a given well or channel, along with suitable growth media, growth factors, and other nutrients suitable for the culture of the cells, the cells grow to form a tissue strand that surrounds and/or integrates with the perfusable scaffold and the bendable elements. In use, nutrients and growth factors, as well as test agents (e.g., drugs, proteins, toxins etc.) may be delivered to the tissue strand via the perfusable lumen which is integrated with a means for delivering such materials (e.g., a reservoir element connected to the luman via a tube or vessel). In addition, the bioreactor system may also include in various embodiments a passage that exits from the perfusable lumen, e.g., a drain or otherwise terminal reservoir that allows waste and otherwise metabolic products to diffuse from the tissue strand into the perfusable lumen and out through to the terminal reservoir. In various embodiments involving cardiac cells (or other electrically-stimulated cells), the bioreactor can be further configured to include electrodes configured to generate an electric field across the channel of the bioreactor. The direction of the electric field can be in any direction, but preferably in a direction that is parallel to the longitudinal axis of the tissue strand that forms along the length of the perfusuable luminal element.

Although five particular aspects are described above, and further described herein, the present invention is not limited to these aspect and embodiments thereof. The disclosure contemplates any other suitable variation of these aspects and embodiments, and combinations of thereof.

In any of the embodiments contemplated, the three-dimensional tissues grown by the bioreactors described herein can be formed from any single cell type, such as cells from cardiac tissue, liver tissue, kidney tissue, cartilage tissue, skin, bone marrow tissue, or combinations of such tissues, or the like. The cells used to grow the three-dimensional tissues can be sourced from anywhere, including from any commercial source, or even sourced from individual subjects or patients. For example, a tissue strand of the invention may be grown starting from a seed of a commercially available hepatic cell line. In another example, a tissue strand of the invention may be grown starting from a seed of cells obtained directly from a subject, e.g., cells isolated from a biopsy. In other embodiments, the three-dimensional tissues of the invention can be grown from a mixture of different cells. Such mixtures of cells can include mixtures of healthy or diseased cells from the same or different tissues, mixtures of cells from different sources or patients, or mixtures of cells from both patients and from commercial sources. The cells used to grow the tissues of the invention can also be genetically engineered cells, such as drug-resistant or drug-sensitive engineered cell lines.

In other embodiments, the cells used to grow the three-dimensional tissues of the invention can be stem cells, including embryonic stem cells ("ESCs"), fetal stem cells ("FSCs"), and adult (or somatic) stem cells ("SSCs"). The stem cells, in terms of potency potential, can be totipotent (a.k.a. omnipotent) (stem cells that can differentiate into embryonic and extra-embryonic cell types), pluripotent stem cells (can differentiate into nearly all cells), multipotent stem cells (can differentiate into a number of cell types), oligopotent stem cells (can differentiate into only a few cell types), or unipotent cells (can produce only one cell type). Stem cells can be obtained commercially, or obtained/isolated directly from patients, or from any other suitable source.

In still other embodiments, any suitable experimental drug or pharmacologic test agent may be tested by the three-dimensional systems of the invention, including opioid analgesics, anti-inflammatory drugs such as antihistamines and non-steroidal anti-inflammatory drugs (NSAIDs), diuretics such as carbonic anhydrase inhibitors, loop diuretics, high-ceiling diuretics, thiazide and thiazide-like agents, and potassium-sparing diuretics, agents that impinge on the renal and cardiovascular systems such as angiotensin converting enzyme inhibitors, cardiac drugs such as organic nitrates, calcium channel blockers, sympatholytic agents, vasodilators, beta-adrenergic receptor agonists and antagonists, .alpha.-adrenergic receptor agonists and antagonists, cardiac glycosides, anti-arrhythmic drugs, agents that affect hyperlipoproteinemias such as 3-hydroxymethylglutaryl-coenzyme A (HMG-CoA) inhibitors, anti-neoplastic agents such as alkylating agents, antimetabolites, natural products, antibiotics, and other drugs, immunomodulators, anti-diabetic agents, and anti-microbial agents such as antibacterial agents, antiviral agents, antifungal agents, antiprotozoal agents, and antihelminthic agents.

In any of the embodiments of the invention, the scaffolds, matrices, or otherwise bendable elements may be made from any suitable material, including, for example, poly(dimethylsiloxane (PDMS)), poly(methylmethacrylate (PMMA)), polystyrene, polystyrene. The scaffold may be made of a biodegradable material. Other suitable materials may include poly(glycerol sebacate), POMac without citric acid, poly(lactic acid), poly(glycolic acid), poly(ε-caprolactone), various polyurethanes as well as co-polymers thereof, silk, microstructured, nanofabricated materials, and/or materials doped with nanostructures such as nanorods or quantum dots, among others. Optionally in certain embodiments, the scaffold material can be perfusable to allow exchange and/or passage of water and molecules, including proteins, drugs, nutrients, and metabolic waste materials. In certain other embodiments, perfusability may be implemented through the formation of pores in the scaffold material. In still other embodiments, the scaffolds may be fabricated by any suitable means, including microfabrication, soft lithography processes (including, but not limited to step-and-flash imprint lithography (SFIL), 3D printing (i.e., additive manufacturing), hot embossing, extrusion, injection molding, phase-shifting edge lithography, and nanoskiving.

In a particular aspect, the present invention relates to a bioreactor for cultivation of a tissue strand, comprising a plurality of wells, each well comprising a longitudinal chamber suitable for growing a three-dimensional tissue strand therein and a pair of linear and pliable scaffolds affixed to each longitudinal chamber in a substantially perpendicular orientation.

In another aspect, the invention provides a multiwell bioreactor for measuring contractile force of a tissue strand, comprising: a device having a plurality of sealed wells arranged in a pattern over a plane; a plurality of growth chambers each suitable for growing a tissue strand from cells seeded therein, wherein each sealed well is configured with a single growth chamber; a plurality of linear scaffolds flexibly connected to each growth chamber, wherein the linear scaffolds are configured to be encapsulated by the tissue strands once formed in the growth chambers.

In still another aspect, the invention relates to a device for cultivation of a tissue strand, the device comprising: a longitudinal bioreactor channel for receiving seed cells for a tissue culture; and a longitudinal scaffold supported to be suspended over the length of the bioreactor channel, the scaffold providing a support for the seed cells to form a tissue structure along the length of the scaffold.

In yet another aspect, the invention relates to a device for cultivation of a tissue strand, the device comprising: a longitudinal bioreactor channel for receiving seed cells for a tissue culture; and a longitudinal scaffold supported to be suspended over the length of the bioreactor channel, the scaffold providing a support for the seed cells to form a tissue structure along the length, the scaffold having a lumen and enabling perfusion of the tissue structure via the lumen.

In still another aspect, the invention provides a device for cultivation of a branched tissue, the device comprising: a bioreactor chamber for receiving seed cells for a tissue culture; and a scaffold received in the bioreactor chamber, the scaffold comprising a three-dimensional network of struts and perfusion channels, the scaffold providing a support for the seed cells to form a tissue structure about the three-dimensional network.

In certain embodiments, the bioreactor is a multiwell plate.

In certain embodiments, the bioreactor is a multiwall plate with 12 wells, 96 wells, 384 wells, or 1536 wells.

In certain embodiments, the bioreactor is comprised of a polymer.

In certain embodiments, the polymer is a biodegradable polymer. The biodegradable polymer can be polylactic acid, poly(lactic-co-glycolic) acid, or poly(caprolactone), polyglycolide, polylactide, polyhydroxybutyrate, polyhydroxyalcanoic acids, chitosan, hyaluronic acid, hydrogels, poly(2-hydroxyethyl-methacrylate), poly(ethylene glycol), poly(L-lactide) (PLA), or any combination thereof. The polymer can be poly(dimethysiloxane (PDMS)), poly(methylmethacrylate (PMMA)), polystyrene, poly(glycerol sebacate), POMac without citric acid, poly(ε-caprolactone), polyurethane, silk, or nanofabricated materials, or a polymer created by polycondensation reaction, or a co-polymer or blended polymer thereof. The polymer can be doped with a nanostructure.

In various embodiments, the scaffolds are comprised of metal, silk, or a polymer. In certain embodiments, the scaffolds are comprised of intestinal material, monocryl, polyglycolide, prolene, polyglactin, polydioxanone, polypropylene, nylon, or polyester.

The longitudinal chamber in certain embodiments is configured to be seeded by a cell.

In various embodiments, the cells can be a cardiomyocyte, a hepatocyte, renal cell, chondrocyte, skin cell, contractile cell, blood cell, immune system cell, germ cell, neural cell, epithelial cell, hormone secreting cell, bone marrow cell, or a stem cell.

In various embodiments, the scaffolds affixed to each longitudinal chamber are in a substantially perpendicular orientation, a substantially parallel orientation, or a substantially diagonal orientation relative to the orientation of the longitudinal chamber. The scaffolds can be configured to become embedded or partially embedded by the tissue strand upon the growth of the tissue strand. The scaffolds can be configured to be encapsulated or partially encapsulated by a grown tissue strand and attached thereto such that the tissue strand moves in conjunction with the movement of the scaffold.

In various embodiments, the bioreactors of the invention can comprise a pair of electrodes (or a plurality of electrodes) configured to create an electrical current through the growth chamber of the bioreactor.

In certain embodiments, the scaffolds flexibly connected to each longitudinal chamber are in a substantially perpendicular orientation, a substantially parallel orientation, or a substantially diagonal orientation relative to the orientation of the longitudinal chamber. Such scaffolds, once encapsulated or partially encapsulated by a grown tissue strand, are attached thereto and move in conjunction with the movement of the scaffold.

In certain embodiments, the bioreactors can be used for measuring the effect on contractility of the tissue strand formed therein resulting from exposure to a therapeutic agent or a toxin or a test agent of interest.

In various embodiments, the bioreactors of the invention can be used for (a) testing of the efficacy and safety (including toxicity) of an experimental pharmacologic agent, (b) defining the pharmacokinetics and/or pharmacodynamics of a pharmacologic agent, (c) characterizing the properties and therapeutic effects of a pharmacologic agent on a subject, (d) screening a new pharmacologic agents, and (e) providing implantable engineered tissues for use in regenerative medicine for treating damaged and/or diseased tissues.

In another aspect, the invention relates to a method for measuring the effect of a test agent on the contractile force of a tissue, comprising: (a) measuring contractile force of the tissue strand of a bioreactor, (b) contacting the tissue strand of the bioreactor with a test agent under conditions sufficient for the test agent to affect contractile force; (c) measuring contractile force of the tissue strand after expore to the test agent; determining whether the test agent affects contractile force by comparing (a) and (c), wherein measuring contractile force comprises measuring the amount of force imposed by the tissue strand on the longitudinal scaffold when moving the longitudinal scaffold from a resting position to a second position using an external force.

In certain embodiments, the contractile force is measured by a bending test in conjunction with electron microscopy imaging.

In another aspect, the invention provides a method for evaluating the safety and efficacy of a test agent on a tissue, comprising: (a) contacting the tissue strand of a bioreactor with a test agent; (b) measuring the effect on one or more physiological parameters indicative of safety and/or efficacy; comparing (b) to the same physiological parameter measured from a control bioreactor not exposed to the test agent, wherein a statistically significant change in the physiological parameter in (b) as compared to (c) indicates that the test agent lacks safety and/or efficacy.

In yet another aspect, the invention relates to a method for fabricating a bioreactor for cultivation of a tissue strand, comprising the steps of: microfabricating a plate comprising an array of sealed wells, each being formed with a longitudinal chamber suitable for growing a three-dimensional tissue strand therein; affixing a pair of linear scaffolds to each longitudinal chamber, wherein the linear scaffolds are configured to become encapsulated by the tissue strand, once formed in the longitudinal chamber, wherein the linear scaffolds are oriented in a generally longitudinal direction in relation to the longitudinal chamber.

Where applicable or not specifically disclaimed, any one of the embodiments described herein are contemplated to be able to combine with any other one or more embodiments, even though the embodiments are described under different aspects of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings. Reference will now be made, by way of example, to the accompanying drawings which show example embodiments of the present application.

FIG. 26 shows a table of measurements performed on tissues generated in accordance with an exemplary biowire system of the disclosure.

FIG. 27 shows a table of changes in Ca2+ handling properties in tissues cultivated using an example of the disclosed devices.

FIG. 28 shows a table of example oligonucleotide sequences used for generation of tissues, according to an example of the present disclosure.

FIG. 51(b) provides a schematic of the AngioChip scaffold micro-fabrication process using 3-D stamping. FIG. 51(c) depicts the seeding of the AngioChip surface with a gel/cell preparation (2) followed by gel compaction (3) around and within the AngioChip. The right figure (ii) depicts a bioreactor comprising three separate chambers for growing AngioChip. FIG. 51(d) provides SEM images showing the micro-structure of the AngioChip scaffold of different configurations and pore sizes. FIG. 51(e) provides SEM images of AngioChip scaffolds with 10 micron micro-holes. (A) provides image of an AngioChip scaffold with 10 micron through-holes patterned throughout its network wall. Scale bar: 600 microns. Image was stitched from multiple images. (B) SEM of an AngioChip scaffold with 10 micron through-holes viewed from different angles. Scale bars are shown in images. FIG. 51(f) provides microCT of 3-D AngioChip scaffolds. (A) MicroCT scans of the cross-section of a 3-D AngioChip scaffold from its inlet to the branches along the long-edge direction of the scaffold. Scale bar: 400 microns. (B) MicroCT of the internal network of an AngioChip view from different angles. The scaffold was perfused with barium sulfate solution through its internal network hence increasing its density for improved visualization. The thickness of the scaffold network wall was 50 μm. The inlet, outlet, and the first order branch had an inner luminal dimension of 50 μm by 200 μm. The second order branch had an inner luminal dimension of 50 μm by 100 μm. The network was designed so that the endothelial cells in the first and second order branches experienced the same level of shear stress. The networks on each layer were connected through a vertical channel and were 300 μm apart in z-axis. The scaffold mesh was made of 50 μm struts. The struts were spaced 250 μm apart in the long-edge direction, 100 μm apart in the short-edge direction, and 50 μm apart in the z-axis. FIG. 51(g) provides the molecular structural characterization of POMac polymer solution. (A) Fourier transform infrared (FT IR) spectroscopy. (B) Nuclear magnetic resonance (NMR) spectroscopy.

The arrow indicates the flow direction. h-i, SEM of (h) the luminal surface of an untreated scaffold network and (i) the luminal surface of an endothelialized network after perfused with heparinized human whole blood at 15 dynes/cm$^2$ for 30 min. Scale bar: (h, i) 100 μm, and (inset) 50 μm. White arrows label representative platelets. j, Quantification of the luminal surface area of the scaffold network covered by the platelets (average±s.d., n=3). (k) Schematic of the perfusion of macrophages through the endothelialized network. l, Fluorescent image showing adhesion and accumulation of fluorescently labeled RAW 267 cells in the network branches. Scale bar: 200 μm. White arrows indicate macrophage aggregates. (m), Time-lapse images of a fluorescently labeled macrophage migrating laterally on the endothelialized surface of a scaffold network. Scale bar: 10 μm. White arrows indicate the direction of macrophage migration. White dots indicate the position of the tracked cell in a previous captured frame. (n), Trans-wall migration of fluorescently labeled macrophages through the 10 μm micro-holes on the channel wall. Scale bar: 100 μm. (Inset) scale bar: 50 μm. White arrows indicate migrating macrophages.

Figure 59:
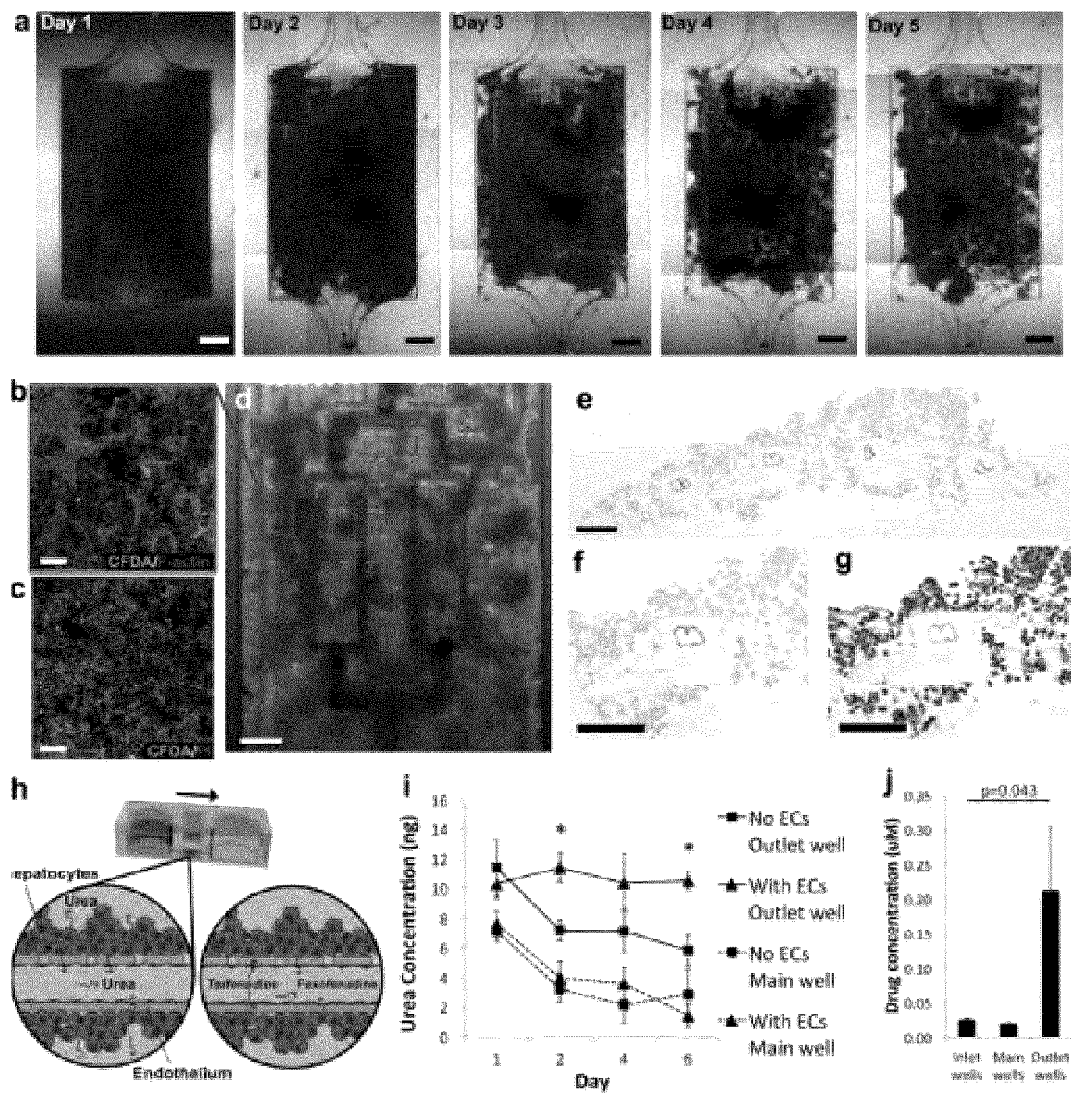

FIG. 59 Vascularized hepatic tissue assembly. (a), Time-lapse images of the tissue remodelling process of rat hepatocytes on an exemplary AngioChip scaffold over 5 days. Scale bar: 800 μm. Final images were stitched from multiple images. (b), Immunostaining (F-actin) of a hepatic tissue, fluorescently labeled with CFDA, shows the distribution and morphology of rat fibroblasts around hepatocytes. Scale bar: 200 μm. c, Fluorescent image of a CFDA and propidium iodide (PI) stained hepatic tissue shows a high cell viability. Scale bar: 200 μm. (d), Bright-field image of a hepatic tissue perfused with blue color dye. Scale bar: 600 μm. (e-g), Histology cross-section of a hepatic tissue stained for (e,f) CD31 to identify endothelial cells (scale bar: 200 μm) and (g) albumin to identify hepatocytes (scale bar: 200 μm). (h), Schematic of urea secretion from the hepatic tissue and terfenadine diffusing through the vessel wall into the hepatic tissue and then subsequently being converted into fexofenadine and released back into the vasculature. (i), Quantification of urea secretion into the bioreactor main well and outlet well over time (average±s.e.m., n=4). *, significant difference between groups with p<0.05. (j), Concentration of fexofenadine in the bioreactor inlet, main, and outlet wells after 24 hr perfusion of terfenadine at 10 μM from inlet wells (average±s.e.m., n=4).

Figure 60:
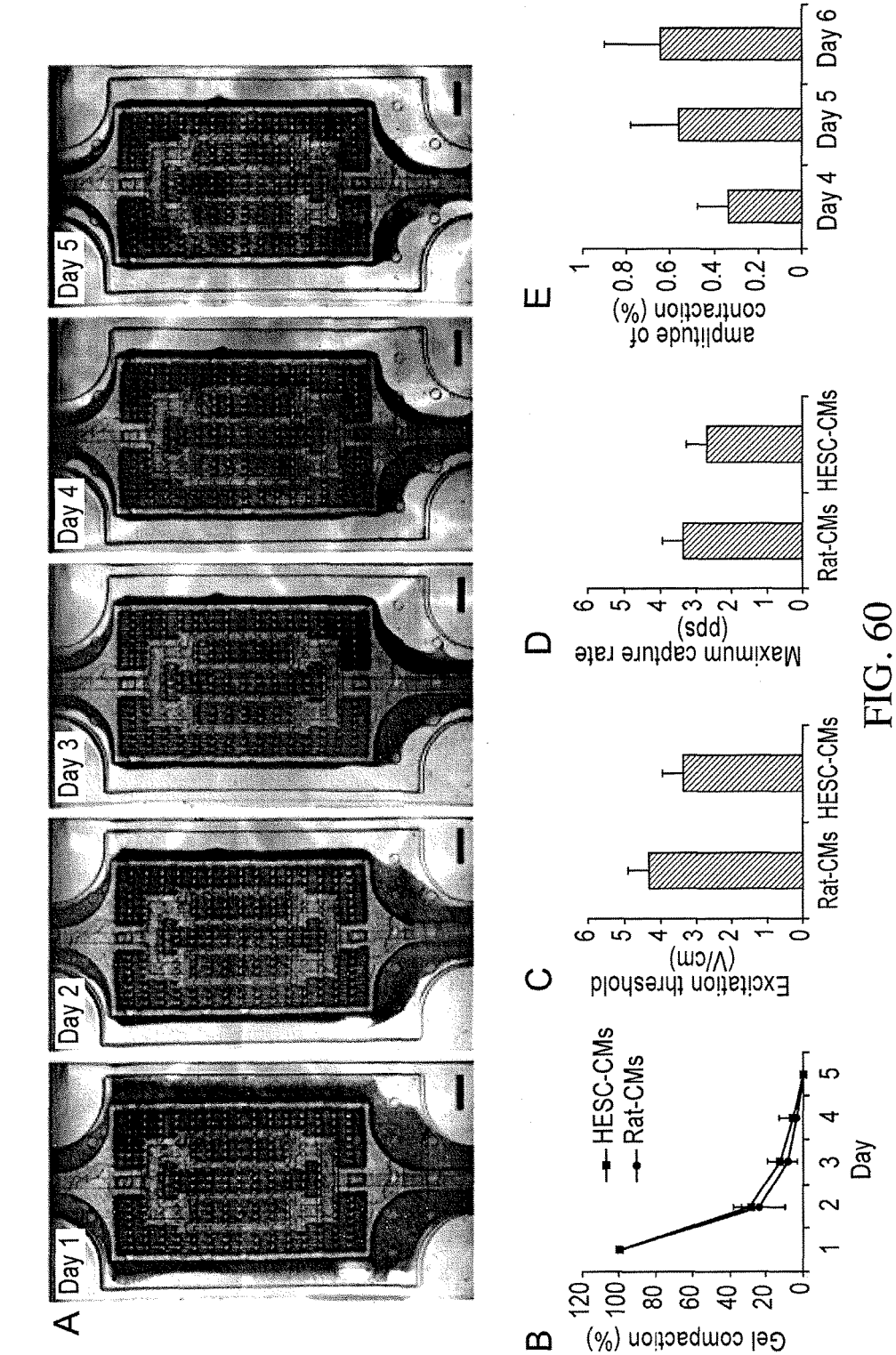
Figure 60:
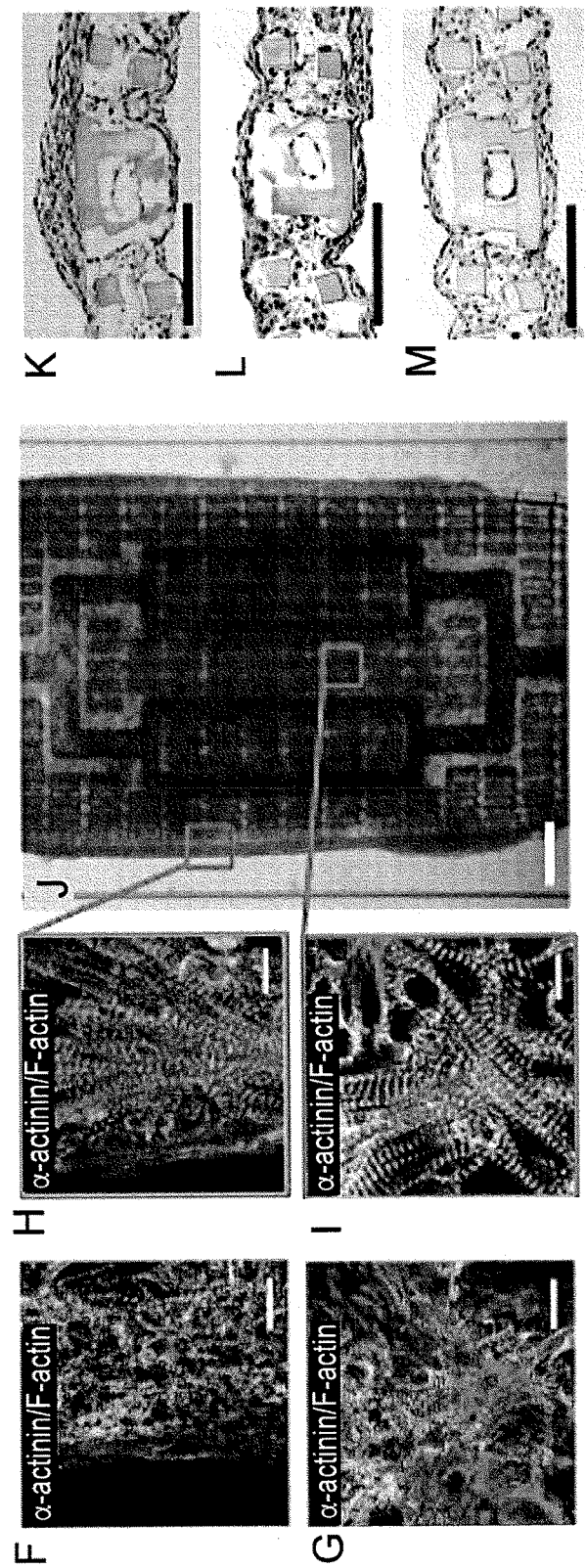
Figure 60:
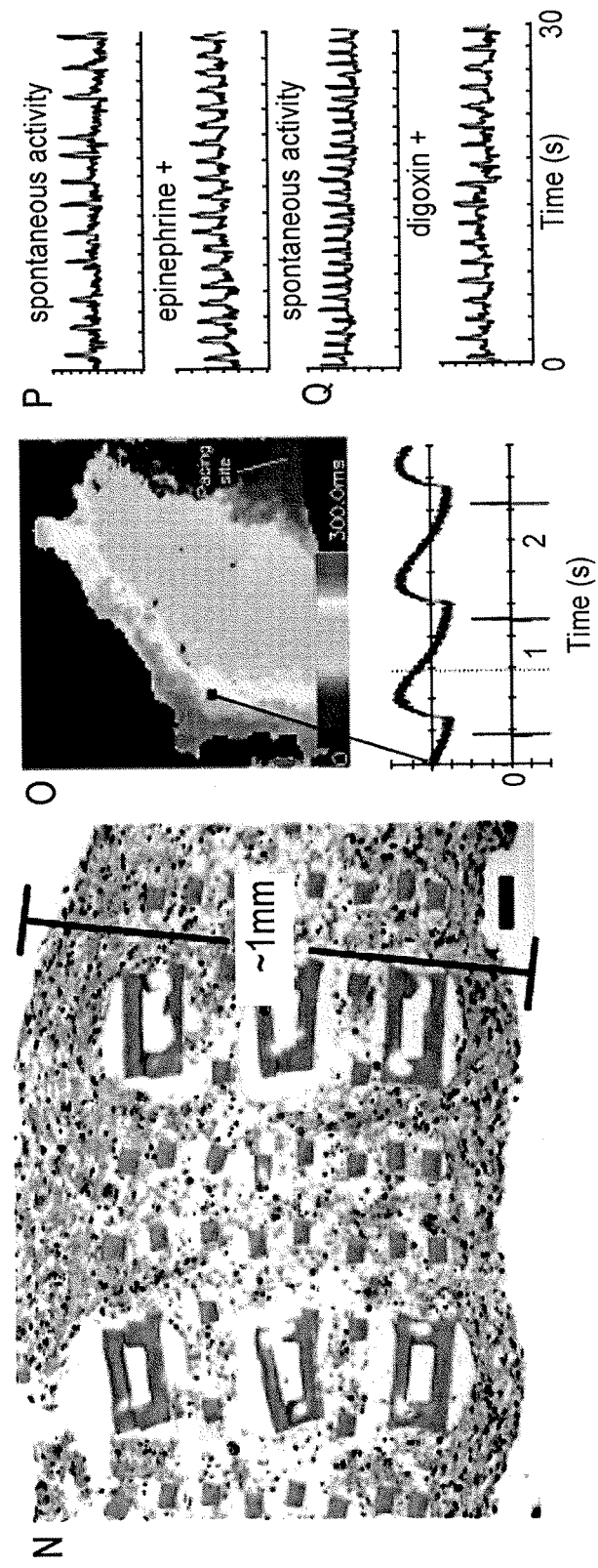
Figure 60:
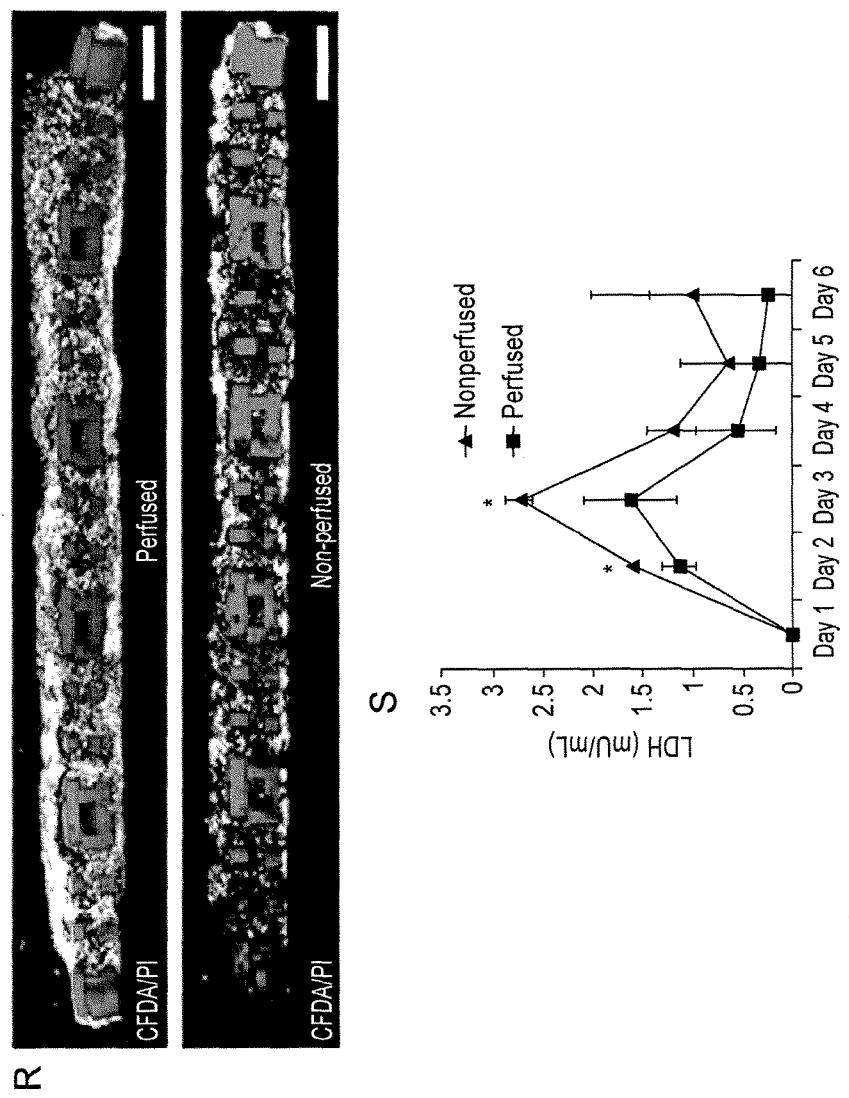

FIG. 60 Vascularized cardiac tissue assembly. (a), Time-lapse of rat cardiac tissue remodelling over 5 days. (b), Quantification of decreasing tissue width due to tissue compaction for both rat (rat-CMs) and human cardiomyocytes (HESC-CMs) (average±s.d., n=3). (c-d), Electrical excitability parameters (average±s.d., n=3). (e), The percent amplitude of contraction of the human cardiac tissues between day 4-6 (average±s.e.m., n=4). (f-i), Immunostaining of sarcomeric-α-actinin and F-actin on (f, g) a human cardiac tissue (scale bar: 20 μm) and (h, i) a rat cardiac tissue (scale bar: 10 μm). (j), Bright-field image of a human cardiac tissue patch perfused with color dye. Scale bar: 400 μm. (k-m), Histological cross-sections of human cardiac tissues stained with (k) Hematoxylin and Eosin (H&E), (l) Masson's Trichrome, and (m) CD31 to identify endothelial cells. Scale bar: 200 μm. (n), Histology cross-section of a ~1 mm thick human cardiac tissue stained with H&E. Scale bar: 100 μm. (o), Conduction velocity activation map of hESC-derived cardiac tissue. (inset) Electrical activity response to electrical stimulation. (p-q), Initial spontaneous contraction trace and drug stimulated contraction trace of a human cardiac tissue perfused with (p) 10 μM epinephrine or (q) 10 μM digoxin. r, CFDA and PI stained images of the cross-section of rat cardiac tissues cultivated with or without medium perfusion. Scale bar: 200 μm. (s), Quantification of lactate dehydrogenase (LDH) secretion from rat cardiac tissues cultivated with or without medium perfusion (average±s.d., n=4). *, significant difference between groups with p<0.05.

Figure 61:
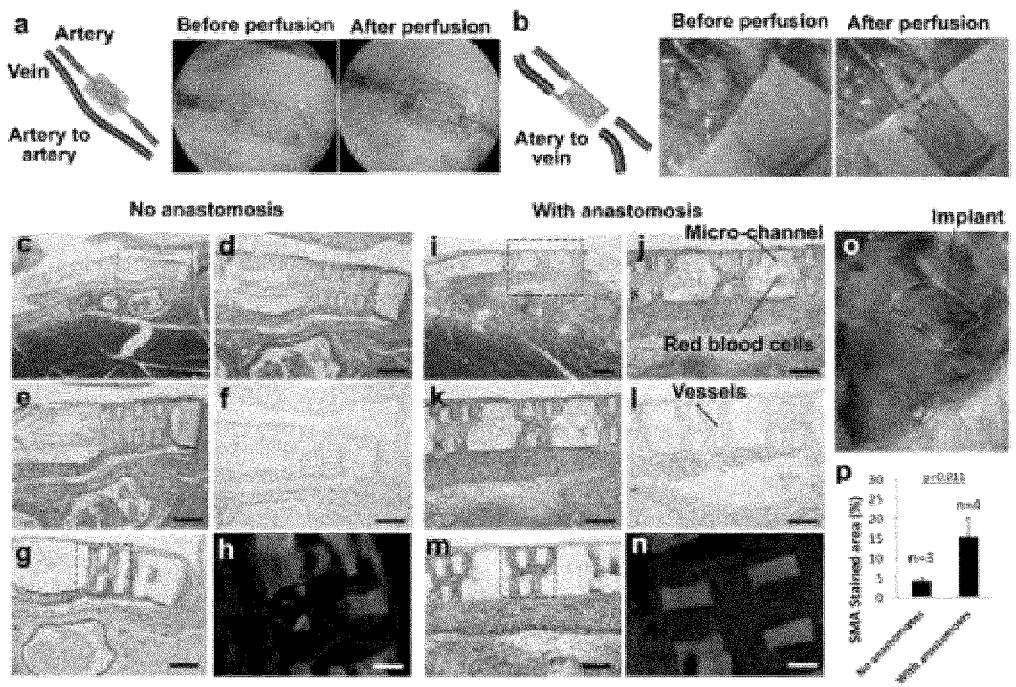

FIG. 61 Surgical anastomoses of the cardiac tissue. a-b, Surgical anastomoses of the AngioChip cardiac tissue on the rat femoral vessels in the configuration of (a) artery-to-artery graft and (b) artery-to-vein graft. Blood perfusion was established immediately after anastomoses. Papers were placed under the implants during imaging for better visual contrast. (c-n), Cross-section of the rat cardiac tissue implants, 1 week after surgery (c-h) without or (i-n) with direct anastomoses in the configuration of artery-to-vein graft. The sections were stained with (c-d, i-j) Masson's Trichrome, (e, k) H&E, (f,l) CD31, (g, m) smooth muscle actin. Scale bar: (c, i) 200 μm and (d-h, j-n) 100 μm. Immuno-staining for cardiac troponin T and DAPI on the cross-section of the rat cardiac tissue implants, 1 week after surgery (h) without or (n) with direct anastomoses in the configuration of artery-to-vein graft. (h, n) Scale bar: 50 μm. o, Image of an implant on rat hind limb 1 week after surgery with direct anastomosis in the configuration of artery-to-vein graft. White dotted line outlines the AngioChip implant. p, Quantification of area stained by smooth muscle actin (average±s.d.).

FIG. 62 Summary of the effective stiffness (ELD, ESD), anisotropic ratio (ELD/ESD), ultimate tensile stress (UT-SLD, UTSSD) and strain-to-failure (εfLD and εfSD) measured in uniaxial direction for AngioChip scaffolds of different designs (average±s.d.). Corresponding properties for adult rat myocardium are shown for comparison. Long-edge direction (LD) and short-edge direction (SD) respectively corresponds to the circumferential and longitudinal axes of the heart.

Figure 63:
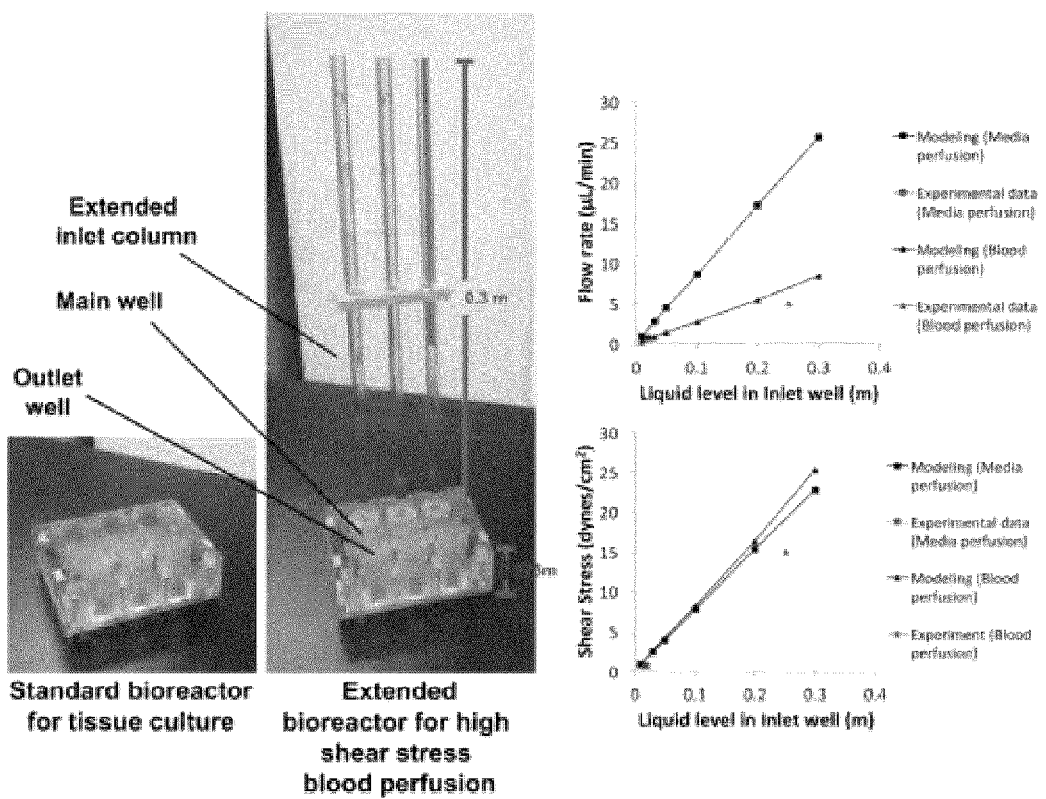

FIG. 63 Characterization of culture media and blood perfusion with the standard and the extended bioreactor setup. To model the flow rate through the AngioChip scaffold with a given pressure head level, the pressure generated from a fluid column with a given height was first calculated based on the equation, P=h g p, where P stands for pressure, h stands for height, g is the gravitational constant, and p stands for density of the fluid. Then the inlet pressure head value was entered into COMSOL multi-physics where a geometrical model of the AngioChip network was created. Using the built-in Navier-Stokes equation, the volumetric flow rate through the network was then derived from the model. The wall shear stress was calculated from the derived volumetric flow rate based on the equation, $$\tau = \frac{6\mu Q}{wH^2},$$

where i stands for shear stress, μ stands for viscosity, w and H stand for the width and H stands for the width and the height of the channel, and Q stands for the volumetric flow rate. The experimental volumetric flow rate was derived from the amount of fluid collected after one day of perfusion and the shear stress was derived from the corresponding volumetric flow rate.

Figure 64:
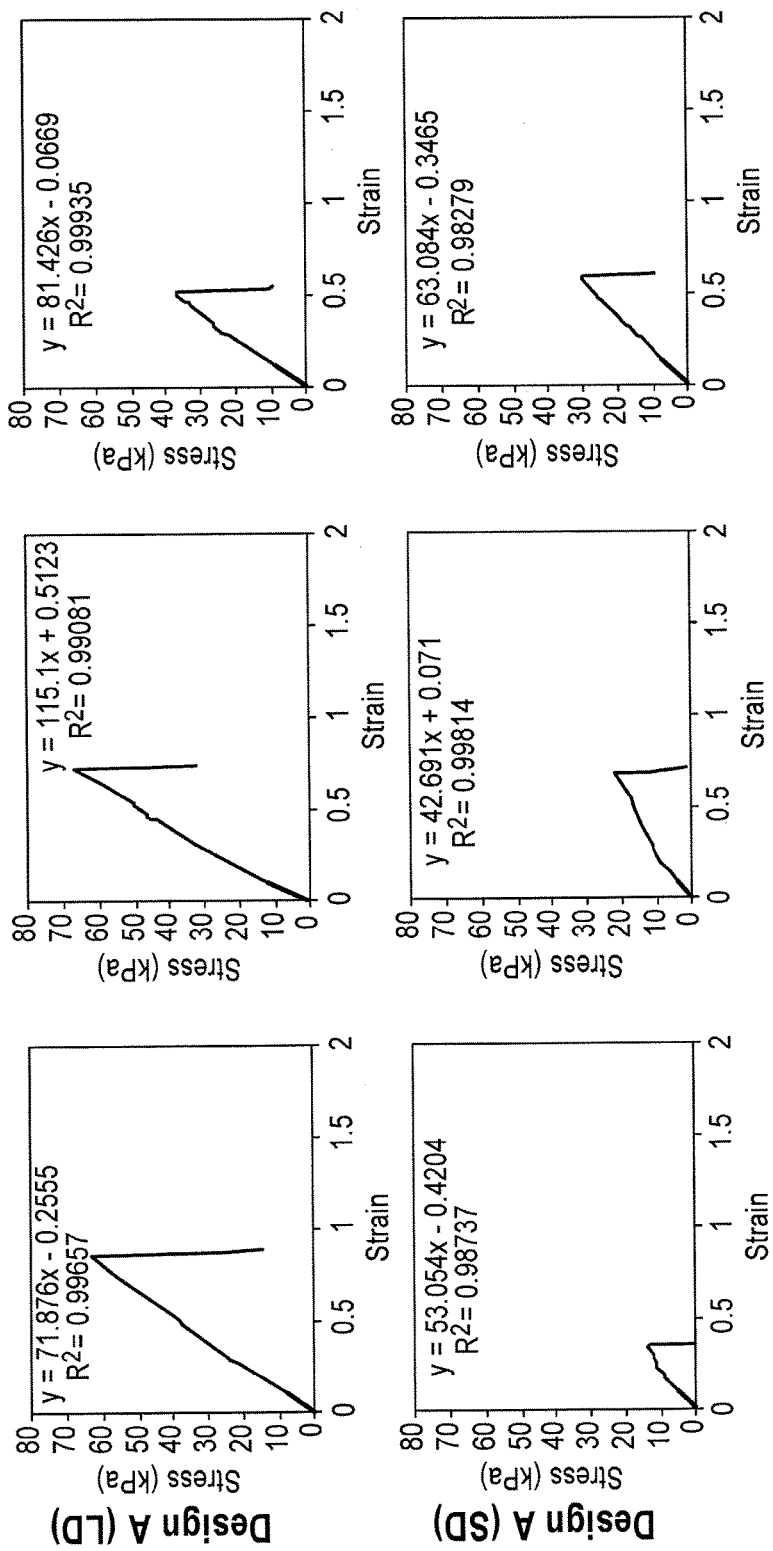
Figure 64:
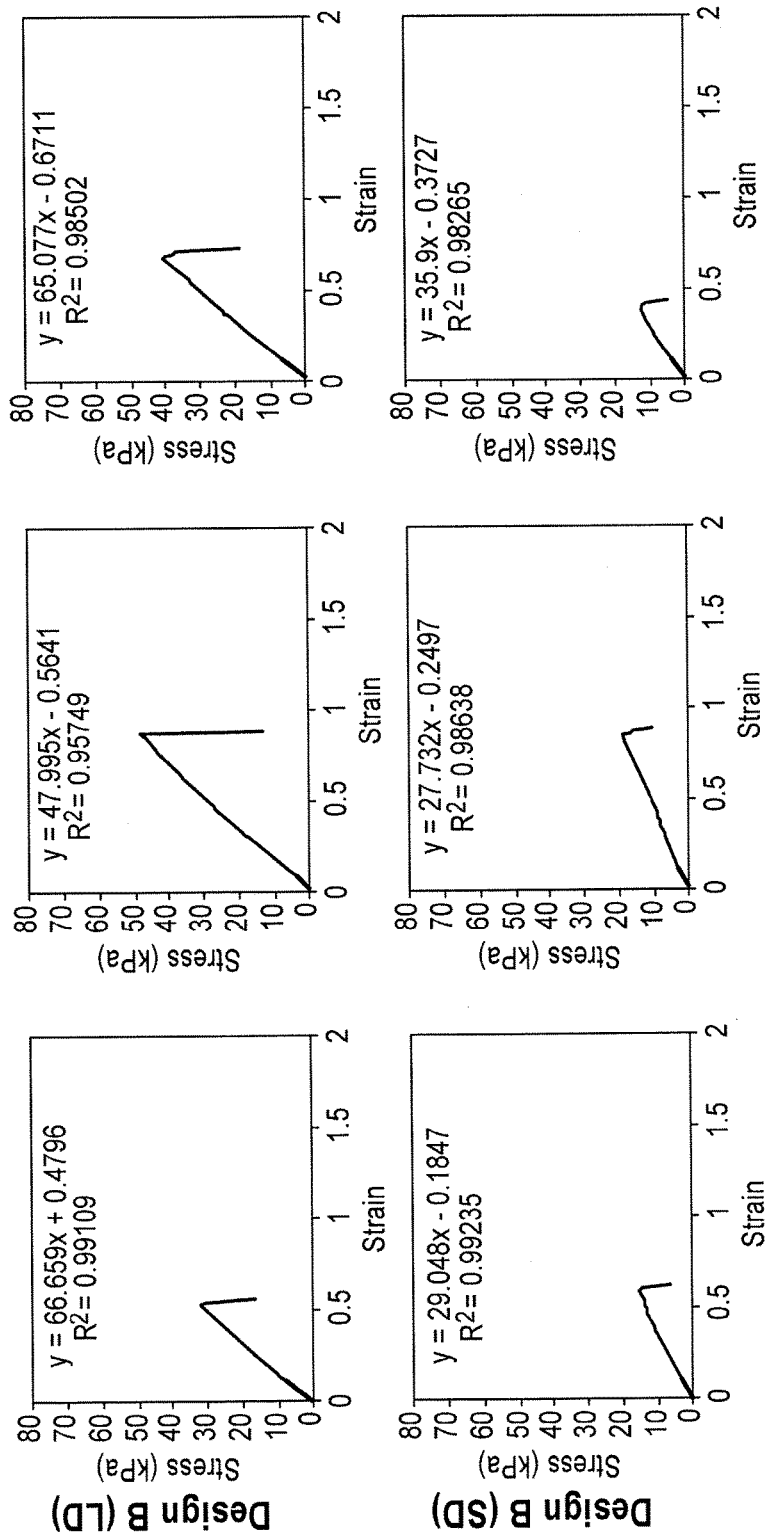
Figure 64:
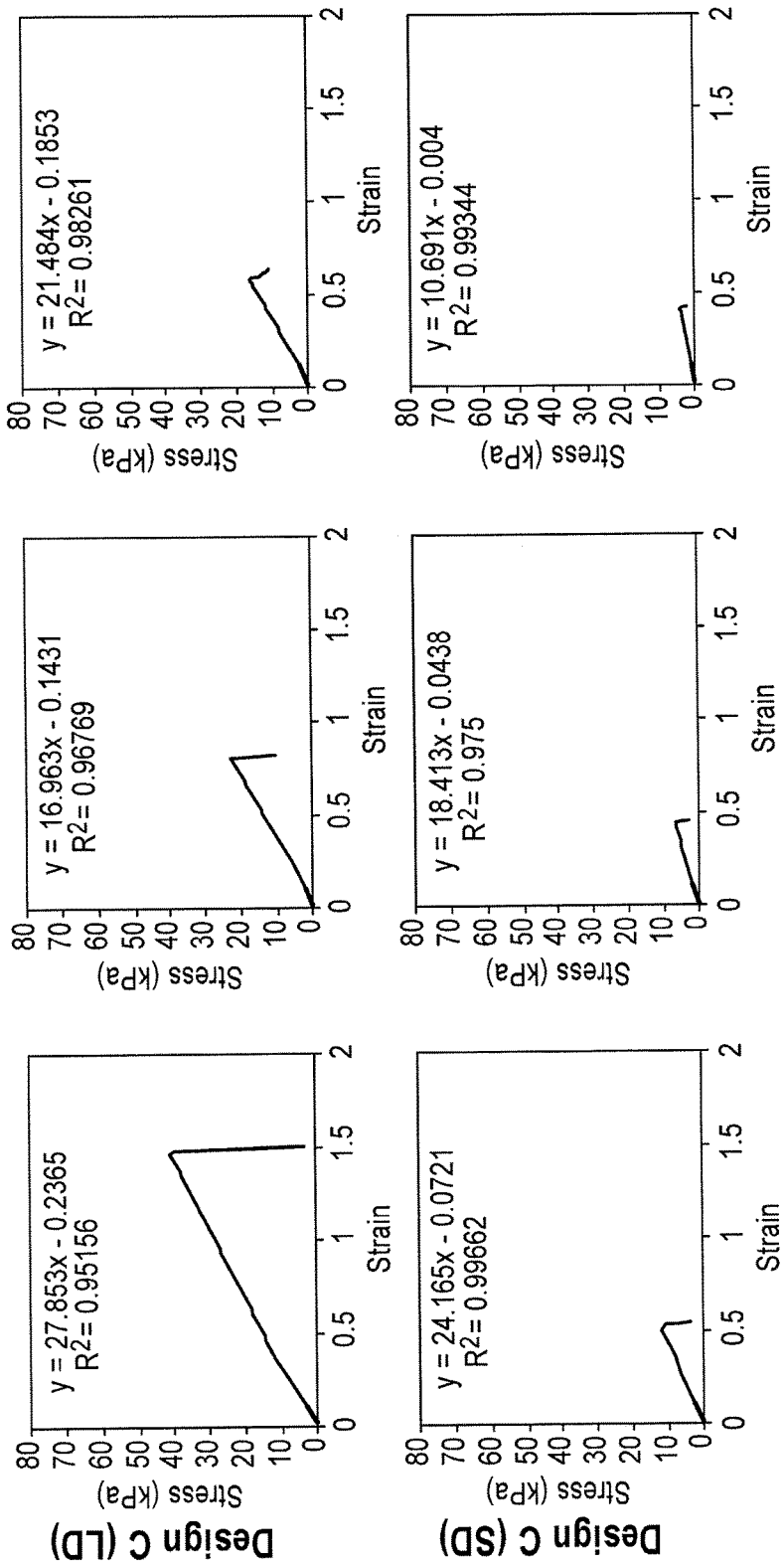

FIG. 64 Uniaxial tensile stress-strain plots of AngioChip scaffolds with the three different lattice designs. The segments of the plots between strains of 0 to 0.1 were fitted with linear regression to calculate the effective stiffness (E). The Linear regression equations and the R-values are shown. The last data point before a significant drop in tensile stress was used to calculate the ultimate tensile stress (UTS) and the strains-to-failure (εf).

Figure 65:
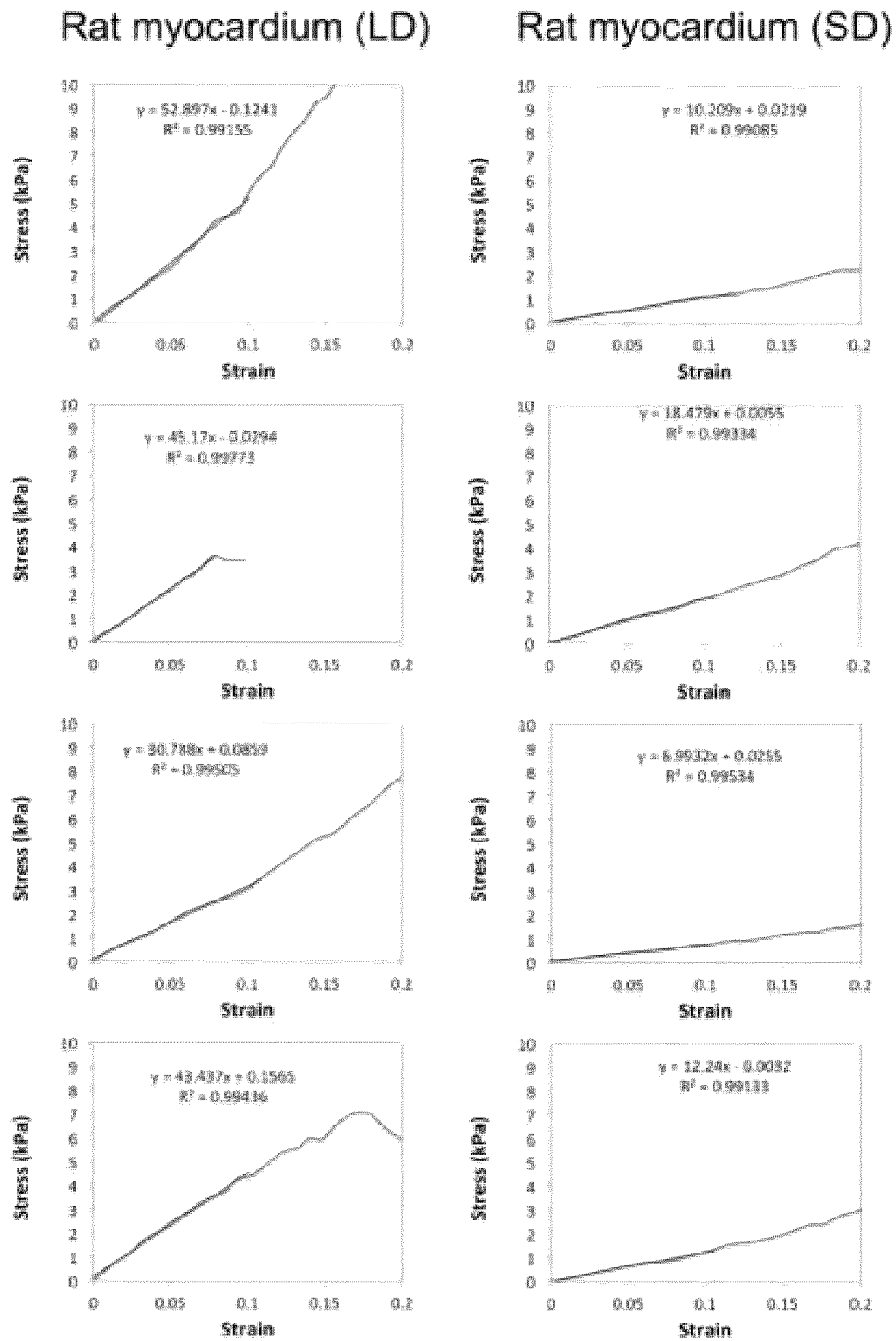

FIG. 65 Uniaxial tensile stress-strain plots of the rat adult ventricular myocardium. Long-edge direction (LD) and short-edge direction (SD) respectively corresponds to the circumferential and longitudinal axes of the heart. The segments of the plots between strains of 0 to 0.1 were fitted with linear regression to calculate the effective stiffness. The linear regression equations and the R-values are shown.

Figure 66:
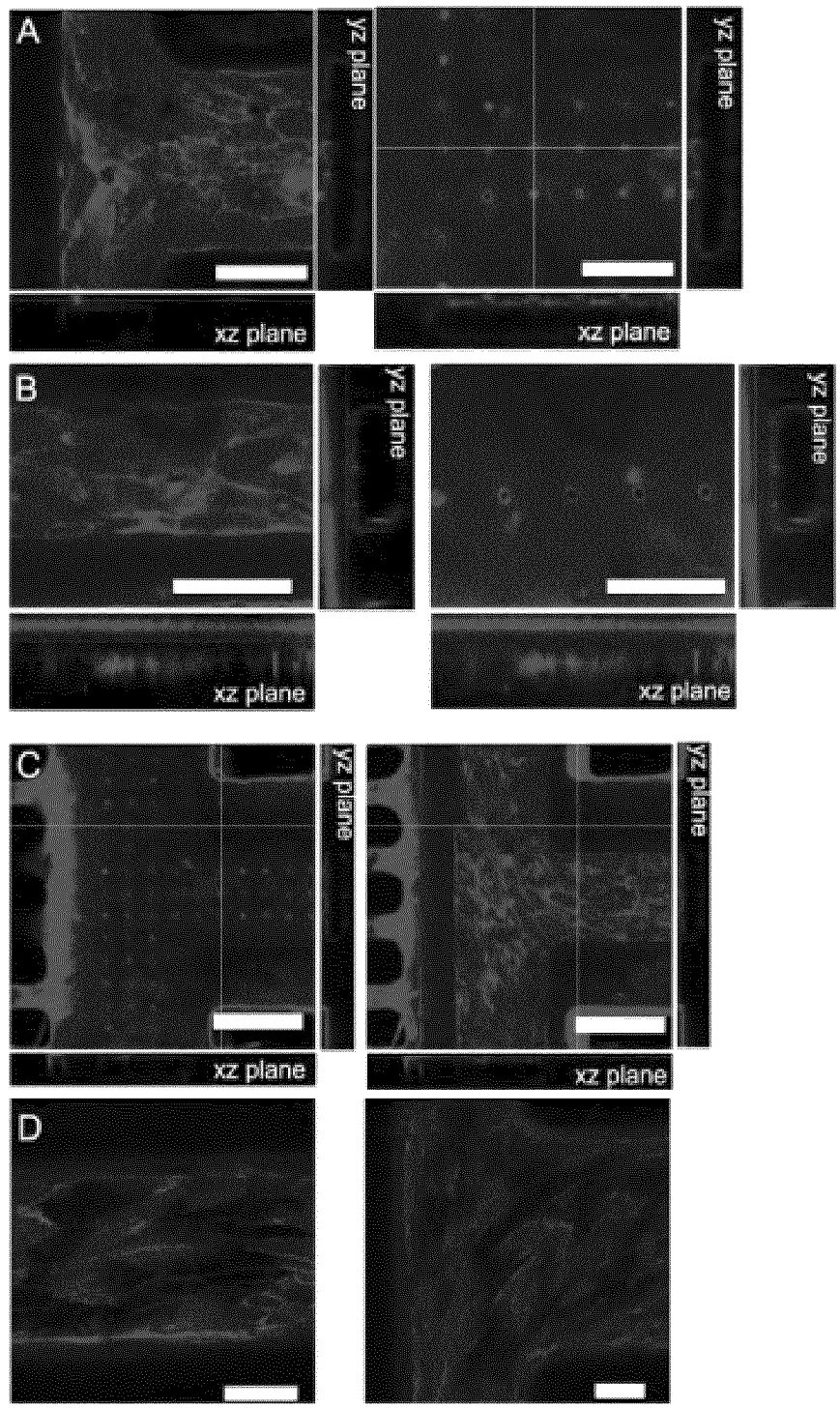

FIG. 66 Endothelization of AngioChip scaffold network. (A-C) Confocal scan of the endothelial cell (CD31 immunostained) coverage on the scaffold network with 10 μm micro-holes patterned on the network wall. Scale bar: (A) 100 μm, (B) 100 μm, (C) 200 μm. (D) Confocal scan of the endothelial cell (VE-cadherin immunostained) coverage on the scaffold network. Scale bar: 50 μm.

Figure 67:
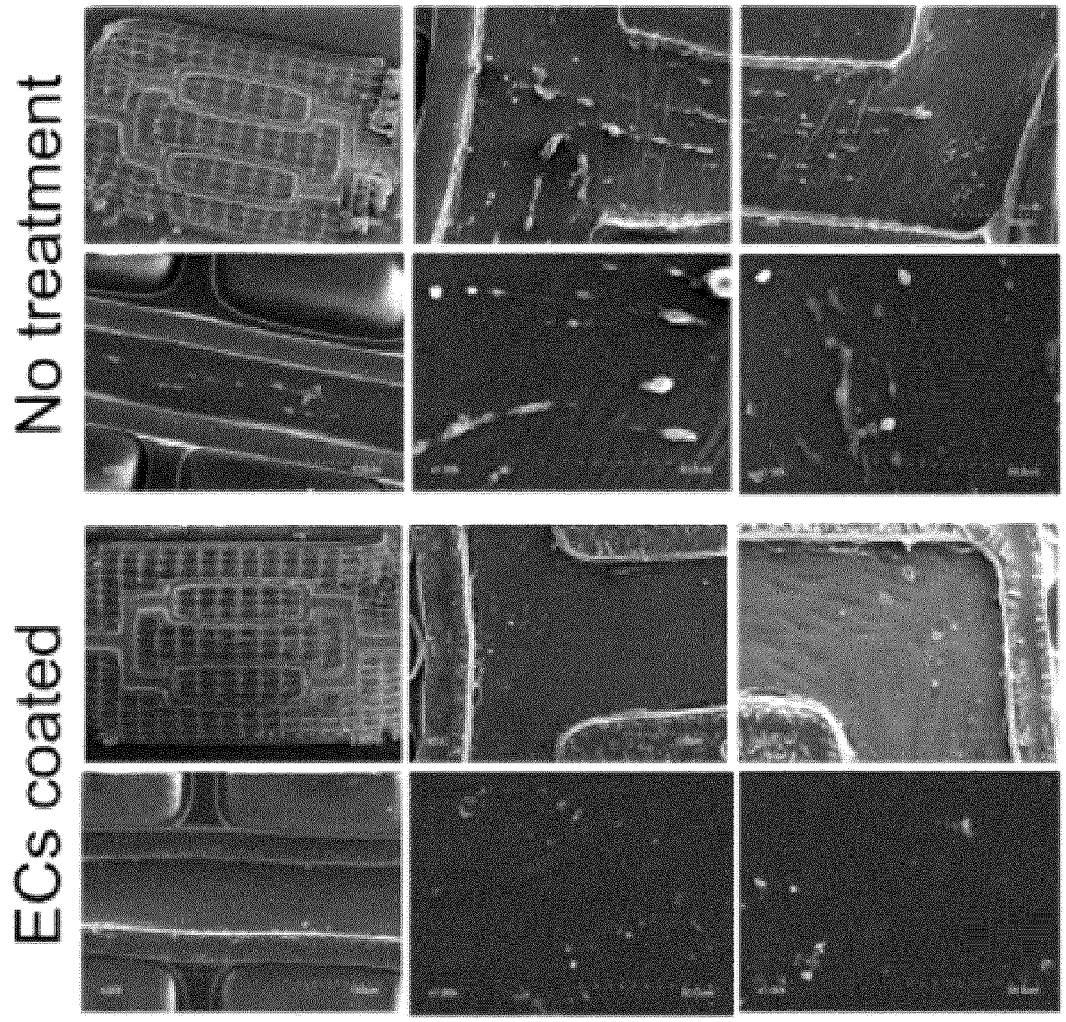

FIG. 67 Representative SEM of the luminal surface of the AngioChip scaffold networks, with or without endothelial cell coating, after the perfusion of human whole blood at 15 dynes/cm$^2$ for 30 min. Human blood was heparinized with 1% heparin (v/v) to prevent clotting during handling. Scale bars are shown in images.

Figure 68:
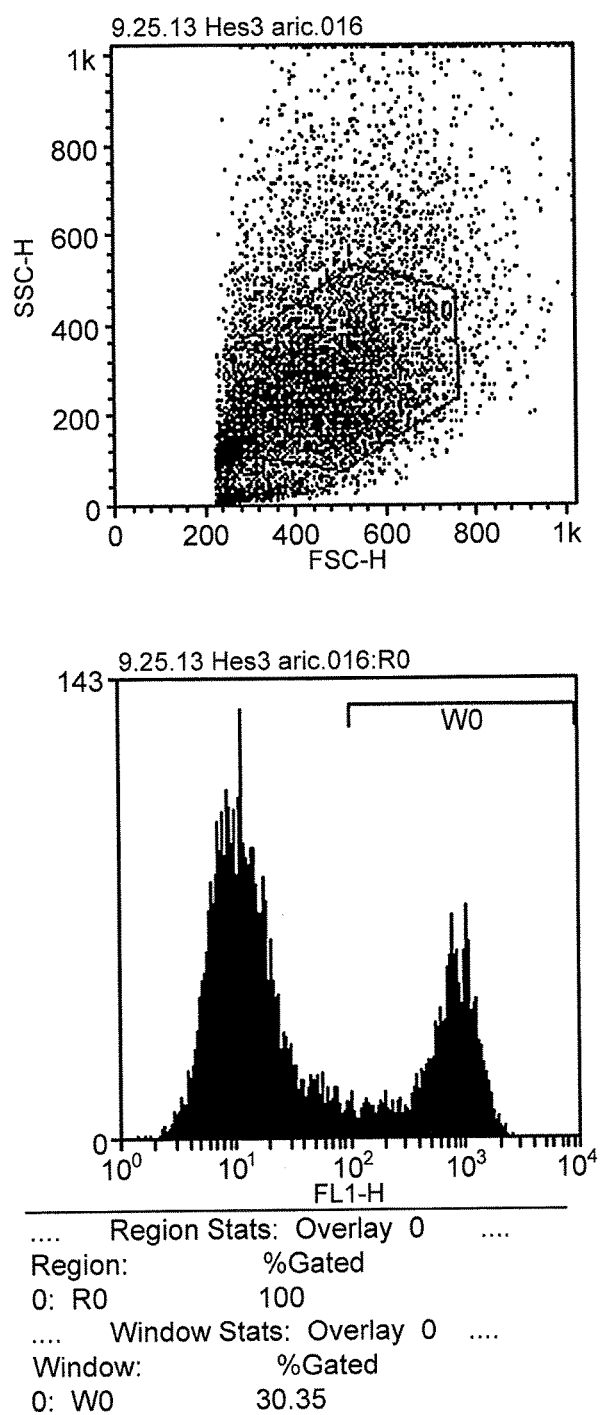
Figure 68:
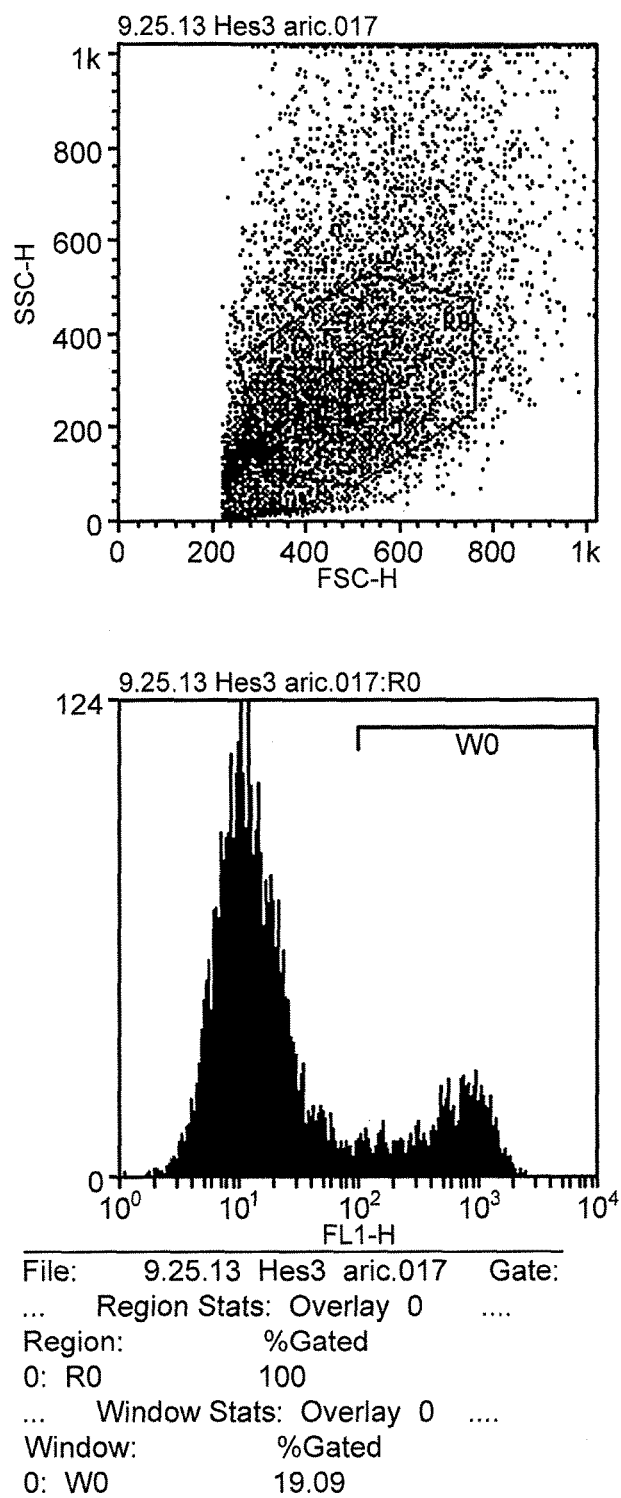
Figure 68:
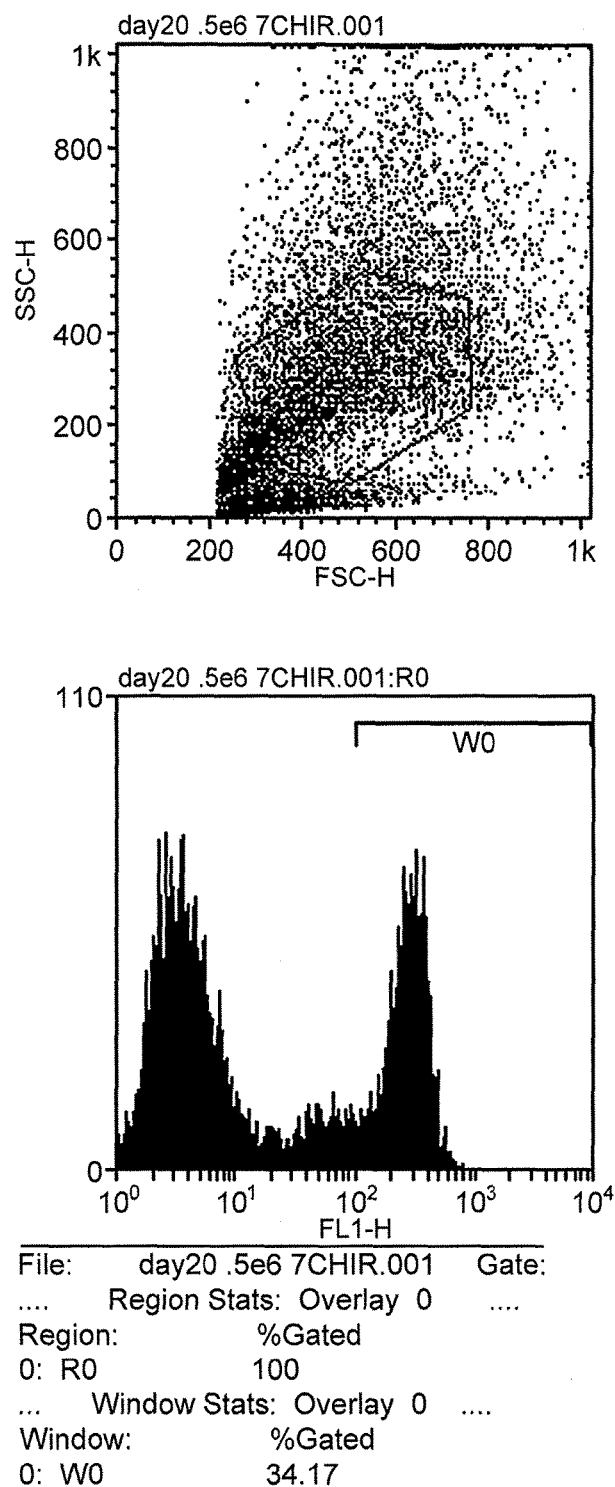
Figure 68:
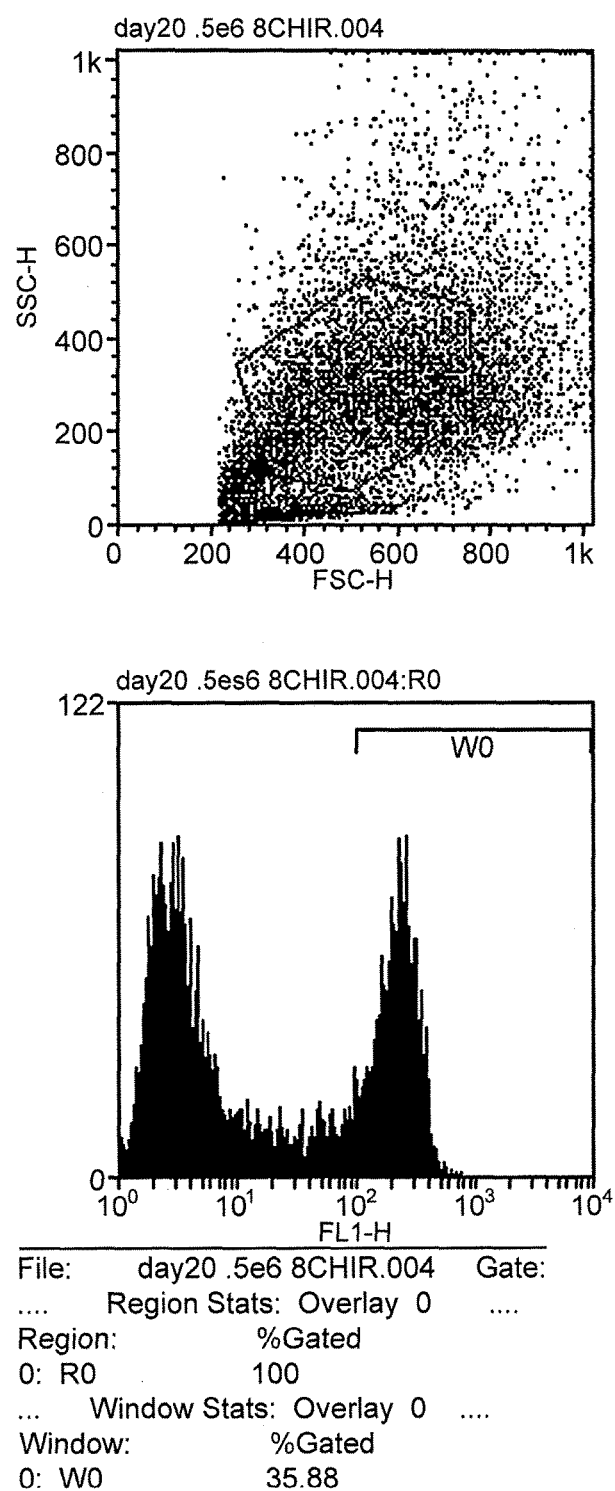
Figure 68:
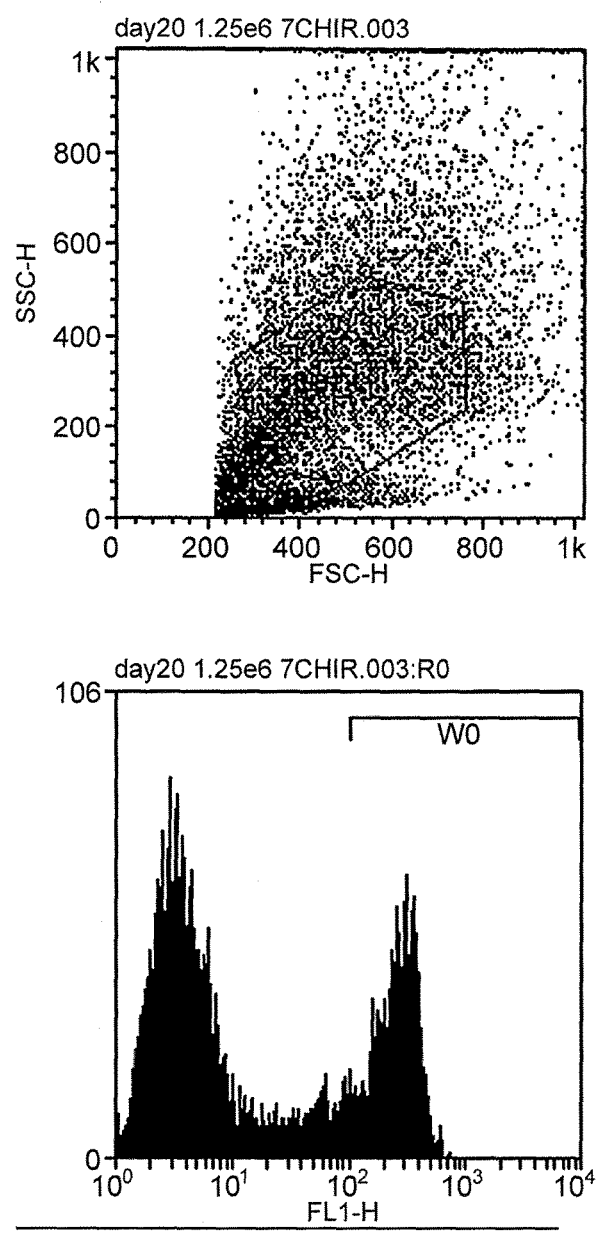
Figure 68:
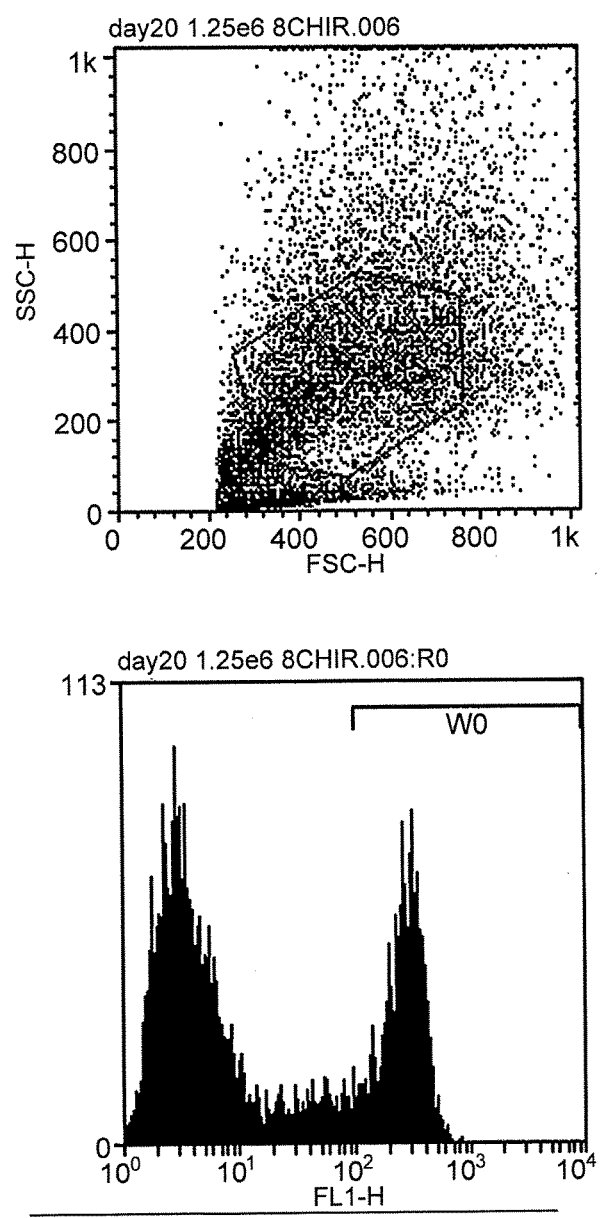
Figure 68:
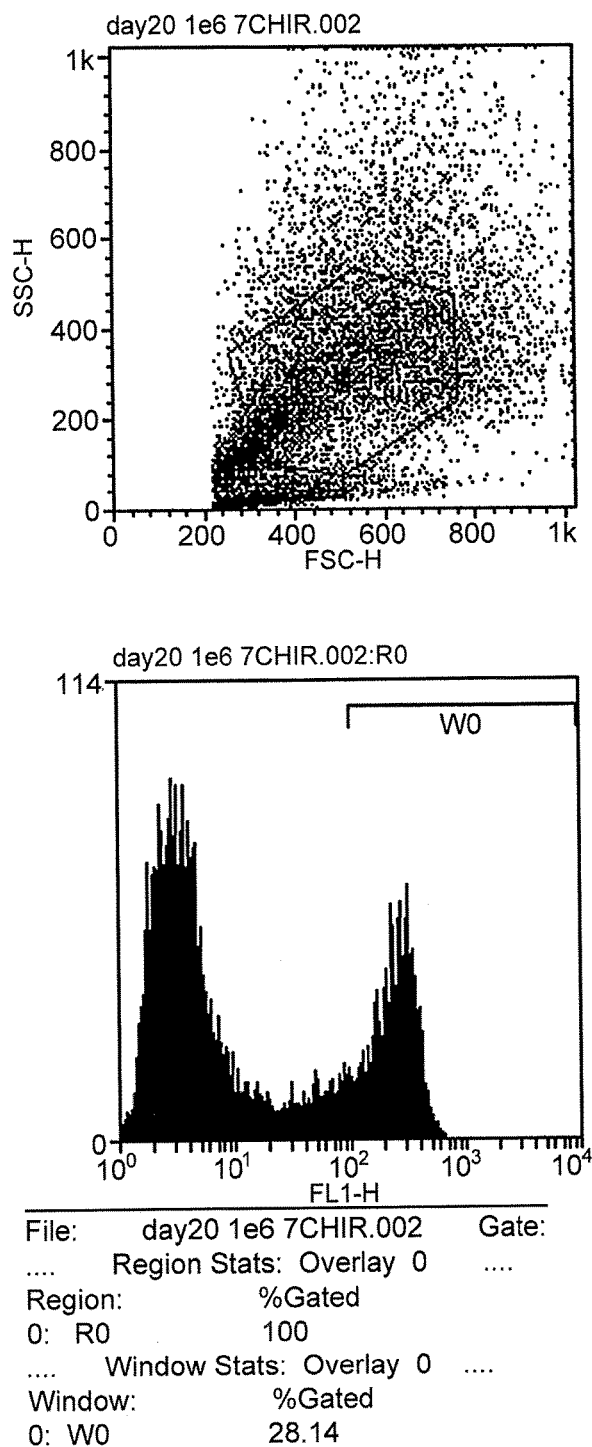
Figure 68:
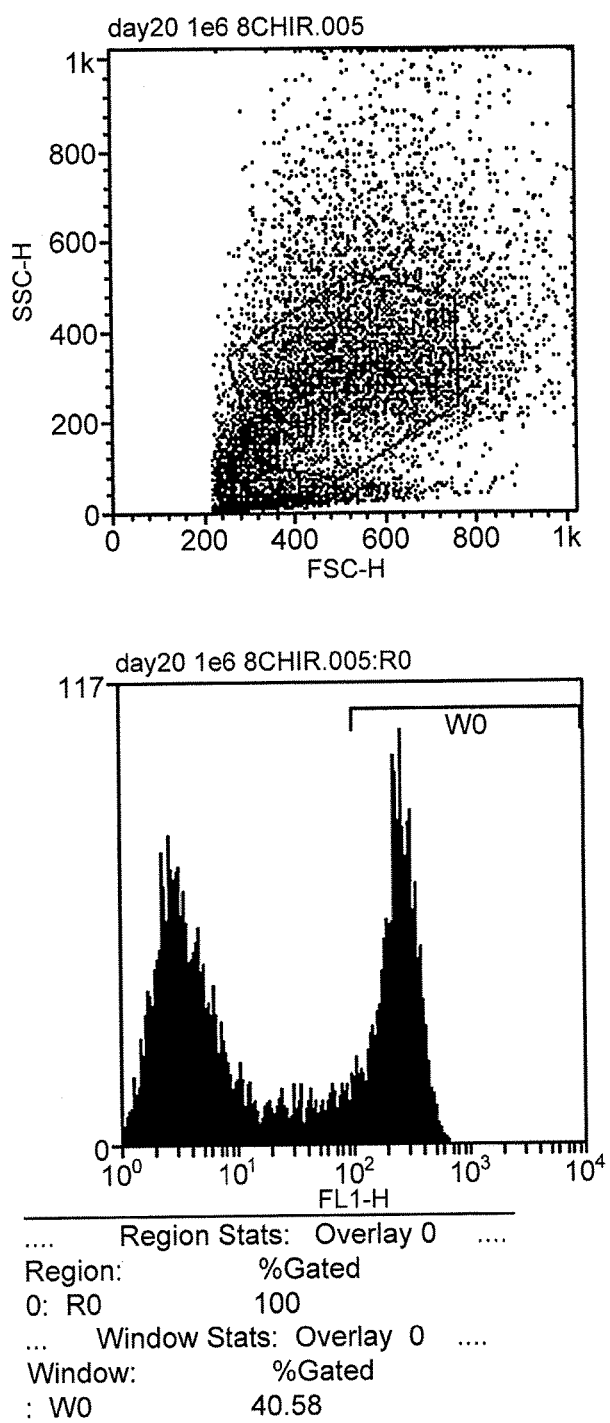

FIG. 68 Flow cytometry analysis of HES-3 NKX2-5 GFP positive cells derived cardiomyocytes cell mixture. FL1-H corresponds to NKX2-5 expression. NKX2-5 positive cells were considered to be cardiomyocytes. Percent of cardiomyocytes in each cell mixture were determined by the W0 gated region.

Figure 69:
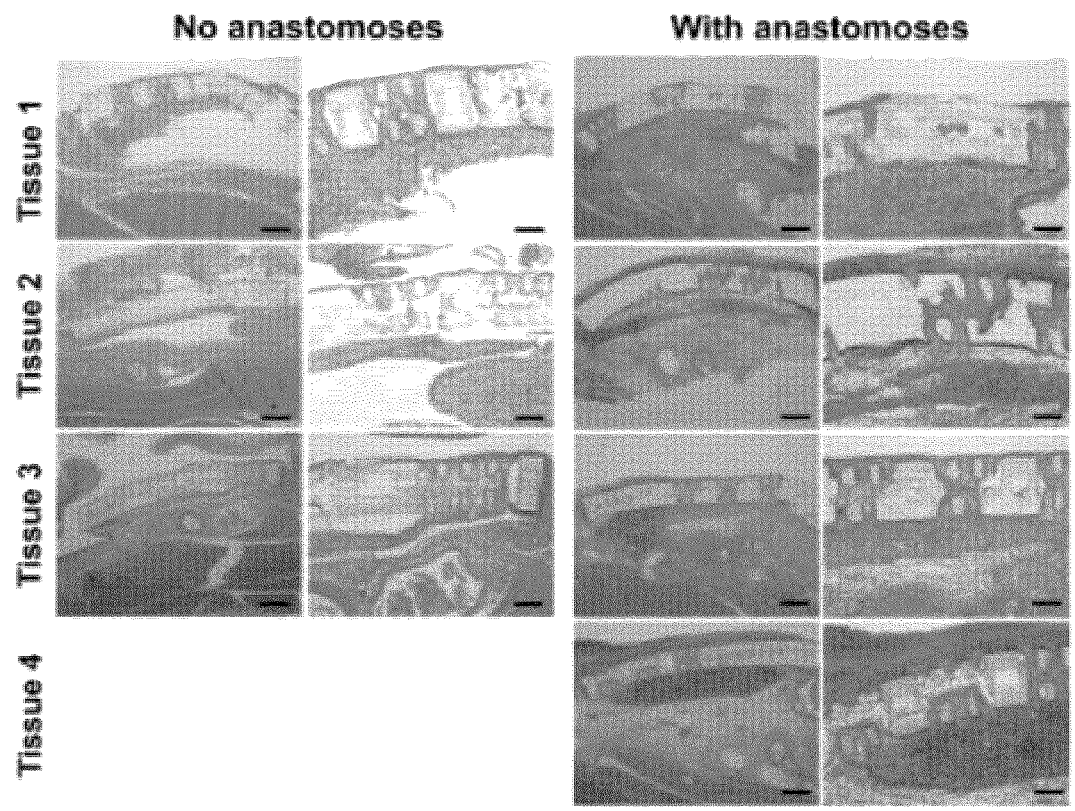

FIG. 69 H&E stained histology cross-section of the cardiac tissue implants after 1 week with or without the direct surgical anastomoses in the configuration of artery-to-vein graft. Low magnification images are shown in the left column. Scale bar: 400 μm. High magnification images are shown in the right column. Scale bar: 150 μm.

Figure 70:
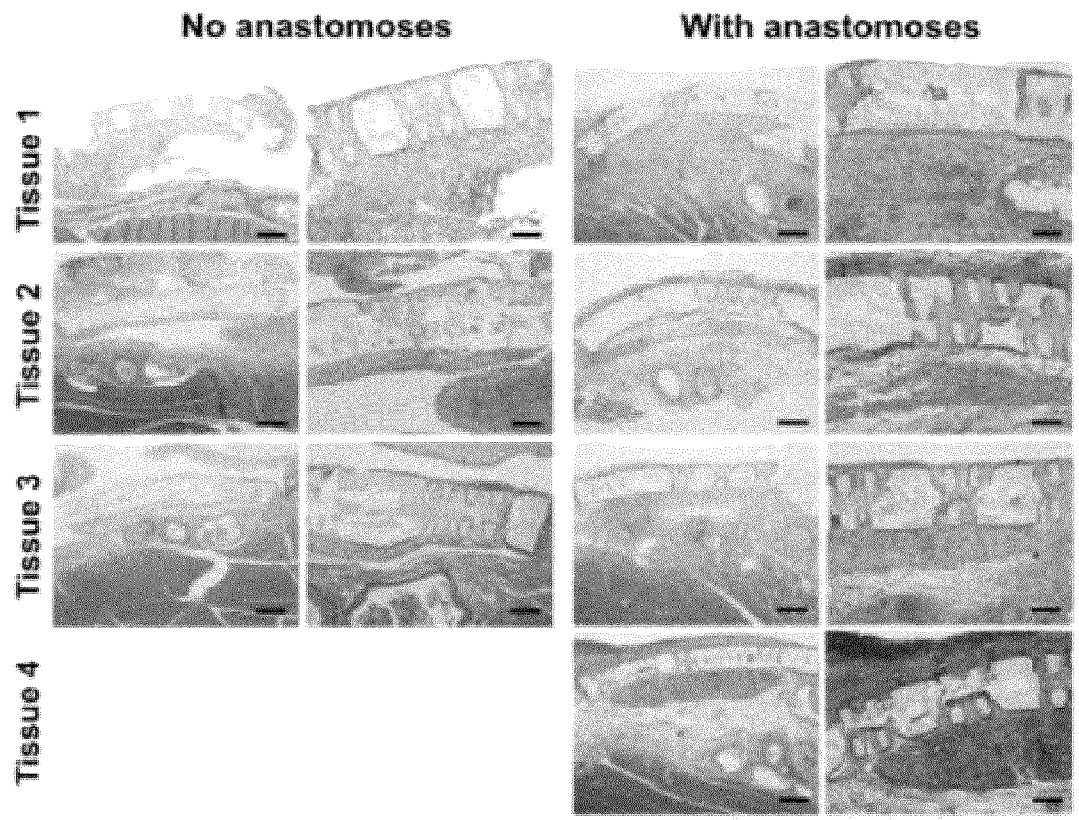

FIG. 70 Masson's trichrome stained histology cross-section of the cardiac tissue implants after 1 week with or without the direct surgical anastomoses in the configuration of artery-to-vein graft. Low magnification images are shown in the left column. Scale bar: 400 μm. High magnification images are shown in the right column. Scale bar: 150 μm.

Figure 71:
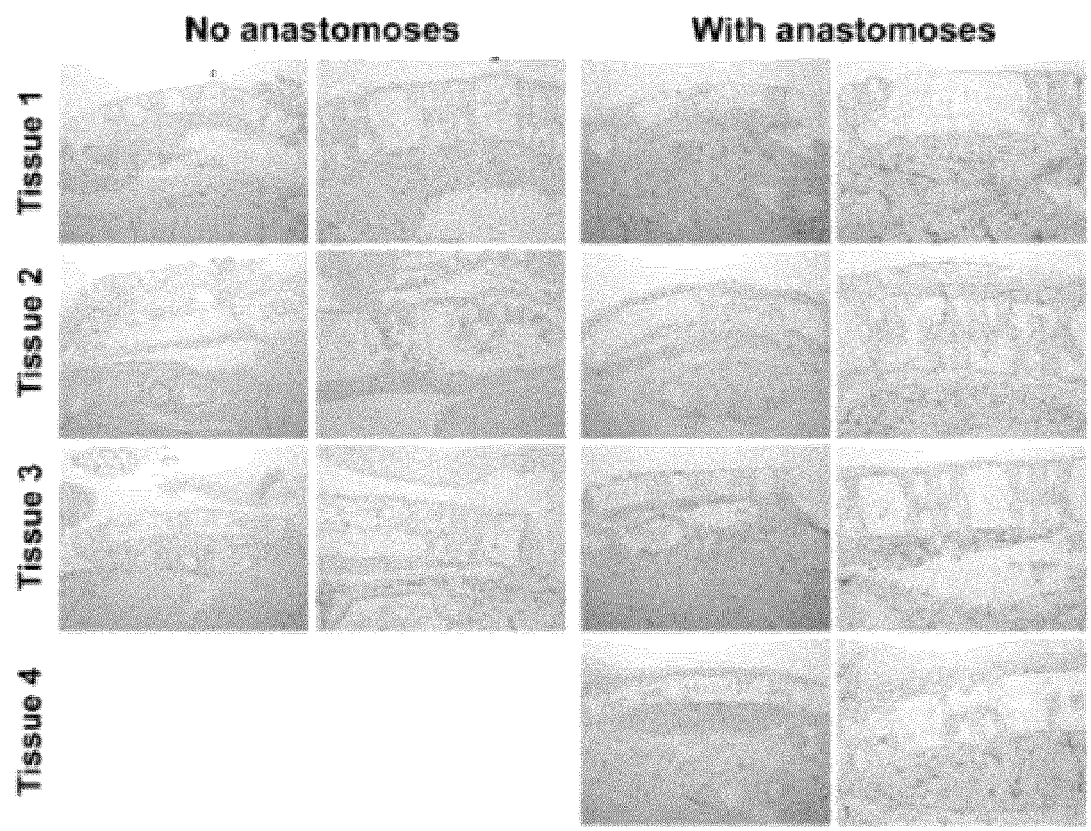

FIG. 71 CD31 stained histology cross-section of the cardiac tissue implants after 1 week with or without the direct surgical anastomoses in the configuration of artery-to-vein graft. Low magnification images are shown in the left column. Scale bar: 400 μm. High magnification images are shown in the right column. Scale bar: 150 μm.

Figure 72:
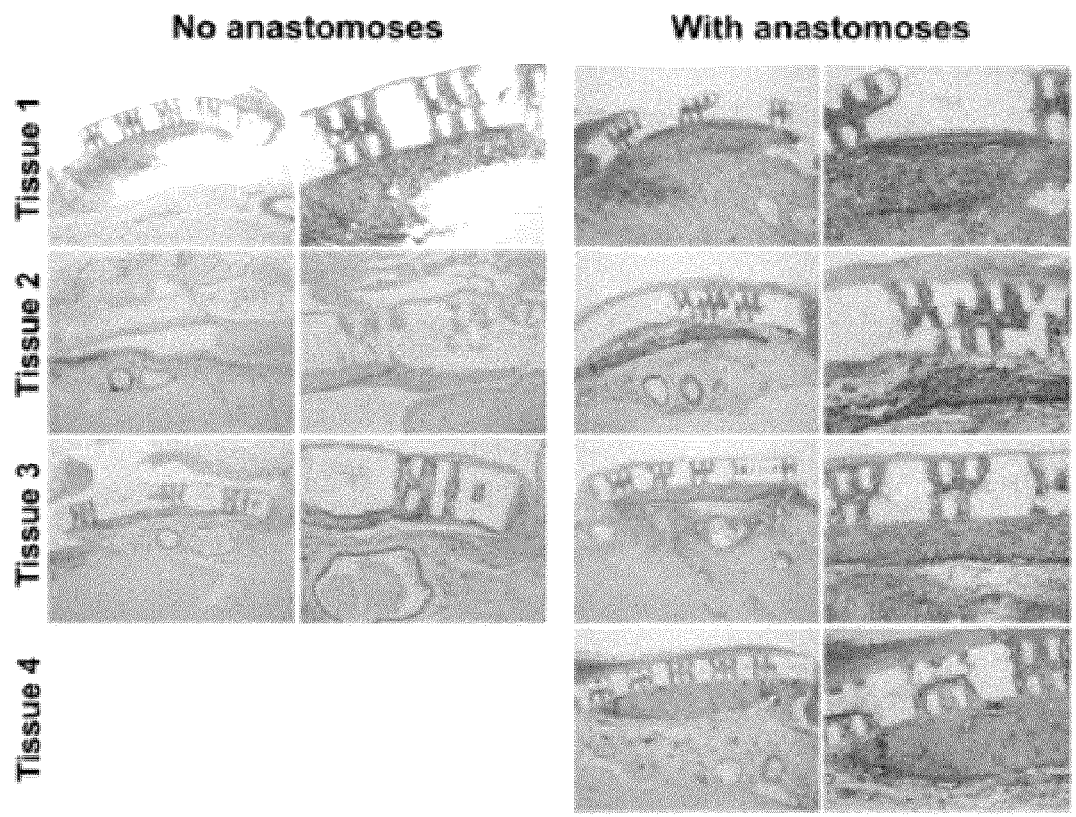

FIG. 72 Smooth muscle actin (SMA) stained histology cross-section of the cardiac tissue implants after 1 week with or without the direct surgical anastomoses in the configuration of artery-to-vein graft. Low magnification images are shown in the left column. Scale bar: 400 μm. High magnification images are shown in the right column. Scale bar: 150 μm.

FIG. 73 Immunostaining of the cross-section of the cardiac tissue implants after 1 week with or without the direct surgical anastomoses in the configuration of artery-to-vein graft. Troponin T, DAPI. Scale bar: 50 μm.

Figure 74:
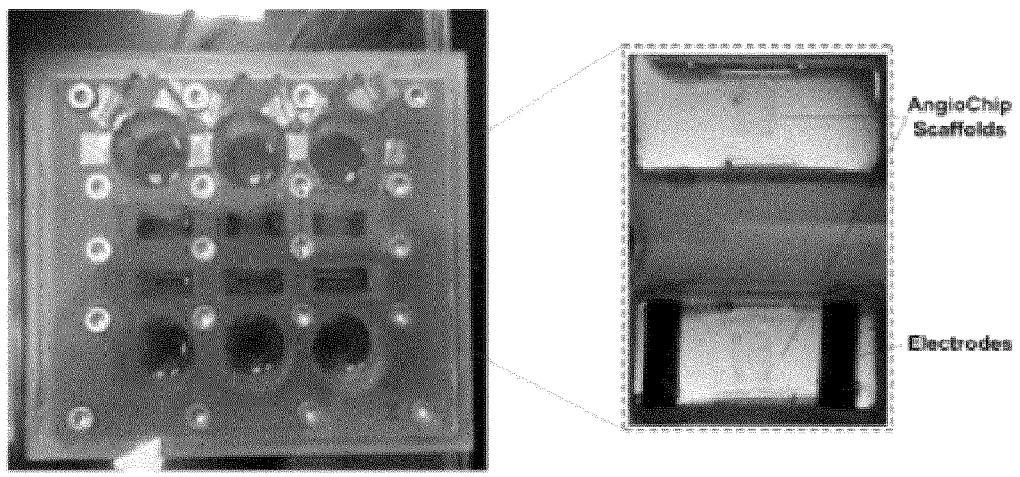

FIG. 74 Image of a dual-well bioreactor where two main wells were included between each inlet well and outlet well. Two AngioChip scaffolds can be connected in series and perfused sequentially from the inlet well to the outlet well. (inset) Magnified image of the dual-well where two AngioChip scaffolds were installed. Hepatocytes can be seeded onto the first scaffold while cardiomyocytes can be seeded onto the second scaffold to created an "organ-on-a-chip" system for probing organ level drug interaction. A pair of electrodes were installed in the second chamber for stimulating cardiac tissues.

Figure 75:
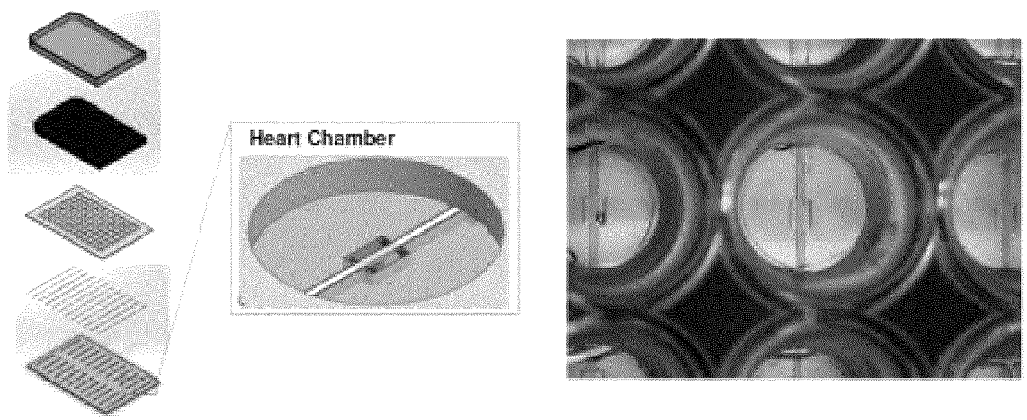

FIG. 75 provides schematic of an exemplary AngioTube system of the disclosure comprising a multi-well perfusable system comprising an array of chambers, wherein each chamber contains one or more wells for seeding and growing 3D tissue strands around a permeable/perfusable tube positioned within the wells. Each chamber may also contain at least two opposing elements for anchoring the tissue stand and whose movements may be discerned and measured during contraction/relaxation cycles of the 3D tissue strands. The chambers may also be configured with electrodes for stimulating cardiac tissues.

Figure 76:
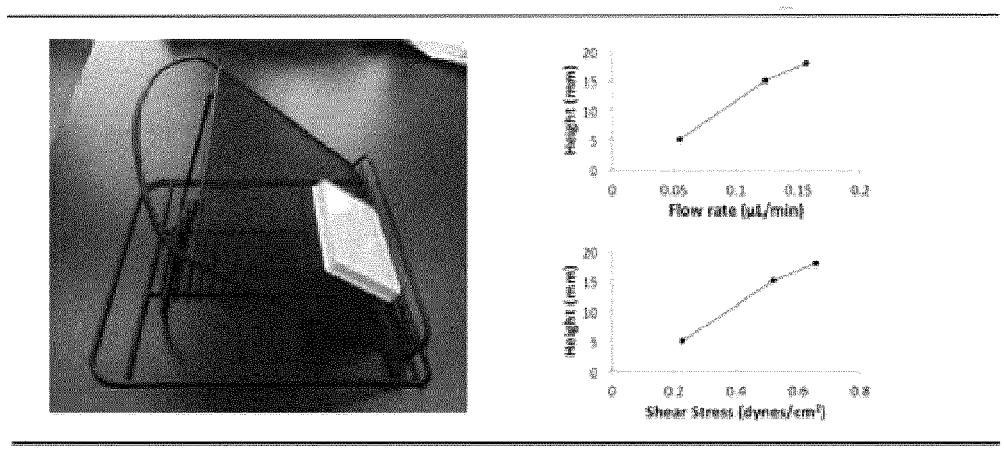

FIG. 76 demonstrates the results of passive perfusion of an exemplary AngioTube multi-well perfusable bioreactor as measured by flow rate (μl/min) or shear stress (dynes/cm$^2$) as a function of the tilt height of the bioreactor.

Figure 77:
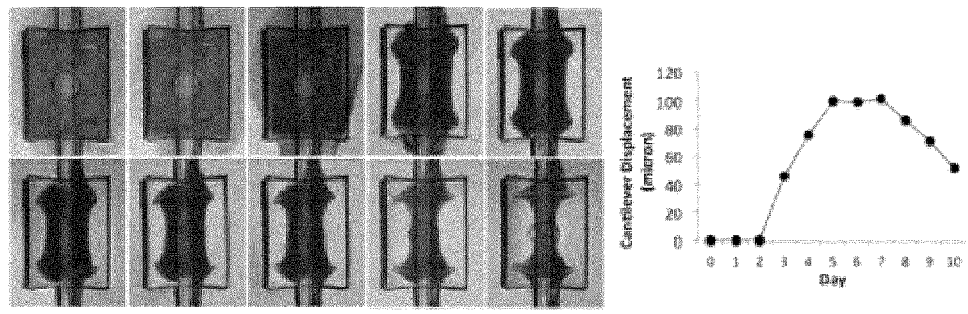

FIG. 77 shows a time course of the development of a 3D tissue strand in a single chamber of an exemplary AngioTube bioreactor. The first image in the series shows the point at which the cells are first seeded into the bioreactor chamber. As time progresses, the cells grow and begin to cluster towards the two flexible cantilever elements in the chamber, while maintaining a tissue connection between the flexible elements. The particular embodiment shown in the photographs is an embodiment only and other configurations are contemplated by the invention. For example, the flexible cantilever elements may be formed having a different shape and/or length (e.g., curved, rounded, nonlinear, flat, round, bent, thickness) and attached to the permeable tubular element at a different angle or orientation such that measurement and/or detection of cantilever displacement can be detected. The chamber may also contain electrodes for stimulating cardiac cells. The bar at the right demonstrates the degree of cantilever displacement that can be observed during the formation of the 3D tissue strand.

Figure 78:
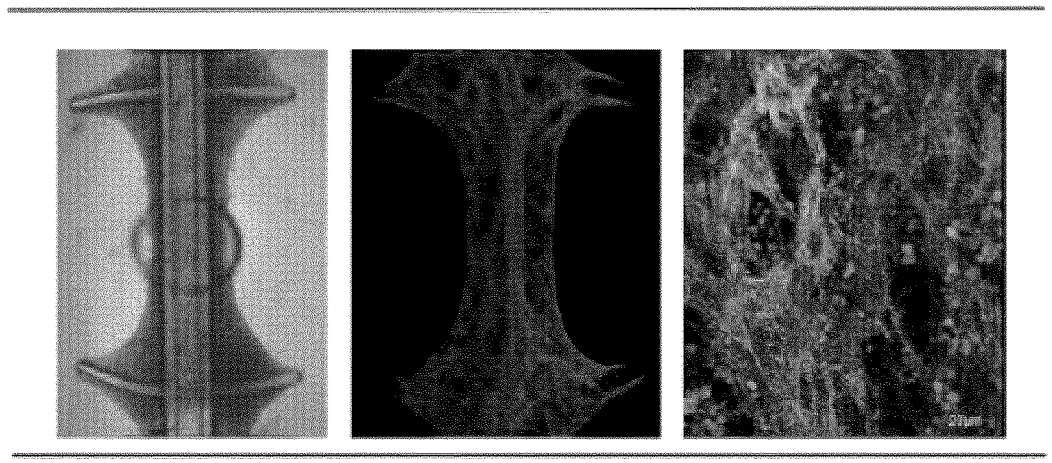

FIG. 78 Tissue visualization of a 3D tissue strand formed in an exemplary AngioTube bioreactor chamber showing. Light microscopy image of a tissue strand (left image). The same tissue strand stained with F-actin (middle image). Immunostaining of cells of the 3D tissue strand with CFDA to show the distribution and morphology and orientation of cells of the tissue strand.

Figure 79:
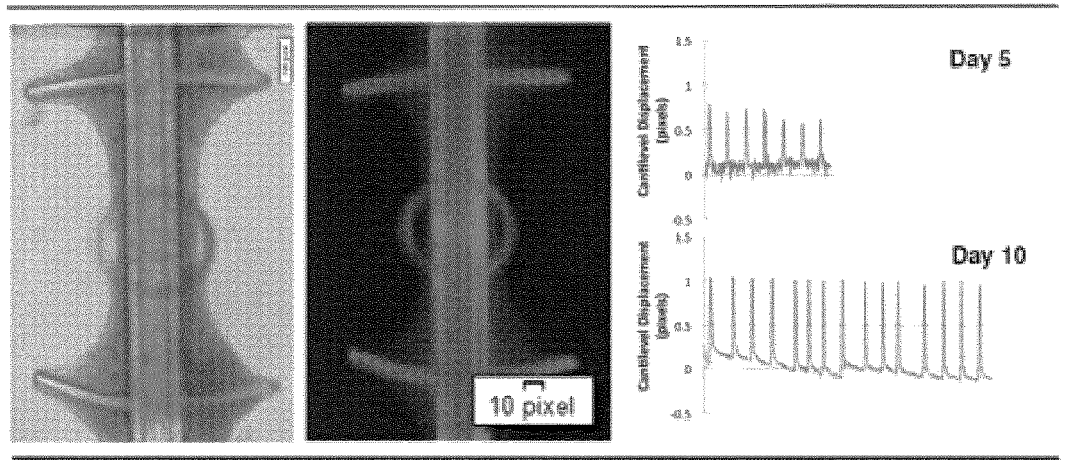

FIG. 79 measures cantilever displacement (as measured by pixels) of a 3D tissue strand after 5 days and after 10 days of growth post-seeding.

Figure 80:
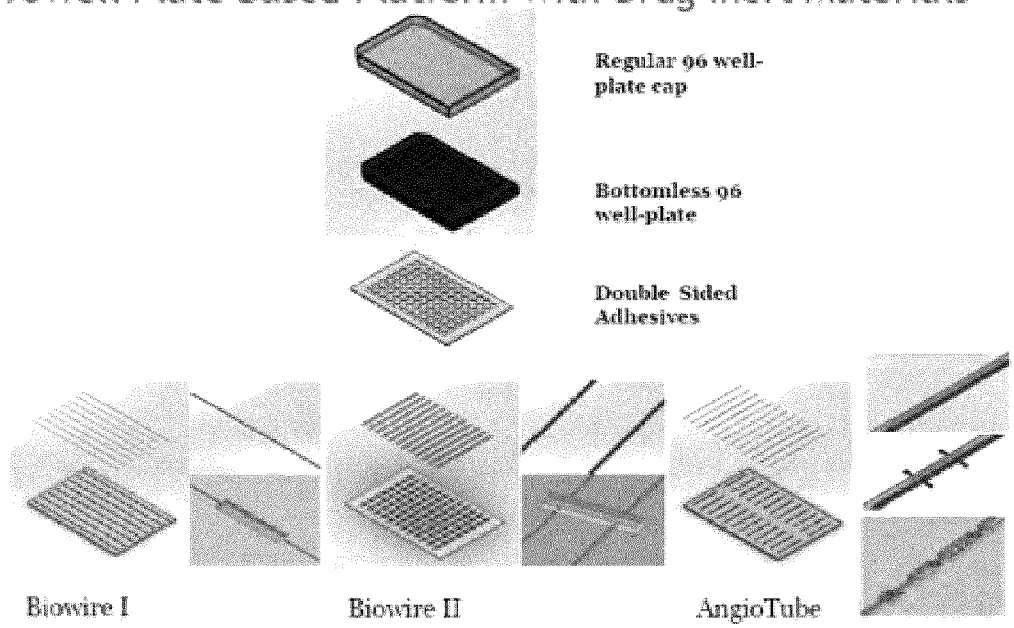

FIG. 80 compares exemplary biowire, biorod, and angiotube systems, each configured to be compatible with a 96-well plate format.

Figure 81:
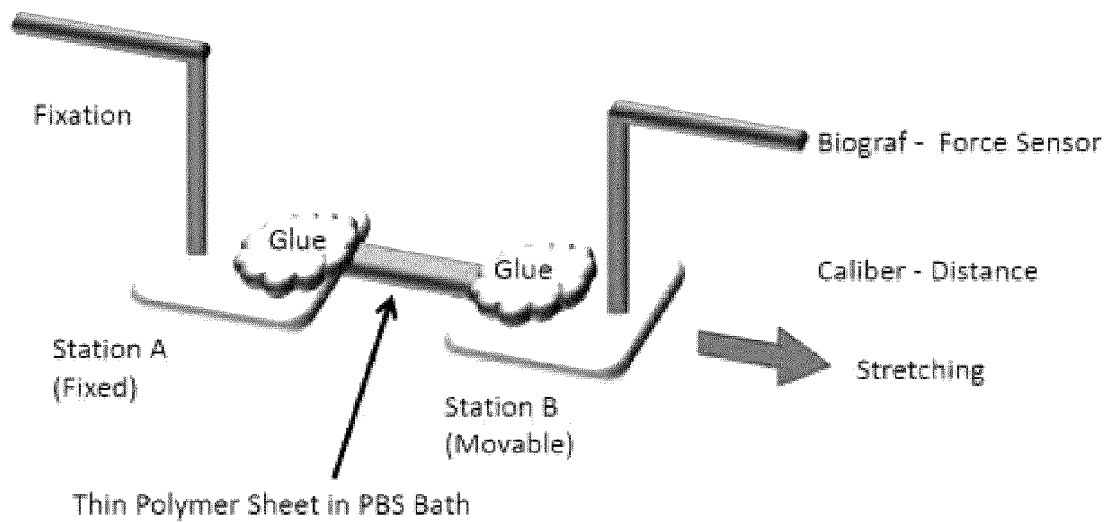

FIG. 81 provides a schematic of a system for measuring the mechanical properties of a polymer sheet comprising a fixed station (A) and a movable station (B).

Figure 82:
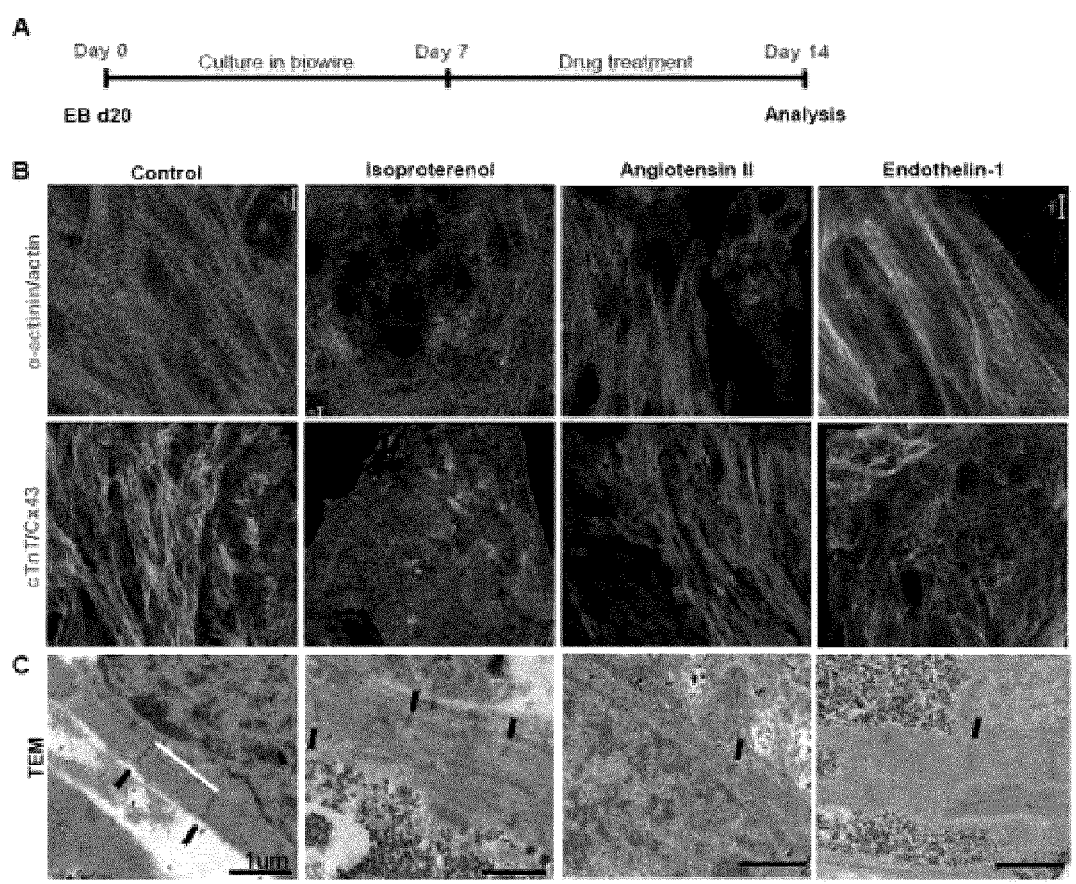

FIG. 82 Light and fluorescence microscopy of biowires treated with different compounds.

Figure 83:
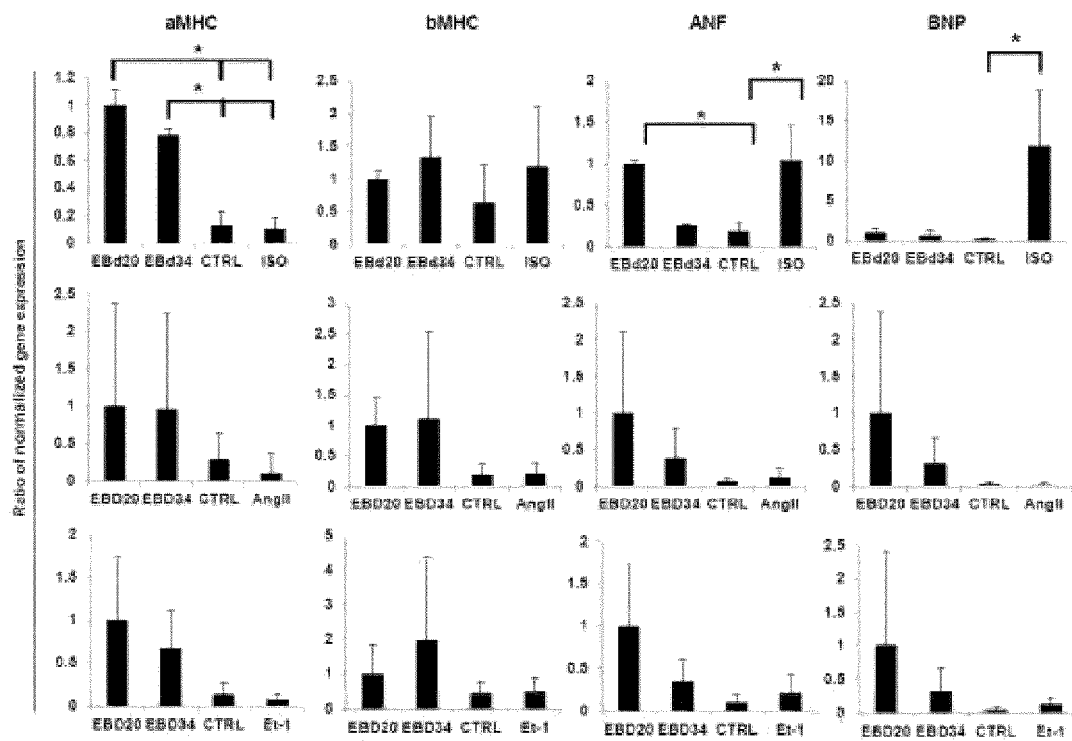

FIG. 83 depicts effects of chronic drug exposure on gene expression.

Figure 84:
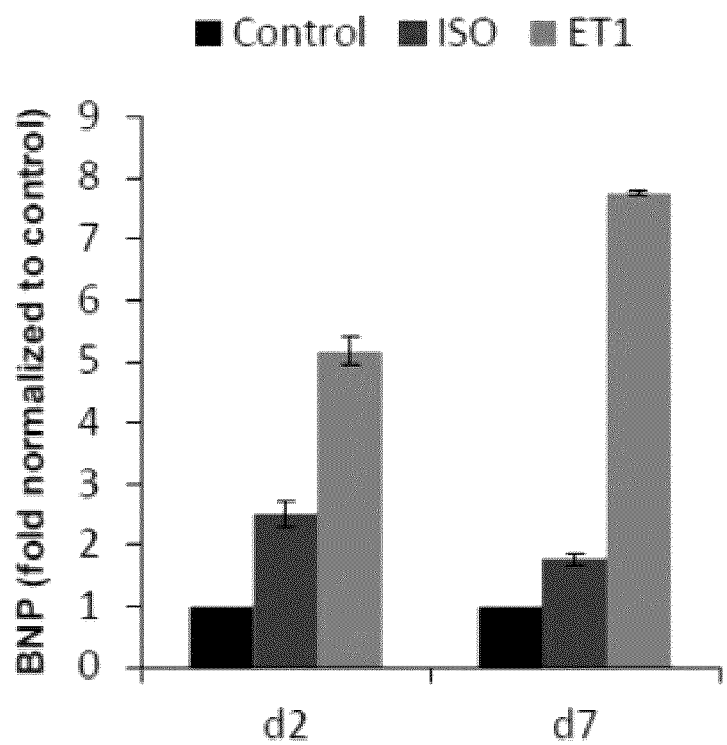

FIG. 84 Quantification of soluble human BNP in conditioned media of untreated hESC-microtissues (control) or treated with different hypertrophic drugs by ELISA. N=3. Average+/−standard deviation. Due to cross-reactivity issues, we were unable to quantify BNP in the AngII-treated samples.

FIG. 85 Treatment of biowires with ISO, Et-1 and AngII induces cardiomyocyte hypertrophy. Measurements performed on single Hes2 hESC derived cardiomyocytes dissociated from biowires at the end of cultivation. Cell area ($\mu m^2$), average+/−s.e.m., n=3.

Figure 86:
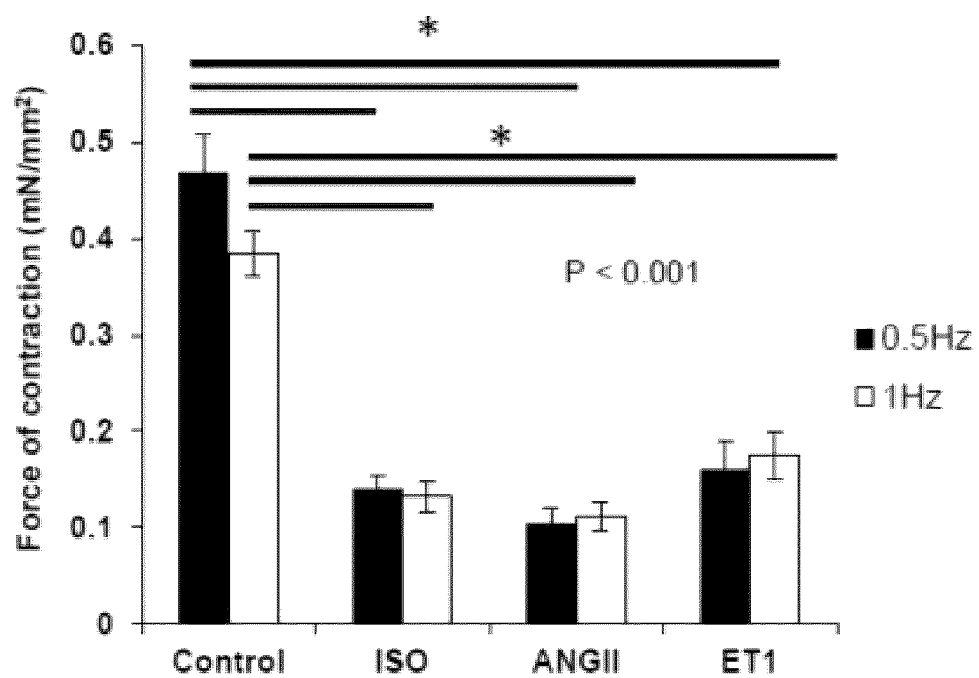

FIG. 86 Shows effects on force of contraction in ISO, AngII, and ET-1-treated biowire samples.

Figure 87:
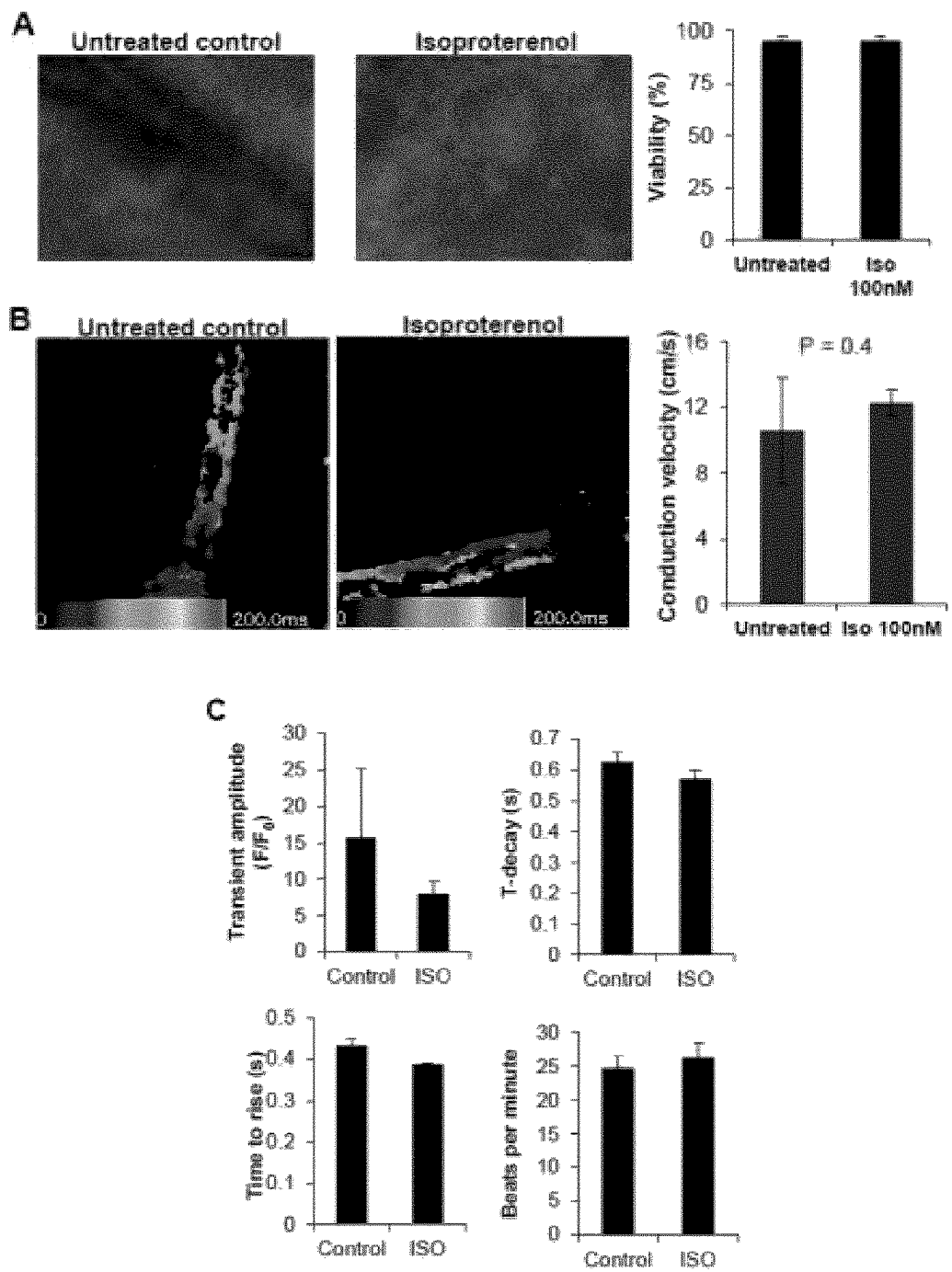

FIG. 87 Representative conduction velocity activation maps in biowires.

DETAILED DESCRIPTION

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention.

All publications, patent applications, patents, figures and other references cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

Unless defined otherwise, all technical and scientific terms used herein have the meaning commonly understood by a person skilled in the art to which this invention belongs. The following references, the entire disclosures of which are incorporated herein by reference, provide one of skill with a general definition of many of the terms (unless defined otherwise herein) used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, the Harper Collins Dictionary of Biology (1991). Generally, the procedures of molecular biology methods described or inherent herein and the like are common methods used in the art. Such standard techniques can be found in reference manuals such as for example Sambrook et al., (2000, Molecular Cloning—A Laboratory Manual, Third Edition, Cold Spring Harbor Laboratories); and Ausubel et al., (1994, Current Protocols in Molecular Biology, John Wiley & Sons, New-York).

The following terms may have meanings ascribed to them below, unless specified otherwise. However, it should be understood that other meanings that are known or understood by those having ordinary skill in the art are also possible, and within the scope of the present invention. All publications, patent applications, patents, and other references mentioned herein are incorporated by reference in their entirety. In the case of conflict, the present specification, including definitions, will control. In addition, the materials, methods, and examples are illustrative only and not intended to be limiting.

Definitions

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

An "agonist" is a drug, agent, or compound that binds to and activates its cognate receptor in some fashion, which directly or indirectly brings about a physiological effect.

An "antagonist" is an agent that binds to a receptor, and which in turn prevents binding by other molecules.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items.

In the pharmaceutical arts, the term "efficacy" can describe the strength of a response in a tissue produced from a single drug-receptor complex. In the context of this disclosure, "efficacy" can also be defined as a response elicited by a drug or test agent that improves the phenotype of a cell or tissue.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments. Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

As used herein, the term "hydrogel" refers to a physically or chemically cross-linked polymer network that is able to absorb large amounts of water and is a common material for forming tissue engineering scaffolds. They can be classified into different categories depending on various parameters including the preparation method, the charge, and the mechanical and structural characteristics. Reference can be made to S. Van Vlierberghe et al., "Biopolymer-Based Hydrogels As Scaffolds for Tissue Engineering Applications: A Review," Biomacromolecules, 2011, 12(5), pp. 1387-1408, which is incorporated herein by reference.

As used herein, the term "microfabrication" is a concept that includes fabrication on a nanometer or micrometer level, including microfabrication and nanofabrication. Methods for microfabrication are well known in the art. Reference to certain microfabrication techniques that may be applicable in the invention include, for example, U.S. Pat. Nos. 8,715,436, 8,609,013, 8,445,324, 8,236,480, 8,003,300, as well as Introduction to Microfabrication (2004) by S. Franssila. ISBN 0-470-85106-6, each of which are incorporated herein by reference.

The term "microfabricated structure" as used herein is a concept that includes one or more structures occupying a two- or three-dimensional space, including a structure fabricated on a nanometer or micrometer scale. The term "two-dimensional" means on a surface in either vertical or horizontal space.

As used herein, the term "pharmacokinetics" refers to the actions of the body on a drug. Pharmacokinetic processes include, but are not limited to, absorption, distribution, metabolism, and elimination of drugs.

As used herein, the term "pharmacodynamics" refers to the actions of a drug on the body. Because certain classes of drugs exhibit similar effects on the body, pharmacodynamic properties determine the group in which a drug or agent is classified.

As used here, the term "PDMS" refers to the polymer poly(dimethylsiloxane). Polydimethylsiloxane (PDMS) belongs to a group of polymeric organosilicon compounds that are commonly referred to as silicones. PDMS is the most widely used silicon-based organic polymer, and is particularly known for its unusual rheological (or flow) properties. PDMS is optically clear, and, in general, inert, non-toxic, and non-flammable. It is also called dimethicone and is one of several types of silicone oil (polymerized siloxane).

As used herein, the term "PMMA" refers to poly(methyl methacrylate). Poly(methyl methacrylate) (PMMA) is a transparent thermoplastic often used as a lightweight or shatter-resistant alternative to glass. Although it is not technically a type of glass, the substance has sometimes historically been called acrylic glass and is known as Plexiglas, Acrylite, Lucite, and Perspex. Chemically, it is the synthetic polymer of methyl methacrylate. PMMA is an economical alternative to polycarbonate (PC) when extreme strength is not necessary. Additionally, PMMA does not contain the potentially harmful bisphenol-A subunits found in polycarbonate. Non-modified PMMA behaves in a brittle manner when loaded, especially under an impact force, and is more prone to scratching than conventional inorganic glass, but modified PMMA can achieve high scratch and impact resistance.

As used herein, the term "POMac" refers to poly(octamethylene maleate (anhydride) citrate) (POMaC) or the POMac prepolymer which comprises a mixture of 1,8-octandiol, citrate acid, and maleic anhydride. Reference can be made to Tran et al., "Synthesis and characterization of a biodegradable elastomer featuring a dual crosslinking mechanism," Soft Matter, Jan. 1, 2010; 6(11): 2449-2461, which is incorporated herein by reference in its entirety.

A "test agent" is any substance that is evaluated for its ability to diagnose, cure, mitigate, treat, or prevent disease in a subject, or is intended to alter the structure or function of the body of a subject. A test agent in an embodiment can be a "drug" as that term is defined under the Food Drug and Cosmetic Act, Section 321(g)(1). Test agents include, but are not limited to, chemical compounds, biologic agents, proteins, peptides, antibodies, nucleic acids, lipids, polysaccharides, supplements, diagnostic agents and immune modulators and may also be referred to as "pharmacologic agents."

As used herein, the term "toxicity" is defined as any unwanted effect on human cells or tissue caused by a test agent, or test agent used in combination with other pharmaceuticals, including unwanted or overly exaggerated pharmacological effects. An analogous term used in this context is "adverse reaction."

As used herein, the term "tissue strand" refers to a three-dimensional tissue culture which is formed by first seeding a growth chamber or the like in various embodiments, e.g., the Biowire, Biotube, Biorod, or Angiotube embodiments, wherein the growth chamber comprises one or more suspended growth surfaces, e.g., wires, tubes, sufficient for growing a tissue strand. The tissue strand can grow or form around a single growth surface, e.g., a polymer wire or tube, or the tissue strand can grow between one or more growth elements, e.g., as in the Biorod embodiment.

As used herein, the term "tunability" as it is used in reference to a "tunable" polymer, e.g., POMac, refers to the capability of adjusting the process of polymerization of a polymer in a manner that allows for the formation of a resultant polymer product to have different mechanical and/or physical properties, such as elasticity, stiffness, and/or reactivity, or other properties. This concept is referred to in the context of certain polymers, such as POMac, that may be advantageously used in various embodiments/devices of the present invention, including the Biowire, Biotube, Biorod, Angiochip, and Angiotube embodiments to form the various components of the devices of the invention, e.g., polymer wires, scaffolds, scaffold layers, and other components. Tunable polymers, such as POMac, may have adjustable or "tunable" properties by adjusting, for example, (a) the degree or quantity of UV crosslinking or (b) the ratio of pre-polymer units that form the polymer, e.g., the ratio of 1,8-octanediol, citric acid, and maleic anhydride in the case of POMac. In addition, certain embodiments, such as the Angiochip embodiment, comprise polymer scaffolds that are formed with pores of various sizes. The controlled formation of pores can also be regarded as an aspect of tunability, and in particular, pore size may be controlled as exemplified herein by the include of different amounts of polyethylene glycol dimethyle ether (PEGDME) or an equivalent during the UV crosslinking stage, wherein the PEGDME will act as a spacer for the forming crosslinked network, thereby, inparting pores of various pores.

Tissue Culture Devices

The present invention contemplates various tissue culture systems for making and using three-dimensional biological tissues that accurately mimic native physiology, tissue architecture, vasculature, and other properties of native tissues. The mimicked tissues may include, but are not limited to, cardiac, hepatic, neural, vascular, kidney, and muscle tissues. The methods, composition, and devices may be used in a variety of applications that include drug testing, tissue repair and/or treatment, and regenerative medicine. The tissue culture devices of the invention can be used particularly for methods that include: (a) the testing of the efficacy and safety (including toxicity) of experimental pharmacologic agents (including, but not limited to, small molecule drugs, biologics, nucleic acid-based agents), (b) the defining of pharmacokinetics and/or pharmacodynamics of pharmacologic agents (including, but not limited to, small molecule drugs, biologics, nucleic acid-based agents), (c) characterizing the properties and therapeutic effects of pharmacologic agents (including, but not limited to, small molecule drugs, biologics, nucleic acid-based agents) on a subject, (d) screening of new pharmacologic agents, (e) provide implantable engineered tissues for use in regenerative medicine for treating damaged and/or diseased tissues, (e.g., use of the tissue constructs, devices, and/or systems of the disclosure to study cardiac disease states, including patients with electrical conduction defects (iPSC-CM)), and (f) personalized medicine.

In one aspect, the present disclosure provides a bioreactor system that may combine architectural and electrical cues to generate a microenvironment conducive to maturation of three-dimensional (3D) cardiac tissues or other contractile tissues. The present disclosure also provides methods and techniques for fabricating the disclosed devices, for using the disclosed devices to cultivate tissues, and for using the resulting tissues for implantation and other applications.

Another aspect relates to a bioreactor system in which cells are seeded in a hydrogel, e.g., a collagen gel, around a scaffold (e.g., a template suture) in a bioreactor channel or chamber (e.g., a microfabricated well). The seed cells in this example (in particular, where the cells have electrical characteristics, such as cardiac cells) can be subjected to electrical field stimulation according to a defined regimen defining specific frequency of stimulation at specific times (e.g., progressive frequency increase over several days). Consistent with maturation, the generated tissues (e.g., cardiac tissues) exhibit a significant degree of ultrastructural organization, improved conduction velocity and enhanced Ca2+ handling and electrophysiological properties.

In other aspect, perfusable bioreactor systems may be generated in which a perfusable scaffold having a lumen (e.g., a tubing template, such as a polytetrafluoroethylene (PTFE) tubing template) is suspended in the bioreactor channel or chamber (e.g., a microfabricated bioreactor channel). The scaffold may provide guidance for cells to align and elongate. To demonstrate the feasibility of such a device for drug testing, nitric oxide (NO) can be supplied in the cell culture channel to provide biochemical stimulation to cardiomyocytes within the cardiac tissue. NO was released from perfused sodium nitroprusside (SNP) solution and perfused from the scaffold lumen to the tissue culture (e.g., NO passed through the tubing wall) to reach the tissue space with cardiomyocytes. An example of the disclosed bioreactor device can also be integrated with electrical stimulation, which may further improve phenotype of the cells, e.g., cardiomyocytes.

In other aspects, the disclosure provides devices that enable measurement of the contraction force of cultivated tissues. In some examples, the device may have a multi-well configuration (e.g., configured as a 96 well plate), which may enable the device to be compatible with drug screening and/or non-invasive on-line monitoring of function.

In still other aspect, the disclosure provides a hybrid approach to create a microfluidic tissue. Such an approach may include providing an example device having a 3-D branched micro-channel network with thin channel walls to provide mechanical support to the built-in vasculatures (e.g., composed of the biodegradable elastomer, (poly(octamethylene maleate (anhydride) citrate) (POMaC))). A hydrogel (e.g., collagen based hydrogel) embedded with seed cells (e.g., cardiac cells) may be cast around the network such that the cardiac cells may remodel the aqueous matrix and compact around the built-in vasculature of the 3-D network to form macroscopically contracting vascularized cardiac muscle with physiological cell density. The resulting branched tissue, or the branching permeable polymer scaffold alone, may be used for implantation.

In still other aspects, the disclosed bioreactor systems may be similar to or reproduce the complexity of the native tissue architecture in vitro, thus enabling the cultivated cells to assume the structure which they would be expected to assume in vivo. Reproducing this structure may enable the cells to mature and to assume a similar function they would have in vivo. In various examples, the disclosed devices may be suitable for culture of muscle cells such as cardiomyocytes, skeletal muscle cells, smooth muscle cells as well as excitable tissues such as neurons and cells that may require rich vasculature such as hepatocytes, among others. In various examples, the disclosed devices may be suitable for drug-testing in vitro, for building a human-on-a-chip with several different compartments as well as for direct anastomosis and/or implantation into an animal or a human patient, among other applications. Implantation may include using the permeable polymer scaffold alone as a surgical cuff, bypass graft, fistula or arterio-ventricular shunt, among others. Implanting the cultivated tissue with direct anastomosis (e.g., in the form of an arterio-ventricular shunt) or without direct anastomosis at the desired target tissue location may be also possible.

Reference will now be made in detail to exemplary aspects of the disclosure. In particular, the following Examples discloses five (5) exemplary aspects of the present disclosure which may be referred to as Biowire systems (Example 1, a single-wire tissue culture embodiment), Biotube systems (Example 2, a perfusable wire tissue culture embodiment), Biorod/Biowirell systems (Example 3, a contractile force tissue culture embodiment), Biobranch/Angiochip systems (Example 4, a vascularized tissue culture embodiment), and Angiotube systems (Example 5, a perfusable contractile force tissue culture embodiment). While the disclosure will be described in conjunction with the exemplary aspects, it will be understood that it is not intended to limit the disclosure to these aspects. To the contrary, it is intended to cover alternatives, modifications, combinations of embodiments, and equivalents as may be included within the spirit and scope of the invention.

Biowire Systems

As may be used herein, the first aspect of the bioreactors systems of the disclosure can be referred to as "biowire systems or devices" and is intended to refer to the bioreactor system comprising the features and components described herein. The tissue culture that forms in the biowire systems of the invention may be referred to as a "biowire." It will be understood that herein description of the biowire systems is not intended to limit the disclosure to these aspects or any particular embodiment. To the contrary, it is intended to cover alternatives, modifications, combinations of embodiments, and equivalents as may be included within the spirit and scope of the invention.

In a first aspect, the disclosure relates to a bioreactor system comprising a bioreactor having a well or channel, a longitudinal scaffold, suture, or otherwise cell growth element supported or suspended across the well or channel. The well or channel is configured to receive cells seeded therein, as well as growth media and/or nutrient and/or factors. The cells, once seeded, cultivate to form a tissue culture, and preferable in certain embodiments, a three-dimensional tissue strand contained on, around, over, and/or integrated with the longitudinal scaffold, stuture, or otherwise cell growth element.

In certain embodiments of the first aspect, the longitudinal scaffold, suture, or otherwise cell growth element is elevated off of the bottom surface of the well or channel.

In various embodiments of the first aspect, the longitudinal scaffold, suture, or otherwise cell growth element can be any suitable material, which can include natural materials, such as collagen and collagen derivatives, natural suture material (e.g., animal intestines), cellulose and cellulose derivatives, proteoglycans, heparin sulfate, chondroitin sulfate, keratin sulfates, hyaluronic acid, elastin, fibronectin, and lamanin, etc., as well as synthetic materials, including various polymers and nanomaterials.

In certain embodiments of the first aspect, those having ordinary skill in the art would appreciate the criteria for selecting an appropriate material as biomaterials for use in the scaffolds of the invention. Such choices can be based on a variety of parameters, which can include their material chemistry, molecular weight, solubility, shape and structure, hydrophilicity/hydrophobicity, lubricity, surface energy, water absorption degradation, and erosion mechanism.

In certain embodiments of the first aspect, the scaffolds of the invention can be polymeric scaffolds. Such scaffolds, in general, are drawing a great attention due to their unique properties such as high surface-to-volume ratio, high porosity with very small pore size, biodegradation, and mechanical property. They offer distinct advantages of biocompatibility, versatility of chemistry, and the biological properties which are significant in the application of tissue engineering and organ substitution.

Scaffold materials can be synthetic or biologic, degradable or nondegradable. The properties of polymers depend on the composition, structure, and arrangement of their constituent macromolecules. It can be categorized into different types in terms of their structural, chemical, and biological characteristics, for example, ceramics, glasses, polymers, and so forth. Naturally occurring polymers, synthetic biodegradable, and synthetic nonbiodegradable polymers can all be used as polymers to form the scaffolds of the invention.

It will be appreciated that natural polymers can be used as the scaffold or cell growth substrates of the herein described bioreactor systems. Natural materials, owing to the bioactive properties, potentially may have better interactions with cells which allow them to enhance the cells' performance in biological systems described herein. Natural polymers can be classified as proteins (silk, collagen, gelatin, fibrinogen, elastin, keratin, actin, and myosin), polysaccharides (cellulose, amylose, dextran, chitin, and glycosaminoglycans), or polynucleotides (DNA, RNA), etc., or combinations of these materials.

The scaffolds used in the bioreactor systems of the invention can also include synthetic biomaterials, which may facilitate restoration of structure and function of damaged or diseased tissues. Synthetic polymers are highly useful in biomedical field since their properties (e.g., porosity, degradation time, and mechanical characteristics) can be tailored for specific applications. Synthetic polymers are often cheaper than biologic scaffolds; it can be produced in large uniform quantities and have a long shelf time. Many commercially available synthetic polymers show physicochemical and mechanical properties comparable to those of biological tissues. Synthetic polymers represent the largest group of biodegradable polymers, and they can be produced under controlled conditions. They exhibit, in general, predictable and reproducible mechanical and physical properties such as tensile strength, elastic modulus, and degradation rate. PLA, PGA, and PLGA copolymers are among the most commonly used synthetic polymers in tissue engineering. PHA belongs to a class of microbial polyesters and is being increasingly considered for applications in tissue engineering. All of these synthetic polymers are contemplated herein.

In addition, the bioreactor systems of the first aspect of the disclosure may also use semi-synthetic, such as those disclosed in Rosso et al., "Smart materials as scaffolds for tissue engineering," J Cell Physiol. 2006 December; 209(3): 1054. Such scaffolds may contain oligopeptide cleaving sequences specific for matrix metalloproteinases (MMPs), integrin binding domains, growth factors, anti-thrombin sequences, plasmin degradation sites, and morphogenetic proteins. Such semi-synthetic materials aim to confer "intelligent" semi-synthetic biomaterials, having advantages offered by both the synthetic materials (e.g., processability, mechanical strength) and by the natural materials (e.g., specific cell recognition, cellular invasion, and the ability to supply differentiation/proliferation signals). Due to their characteristics, these semi-synthetic biomaterials represent a new and versatile class of biomimetic hybrid materials that hold clinical promise in serving as a source of materials for the scaffolds described herein.

As a point of reference, the following polymers and materials are contemplated for use in the bioreactors described herein:

PU:PolyurethanePS:PolysulfoneCP:Calcium phosphate;
HA:Hyaluronic acidPP:PolypropyleneBG:Bioactive glassECM:Extracellular matrix;
PVA:Polyvinyl alcoholPGA:PolyglycolidePLA:PolylactidePPF:Poly(propylene fumarate);
PCA:PolycyanoacrylatePCL:Poly(ε-caprolactone);
PDO:PolydioxanonePHA:Polyhydroxyalkanoates;
POE:Poly(ortho ester);
PEE:Poly(ether ester);
PEO:Poly(ethylene oxide);
PBT:Polybutylene terephthalate;
HAP:Hydroxyapatite;
TCP:Tricalcium phosphate;
PEG:Poly(ethylene glycol);
PEU:Poly(ester urethane);
PAA:Poly(acrylic acid);
LDI:Lysine diisocyanate;
BCP:Biphasic calcium phosphate;
PAam:Polyacrylamide;
PMMA:Polymethylmethacrylate;
PLLA:Poly(L-lactic acid);
PLGA:Poly(l-lactide-co-glycolide);
PTMC:Poly(trimethylene carbonate);
PDMS:Polydimethylsiloxane;

PTFE:Polytetrafluoroethylene;
PEVA:Poly(ethylene-co-vinylacetate);
PGCL:Poly(glycolide-co-ε-caprolactone);
PLCL:Poly(l-lactide-co-caprolactone);
PDLLA:Poly(DL-lactide);
PLDLA:Poly-L/D-lactide;
PLAGA:Poly(lactic acid-glycolic acid);
PHBHV:Poly(3-hydroxybutyrate) 3-hydroxyvalerate;
PCLTMC:Poly(caprolactone-co-trimethylene carbonate);
PNIPAAm:Poly(N-isopropylacrylamide);
PDMAEM:Poly(dimethylaminoethylmethacrylate) hydrochloride;
PDLLA-CL:Poly(D,L-lactide-co-caprolactone);
PLLA-CL:Poly(l-lactide-co-ε-caprolactone); and
TCP:Tricalcium phosphate.
POMac.

In particular embodiments, the scaffolds described herein may made from poly(dimethysiloxane (PDMS)), poly(m-ethylmethacrylate (PMMA)), polystyrene, or polystyrene, or combinations thereof. The scaffold may be made of a biodegradable material. Other suitable materials may include poly(glycerol sebacate), POMac without citric acid, poly(lactic acid), poly(glycolic acid), poly(ε-caprolactone), various polyurethanes as well as co-polymers thereof, silk, microstructured, nanofabricated materials, and/or materials doped with nanostructures such as nanorods or quantum dots, among others. Optionally in certain embodiments, the scaffold material can be perfusable to allow exchange and/or passage of water and molecules, including proteins, drugs, nutrients, and metabolic waste materials.

The skilled artisan will appreciate that reference can be made to resources available in the state of the art regarding the making and use of tissue engineering scaffolds and, in particular, reference case be made to the scaffold materials described in Dhandayuthapani et al., "Polymeric Scaffolds in Tissue Engineering Application: A Review; International Journal of Polymer Science, Vol. 2011 (2011), pages 1-19.

The shape of the well or channel is not limited in any particular manner and can be square, rectangular, circular, oval, oblong, triangular, or any combination of shapes. The other dimensions of the well or channel also may vary in any suitable manner. For example, the depth of the channel, height of the walls, and length of the channel, and the overall volume of the channel may be varied in any suitable way.

For example, the length, height, and width of the channel can be from about 0.1-1 mm, or about 0.2-2 mm, or about 0.3-3 mm, or about 0.4-4 mm, or about 0.5-5 mm, or about 0.6-6 mm, or about 0.7-7 mm, or about 0.8-8 mm, or about 0.9-9 mm, or about 1-10 mm, or more.

The surface of the channel may also be modified with any suitable surface treatments, including chemical modifications (such as, for example, ligands, charged substances, bind agents, growth factors, antibiotics, antifungal agents), or physical modifications (such as, for example, spikes, curved portions, folds, pores, uneven portions, or various shapes and topographies) which may facilitate the tissue culture process.

In various embodiments of the first aspect, the cells that may be seeded and cultivated in the tissue culture systems disclosed herein may include, but are not limited to, cardiac cells, liver cells, kidney cells, cartilage cells, skin cells, bone marrow cells, or combinations of such tissues. In particular embodiments, the tissue culture systems disclosed herein are suitable for growing cardiac tissue, hepatic tissue, or kidney tissue. In certain embodiments, the tissues formed in the systems described herein are three-dimensional tissues.

In various other embodiments of the first aspect, the bioreactor systems disclosed herein may be seeded with stem cells or otherwise pregenitor cells which are capable of developing into mature tissue types, e.g., mature cardiac, hepatic, or kidney tissue. Stem cells may include, but are not limited to embryonic stem cells and adult stem cells. In addition, stem cells contemplated for use with the herein described devices may have any degree of potency, including totipotent/omnipotent cells, pluripotent cells, multipotent cells, oligopotent cells, or unipotent cells (e.g., progenitor cells).

In embodiments involving cardiac cells (or other electrically-stimulated cells), the bioreactor systems described herein can be further configured to include electrodes configured to generate an electric field across the channel of the bioreactor system. The direction of the electric field can be in any direction, but preferably in a direction that is generally parallel to the longitudinal axis of the channel (and the resulting tissue strand once grown on and around the scaffold in the channel), or which is generally perpendicular to the longitudinal axis of the channel (and the resulting tissue strand). However, the orientation of the electric field is not limited and the positioning of the electrodes can be in any suitable format such that a suitable electric field can be generated. In certain embodiments, e.g., cardiac cells, the electric field facilitates that maturation of the cells to form tissue that more closely mimicks the physiological and electrical properties of actual tissue, e.g., cardiac tissue.

In certain embodiments of the first aspect, the bioreactors disclosed herein may be assembled as a plurality of individual bioreactors, e.g., in the format of multi-well plates, such as 6-well, 12-well, 24-well, 96-well, 384-well, and 1536-well plates, such that a plurality of tissue strands may be grown, tested, measured, and evaluated, etc., in a simultaneous manner.

In yet another embodiments of the first aspect, the present disclosure relates to methods of using the three-dimensional tissue constructs, the devices, and/or the systems of the disclosure in various applications, including, but not limited to, (a) the testing of the efficacy and safety (including toxicity) of experimental pharmacologic agents (including, but not limited to, small molecule drugs, biologics, nucleic acid-based agents), (b) the defining of pharmacokinetics and/or pharmacodynamics of pharmacologic agents (including, but not limited to, small molecule drugs, biologics, nucleic acid-based agents), (c) characterizing the properties and therapeutic effects of pharmacologic agents (including, but not limited to, small molecule drugs, biologics, nucleic acid-based agents) on a subject, (d) screening of new pharmacologic agents, (e) providing implantable engineered tissues for use in regenerative medicine for treating damaged and/or diseased tissues (e.g., use of the tissue constructs, devices, and/or systems of the disclosure to study cardiac disease states, including patients with electrical conduction defects (iPSC-CM)), and (f) personalized medicine.

The biowire systems may also be formed with or include hydrogels. Hydrogels are physically or chemically cross-linked polymer networks that are able to absorb large amounts of water. They can be classified into different categories depending on various parameters including the preparation method, the charge, and the mechanical and structural characteristics. Hydrogels are an appealing scaffold material because they are structurally similar to the extracellular matrix of many tissues, can often be processed under relatively mild conditions, and may be delivered in a minimally invasive manner. Consequently, hydrogels can be utilized as scaffold materials herein. Hydrogels can include polyvinyl alcohol, sodium polyacrylate, acrylate polymers and copolymers with an abundance of hydrophilic groups, among other materials. Natural hydrogel materials include agarose, methylcellulose, hyaluronan, and other naturally derived polymers.

Biotube Systems

As may be used herein, the second aspect of the bioreactors systems of the disclosure can be referred to as "biotube systems or devices" and is intended to refer to the bioreactor systems comprising the features and components described herein. The tissue culture that forms in the biotube systems of the disclosure may be referred to as a "biotubes." It will be understood that herein description of the biotube systems is not intended to limit the disclosure to these aspects or any particular embodiment. To the contrary, it is intended to cover alternatives, modifications, combinations of embodiments, and equivalents as may be included within the spirit and scope of the invention.

In a second aspect, the disclosure relates to a bioreactor system for growing a tissue culture, e.g., a three dimensional tissue strand with a perfusable lumen. The bioreactor system includes a well or channel suitable for seeding cells and a perfusable scaffold with one or more lumens and which is supported or suspended over the well or channel, e.g., along the longitudinal axis of the well or channel. Once cells are seeded into the well or channel, along with suitable growth media, growth factors, and other nutrients suitable for the culture of the cells, the cells grow to form a tissue strand that surrounds and/or integrates with the perfusable scaffold. In use, nutrients and growth factors, as well as test agents (e.g., drugs, proteins, toxins etc.) may be delivered to the tissue strand via the perfusable lumen which is integrated with a means for delivering such materials (e.g., a reservoir element connected to the luman via a tube or vessel). In addition, the bioreactor system may also include in various embodiments a passage that exits from the perfusable lumen, e.g., a drain or otherwise terminal reservoir that allows waste and otherwise metabolic products to diffuse from the tissue strand into the perfusable lumen and out through to the terminal reservoir. In various embodiments involving cardiac cells (or other electrically-stimulated cells), the bioreactor can be further configured to include electrodes configured to generate an electric field across the channel of the bioreactor. The direction of the electric field can be in any direction, but preferably in a direction that is parallel to the longitudinal axis of the tissue strand that forms along the length of the perfusuable luminal element.

In certain embodiments of the second aspect, the perfusable longitudinal scaffold, suture, or otherwise cell growth element is elevated off of the bottom surface of the well or channel.

In various embodiments of the second aspect, the perfusable longitudinal scaffold, suture, or otherwise cell growth element can be any suitable material, which can include natural materials, such as collagen and collagen derivatives, natural suture material (e.g., animal intestines), cellulose and cellulose derivatives, proteoglycans, heparin sulfate, chondroitin sulfate, keratin sulfates, hyaluronic acid, elastin, fibronectin, and lamanin, etc., as well as synthetic materials, including various polymers and nanomaterials (e.g., POMac).

In certain embodiments of the second aspect, those having ordinary skill in the art would appreciate the criteria for selecting an appropriate material as biomaterials for use in the perfusable scaffolds of the invention. Such choices can be based on a variety of parameters, which can include their material chemistry, molecular weight, solubility, shape and structure, hydrophilicity/hydrophobicity, lubricity, surface energy, water absorption degradation, and erosion mechanism.

In certain embodiments of the second aspect, the perfusable scaffolds of the invention can be polymeric scaffolds. Such scaffolds, in general, are drawing a great attention due to their unique properties such as high surface-to-volume ratio, high porosity with very small pore size, biodegradation, and mechanical property. They offer distinct advantages of biocompatibility, versatility of chemistry, and the biological properties which are significant in the application of tissue engineering and organ substitution.

Perfusable scaffold materials can be synthetic or biologic, degradable or nondegradable. The properties of the polymers depends on the composition, structure, and arrangement of their constituent macromolecules. It can be categorized into different types in terms of their structural, chemical, and biological characteristics, for example, ceramics, glasses, polymers, and so forth. Naturally occurring polymers, synthetic biodegradable, and synthetic non-biodegradable polymers can all be used as polymers to form the scaffolds of the invention.

It will be appreciated that natural polymers can be used as the perfusable scaffold or cell growth substrates of the herein described bioreactor systems. Natural materials, owing to the bioactive properties, potentially may have better interactions with cells which allow them to enhance the cells' performance in biological systems described herein. Natural polymers can be classified as proteins (silk, collagen, gelatin, fibrinogen, elastin, keratin, actin, and myosin), polysaccharides (cellulose, amylose, dextran, chitin, and glycosaminoglycans), or polynucleotides (DNA, RNA), etc., or combinations of these materials.

The perfusable scaffolds used in the bioreactor systems of the invention can also include synthetic biomaterials, which may facilitate restoration of structure and function of damaged or diseased tissues. Synthetic polymers are highly useful in biomedical field since their properties (e.g., porosity, degradation time, and mechanical characteristics) can be tailored for specific applications. Synthetic polymers are often cheaper than biologic scaffolds; it can be produced in large uniform quantities and have a long shelf time. Many commercially available synthetic polymers show physico-chemical and mechanical properties comparable to those of biological tissues. Synthetic polymers represent the largest group of biodegradable polymers, and they can be produced under controlled conditions. They exhibit, in general, predictable and reproducible mechanical and physical properties such as tensile strength, elastic modulus, and degradation rate. PLA, PGA, and PLGA copolymers are among the most commonly used synthetic polymers in tissue engineering. PHA belongs to a class of microbial polyesters and is being increasingly considered for applications in tissue engineering. All of these synthetic polymers are contemplated herein.

In addition, the bioreactor systems of the first aspect of the disclosure may also use semi-synthetic, such as those disclosed in Rosso et al., "Smart materials as scaffolds for tissue engineering," J Cell Physiol. 2006 December; 209(3): 1054. Such scaffolds may contain oligopeptide cleaving sequences specific for matrix metalloproteinases (MMPs), integrin binding domains, growth factors, anti-thrombin sequences, plasmin degradation sites, and morphogenetic proteins. Such semi-synthetic materials aim to confer "intelligent" semi-synthetic biomaterials, having advantages offered by both the synthetic materials (e.g., processability, mechanical strength) and by the natural materials (e.g., specific cell recognition, cellular invasion, and the ability to supply differentiation/proliferation signals). Due to their characteristics, these semi-synthetic biomaterials represent a new and versatile class of biomimetic hybrid materials that hold clinical promise in serving as a source of materials for the scaffolds described herein.

As a point of reference, the following polymers and materials are contemplated for use in the second aspect bioreactors described herein:
PU:PolyurethanePS:PolysulfoneCP:Calcium phosphate;
HA:Hyaluronic acidPP:PolypropyleneBG:Bioactive glassECM:Extracellular matrix;
PVA:Polyvinyl alcoholPGA:PolyglycolidePLA:PolylactidePPF:Poly(propylene fumarate);
PCA:PolycyanoacrylatePCL:Poly(ε-caprolactone);
PDO:PolydioxanonePHA:Polyhydroxyalkanoates;
POE:Poly(ortho ester);
PEE:Poly(ether ester);
PEO:Poly(ethylene oxide);
PBT:Polybutylene terephthalate;
HAP:Hydroxyapatite;
TCP:Tricalcium phosphate;
PEG:Poly(ethylene glycol);
PEU:Poly(ester urethane);
PAA:Poly(acrylic acid);
LDI:Lysine diisocyanate;
BCP:Biphasic calcium phosphate;
PAam:Polyacrylamide;
PMMA:Polymethylmethacrylate;
PLLA:Poly(L-lactic acid);
PLGA:Poly(l-lactide-co-glycolide);
PTMC:Poly(trimethylene carbonate);
PDMS:Polydimethylsiloxane;
PTFE:Polytetrafluoroethylene;
PEVA:Poly(ethylene-co-vinylacetate);
PGCL:Poly(glycolide-co-ε-caprolactone);
PLCL:Poly(l-lactide-co-caprolactone);
PDLLA:Poly(DL-lactide);
PLDLA:Poly-L/D-lactide;
PLAGA:Poly(lactic acid-glycolic acid);
PHBHV:Poly(3-hydroxybutyrate) 3-hydroxyvalerate;
PCLTMC:Poly(caprolactone-co-trimethylene carbonate);
PNIPAAm:Poly(N-isopropylacrylamide);
PDMAEM:Poly(dimethylaminoethylmethacrylate) hydrochloride;
PDLLA-CL:Poly(D,L-lactide-co-caprolactone);
PLLA-CL:Poly(l-lactide-co-ε-caprolactone); and
TCP:Tricalcium phosphate.
POMac.

In particular embodiments of the second aspect, the perfusable scaffolds described herein may made from poly (dimethysiloxane (PDMS)), poly(methylmethacrylate (PMMA)), polystyrene, or polystyrene, or combinations thereof. The scaffold may be made of a biodegradable material. Other suitable materials may include poly(glycerol sebacate), POMac without citric acid, poly(lactic acid), poly(glycolic acid), poly(ε-caprolactone), various polyurethanes as well as co-polymers thereof, silk, microstructured, nanofabricated materials, and/or materials doped with nanostructures such as nanorods or quantum dots, among others. Optionally in certain embodiments, the scaffold material can be perfusable to allow exchange and/or passage of water and molecules, including proteins, drugs, nutrients, and metabolic waste materials.

The skilled artisan will appreciate that reference can be made to resources available in the state of the art regarding the making and use of tissue engineering scaffolds and, in particular, reference case be made to the scaffold materials described in Dhandayuthapani et al., "Polymeric Scaffolds in Tissue Engineering Application: A Review; International Journal of Polymer Science, Vol. 2011 (2011), pages 1-19

The shape of the well or channel is not limited in any particular manner and can be square, rectangular, circular, oval, oblong, triangular, or any combination of shapes. The other dimensions of the well or channel also may vary in any suitable manner. For example, the depth of the channel, height of the walls, and length of the channel, and the overall volume of the channel may be varied in any suitable way.

For example, the length, height, and width of the channel can be from about 0.1-1 mm, or about 0.2-2 mm, or about 0.3-3 mm, or about 0.4-4 mm, or about 0.5-5 mm, or about 0.6-6 mm, or about 0.7-7 mm, or about 0.8-8 mm, or about 0.9-9 mm, or about 1-10 mm, or more.

The surface of the channel may also be modified with any suitable surface treatments, including chemical modifications (such as, for example, ligands, charged substances, bind agents, growth factors, antibiotics, antifungal agents), or physical modifications (such as, for example, spikes, curved portions, folds, pores, uneven portions, or various shapes and topographies) which may facilitate the tissue culture process.

In various embodiments of the second aspect, the cells that may be seeded and cultivated in the tissue culture systems disclosed herein may include, but are not limited to, cardiac cells, liver cells, kidney cells, cartilage cells, skin cells, bone marrow cells, or combinations of such tissues. In particular embodiments, the tissue culture systems disclosed herein are suitable for growing cardiac tissue, hepatic tissue, or kidney tissue. In certain embodiments, the tissues formed in the systems described herein are three-dimensional tissues.

In various other embodiments of the second aspect, the bioreactor systems disclosed herein may be seeded with stem cells or otherwise pregenitor cells which are capable of developing into mature tissue types, e.g., mature cardiac, hepatic, or kidney tissue. Stem cells may include, but are not limited to embryonic stem cells and adult stem cells. In addition, stem cells contemplated for use with the herein described devices may have any degree of potency, including totipotent/omnipotent cells, pluripotent cells, multipotent cells, oligopotent cells, or unipotent cells (e.g., progenitor cells).

In embodiments involving cardiac cells (or other electrically-stimulated cells), the bioreactor systems described herein can be further configured to include electrodes configured to generate an electric field across the channel of the bioreactor system. The direction of the electric field can be in any direction, but preferably in a direction that is generally parallel to the longitudinal axis of the channel (and the resulting tissue strand once grown on and around the scaffold in the channel), or which is generally perpendicular to the longitudinal axis of the channel (and the resulting tissue strand). However, the orientation of the electric field is not limited and the positioning of the electrodes can be in any suitable format such that a suitable electric field can be generated. In certain embodiments, e.g., cardiac cells, the electric field facilitates that maturation of the cells to form tissue that more closely mimicks the physiological and electrical properties of actual tissue, e.g., cardiac tissue.

In certain embodiments of the second aspect, the bioreactors disclosed herein may be assembled as a plurality of individual bioreactors, e.g., in the format of multi-well plates, such as 6-well, 12-well, 24-well, 96-well, 384-well, and 1536-well plates, such that a plurality of tissue strands may be grown, tested, measured, and evaluated, etc., in a simultaneous manner.

In yet another embodiments of the second aspect, the present disclosure relates to methods of using the three-dimensional tissue constructs, the devices, and/or the systems of the invention in various applications, including, but not limited to, (a) the testing of the efficacy and safety (including toxicity) of experimental pharmacologic agents (including, but not limited to, small molecule drugs, biologics, nucleic acid-based agents), (b) the defining of pharmacokinetics and/or pharmacodynamics of pharmacologic agents (including, but not limited to, small molecule drugs, biologics, nucleic acid-based agents), (c) characterizing the properties and therapeutic effects of pharmacologic agents (including, but not limited to, small molecule drugs, biologics, nucleic acid-based agents) on a subject, (d) screening of new pharmacologic agents, (e) providing implantable engineered tissues for use in regenerative medicine for treating damaged and/or diseased tissues, (e.g., use of the tissue constructs, devices, and/or systems of the disclosure to study cardiac disease states, including patients with electrical conduction defects (iPSC-CM)), and (f) personalized medicine.

In certain embodiments, the longitudinal element may comprise a plurality of lumens. The thickness and/or diameter of the element may vary in any suitable way. The diameter of the lumen may vary in size over any suitable range, including, for example between 0.1-5 microns, 0.2-10 microns, 0.3-15 microns, 0.4-20 microns, 0.5-30 microns, 0.5-50 microns, 1.0-100 micron, 2.0-200 microns, 3.0-500 microns, 4.0-800 microns, 5.0 microns-1 millimeter, or 1-10 millimeters or more. The lumen may have a constant diameter, or the diameter may vary over the length of the longitudinal element. The surface of the longitudinal element may have any suitable properties, including having a smooth surface, rough surface, barbed surface, or the like. In addition, the element may be covalently or noncovalently coupled with additional components such as ligands, antibodies, charged molecules, hydrophobic molecules, or the like which may assist cells that come into contact with the element to adhere to the longitudinal element.

Orientation of the scaffold, and in particular, the orientation of the perfusable longitudinal elements may be varied with respect to the orientation of the growth chamber in the well. In one embodiment, the growth chamber may be a generally longitudinal growth chamber that may be orientated generally perpendicular to the orientation of the longitudinal elements. In another embodiment, the longitudinal elements may be orientated in a generally perpendicular orientation relative to the orientation of the growth chamber. In still another embodiment, the longitudinal elements may be orientated in a generally parallel orientation relative to the orientation of the growth chamber. In yet other embodiments, the longitudinal elements may be orientated in a generally diagonal orientation relative to the orientation of the growth chamber.

The attachment of the longitudinal elements to the wells of the bioreactor plates can be by any suitable means, e.g., adhesives, welding, or otherwise mechanical means. The points of attachment between the wells and the longitudinal elements can be ordered, random, continuous, or non-continuous.

The longitudinal elements can also, in certain embodiments, comprise perfusable materials, that allow the passage of nutrients, metabolic waste material, proteins, or even whole cells. Perfusability may be established by any suitable means including as a property of the material used to form the elements, or by forming one or more pores in the material forming the elements. Perfusable materials will allow free movement of nutrients, metabolic waste, and even whole cells to freely move between the lumen of the biotube and the growth chamber of the bioreactor.

The bioreactor components (e.g., reactor body, lids, covers, growth chambers, scaffolds, longitudinal elements, etc.) of any of the bioreactors of the disclosure may be made from any suitable materials, including a variety of polymers (including those that are FDA approved), such as, polylactones, such as poly(L-lactide) (PLA), poly(glycolide) (PGA), and their copolymers (PLGA), PDMS (poly(dimethylsiloxane)), PMMA (poly(methyl methacrylate)), and biodegradable polymers, including POMac (poly(octamethylene maleate (anhydride) citrate, a mixture of 1,8-octandiol, citrate acid, and maleic anhydride units). Reference can be made to Tran et al., "Synthesis and characterization of a biodegradable elastomer featuring a dual crosslinking mechanism," Soft Matter, Jan. 1, 2010; 6(11): 2449-2461, which is incorporated herein by reference in its entirety. The polymers can be any suitable naturally occurring polymer (such as, but not limited to cellulose, silk, shellac, rubber or derivatives thereof) or any suitable synthetic polymer (including, but not limited to, nylon, polyvinyl chloride (PVC or vinyl), polystyrene, polyethylene, polypropylene, polyacrylonitrile, PVB, silicone, and derivatives thereof). The polymers may be modified covalently or noncovalently with additional components such as ligands, antibodies, charged molecules, hydrophobic molecules, or the like which may facilitate growth and/or maintenance of tissues in the bioreactor. It will be appreciated that the particular types of polymers, their modifications, and the like hinges on finding an appropriate material to address the critical physical, mass transport, and biological design variables inherent to each application as described herein.

The bioreactors described herein may also include with hydrogels for seeding of cells or for structural components of the scaffolds. Hydrogels are physically or chemically cross-linked polymer networks that are able to absorb large amounts of water. They can be classified into different categories depending on various parameters including the preparation method, the charge, and the mechanical and structural characteristics. Hydrogels are an appealing scaffold material because they are structurally similar to the extracellular matrix of many tissues, can often be processed under relatively mild conditions, and may be delivered in a minimally invasive manner. Consequently, hydrogels can be utilized as scaffold materials herein. Hydrogels can include polyvinyl alcohol, sodium polyacrylate, acrylate polymers and copolymers with an abundance of hydrophilic groups, among other materials. Natural hydrogel materials include agarose, methylcellulose, hyaluronan, and other naturally derived polymers.

Biorod Systems

As may be used herein, the third aspect of the bioreactors systems of the disclosure can be referred to as "biorod systems or devices" and is intended to refer to the bioreactor systems comprising the features and components described herein. The tissue culture that forms in the biotube systems of the disclosure may be referred to as a "biorods." It will be understood that herein description of the biotube systems is not intended to limit the disclosure to these aspects or any particular embodiment. To the contrary, it is intended to cover alternatives, modifications, combinations of embodiments, and equivalents as may be included within the spirit and scope of the invention.

In the third aspect, the invention relates to a bioreactor system for growing a tissue culture, e.g., a three-dimensional tissue strand, that is suitable for measuring contractile forces. This aspect of the invention can comprise a bioreactor having a well or channel and at least one set of opposing scaffold elements (which can be formed from a single scaffold or separate scaffolds) that are disposed within the well or chamber and function to form at least two anchor points for a three-dimensional tissue strand formed therebetween. Preferably, the at least one set of opposing scaffold elements are reversibly affixed to the walls of the well or channel but suspended thereover such that there is a gap between the bottom of the well or chamber and the elements. The bioreactor of the third aspect is not limited to having two such elements, but may include more than two, such as, three, four, five, six, seven, eight, nine, or ten, or more such elements. Any number of elements per channel may be provided so long as there is the ability to (a) form a three dimensional tissue strand that forms around each of the opposing elements and becomes joined therebetween such that the tissue strand becomes disposes between the opposing set or sets of scaffold elements and is suspended above the channel or well.

The scaffold elements are preferably deflectable, deformable, bendable, or the like, which are further configured to allow the measurement of contractile forces exerted by the tissue strand on the scaffold elements.

In a preferred embodiment of the third aspect, each of the well or channels is configured with a set (two) or opposing scaffold elements, and preferably whereby a single scaffold element is disposed at or near the opposing ends of the longitudinal axis of the well or channel.

In certain embodiments of the third aspect, the scaffold elements are elevated off of the bottom surface of the well or channel.

In various embodiments of the third aspect, the scaffold elements can be made from any suitable material, which can include natural materials, such as collagen and collagen derivatives, natural suture material (e.g., animal intestines), cellulose and cellulose derivatives, proteoglycans, heparin sulfate, chondroitin sulfate, keratin sulfates, hyaluronic acid, elastin, fibronectin, and lamanin, etc., as well as synthetic materials, including various polymers and nanomaterials (e.g., POMac).

In certain embodiments of the third aspect, those having ordinary skill in the art would appreciate the criteria for selecting an appropriate material as biomaterials for use in the scaffold elements of the invention. Such choices can be based on a variety of parameters, which can include their material chemistry, molecular weight, solubility, shape and structure, hydrophilicity/hydrophobicity, lubricity, surface energy, water absorption degradation, and erosion mechanism, and in particular, their deformability, flexibility, and bendability, and the like.

In certain embodiments of the third aspect, the scaffold elements can be polymeric scaffolds. Such scaffolds, in general, are drawing a great attention due to their unique properties such as high surface-to-volume ratio, high porosity with very small pore size, biodegradation, and mechanical property. They offer distinct advantages of biocompatibility, versatility of chemistry, and the biological properties which are significant in the application of tissue engineering and organ substitution.

The scaffold elements can be synthetic or biologic, degradable or nondegradable. The properties of polymers depends on the composition, structure, and arrangement of their constituent macromolecules. It can be categorized into different types in terms of their structural, chemical, and biological characteristics, for example, ceramics, glasses, polymers, and so forth. Naturally occurring polymers, synthetic biodegradable, and synthetic nonbiodegradable polymers can all be used as polymers to form the scaffolds of the invention.

It will be appreciated that natural polymers can be used as the scaffold elements of the herein described bioreactor systems. Natural materials, owing to the bioactive properties, potentially may have better interactions with cells which allow them to enhance the cells' performance in biological systems described herein. Natural polymers can be classified as proteins (silk, collagen, gelatin, fibrinogen, elastin, keratin, actin, and myosin), polysaccharides (cellulose, amylose, dextran, chitin, and glycosaminoglycans), or polynucleotides (DNA, RNA), etc., or combinations of these materials.

The scaffold elements used in the bioreactor systems of the invention can also include synthetic biomaterials, which may facilitate restoration of structure and function of damaged or diseased tissues. Synthetic polymers are highly useful in biomedical field since their properties (e.g., porosity, degradation time, and mechanical characteristics) can be tailored for specific applications. Synthetic polymers are often cheaper than biologic scaffolds; it can be produced in large uniform quantities and have a long shelf time. Many commercially available synthetic polymers show physicochemical and mechanical properties comparable to those of biological tissues. Synthetic polymers represent the largest group of biodegradable polymers, and they can be produced under controlled conditions. They exhibit, in general, predictable and reproducible mechanical and physical properties such as tensile strength, elastic modulus, and degradation rate. PLA, PGA, and PLGA copolymers are among the most commonly used synthetic polymers in tissue engineering. PHA belongs to a class of microbial polyesters and is being increasingly considered for applications in tissue engineering. All of these synthetic polymers are contemplated herein.

In addition, the bioreactor systems of the third aspect of the disclosure may also use semi-synthetic, such as those disclosed in Rosso et al., "Smart materials as scaffolds for tissue engineering," J Cell Physiol. 2006 December; 209(3): 1054. Such scaffolds may contain oligopeptide cleaving sequences specific for matrix metalloproteinases (MMPs), integrin binding domains, growth factors, anti-thrombin sequences, plasmin degradation sites, and morphogenetic proteins. Such semi-synthetic materials aim to confer "intelligent" semi-synthetic biomaterials, having advantages offered by both the synthetic materials (e.g., processability, mechanical strength) and by the natural materials (e.g., specific cell recognition, cellular invasion, and the ability to supply differentiation/proliferation signals). Due to their characteristics, these semi-synthetic biomaterials represent a new and versatile class of biomimetic hybrid materials that hold clinical promise in serving as a source of materials for the scaffolds described herein.

As a point of reference, the following polymers and materials are contemplated for use in the third aspect bioreactors described herein:

PU:PolyurethanePS:PolysulfoneCP:Calcium phosphate;
HA:Hyaluronic acidPP:PolypropyleneBG:Bioactive glassECM:Extracellular matrix;
PVA:Polyvinyl alcoholPGA:PolyglycolidePLA:PolylactidePPF:Poly(propylene fumarate);
PCA:PolycyanoacrylatePCL:Poly(ε-caprolactone);
PDO:PolydioxanonePHA:Polyhydroxyalkanoates;

POE:Poly(ortho ester);
PEE:Poly(ether ester);
PEO:Poly(ethylene oxide);
PBT:Polybutylene terephthalate;
HAP:Hydroxyapatite;
TCP:Tricalcium phosphate;
PEG:Poly(ethylene glycol);
PEU:Poly(ester urethane);
PAA:Poly(acrylic acid);
LDI:Lysine diisocyanate;
BCP:Biphasic calcium phosphate;
PAam:Polyacrylamide;
PMMA:Polymethylmethacrylate;
PLLA:Poly(L-lactic acid);
PLGA:Poly(l-lactide-co-glycolide);
PTMC:Poly(trimethylene carbonate);
PDMS:Polydimethylsiloxane;
PTFE:Polytetrafluoroethylene;
PEVA:Poly(ethylene-co-vinylacetate);
PGCL:Poly(glycolide-co-ε-caprolactone);
PLCL:Poly(l-lactide-co-caprolactone);
PDLLA:Poly(DL-lactide);
PLDLA:Poly-L/D-lactide;
PLAGA:Poly(lactic acid-glycolic acid);
PHBHV:Poly(3-hydroxybutyrate) 3-hydroxyvalerate;
PCLTMC:Poly(caprolactone-co-trimethylene carbonate);
PNIPAAm:Poly(N-isopropylacrylamide);
PDMAEM:Poly(dimethylaminoethylmethacrylate) hydrochloride;
PDLLA-CL:Poly(D,L-lactide-co-caprolactone);
PLLA-CL:Poly(l-lactide-co-ε-caprolactone); and
TCP:Tricalcium phosphate.
POMac.

In particular embodiments of the third aspect, the scaffold elements described herein may be made from poly(dimethysiloxane (PDMS)), poly(methylmethacrylate (PMMA)), polystyrene, or polystyrene, or combinations thereof. The scaffolds may be made of a biodegradable material. Other suitable materials may include poly(glycerol sebacate), POMac without citric acid, poly(lactic acid), poly(glycolic acid), poly(ε-caprolactone), various polyurethanes as well as co-polymers thereof, silk, microstructured, nanofabricated materials, and/or materials doped with nanostructures such as nanorods or quantum dots, among others. Optionally in certain embodiments, the scaffold material can be perfusable to allow exchange and/or passage of water and molecules, including proteins, drugs, nutrients, and metabolic waste materials.

The skilled artisan will appreciate that reference can be made to resources available in the state of the art regarding the making and use of tissue engineering scaffolds and, in particular, reference case be made to the scaffold materials described in Dhandayuthapani et al., "Polymeric Scaffolds in Tissue Engineering Application: A Review; International Journal of Polymer Science, Vol. 2011 (2011), pages 1-19.

The shape, thickness, length, orientation, and surface topographical properties of the scaffold elements can vary any number of suitable ways so long as the scaffold elements are capable of deforming, bending, or otherwise changing shape in response to the contractile action or activity of the tissue strand connected therebetween, and that such deforming, bending, or otherwise shape changing can be reliably measured.

The shape of the well or channel is not limited in any particular manner and can be square, rectangular, circular, oval, oblong, triangular, or any combination of shapes. The other dimensions of the well or channel also may vary in any suitable manner. For example, the depth of the channel, height of the walls, and length of the channel, and the overall volume of the channel may be varied in any suitable way.

For example, the length, height, and width of the channel can be from about 0.1-1 mm, or about 0.2-2 mm, or about 0.3-3 mm, or about 0.4-4 mm, or about 0.5-5 mm, or about 0.6-6 mm, or about 0.7-7 mm, or about 0.8-8 mm, or about 0.9-9 mm, or about 1-10 mm, or more.

The surface of the channel may also be modified with any suitable surface treatments, including chemical modifications (such as, for example, ligands, charged substances, bind agents, growth factors, antibiotics, antifungal agents), or physical modifications (such as, for example, spikes, curved portions, folds, pores, uneven portions, or various shapes and topographies) which may facilitate the tissue culture process.

In various embodiments of the third aspect, the cells that may be seeded and cultivated in the tissue culture systems disclosed herein may include, but are not limited to, cardiac cells, liver cells, kidney cells, cartilage cells, skin cells, bone marrow cells, or combinations of such tissues. In particular embodiments, the tissue culture systems disclosed herein are suitable for growing cardiac tissue, hepatic tissue, or kidney tissue. In certain embodiments, the tissues formed in the systems described herein are three-dimensional tissues.

In various other embodiments of the third aspect, the bioreactor systems disclosed herein may be seeded with stem cells or otherwise pregenitor cells which are capable of developing into mature tissue types, e.g., mature cardiac, hepatic, or kidney tissue. Stem cells may include, but are not limited to embryonic stem cells and adult stem cells. In addition, stem cells contemplated for use with the herein described devices may have any degree of potency, including totipotent/omnipotent cells, pluripotent cells, multipotent cells, oligopotent cells, or unipotent cells (e.g., progenitor cells).

In embodiments involving cardiac cells (or other electrically-stimulated cells), the bioreactor systems described herein can be further configured to include electrodes configured to generate an electric field across the channel of the bioreactor system. The direction of the electric field can be in any direction, but preferably in a direction that is generally parallel to the longitudinal axis of the channel (and the resulting tissue strand once grown on and around the scaffold in the channel), or which is generally perpendicular to the longitudinal axis of the channel (and the resulting tissue strand). However, the orientation of the electric field is not limited and the positioning of the electrodes can be in any suitable format such that a suitable electric field can be generated. In certain embodiments, e.g., cardiac cells, the electric field facilitates that maturation of the cells to form tissue that more closely mimicks the physiological and electrical properties of actual tissue, e.g., cardiac tissue.

In certain embodiments of the third aspect, the bioreactors disclosed herein may be assembled as a plurality of individual bioreactors, e.g., in the format of multi-well plates, such as 6-well, 12-well, 24-well, 96-well, 384-well, and 1536-well plates, such that a plurality of tissue strands may be grown, tested, measured, and evaluated, etc., in a simultaneous manner.

In yet another embodiments of the third aspect, the present disclosure relates to methods of using the three-dimensional tissue constructs, the devices, and/or the systems of the invention in various applications, including, but not limited to, (a) the testing of the efficacy and safety (including toxicity) of experimental pharmacologic agents (including, but not limited to, small molecule drugs, biologics, nucleic acid-based agents), (b) the defining of pharmacokinetics and/or pharmacodynamics of pharmacologic agents (including, but not limited to, small molecule drugs, biologics, nucleic acid-based agents), (c) characterizing the properties and therapeutic effects of pharmacologic agents (including, but not limited to, small molecule drugs, biologics, nucleic acid-based agents) on a subject, (d) screening of new pharmacologic agents, (e) providing implantable engineered tissues for use in regenerative medicine for treating damaged and/or diseased tissues, (e.g., use of the tissue constructs, devices, and/or systems of the disclosure to study cardiac disease states, including patients with electrical conduction defects (iPSC-CM)), and (f) personalized medicine. As it relates particularly to the third aspect, the bioreactor system can be used especially for measuring the contractile force of a tissue strand, e.g., a cardiac tissue strand. Such measurements may be in conjunction with the introduction of pharmaceutical agents, genetic modifications, presence of diseased cells or tissues, toxins, or agents which may affect the physiology of the tissue under study.

The biorod systems of the third aspect may also be formed with or include hydrogels. Hydrogels are physically or chemically cross-linked polymer networks that are able to absorb large amounts of water. They can be classified into different categories depending on various parameters including the preparation method, the charge, and the mechanical and structural characteristics. Hydrogels are an appealing scaffold material because they are structurally similar to the extracellular matrix of many tissues, can often be processed under relatively mild conditions, and may be delivered in a minimally invasive manner. Consequently, hydrogels can be utilized as scaffold materials herein. Hydrogels can include polyvinyl alcohol, sodium polyacrylate, acrylate polymers and copolymers with an abundance of hydrophilic groups, among other materials. Natural hydrogel materials include agarose, methylcellulose, hyaluronan, and other naturally derived polymers.

Angiochip Systems

As may be used herein, the fourth aspect of the bioreactors systems of the disclosure can be referred to as "angiochip systems or devices" and is intended to refer to the bioreactor systems comprising the features and components described herein. The tissue culture that forms in the angiochip systems of the disclosure may be referred to as a "angiochips or biobranches." It will be understood that herein description of the biotube systems is not intended to limit the disclosure to these aspects or any particular embodiment. To the contrary, it is intended to cover alternatives, modifications, combinations of embodiments, and equivalents as may be included within the spirit and scope of the invention.

In the fourth aspect, the invention relates to a bioreactor system for growing a three-dimensional tissue comprising a three-dimensional branched tissue scaffold or matrix having one or more luminal passageways (e.g., mimicking a vascularized three-dimensional tissue structure) integrated therein. The three-dimensional scaffold or matrix may contain a first portion for growing seeded cells and a second portion for providing interconnected channels that pass through the first portion. Preferably, the interconnected channels are perfusable with respect to the first portion and may be configured to mimic a biological vasculature. The first portion can contain one or more open regions or chambers, thereby providing an open network of chambers for growing cells and/or tissues. The three-dimensional scaffold or matrix may also contain pores or open connections between all of the components. For example, the open pores or connections can be positioned between the open network of chambers for growing cells. In addition, open pores or connections can be positioned or integrated with the one or more luminal passageways. The open pores or connections facilitate movement of cells, media, growth factors, nutrients, and waste through the bioreactor system. The bioreactor can be further configured to include electrodes configured to generate an electric field across the bioreactor system. The direction of the electric field can be in any direction, but preferably in a direction.

In various embodiments of the fourth aspect, the three-dimensional scaffold or matrix can be made from any suitable material, which can include natural materials, such as collagen and collagen derivatives, natural suture material (e.g., animal intestines), cellulose and cellulose derivatives, proteoglycans, heparin sulfate, chondroitin sulfate, keratin sulfates, hyaluronic acid, elastin, fibronectin, and lamanin, etc., as well as synthetic materials, including various polymers and nanomaterials (e.g., POMac).

In certain embodiments of the fourth aspect, those having ordinary skill in the art would appreciate the criteria for selecting an appropriate material as biomaterials for use in the three-dimensional scaffold or matrix. Such choices can be based on a variety of parameters, which can include their material chemistry, molecular weight, solubility, shape and structure, hydrophilicity/hydrophobicity, lubricity, surface energy, water absorption degradation, and erosion mechanism, and in particular, their deformability, flexibility, and bendability, and the like.

In certain embodiments of the fourth aspect, the three-dimensional scaffold or matrix can be made from polymeric scaffolds. Such scaffolds, in general, are drawing a great attention due to their unique properties such as high surface-to-volume ratio, high porosity with very small pore size, biodegradation, and mechanical property. They offer distinct advantages of biocompatibility, versatility of chemistry, and the biological properties which are significant in the application of tissue engineering and organ substitution.

The three-dimensional scaffold or matrix can be synthetic or biologic, degradable or nondegradable. The properties of polymers depends on the composition, structure, and arrangement of their constituent macromolecules. It can be categorized into different types in terms of their structural, chemical, and biological characteristics, for example, ceramics, glasses, polymers, and so forth. Naturally occurring polymers, synthetic biodegradable, and synthetic non-biodegradable polymers can all be used as polymers to form the scaffolds of the invention.

It will be appreciated that natural polymers can be used as the scaffold elements of the herein described bioreactor systems. Natural materials, owing to the bioactive properties, potentially may have better interactions with cells which allow them to enhance the cells' performance in biological systems described herein. Natural polymers can be classified as proteins (silk, collagen, gelatin, fibrinogen, elastin, keratin, actin, and myosin), polysaccharides (cellulose, amylose, dextran, chitin, and glycosaminoglycans), or polynucleotides (DNA, RNA), etc., or combinations of these materials.

The three-dimensional scaffold or matrix can also include synthetic biomaterials, which may facilitate restoration of structure and function of damaged or diseased tissues. Synthetic polymers are highly useful in biomedical field since their properties (e.g., porosity, degradation time, and mechanical characteristics) can be tailored for specific applications. Synthetic polymers are often cheaper than biologic scaffolds; it can be produced in large uniform quantities and have a long shelf time. Many commercially available synthetic polymers show physicochemical and mechanical properties comparable to those of biological tissues. Synthetic polymers represent the largest group of biodegradable polymers, and they can be produced under controlled conditions. They exhibit, in general, predictable and reproducible mechanical and physical properties such as tensile strength, elastic modulus, and degradation rate. PLA, PGA, and PLGA copolymers are among the most commonly used synthetic polymers in tissue engineering. PHA belongs to a class of microbial polyesters and is being increasingly considered for applications in tissue engineering. All of these synthetic polymers are contemplated herein.

In addition, the bioreactor systems of the fourth aspect of the disclosure may also use semi-synthetic, such as those disclosed in Rosso et al., "Smart materials as scaffolds for tissue engineering," J Cell Physiol. 2006 December; 209(3): 1054. Such scaffolds may contain oligopeptide cleaving sequences specific for matrix metalloproteinases (MMPs), integrin binding domains, growth factors, anti-thrombin sequences, plasmin degradation sites, and morphogenetic proteins. Such semi-synthetic materials aim to confer "intelligent" semi-synthetic biomaterials, having advantages offered by both the synthetic materials (e.g., processability, mechanical strength) and by the natural materials (e.g., specific cell recognition, cellular invasion, and the ability to supply differentiation/proliferation signals). Due to their characteristics, these semi-synthetic biomaterials represent a new and versatile class of biomimetic hybrid materials that hold clinical promise in serving as a source of materials for the scaffolds described herein.

As a point of reference, the following polymers and materials are contemplated for use in the fourth aspect bioreactors described herein:

PU:PolyurethanePS:PolysulfoneCP:Calcium phosphate;
HA:Hyaluronic acidPP:PolypropyleneBG:Bioactive glassECM:Extracellular matrix;
PVA:Polyvinyl alcoholPGA:PolyglycolidePLA:PolylactidePPF:Poly(propylene fumarate);
PCA:PolycyanoacrylatePCL:Poly($\varepsilon$-caprolactone);
PDO:PolydioxanonePHA:Polyhydroxyalkanoates;
POE:Poly(ortho ester);
PEE:Poly(ether ester);
PEO:Poly(ethylene oxide);
PBT:Polybutylene terephthalate;
HAP:Hydroxyapatite;
TCP:Tricalcium phosphate;
PEG:Poly(ethylene glycol);
PEU:Poly(ester urethane);
PAA:Poly(acrylic acid);
LDI:Lysine diisocyanate;
BCP:Biphasic calcium phosphate;
PAam:Polyacrylamide;
PMMA:Polymethylmethacrylate;
PLLA:Poly(L-lactic acid);
PLGA:Poly(l-lactide-co-glycolide);
PTMC:Poly(trimethylene carbonate);
PDMS:Polydimethylsiloxane;
PTFE:Polytetrafluoroethylene;
PEVA:Poly(ethylene-co-vinylacetate);
PGCL:Poly(glycolide-co-$\varepsilon$-caprolactone);
PLCL:Poly(l-lactide-co-caprolactone);
PDLLA:Poly(DL-lactide);
PLDLA:Poly-L/D-lactide;
PLAGA:Poly(lactic acid-glycolic acid);
PHBHV:Poly(3-hydroxybutyrate) 3-hydroxyvalerate;
PCLTMC:Poly(caprolactone-co-trimethylene carbonate);
PNIPAAm:Poly(N-isopropylacrylamide);
PDMAEM:Poly(dimethylaminoethylmethacrylate) hydrochloride;
PDLLA-CL:Poly(D,L-lactide-co-caprolactone);
PLLA-CL:Poly(l-lactide-co-$\varepsilon$-caprolactone); and
TCP:Tricalcium phosphate.
POMac.

In particular embodiments of the fourth aspect, the scaffold elements described herein may be made from poly (dimethysiloxane (PDMS)), poly(methylmethacrylate (PMMA)), polystyrene, or polystyrene, or combinations thereof. The scaffolds may be made of a biodegradable material. Other suitable materials may include poly(glycerol sebacate), POMac without citric acid, poly(lactic acid), poly(glycolic acid), poly($\varepsilon$-caprolactone), various polyurethanes as well as co-polymers thereof, silk, microstructured, nanofabricated materials, and/or materials doped with nanostructures such as nanorods or quantum dots, among others. Optionally in certain embodiments, the scaffold material can be perfusable to allow exchange and/or passage of water and molecules, including proteins, drugs, nutrients, and metabolic waste materials.

The skilled artisan will appreciate that reference can be made to resources available in the state of the art regarding the making and use of tissue engineering scaffolds and, in particular, reference case be made to the scaffold materials described in Dhandayuthapani et al., "Polymeric Scaffolds in Tissue Engineering Application: A Review; International Journal of Polymer Science, Vol. 2011 (2011), pages 1-19.

The shape, thickness, length, orientation, and surface topographical properties of the scaffold matrix and the various elements within (e.g., the integrated luminal portions, and the interconnected network of growth chambers or cells) can vary any number of suitable ways so long as scaffold or matrix may support the growth of a three-dimensional tissue.

The shape of the wells or growth chambers comprising the network is not limited in any particular manner and can be square, rectangular, circular, oval, oblong, triangular, or any combination of shapes. The other dimensions of the wells or channels also may vary in any suitable manner. For example, the depth of the channel, height of the walls, and length of the channel, and the overall volume of the channel may be varied in any suitable way.

For example, the length, height, and width of the cells can be from about 0.1-1 mm, or about 0.2-2 mm, or about 0.3-3 mm, or about 0.4-4 mm, or about 0.5-5 mm, or about 0.6-6 mm, or about 0.7-7 mm, or about 0.8-8 mm, or about 0.9-9 mm, or about 1-10 mm, or more.

The surface of the cells, wells, or channels may also be modified with any suitable surface treatments, including chemical modifications (such as, for example, ligands, charged substances, bind agents, growth factors, antibiotics, antifungal agents), or physical modifications (such as, for example, spikes, curved portions, folds, pores, uneven portions, or various shapes and topographies) which may facilitate the tissue culture process.

In various embodiments of the fourth embodiment, the tissue culture system may be used to grow tissues based from cardiac cells, liver cells, kidney cells, cartilage cells, skin cells, bone marrow cells, or combinations of such cells. In particular embodiments, the tissue culture systems disclosed herein are suitable for growing cardiac tissue, hepatic tissue, or kidney tissue. In certain embodiments, the tissues formed in the systems described herein are three-dimensional tissues.

In various other embodiments of the fourth aspect, the bioreactor systems disclosed herein may be seeded with stem cells or otherwise pregenitor cells which are capable of developing into mature tissue types, e.g., mature cardiac, hepatic, or kidney tissue. Stem cells may include, but are not limited to embryonic stem cells and adult stem cells. In addition, stem cells contemplated for use with the herein described devices may have any degree of potency, including totipotent/omnipotent cells, pluripotent cells, multipotent cells, oligopotent cells, or unipotent cells (e.g., progenitor cells).

In embodiments involving cardiac cells (or other electrically-stimulated cells), the bioreactor systems described herein can be further configured to include electrodes configured to generate an electric field across the channel of the bioreactor system. The direction of the electric field can be in any direction, but preferably in a direction that is generally parallel to the longitudinal axis of the bioreactor system. However, the orientation of the electric field is not limited and the positioning of the electrodes can be in any suitable format such that a suitable electric field can be generated. In certain embodiments, e.g., cardiac cells, the electric field facilitates that maturation of the cells to form tissue that more closely mimicks the physiological and electrical properties of actual tissue, e.g., cardiac tissue.

In yet another embodiments of the fourth aspect, the present disclosure relates to methods of using the three-dimensional tissue systems, the devices, and/or the systems of the invention in various applications, including, but not limited to, (a) the testing of the efficacy and safety (including toxicity) of experimental pharmacologic agents (including, but not limited to, small molecule drugs, biologics, nucleic acid-based agents), (b) the defining of pharmacokinetics and/or pharmacodynamics of pharmacologic agents (including, but not limited to, small molecule drugs, biologics, nucleic acid-based agents), (c) characterizing the properties and therapeutic effects of pharmacologic agents (including, but not limited to, small molecule drugs, biologics, nucleic acid-based agents) on a subject, (d) screening of new pharmacologic agents, (e) providing implantable engineered tissues for use in regenerative medicine for treating damaged and/or diseased tissues, (e.g., use of the tissue constructs, devices, and/or systems of the disclosure to study cardiac disease states, including patients with electrical conduction defects (iPSC-CM)), and (f) personalized medicine. In certain embodiments of the fourth aspect, two or more bioreactor systems may be connected to one another such that they are functionally interactive. The two or more bioreactors systems joined together, e.g., end to end in series, may be formed of the same types of tissues or entirely different tissues. For example, a system is contemplated where a first bioreactor systems comprising cardiac tissue is joined in series with a hepatic second bioreactor system. This pair of systems can be further modified with one or more additional bioreactor systems joined further in series with the first two systems. In another example, a first bioreactor system comprising healthy cardiac tissue can be joined in series with a second bioreactor system comprising diseased cardiac tissue. In this way, one can test not only the effects of a drug, toxin, or otherwise test agent on a first bioreactor system comprising a first tissue, but also the effect of the metabolized drug, toxin, or otherwise agent on the downstream second bioreactor system, e.g., hepatic tissue.

The scaffold elements and other elements of the bioreactor may also be formed with hydrogels. Hydrogels are physically or chemically cross-linked polymer networks that are able to absorb large amounts of water. They can be classified into different categories depending on various parameters including the preparation method, the charge, and the mechanical and structural characteristics. Hydrogels are an appealing scaffold material because they are structurally similar to the extracellular matrix of many tissues, can often be processed under relatively mild conditions, and may be delivered in a minimally invasive manner. Consequently, hydrogels can be utilized as scaffold materials herein. Hydrogels can include polyvinyl alcohol, sodium polyacrylate, acrylate polymers and copolymers with an abundance of hydrophilic groups, among other materials. Natural hydrogel materials include agarose, methylcellulose, hyaluronan, and other naturally derived polymers.

In various embodiments, a plurality of Angiochip systems may be configured in series, whereby a first Angiochip is formed of one type of cell or tissue (e.g., cardiac) and a second "downstream" or "upstream" Angiochip is formed of a second type of cell or tissue (e.g., diseased cardiac, or hepatic). In this manner, the interaction of drugs may be tested in the context of multiple organ or tissue systems. For example, a test agent may be introduced into an Angiochip prepared from hepatic tissue, which may be linked downstream to a second Angiochip prepared from cardiac tissue. In this manner, the drug may first interact with the hepatic tissue, and any metabolic products resulting therefrom may flow downstream to the cardiac tissue Angiochip, thereby facilitating one to test the effect of the drug's metabolism on cardiac function. Thus, the invention contemplates a plurality of Angiochip devices arranged in a tandem (i.e., in series) manner for use in testing inter-organ drug interactions in the body. Any conceivable combination of tissues could be tested in tandem, for example, cardiac/hepatic or hepatic/cardiac.

Angiotube Systems

As may be used herein, the fifth aspect of the bioreactors systems of the disclosure can be referred to as "angiotube systems or devices" and is intended to refer to the bioreactor systems comprising the features and components described herein. The tissue culture that forms in the angiochip systems of the disclosure may be referred to as "angiotubes." It will be understood that herein description of the angiotube systems is not intended to limit the disclosure to these aspects or any particular embodiment. To the contrary, it is intended to cover alternatives, modifications, combinations of embodiments, and equivalents as may be included within the spirit and scope of the invention.

In the fifth aspect, the disclosure relates to a bioreactor system for growing a tissue culture, e.g., a three dimensional tissue strand, that is suitable for measuring contractile forces. The bioreactor system includes a well or channel suitable for seeding cells and a perfusable scaffold with one or more lumens and which is supported or suspended over the well or channel, e.g., along the longitudinal axis of the well or channel. In addition, the perfusable scaffold is configured with one set or more of opposing scaffold elements (which can be formed from a single scaffold or separate scaffolds) that are disposed within the well or chamber along the longitudinal axis of the perfusable scaffold and function to form at least two anchor points for a three-dimensional tissue strand formed therebetween and which are capable of deforming or bending in response to the contractile state of the tissue strand. The bioreactor of the fifth aspect is not limited to having two such deformable elements, but may include more than two, such as, three, four, five, six, seven, eight, nine, or ten, or more such elements. Any number of elements per channel may be provided so long as there is the ability to form a three dimensional tissue strand that forms around each of the opposing elements and along the longitudinal length of the perfusable element and becomes joined therebetween such that the tissue strand becomes disposed between the opposing set or sets of scaffold elements and is suspended above the channel or well.

The scaffold elements are preferably deflectable, deformable, bendable, or the like, which are further configured to allow the measurement of contractile forces exerted by the tissue strand on the scaffold elements.

In a preferred embodiment of the fifth aspect, each of the well or channels is configured with a set (two) or opposing scaffold elements, and preferably whereby a single scaffold element is disposed at or near the opposing ends of the longitudinal axis of the well or channel.

Once cells are seeded into the well or channel, along with suitable growth media, growth factors, and other nutrients suitable for the culture of the cells, the cells grow to form a tissue strand that surrounds and/or integrates with the perfusable scaffold and the bendable elements. In use, nutrients and growth factors, as well as test agents (e.g., drugs, proteins, toxins etc.) may be delivered to the tissue strand via the perfusable lumen which is integrated with a means for delivering such materials (e.g., a reservoir element connected to the luman via a tube or vessel). In addition, the bioreactor system may also include in various embodiments a passage that exits from the perfusable lumen, e.g., a drain or otherwise terminal reservoir that allows waste and otherwise metabolic products to diffuse from the tissue strand into the perfusable lumen and out through to the terminal reservoir. In various embodiments involving cardiac cells (or other electrically-stimulated cells), the bioreactor can be further configured to include electrodes configured to generate an electric field across the channel of the bioreactor. The direction of the electric field can be in any direction, but preferably in a direction that is parallel to the longitudinal axis of the tissue strand that forms along the length of the perfusuable luminal element.

In certain embodiments of the fifth aspect, the perfusable longitudinal scaffold and the bendable elements are elevated off of the bottom surface of the well or channel such that a three-dimensional tissue strand may form thereon.

In various embodiments of the fifth aspect, the perfusable longitudinal scaffolds and bendable elements can be any suitable material (and can be the same or different materials), which can include natural materials, such as collagen and collagen derivatives, natural suture material (e.g., animal intestines), cellulose and cellulose derivatives, proteoglycans, heparin sulfate, chondroitin sulfate, keratin sulfates, hyaluronic acid, elastin, fibronectin, and lamanin, etc., as well as synthetic materials, including various polymers and nanomaterials (e.g., POMac).

In certain embodiments of the fifth aspect, those having ordinary skill in the art would appreciate the criteria for selecting an appropriate material as biomaterials for use in the perfusable scaffolds or bendable elements of the invention. Such choices can be based on a variety of parameters, which can include their material chemistry, molecular weight, solubility, shape and structure, hydrophilicity/hydrophobicity, lubricity, surface energy, water absorption degradation, bendability/deformability, and erosion mechanism.

In certain embodiments of the fifth aspect, the perfusable scaffolds and bendable elements can be polymeric scaffolds. Such scaffolds, in general, are drawing great attention due to their unique properties such as high surface-to-volume ratio, high porosity with very small pore size, biodegradation, and mechanical property. They offer distinct advantages of biocompatibility, versatility of chemistry, and the biological properties which are significant in the application of tissue engineering and organ substitution.

Perfusable scaffold materials and bendable elements can be synthetic or biologic, degradable or nondegradable. The properties of the polymers depend on the composition, structure, and arrangement of their constituent macromolecules. It can be categorized into different types in terms of their structural, chemical, and biological characteristics, for example, ceramics, glasses, polymers, and so forth. Naturally occurring polymers, synthetic biodegradable, and synthetic nonbiodegradable polymers can all be used as polymers to form the scaffolds of the invention.

It will be appreciated that natural polymers can be used as the perfusable scaffold or the bendable elements of the herein described bioreactor systems. Natural materials, owing to the bioactive properties, potentially may have better interactions with cells which allow them to enhance the cells' performance in biological systems described herein. Natural polymers can be classified as proteins (silk, collagen, gelatin, fibrinogen, elastin, keratin, actin, and myosin), polysaccharides (cellulose, amylose, dextran, chitin, and glycosaminoglycans), or polynucleotides (DNA, RNA), etc., or combinations of these materials.

The perfusable scaffolds and bendable elements used in the bioreactor systems of the invention can also include synthetic biomaterials, which may facilitate restoration of structure and function of damaged or diseased tissues. Synthetic polymers are highly useful in biomedical field since their properties (e.g., porosity, degradation time, and mechanical characteristics) can be tailored for specific applications. Synthetic polymers are often cheaper than biologic scaffolds; it can be produced in large uniform quantities and have a long shelf time. Many commercially available synthetic polymers show physicochemical and mechanical properties comparable to those of biological tissues. Synthetic polymers represent the largest group of biodegradable polymers, and they can be produced under controlled conditions. They exhibit, in general, predictable and reproducible mechanical and physical properties such as tensile strength, elastic modulus, and degradation rate. PLA, PGA, and PLGA copolymers are among the most commonly used synthetic polymers in tissue engineering. PHA belongs to a class of microbial polyesters and is being increasingly considered for applications in tissue engineering. All of these synthetic polymers are contemplated herein.

In addition, the bioreactor systems of the fifth aspect of the disclosure may also use semi-synthetic, such as those disclosed in Rosso et al., "Smart materials as scaffolds for tissue engineering," J Cell Physiol. 2006 December; 209(3): 1054. Such scaffolds may contain oligopeptide cleaving sequences specific for matrix metalloproteinases (MMPs), integrin binding domains, growth factors, anti-thrombin sequences, plasmin degradation sites, and morphogenetic proteins. Such semi-synthetic materials aim to confer "intelligent" semi-synthetic biomaterials, having advantages offered by both the synthetic materials (e.g., processability, mechanical strength) and by the natural materials (e.g., specific cell recognition, cellular invasion, and the ability to supply differentiation/proliferation signals). Due to their characteristics, these semi-synthetic biomaterials represent a new and versatile class of biomimetic hybrid materials that hold clinical promise in serving as a source of materials for the scaffolds described herein.

As a point of reference, the following polymers and materials are contemplated for use in the fifth aspect bioreactors described herein:

PU:PolyurethanePS:PolysulfoneCP:Calcium phosphate;
HA:Hyaluronic acidPP:PolypropyleneBG:Bioactive glassECM:Extracellular matrix;
PVA:Polyvinyl alcoholPGA:PolyglycolidePLA:PolylactidePPF:Poly(propylene fumarate);
PCA:PolycyanoacrylatePCL:Poly(ε-caprolactone);
PDO:PolydioxanonePHA:Polyhydroxyalkanoates;
POE:Poly(ortho ester);
PEE:Poly(ether ester);
PEO:Poly(ethylene oxide);
PBT:Polybutylene terephthalate;
HAP:Hydroxyapatite;
TCP:Tricalcium phosphate;
PEG:Poly(ethylene glycol);
PEU:Poly(ester urethane);
PAA:Poly(acrylic acid);
LDI:Lysine diisocyanate;
BCP:Biphasic calcium phosphate;
PAam:Polyacrylamide;
PMMA:Polymethylmethacrylate;
PLLA:Poly(L-lactic acid);
PLGA:Poly(l-lactide-co-glycolide);
PTMC:Poly(trimethylene carbonate);
PDMS:Polydimethylsiloxane;
PTFE:Polytetrafluoroethylene;
PEVA:Poly(ethylene-co-vinylacetate);
PGCL:Poly(glycolide-co-ε-caprolactone);
PLCL:Poly(l-lactide-co-caprolactone);
PDLLA:Poly(DL-lactide);
PLDLA:Poly-L/D-lactide;
PLAGA:Poly(lactic acid-glycolic acid);
PHBHV:Poly(3-hydroxybutyrate) 3-hydroxyvalerate;
PCLTMC:Poly(caprolactone-co-trimethylene carbonate);
PNIPAAm:Poly(N-isopropylacrylamide);
PDMAEM:Poly(dimethylaminoethylmethacrylate) hydrochloride;
PDLLA-CL:Poly(D,L-lactide-co-caprolactone);
PLLA-CL:Poly(l-lactide-co-ε-caprolactone); and
TCP:Tricalcium phosphate.
POMac.

In particular embodiments of the fifth aspect, the perfusable scaffolds and bendable elements described herein may made from poly(dimethysiloxane (PDMS)), poly(methylmethacrylate (PMMA)), polystyrene, or polystyrene, or combinations thereof. The scaffold may be made of a biodegradable material. Other suitable materials may include poly(glycerol sebacate), POMac without citric acid, poly(lactic acid), poly(glycolic acid), poly(ε-caprolactone), various polyurethanes as well as co-polymers thereof, silk, microstructured, nanofabricated materials, and/or materials doped with nanostructures such as nanorods or quantum dots, among others. Optionally in certain embodiments, the scaffolds and bendable elements can be perfusable to allow exchange and/or passage of water and molecules, including proteins, drugs, nutrients, and metabolic waste materials.

The skilled artisan will appreciate that reference can be made to resources available in the state of the art regarding the making and use of tissue engineering scaffolds and, in particular, reference case be made to the scaffold materials described in Dhandayuthapani et al., "Polymeric Scaffolds in Tissue Engineering Application: A Review; International Journal of Polymer Science, Vol. 2011 (2011), pages 1-19

The shape of the well or channel is not limited in any particular manner and can be square, rectangular, circular, oval, oblong, triangular, or any combination of shapes. The other dimensions of the well or channel also may vary in any suitable manner. For example, the depth of the channel, height of the walls, and length of the channel, and the overall volume of the channel may be varied in any suitable way.

For example, the length, height, and width of the channel can be from about 0.1-1 mm, or about 0.2-2 mm, or about 0.3-3 mm, or about 0.4-4 mm, or about 0.5-5 mm, or about 0.6-6 mm, or about 0.7-7 mm, or about 0.8-8 mm, or about 0.9-9 mm, or about 1-10 mm, or more.

The surface of the channel may also be modified with any suitable surface treatments, including chemical modifications (such as, for example, ligands, charged substances, bind agents, growth factors, antibiotics, antifungal agents), or physical modifications (such as, for example, spikes, curved portions, folds, pores, uneven portions, or various shapes and topographies) which may facilitate the tissue culture process.

In various embodiments of the fifth aspect, the cells that may be seeded and cultivated in the tissue culture systems disclosed herein may include, but are not limited to, cardiac cells, liver cells, kidney cells, cartilage cells, skin cells, bone marrow cells, or combinations of such tissues. In particular embodiments, the tissue culture systems disclosed herein are suitable for growing cardiac tissue, hepatic tissue, or kidney tissue. In certain embodiments, the tissues formed in the systems described herein are three-dimensional tissues.

In various other embodiments of the fifth aspect, the bioreactor systems disclosed herein may be seeded with stem cells or otherwise pregenitor cells which are capable of developing into mature tissue types, e.g., mature cardiac, hepatic, or kidney tissue. Stem cells may include, but are not limited to embryonic stem cells and adult stem cells. In addition, stem cells contemplated for use with the herein described devices may have any degree of potency, including totipotent/omnipotent cells, pluripotent cells, multipotent cells, oligopotent cells, or unipotent cells (e.g., progenitor cells).

In embodiments involving cardiac cells (or other electrically-stimulated cells), the bioreactor systems described herein can be further configured to include electrodes configured to generate an electric field across the channel of the bioreactor system. The direction of the electric field can be in any direction, but preferably in a direction that is generally parallel to the longitudinal axis of the channel (and the resulting tissue strand once grown on and around the perfusable scaffold in the channel), or which is generally perpendicular to the longitudinal axis of the channel (and the resulting tissue strand). However, the orientation of the electric field is not limited and the positioning of the electrodes can be in any suitable format such that a suitable electric field can be generated. In certain embodiments, e.g., cardiac cells, the electric field facilitates that maturation of the cells to form tissue that more closely mimicks the physiological and electrical properties of actual tissue, e.g., cardiac tissue.

In certain embodiments of the fifth aspect, the bioreactors disclosed herein may be assembled as a plurality of individual bioreactors, e.g., in the format of multi-well plates, such as 6-well, 12-well, 24-well, 96-well, 384-well, and 1536-well plates, such that a plurality of tissue strands may be grown, tested, measured, and evaluated, etc., in a simultaneous manner.

In yet another embodiments of the fifth aspect, the present disclosure relates to methods of using the three-dimensional tissue constructs, the devices, and/or the systems of the invention in various applications, including, but not limited to, (a) the testing of the efficacy and safety (including toxicity) of experimental pharmacologic agents (including, but not limited to, small molecule drugs, biologics, nucleic acid-based agents), (b) the defining of pharmacokinetics and/or pharmacodynamics of pharmacologic agents (including, but not limited to, small molecule drugs, biologics, nucleic acid-based agents), (c) characterizing the properties and therapeutic effects of pharmacologic agents (including, but not limited to, small molecule drugs, biologics, nucleic acid-based agents) on a subject, (d) screening of new pharmacologic agents, (e) providing implantable engineered tissues for use in regenerative medicine for treating damaged and/or diseased tissues, (e.g., use of the tissue constructs, devices, and/or systems of the disclosure to study cardiac disease states, including patients with electrical conduction defects (iPSC-CM)), and (f) personalized medicine.

In certain embodiments of the fifth aspect, two or more bioreactor systems may be connected to one another such that they are functionally interactive. The two or more bioreactors systems joined together, e.g., end to end in series, may be formed of the same types of tissues or entirely different tissues. For example, a system is contemplated where a first bioreactor system comprising cardiac tissue is joined in series with a hepatic second bioreactor system. This pair of systems can be further modified with one or more additional bioreactor systems joined further in series with the first two systems. In another example, a first bioreactor system comprising healthy cardiac tissue can be joined in series with a second bioreactor system comprising diseased cardiac tissue. In this way, one can test not only the effects of a drug, toxin, or otherwise test agent on a first bioreactor system comprising a first tissue, but also the effect of the metabolized drug, toxin, or otherwise agent on the downstream second bioreactor system, e.g., hepatic tissue.

Orientation of the scaffold, and in particular, the orientation of the longitudinal elements and/or the bendable elements may be varied with respect to the orientation of the growth chamber in the well. In one embodiment, the growth chamber may be a generally longitudinal growth chamber that may be orientated generally perpendicular to the orientation of the longitudinal elements. In another embodiment, the longitudinal elements may be orientated in a generally perpendicular orientation relative to the orientation of the growth chamber. In still another embodiment, the longitudinal elements and/or bendable elements may be orientated in a generally parallel orientation relative to the orientation of the growth chamber. In yet other embodiments, the longitudinal elements and/or bendable elements may be oriented in a generally diagonal orientation relative to the orientation of the growth chamber.

In various embodiments, the scaffold comprising the plurality of longitudinal elements is affixed (either permanently, or reversibly) or attached (either permanently or reversibly) to the plurality of wells of the bioreactor such that as cells that are seeded into the growth chamber become cultivated into a tissue strand, the tissue strand grows over all or at least a portion of the longitudinal elements and bendable elements contacting the well. That is, the longitudinal elements and bendable elements become encapsulated or at least a portion of the longitudinal elements become encapsulated or at least contacted by the cells of the tissue strand and the longitudinal elements are fixedly connected to one another. As used herein, the term "fixedly connected" refers to the connection established between the tissue strand and the longitudinal/bendable elements, such that the tissue strand's movement (e.g., beating of cardiac tissue) is reflected in the movement of the bendable elements.

In a preferred embodiment, the bendable elements may be in generally the same orientation, e.g., parallel with one another and perpendicular to the longitudinal element. In other embodiments, the bendable elements may be arranged in a generally criss-crossed format. In still other embodiments, the bendable elements may take the form of sinusoids, zig-zags, curves, or the like.

The attachment of the bendable elements to the longitudinal elements, and the longitudinal elements to the wells of the bioreactor plates can be by any suitable means, e.g., adhesives, welding, or otherwise mechanical means. The points of attachment between the wells and the longitudinal elements can be ordered, random, continuous, or non-continuous.

The longitudinal elements can also, in certain embodiments, comprise perfusable materials, that allow the passage of nutrients, metabolic waste material, proteins, or even whole cells. Perfusability may be established by any suitable means including as a property of the material used to form the elements, or by forming one or more pores in the material forming the elements. This may be useful in certain embodiments where the longitudinal elements upon traversing the growth chambers is situated such that it effectively forms a divisional seal, or partial seal between the intersected portions of the chamber. That is, the longitudinal elements may in certain embodiments be suspended over the width of the growth channels without contacting the base of the channels (i.e., only forming connections to the sides of the channels). In certain other embodiments, the longitudinal elements may pass through the growth chambers in such a way that a connection (or a plurality of connections) is made between the growth channel and the longitudinal element. Perfusable materials will allow free movement of nutrients, metabolic waste, and even whole cells to freely move within the growth chamber, including points where the longitudinal elements contact the chamber.

The bioreactor components (e.g., reactor body, lids, covers, growth chambers, scaffolds, longitudinal elements, bendable elements, etc.) may be made from any suitable materials, including a variety of polymers (including those that are FDA approved), such as, polylactones, such as poly(L-lactide) (PLA), poly(glycolide) (PGA), and their copolymers (PLGA), PDMS (poly(dimethylsiloxane)), PMMA (poly(methyl methacrylate)), and biodegradable polymers, including POMac (poly(octamethylene maleate (anhydride) citrate, a mixture of 1,8-octandiol, citrate acid, and maleic anhydride units). Reference can be made to Tran et al., "Synthesis and characterization of a biodegradable elastomer featuring a dual crosslinking mechanism," Soft Matter, Jan. 1, 2010; 6(11): 2449-2461, which is incorporated herein by reference in its entirety. The polymers can be any suitable naturally occurring polymer (such as, but not limited to cellulose, silk, shellac, rubber or derivatives thereof) or any suitable synthetic polymer (including, but not limited to, nylon, polyvinyl chloride (PVC or vinyl), polystyrene, polyethylene, polypropylene, polyacrylonitrile, PVB, silicone, and derivatives thereof). The polymers may be modified covalently or noncovalently with additional components such as ligands, antibodies, charged molecules, hydrophobic molecules, or the like which may facilitate growth and/or maintenance of tissues in the bioreactor. It will be appreciated that the particular types of polymers, their modifications, and the like hinges on finding an appropriate material to address the critical physical, mass transport, and biological design variables inherent to each application as described herein.

The scaffold elements and other elements of the bioreactor may also be formed with hydrogels. Hydrogels are physically or chemically cross-linked polymer networks that are able to absorb large amounts of water. They can be classified into different categories depending on various parameters including the preparation method, the charge, and the mechanical and structural characteristics. Hydrogels are an appealing scaffold material because they are structurally similar to the extracellular matrix of many tissues, can often be processed under relatively mild conditions, and may be delivered in a minimally invasive manner. Consequently, hydrogels can be utilized as scaffold materials herein. Hydrogels can include polyvinyl alcohol, sodium polyacrylate, acrylate polymers and copolymers with an abundance of hydrophilic groups, among other materials. Natural hydrogel materials include agarose, methylcellulose, hyaluronan, and other naturally derived polymers.

In various embodiments, a plurality of angiotube systems may be configured in series, whereby a first angiotube is formed of one type of cell or tissue (e.g., cardiac) and a second "downstream" or "upstream" angiotube is formed of a second type of cell or tissue (e.g., diseased cardiac, or hepatic). In this manner, the interaction of drugs may be tested in the context of multiple organ or tissue systems. For example, a test agent may be introduced into an angiotube prepared from hepatic tissue, which may be linked downstream to a second angiotube prepared from cardiac tissue. In this manner, the drug may first interact with the hepatic tissue, and any metabolic products resulting therefrom may flow downstream to the cardiac tissue angiotube, thereby facilitating one to test the effect of the drug's metabolism on cardiac function. Thus, the invention contemplates a plurality of angiotube devices arranged in a tandem (i.e., in series) manner for use in testing inter-organ drug interactions in the body. Any conceivable combination of tissues could be tested in tandem, for example, cardiac/hepatic or hepatic/cardiac.

Cells/Tissues

The disclosed devices may be used in conjunction with tissues derived from any cell, such as cells from cardiac tissue, skeletal muscle tissue, smooth muscle tissue, liver tissue, kidney tissue, cartilage tissue, skin, bone marrow tissue, or combinations of such tissues, or the like. The cells used to grow the three-dimensional tissues can be sourced from anywhere, including from any commercial source, or even sourced from individual subjects or patients. For example, a tissue strand of the invention may be grown starting from a seed of a commercially available liver cell line. In another example, a tissue strand of the invention may be grown starting from a seed of cells obtained directly from a subject, e.g., cells isolated from a biopsy. In other embodiments, the three-dimensional tissues of the invention can be grown from a mixture of different cells. Such mixtures of cells can include mixtures of healthy or diseased cells from the same or different tissues, mixtures of cells from different sources or patients, or mixtures of cells from both patients and from commercial sources. The cells used to grow the tissues of the invention can also be genetically engineered cells, such as drug-resistant or drug-sensitive engineered cell lines, or other types of genetically engineered cells, including those that express various biomarkers, such as GFP.

In a particular embodiment, the three-dimensional tissues of the invention prepared by any device contemplated herein may be prepared or grown using cardiomyocytes, e.g., human cardiomyocytes. The cardiomyocytes can be obtained commercially from sources such as GE Healthcare Lifesciences, 3H Biomedical, Sciencell Research Laboratories. The cells may be characterized as expressing particular markers, such as, for example b-myosin heavy chain; a-cardiac actin; Troponin I; Troponin T; the muscle-specific intermediate filament protein, desmin; the cardiomyocyte-specific peptide hormone, atrial natriuretic peptide (ANP); and coupled gap junction proteins, connexin-43 and connexin-40.

In other embodiments, the cells used to grow the three-dimensional tissues of the invention can be stem cells, including embryonic stem cells ("ESCs"), fetal stem cells ("FSCs"), and adult (or somatic) stem cells ("SSCs"). The stem cells, in terms of potency potential, can be totipotent (a.k.a. omnipotent) (stem cells that can differentiate into embryonic and extra-embryonic cell types), pluripotent stem cells (can differentiate into nearly all cells), multipotent stem cells (can differentiate into a number of cell types), oligopotent stem cells (can differentiate into only a few cell types), or unipotent cells (can produce only one cell type). Stem cells can be obtained commercially, or obtained/isolated directly from patients, or from any other suitable source.

As used herein, a "less developmentally potent cell" is a cell that is capable of limited multi-lineage differentiation or capable of single-lineage, tissue-specific differentiation, for example, an untreated mesenchymal stem cell can differentiate into, inter alia, osteocytes and chrondrocytes, i.e., cells of mesenchymal lineage, but has only limited ability to differentiate into cells of other lineages (e.g., neural lineage.).

As used herein, a "more developmentally potent cell" is a cell that is readily capable of differentiating into a greater variety of cell types than its corresponding less developmentally potent cell. For example, a mesenchymal stem cell can readily differentiate into osteocytes and chrondrocytes but has only limited ability to differentiate into neural or retinal lineage cells (i.e., it is a less developmentally potent cell in this context). Mesenchymal stem cells treated according to the methods described herein may in certain embodiments become more developmentally potent because they can readily differentiate into, for example, mesenchymal-lineage and neural-lineage cell types; the plasticity of the cells is increased when treated according to the methods of the invention.

The tissues formed in the devices of the invention will typically include one or more types of functional, mesenchymal or parenchymal cells, such as smooth or skeletal muscle cells, myocytes (muscle stem cells), fibroblasts, chondrocytes, adipocytes, fibromyoblasts, ectodermal cells, including ductile and skin cells, hepatocytes and other liver cells (e.g., Sinusoidal hepatic endothelial cells, Kupffer cells and hepatic stellate cells), kidney cells, pancreatic islet cells, cells present in the intestine, and other parenchymal cells, cells present in lung, osteoblasts and other cells forming bone or cartilage, and hematopoietic cells. In some cases it may also be desirable to include nerve cells. The vasculature will typically be formed from endothelial cells. "Parenchymal cells" include the functional elements of an organ, as distinguished from the framework or stroma. "Mesenchymal cells" include cells in connective and supporting tissues, smooth muscle, vascular endothelium and blood.

The devices may also be pre-seeded with an endothelial cell line to grow an endothelial layer on the outer or intraluminal (in certain embodiments) surfaces of the device prior to seeding the desired cells that ultimate form the three-dimensional tissue.

Cells can be obtained by biopsy or harvested from a living donor, cell culture, or autopsy, all techniques well known in the art. Cells are preferably autologous. Cells to be implanted can be dissociated using standard techniques such as digestion with a collagenase, trypsin or other protease solution and are then seeded into the mold or polymer scaffold immediately or after being maintained in culture. Cells can be normal or genetically engineered to provide additional or normal function. Immunologically inert cells, such as embryonic or fetal cells, stem cells, and cells genetically engineered to avoid the need for immunosuppression can also be used. Methods and drugs for immunosuppression are known to those skilled in the art of transplantation.

Undifferentiated or partially differentiated precursor cells may also be used. For example, the invention may use embryonic germ cells (Gearhart, et al., U.S. Pat. No. 6,245,566), embryonic stem cells (Thomson, U.S. Pat. Nos. 5,843,780 and 6,200,802), mesenchymal stem cells (Caplan, et al. U.S. Pat. No. 5,486,359), neural stem cells (Anderson, et al., U.S. Pat. No. 5,849,553), hematopoietic stem cells (Tsukamoto, U.S. Pat. No. 5,061,620), multipotent adult stem cells (Furcht, et al., WO 01/11011), all of are incorporated by reference. Cells can be kept in an undifferentiated state by co-culture with a fibroblast feeder layer (Thomson, U.S. Pat. Nos. 5,843,780 and 6,200,802), or by feeder-free culture with fibroblast conditioned media (Xu, et al. Nat. Biotechnol., 19, 971 (2001)). Undifferentiated or partially differentiated precursor cells can be induced down a particular developmental pathway by culture in medium containing growth factors or other cell-type specific induction factors or agents known in the art. Some examples of such factors include: vascular endothelial growth factor; Sonic Hedgehog; insulin-like growth factor II; osteogenin; cytotxic T cell differentiation factor; beta-catenin; bone morphogenic protein 2; interleukin 2; transforming growth factor beta; nerve growth factor; interleukin I; fibroblast growth factor 2; retinoic acid; and Wnt3.

A stem cell can be any known in the art, including, but not limited to, embryonic stem cells, adult stem cells, neural stem cells, muscle stem cells, hematopoietic stem cells, mesenchymal stem cells, peripheral blood stem cells and cardiac stem cells. Preferably, the stem cell is human. A "stem cell" is a pluripotent, multipotent or totipotent cell that can undergo self-renewing cell division to give rise to phenotypically and genotypically identical daughter cells for an indefinite time and can ultimately differentiate into at least one final cell type.

The quintessential stem cell is the embryonal stem cell (ES), as it has unlimited self-renewal and multipotent and/or pluripotent differentiation potential, thus possessing the capability of developing into any organ, tissue type or cell type. These cells can be derived from the inner cell mass of the blastocyst, or can be derived from the primordial germ cells from a post-implantation embryo (embryonic germ cells or EG cells). ES and EG cells have been derived from mice, and more recently also from non-human primates and humans. Evans et al. (1981) Nature 292:154-156; Matsui et al. (1991) Nature 353:750-2; Thomson et al. (1995) Proc. Natl. Acad. Sci. USA. 92:7844-8; Thomson et al. (1998) Science 282:1145-1147; and Shamblott et al. (1998) Proc. Natl. Acad. Sci. USA 95:13726-31.

The terms "stem cells," "embryonic stem cells," "adult stem cells," "progenitor cells" and "progenitor cell populations" are to be understood as meaning in accordance with the present invention cells that can be derived from any source of adult tissue or organ and can replicate as undifferentiated or lineage committed cells and have the potential to differentiate into at least one, preferably multiple, cell lineages.

After the bioreactor devices of the invention are prepared, the devices themselves or a scaffold material integrated with the device (e.g., single wire scaffold, double wire scaffold, hollow tubular scaffold, three-dimensional scaffold with integrated channel/vascular system) can be seeded with the desired cells or sets of cells. Cells can be seeded onto the device or scaffold in an ordered manner using methods known in the art, for example, Teebken, et al., Eur J. Vasa Endovasc. Surg. 19, 381 (2000); Ranucci, et al., Biomaterials 21, 783 (2000). Also, tissue-engineered devices can be improved by seeding cells throughout the polymeric scaffolds and allowing the cells to proliferate in vitro for a predetermined amount of time before implantation, using the methods of Burg et al., J. Biomed. Mater. Res 51, 642 (2000).

For purposes of this invention, "animal cells" can comprise endothelial cells, parenchymal cells, bone marrow cells, hematopoietic cells, muscle cells, osteoblasts, stem cells, mesenchymal cells, embryonic stem cells, or fibroblasts. Parenchymal cells can be derived from any organ, including heart, liver, pancreas, intestine, brain, kidney, reproductive tissue, lung, muscle, bone marrow or stem cells.

In one embodiment, the mold or polymer scaffold is first seeded with a layer of parenchymal cells, such as hepatocytes or proximal tubule cells, or endothelial cells. This layer can be maintained in culture for a period of time, e.g., a week or so, in order to obtain a population doubling. It can be maintained in a perfusion bioreactor to ensure adequate oxygen supply to the cells in the interior.

Sets of cells can be added to or seeded into the three-dimensional apparatuses/devices of the invention, which can serve as a template for cell adhesion and growth by the added or seeded cells. The added or seeded cells can be parenchymal cells, such as hepatocytes or proximal tubule cells. Stem cells can also be used. A second set of cells, such as endothelial cells, can be added to or seeded onto the assembled apparatus through other vessels than those used to seed the first set of cells. The cell seeding is performed by slow flow. As a practical matter, the geometry of the apparatus will determine the flow rates. In general, endothelial cells can enter and form vessel walls in micromachined channels that are about 10-50 .mu.m. Thus, in addition to serving as a mechanical framework for the organ, the assembled apparatus provides a template for all of the microstructural complexity of the organ, so that cells have a mechanical map to locate themselves and form subsystems, such as blood vessels in the liver.

Molecules such as growth factors or hormones can be physically trapped or covalently attached to the surface (e.g., by absorption) of the devices/scaffolds to effect growth, division, differentiation or maturation of cells cultured thereon. In other embodiments, the devices/scaffolds of the herein disclosed bioreactor systems may include materials such as growth factor and hormones and other suitable tissue culture agents integrated (e.g., covalent or non-covalently interactions) directly into the polymers that comprise the devices/scaffolds, e.g., forming covalent or non-covalent bonds with the polymer materials, which could be added during bulk processing of the polymers.

Manufacturing Methods

In various embodiments, the disclosed devices can be assembled and/or manufactured using any suitable microfabrication technique. Such methods and techniques are widely known in the art. In addition, exemplary fabrication methods are exemplified in the Examples provided herein.

Microfabrication processes that can be used in making the bioreactor devices disclosed herein include lithography; etching techniques, such as lasers, plasma etching, photolithography, or chemical etching such as wet chemical, dry, and photoresist removal; or by solid free form techniques, including three-dimensional printing (3DP), stereolithography (SLA), selective laser sintering (SLS), ballistic particle manufacturing (BPM) and fusion deposition modeling (FDM); by micromachining; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination or by combinations thereof. See Jaeger, Introduction to Microelectronic Fabrication (Addison-Wesley Publishing Co., Reading Mass. 1988); Runyan, et al., Semiconductor Integrated Circuit Processing Technology (Addison-Wesley Publishing Co., Reading Mass. 1990); Proceedings of the IEEE Micro Electro Mechanical Systems Conference 1987-1998; Rai-Choudhury, ed., Handbook of Microlithography, Micromachining & Microfabrication (SPIE Optical Engineering Press, Bellingham, Wash. 1997). The selection of the material that is used as the mold determines how the surface is configured to form the branching structure. The following methods are preferred for making molds.

For example, state of the art processes for fabrication of Micro Electro Mechanical Systems (MEMS) utilizing photolithographic processes and methods derived from the semiconductor industry may be used. More recently developed methods include "soft lithography" (Whitesides et al, Angew chem. Int ed, 37; 550-575, (1998)) and microfluidic tectonics (U.S. Pat. No. 6,488,872, Beebe et al., Nature; 404:588-59 (2000)). Reviews and other discussions of polymer microdevice fabrication include Madou, M. J. Fundamentals of Microfabrication: The Science of Miniaturization; 2nd ed.; CRC Press: Boca Raton, 1997; Becker, H., and Locascio, L. E. "Polymer microfluidic devices." Talanta, 56(2):267-287, 2002; Quake, S. R., and Scherer, A. "From micro- to nanofabrication with soft materials." Science, 290(5496):1536-1540, 2000; and Whitesides, G. M., and Stroock, A. D. "Flexible methods for microfluidics." Physics Today, 54(6):42-48, 2001, each of which are incorporated herein by reference.

Microstereolithography techniques are also contemplated in fabricating the devices of the invention. Microstereolithography is a technique that incorporates a focused light source with photoactive monomers (Chatwin, C., Farsari, M., Huang, S. P., Heywood, M., Birch, P., Young, R., and Richardson, J. "UV microstereolithography system that uses spatial light modulator technology." Applied Optics, 37(32): 7514-7522, 1998; Cumpston, B. H., Ananthavel, S. P., Barlow, S., Dyer, D. L., Ehrlich, J. E., Erskine, L. L., Heikal, A. A., Kuebler, S. M., Lee, I. Y. S., McCord-Maughon, D., Qin, J. Q., Rockel, H., Rumi, M., Wu, X. L., Marder, S. R., and Perry, J. W. "Two-photon polymerization initiators for three-dimensional optical data storage and microfabrication." Nature, 398(6722):51-54, 1999; Neckers, D. C., Hassoon, S., and Klimtchuk, E. "Photochemistry and photophysics of hydroxyfluorones and xanthenes." Journal of Photochemistry and Photobiology A—Chemistry, 95(1):33-39, 1996), each of which are incorporated herein by reference. Curing sequential cross-sectional layers on top of each other results in three-dimensional structures. Often, this process does not facilitate highly parallel fabrication, and a relatively long time is required for high-resolution microstructure fabrication. Such processes may be used to fabricate the devices of the invention.

The disclosed devices also contemplate techniques involving hot embossing, which is another strategy for polymeric device fabrication (Madou, M. J. Fundamentals of Microfabrication: The Science of Miniaturization; 2nd ed.; CRC Press: Boca Raton, 1997; Becker, H., and Heim, U. "Hot embossing as a method for the fabrication of polymer high aspect ratio structures." Sensors and Actuators A—Physical, 83(1-3):130-135, 2000), each of which are incorporated herein by reference. This requires a metal or semiconductor stamp or mold, known as the embossing tool, which is heated above the glass transition temperature of a polymer substrate. Pressure is applied to the tool and the negative topography is transfer to the softened polymer. The system is cooled, the stamp is removed, and the polymer retains the relief structure of the embossing tool. This leads to highly resolved designs but requires facilities to micromachine the original tool. Furthermore, the design is limited to one layer or multiple layers must be laminated together with precise alignment.

The invention may also employ soft lithography to fabricate the disclosed devices. Soft lithography encompasses a variety of specific techniques. In general, these processes do not require photolithography; an elastomeric master (often poly(dimethylsiloxane), PDMS) is made from any relief structure and used to pattern features onto a number of different surfaces, including polymers (Anderson, J. R., Chiu, D. T., Jackman, R. J., Cherniayskaya, O., McDonald, J. C., Wu, H. K., Whitesides, S. H., and Whitesides, G. M. "Fabrication of topologically complex three-dimensional microfluidic systems in PDMS by rapid prototyping." Analytical Chemistry, 72(14):3158-3164, 2000; Duffy, D. C., McDonald, J. C., Schueller, O. J. A., and Whitesides, G. M. "Rapid prototyping of microfluidic systems in poly(dimethylsiloxane)." Analytical Chemistry, 70(23):4974-4984, 1998; Love, J. C., Anderson, J. R., and Whitesides, G. M. "Fabrication of three-dimensional microfluidic systems by soft lithography." MRS Bulletin, 26(7):523-528, 2001; Wu, H. K., Odom, T. W., Chiu, D. T., and Whitesides, G. M. "Fabrication of complex three-dimensional microchannel systems in PDMS." Journal of the American Chemical Society, 125(2):554-559, 2003; xia, Y. N., and Whitesides, G. M. "Soft lithography." Annual Review of Materials Science, 28:153-184, 1998). The overall method has been classified into a number of specific techniques (e.g., microcontact printing, replica molding (REM), microtransfer molding, micromolding in capillaries (MIMIC), and solvent-assisted micromolding (SAMIM) (Xia, Y. N., and Whitesides, G. M. "Soft lithography." Annual Review of Materials Science, 28:153-184, 1998)). However, all of the individual techniques included within the method of soft lithography require the fabrication of a PDMS master from a relief structure, which is often a surface micromachined silicon wafer. Each of these techniques may be employed in the present invention to microfabricate the disclosed devices.

Micromolding techniques are also contemplated. Micromolding techniques are well known (Anderson, J. R., Chiu, D. T., Jackman, R. J., Cherniayskaya, O., McDonald, J. C., Wu, H. K., Whitesides, S. H., and whitesides, G. M. "Fabrication of topologically complex three-dimensional microfluidic systems in PDMS by rapid prototyping." Analytical Chemistry, 72(14):3158-3164, 2000; Duffy, D. C., McDonald, J. C., Schueller, O. J. A., and Whitesides, G. M. "Rapid prototyping of microfluidic systems in poly(dimethylsiloxane)." Analytical Chemistry, 70(23):4974-4984, 1998; Wu, H. K., Odom, T. W., Chiu, D. T., and Whitesides, G. M. "Fabrication of complex three-dimensional microchannel systems in PDMS." Journal of the American Chemical Society, 125(2):554-559, 2003; Hanemann, T., Ruprecht, R., and Hausselt, J. H. "Micromolding and photopolymerization." Advanced Materials, 9(11):927-929, 1997), each of which are incorporated by reference. In brief, the techniques entail filling recessed regions of a PDMS mold with a monomer or polymer solution and curing or evaporating the solvent to solidify the polymer. In these methods, negative transfer of the mold is obtained. Finally, the master is removed and can be reused in the same manner. Like other soft lithography techniques, each layer requires a separate master. Furthermore, in many cases, adjacent layers are physically adhered. Alternatively, in the case of multilayer PDMS structures, adjacent layers covalently bind upon contact, which suggests that precise alignment prior to contact is critical.

Step-and-flash imprint lithography (S-FIL) is also contemplated. S-FIL is another technique of nanopatterning based on mechanical imprinting, but uses a UV curable liquid material as a liquid resist. With S-FIL, the liquid resist is dispensed in droplet form onto a substrate, and then a template is brought into contact with the substrate and pressed against the substrate to spread out the liquid resist thereby forming a film of the liquid resist. This film is then cured by exposure to UV light. S-FIL can be carried out at room temperature and, therefore, does not require high temperatures like conventional NIL. However, S-FIL is still not ideal because conventional UV curable liquid materials used in S-FIL are typically based on a mechanism involving free radical polymerization of acrylic functional monomers and oligomers. The UV curable liquid materials typically exhibit extensive shrinkage after cure. Furthermore, the UV curable liquid materials are prone to oxygen sensitivity whereby oxygen scavenges free radical species and inhibits polymerization at a surface of the resist film. As a result, the resist film is prone to defect generation in the resultant pattern formed in the resist film.

Direct photolithography of photopolymers is also contemplated. This technique is a robust method for fabrication of polymeric microdevices. The most common application of this technology is in the use of photoresists for any photolithography application. Most photoresists contain three components: a solvent for spreading the resist on a substrate, an organic polymer that resists etchants, and a photosensitizer that causes reaction or solubility (depending on chemistry and processing steps) of the polymer once exposed to UV radiation (Madou, M. J. Fundamentals of Microfabrication: The Science of Miniaturization; 2nd ed.; CRC Press: Boca Raton, 1997). Patterned resists can be used as simple devices or they can be used as a negative mold for another polymer (e.g., the relief structures for soft lithography techniques). Once the desired polymer is cured in the resist mold, then the resist can be removed via standard methods.

Beebe et al. (U.S. Pat. No. 6,488,872) relate to microfabricated devices manufactured from a substrate having microscale fluid channels, where Beebe et al.'s microscale fluid channels have a cross-section diameter of about 1 micron to about 1 millimeter, the disclosed technique of which may be applied in the present invention and are incorporated herein by reference. Polymer components are created inside a cartridge via direct photopatterning of a liquid phase polymerizable mixture. Beebe et al. state that structures that are close together (i.e. approximately 300 microns) typically are not fabricated simultaneously because of a partial polymerization occurring between the objects. Beebe and coworkers (Khoury, C., Mensing, G. A., and Beebe, D. J. "Ultra rapid prototyping of microfluidic systems using liquid phase photopolymerization." Lab On a Chip, 2(1):50-55, 2002; Beebe, D. J., Moore, J. S., Yu, Q., Liu, R. H., Kraft, M. L., Jo, B. H., and Devadoss, C. "Microfluidic tectonics: A comprehensive construction platform for microfluidic systems." Proceedings of the National Academy of Sciences of the United States of America, 97(25):13488-13493, 2000; Beebe, D. J., Moore, J. S., Bauer, J. M., Yu, Q., Liu, R. H., Devadoss, C., and Jo, B. H. "Functional hydrogel structures for autonomous flow control inside microfluidic channels" Nature, 404(6778):588-590, 2000) fabricated channels, valves, and pumps for microfluidic systems using photopolymerization of multifunctional monomers. In particular, Beebe et al. incorporated hydrogel networks (i.e., loosely crosslinked hydrophilic polymers that swell in the presence of water) into hydrophobic polymer channels for various valve and sensor designs. Although swelling kinetics in macroscopic networks are much too slow for valve operations, the significant increase in surface area to volume ratio at the microscale facilitates relatively fast actuation of hydrogel valves—on the order of seconds (De, S. K., Aluru, N. R., Johnson, B., Crone, W. C., Beebe, D. J., and Moore, J. "Equilibrium swelling and kinetics of pH-responsive hydrogels: Models, experiments, and simulations." Journal of Microelectromechanical Systems, 11(5):544-555, 2002). Other groups have used direct photopolymerization of monoliths within channels to form microfluidic valves (Hasselbrink, E. F., Shepodd, T. J., and Rehm, J. E. "High-pressure microfluidic control in lab-on-a-chip devices using mobile polymer monoliths." Analytical Chemistry, 74(19):4913-4918, 2002; Kirby, B. J., Shepodd, T. J., and Hasselbrink, E. F. "Voltage-addressable on/off microvalves for high-pressure microchip separations." Journal of Chromatography A, 979(1-2):147-154, 2002), and separations or combinatorial chemistry platforms (Peters, E. C., Svec, F., Frechet, J. M. J., Viklund, C., and Irgum, K. "Control of porous properties and surface chemistry in "molded" porous polymer monoliths prepared by polymerization in the presence of TEMPO." Macromolecules, 32(19):6377-6379, 1999; Tripp, J. A., Svec, F., and Frechet, J. M. J. "Grafted macroporous polymer monolithic disks: A new format of scavengers for solution-phase combinatorial chemistry." Journal of Combinatorial Chemistry, 3(2):216-223, 2001).

In certain embodiments, a multivinyl monomeric precursor material containing silicon, carbon, and nitrogen (i.e., Ceraset) can be used for microfabrication. (Yang, H., Deschatelets, P., Brittain, S. T., and Whitesides, G. M. "Fabrication of high performance ceramic microstructures from a polymeric precursor using soft lithography." Advanced Materials, 13(1):54-58, 2001; Liew, L. A., Zhang, W. G., Bright, V. M., An, L. N., Dunn, M. L., and Raj, R. "Fabrication of SiCN ceramic MEMS using injectable polymer-precursor technique." Sensors and Actuators A—Physical, 89(1-2):64-70, 2001; Liew, L. A., Liu, Y. P., Luo, R. L., Cross, T., An, L. N., Bright, V. M., Dunn, M. L., Daily, J. W., and Raj, R. "Fabrication of SiCN MEMS by photopolymerization of pre-ceramic polymer?" Sensors and Actuators A—Physical, 95(2-3):120-134, 2002; Liew, L. A., Saravanan, R. A., Bright, V. M., Dunn, M. L., Daily, J. W., and Raj, R. "Processing and characterization of silicon carbonnitride ceramics: application of electrical properties towards MEMS thermal actuators." Sensors and Actuators A—Physical, 103(1-2):171-181, 2003; Seok, W. K., and Sneddon, L. G. "Synthesis and ceramic conversion reactions of decaborane-CERASET polymers: New processable precursors to SiC/Si3N4/BN ceramics." Bulletin of the Korean Chemical Society, 19(12):1398-1402, 1998). After photopolymerization by direct photolithographic UV exposure, the microfabricated polymer can be pyrolyzed to create an amorphous Si—C—N ceramic that has utility for high temperature applications.

Micromachining can be performed on standard bulk single crystal silicon wafers of a diameter ranging between about 50 and 300 millimeters (mm), preferably approximately 100 mm, and of thickness ranging between about 200 and 1200 µm. These wafers can be obtained from a large number of vendors of standard semiconductor material, and are sawn and polished to provide precise dimensions, uniform crystallographic orientation, and highly polished, optically flat surfaces. Wafers made from pyrex borosilicate or other glasses can also be procured and inserted into micromachining processes, with alternative processes used to etch the glassy materials.

The geometry of the bioreactor devices of the invention, in particular the number of different feature depths required, is a factor in determining the specific process sequence for fabrication. The simplest case is that of a single depth dimension for the mold. Specifically, for a silicon substrate, the process sequence is as follows: first, the silicon wafer is cleaned, and a layer of photosensitive material is applied to the surface. Typically, the layer is spun on at a high revolution rate to obtain a coating of uniform thickness. The photoresist is baked, and the wafer is then exposed to ultraviolet or other short-wavelength light though a semitransparent mask. This step can be accomplished using any one of several masking techniques, depending on the desired image resolution. The resist is then developed in an appropriate developer chemistry, and the wafer is then hard-baked to remove excess solvent from the resist. Once the lithographic process has been completed, the wafer can be etched in a plasma reactor using one of several possible chemistries. Etching serves to transfer the two-dimensional pattern into the third dimension: a specified depth into the wafer. Plasma parameters are determined by the desired shape of the resulting trench (semi-circular, straight-walled profile, angled sidewall), as well as by the selectivity of the etchant for silicon over the masking photoresist. Once the etching has been completed, the photoresist can be removed and the wafer prepared for use in the tissue molding process.

The present invention contemplates any suitable microfabrication process for making the devices of the invention, including those specifically identified herein, and any other suitable microfabrication process not expressly disclosed herein but which will be known to those having ordinary skill in the art.

Applications

Three-dimensional tissue systems of the invention are useful for a variety of applications, including but not limited to, (a) the testing of the efficacy and safety (including toxicity) of experimental pharmacologic agents (including, but not limited to, small molecule drugs, biologics, nucleic acid-based agents), (b) the defining of pharmacokinetics and/or pharmacodynamics of pharmacologic agents (including, but not limited to, small molecule drugs, biologics, nucleic acid-based agents), (c) characterizing the properties and therapeutic effects of pharmacologic agents (including, but not limited to, small molecule drugs, biologics, nucleic acid-based agents) on a subject, (d) screening of new pharmacologic agents, (e) providing implantable engineered tissues for use in regenerative medicine for treating damaged and/or diseased tissues, (e.g., use of the tissue constructs, devices, and/or systems of the disclosure to study cardiac disease states, including patients with electrical conduction defects (iPSC-CM)), and (f) personalized medicine.

In certain embodiments, the three-dimensional tissue systems of the invention may be suitable for cultivation and generation of various tissue structures. The disclosed devices may be designed to provide an in vitro platform that mimics or reproduces native tissue architecture found in vivo, to enable cells to mature and function in the way they normally would in vivo.

In other embodiments, the disclosed devices may be suitable for culture of various tissues, including muscle cells such as cardiomyocytes, skeletal muscle cells, smooth muscle cells as well as excitable tissues such as neurons and cells that may require rich vasculature such as hepatocytes, among others.

In still other embodiments, the disclosed devices may be suitable for various applications, including drug-testing in vitro, for building a human-on-a-chip with several different compartments as well as for direct anastomosis and implantation into an animal or a human patient, among other applications.

In certain embodiments, the three-dimensional tissue engineered systems of the invention can be used to metabolism, toxicity and efficacy of test agents. Methods of the invention can be used to screen experimental drugs or "test agents" that have no known metabolic or pharmacokinetic profile, in order to obtain such information, including information necessary to assess toxicity. Toxicity can often occur as a result of drug-to-drug interactions. Thus, methods of the invention can be used to study the combination of test agents with known drugs or other test agents. These methods are particularly relevant to use in clinical settings since many patients are treated with multiple drugs.

In general, test agents can be incubated with the three-dimensional tissue engineered systems of the invention in a dosage range estimated to be therapeutic and for a duration sufficient to produce an effect (e.g., metabolic effects or effects indicating to toxicity or efficacy). The incubation time can range between about 1 hour to 24 hours, or can be extended as necessary for several days or even weeks. The incubation conditions typically involve standard culture conditions known in the art, including culture temperatures of about 37 degrees Celsius, and culture mediums compatible with the particular cell type selected.

Test agents that can be analyzed according to methods of the invention include, but are not limited to, opioid analgesics, anti-inflammatory drugs such as antihistamines and non-steroidal anti-inflammatory drugs (NSAIDs), diuretics such as carbonic anhydrase inhibitors, loop diuretics, high-ceiling diuretics, thiazide and thiazide-like agents, and potassium-sparing diuretics, agents that impinge on the renal and cardiovascular systems such as angiotensin converting enzyme (ACE) inhibitors, cardiac drugs such as organic nitrates, calcium channel blockers, sympatholytic agents, vasodilators, .beta.-adrenergic receptor agonists and antagonists, .alpha.-adrenergic receptor agonists and antagonists, cardiac glycosides, anti-arrhythmic drugs, agents that affect hyperlipoproteinemias such as 3-hydroxymethylglutaryl-coenzyme A (HMG-CoA) inhibitors, anti-neoplastic agents such as alkylating agents, antimetabolites, natural products, antibiotics, and other drugs, immunomodulators, anti-diabetic agents, and anti-microbial agents such as antibacterial agents, antiviral agents, antifungal agents, antiprotozoal agents, and antihelminthic agents, but are not limited to these agents.

For example, the three-dimensional tissue systems of the invention can be used to detect/evaluate toxicity associated with therapeutic agents (e.g., cardio-toxicity, or liver toxicity associated with drug administration). There are three general classes of toxicity. Acute toxicity is a toxic effect that occurs after less than about 24 hours of exposure to the drug. Subacute toxicity occurs later, after about 14 to 90 days of exposure to the drug. Chronic toxicity occurs after about 90 days (or longer) exposure to the drug. Current methods in the art are suboptimal for use in detecting subacute and chronic toxicity due to the requirement for extended periods of monitoring in a living subject. While methods of the invention can encompass these longer intervals of exposure, effects may be detected more rapidly, such that the incubation time for the test agent need not be extended. Accordingly, incubation times can range between about 1 hour to 24 hours, or can be extended as necessary for several days or even weeks.

The undesired effects of toxicity caused by administration of a test agent can be screened in several ways. Tissue engineered systems of the invention can be used to determine the range of toxic dosimetry of a test agent. The effect of increasing concentrations of the test agent (i.e., dose) on tissues of interest can be monitored to detect toxicity. A toxic effect, when observed, can be equated with a measurement of test agent concentration/cells $cm^2$. By calculating the toxic concentration according to the distribution of cells in the tissue engineered system, one of skill in the art can extrapolate to the living system, to estimate toxic doses in subjects of various weights and stages in development.

Using methods of the present invention, various doses of individual test agents and combinations of test agents with other pharmaceuticals will be screened to detect toxic effects, including but not limited to irregular metabolism, cardiotoxicity, liver toxicity, carcinogenicity, kidney and neural toxicity and cell death. To detect irregular changes in metabolism, standard methods known in the art for assaying metabolite production, including but not limited to glucose metabolism and enzymatic assays, can be employed. The particular metabolic pathway assayed, or metabolite measured, can vary according to the tissue type selected.

In detecting carcinogenicity, cells can be screened for a transformed phenotype using methods well known in the art, for example, methods detecting changes in gene expression, protein levels, abnormal cell cycles resulting in proliferation and changes in expression of cell surface markers, including, but not limited to, antigenic determinants. Gene expression patterns can be determined, for example, by evaluating mRNA levels of genes of interest according to standard hybridization techniques, such as RT-PCR, in situ hybridization, and fluorescence in situ hybridization (FISH), Northern analysis or microchip-based analysis. Protein expression patterns can be determined by any methods known in the art, for example, by quantitative Western blot, immunohistochemistry, immunofluorescence, and enzyme-linked immunosorbent assay (ELISA), amino acid sequence analysis, and/or protein concentration assays. For details, see Sambrook, Fritsch and Maniatis, Molecular Cloning, A Laboratory Manual, 2nd Ed., Cold Spring Harbor Laboratory Press, 1989. Cell counting and/or separation techniques, such as FACS analysis, can be employed to measure proliferation or detect aberrant cell surface marker expression.

Standard methods well known in the art can also be used to detect cell death, including but not limited to, tunnel assays. Traditional approaches of in vitro toxicology to toxicological screening has been to measure comparatively late events in the process of cell death, such as lactate dehydrogenase release or differential counting of viable and dead cells using vital dyes, such as trypan blue, 4,6-diaminophenylindole (DAPI), propidium iodide, and LIVE/DEAD stain available from Molecular Probes. Prediction of lethality in vivo is one proposed application of this type of in vitro screen, although cell death is not a common mechanism by which the animal's death is induced following acute exposure to a toxic agent. In contrast, caspase activation is at the center the common features of chronic toxicity, cell death, hyperproliferation and inflammatory reactions. Caspase activity can be measured relatively quickly after a toxic insult (30 min to 4 hr) by fluorescence spectroscopy, thus lending itself to high-throughput screening techniques. Other markers and assays commonly used to monitor apoptosis or necrosis of cells can include, but are not limited to, the presence of phosphatidylserine on the outer leaflet of the plasma membrane of affected cells, annexin V staining, and terminal deoxynucleotidyltransferase nick-end labeling assay (TUNEL).

Using methods of the invention, various doses of individual test agents and combinations of test agents will be screened in panels comprised of tissues having diverse genetic backgrounds to determine the pharmacogenetic toxicity profile of the test agents. For example, multiple doses of, or combinations with, test agents will be screened for toxic effects specific to one or more genetic backgrounds. Toxic effects to be screened for genetic variance include, but are not limited to, irregular metabolism, carcinogenicity and cell death.

Tissue-engineered devices of the present invention can be modified in parallel to generate a comprehensive array of the currently known genetic polymorphisms of different metabolic enzymes. A salient example is the CYP450 monooxygenase system, wherein the population comprises multiple isoforms and polymorphisms that impinge on and complicate predictive models of drug metabolism, drug clearance, and toxicity. For example, in the metabolism of thiopurines, such as thioguanine, the rate-limiting enzyme is a methyltransferase that has different polymorphic forms. Polymorphism in the methyltransferases is known to affect metabolism of the thiopurines. Where the polymorphism gives rise to slower metabolism of the thiopurine, clinical benefit is decreased and where the polymorphism gives rise to an increased rate of metabolism, toxicity can result. Thus, methods of the invention can be used to determine the metabolic profile of various test agents in the presence of various polymorphic forms of an enzyme, such as methyltransferase.

In testing for differential toxicity due to polymorphic variation, or other genetic defects, genetically engineered cells comprising gene knockouts or knock-ins of specific enzymes known to affect drug metabolism and toxicity can be used in the systems of the invention. Cells can be modified using techniques that are known to the skilled artisan, such as RNA interference (RNAi), antisense technology, ribozymes, site-directed mutagenesis, among others.

When evaluating effects on metabolism, levels of metabolites, if known, can be detected using methods well known in the art as a reflection of metabolic activity, such as liquid chromatography. Liquid chromatography coupled with tandem mass spectrometric detection (LC/MS/MS) can be used as an analytical method to monitor early absorption, distribution, metabolism and elimination testing. This method provides excellent sensitivity, specificity and high sample throughput. The quantitative selectivity afforded by reaction monitoring on a triple quadrupole instrument precludes the need for high chromatographic resolution or extensive sample clean up. Using automated sample-processing techniques, such as on-line column switching, combined with high-sample-density microtiter plates, can further maximize analytical throughput. Modern LC/MS/MS also offers limits of detection extending down to the sub-nanogram per ml range using only minimal quantities of biological matrix.

LC/MS/MS enables rapid and sensitive quantitation of new drug candidates, as well as providing important structural information on metabolites. A full scan LC/MS analysis can initially suggest possible oxidative and/or conjugative metabolic transformations on the basis of the ionic species observed. In the MS/MS mode, the instrument can be tuned to a selected precursor ion of interest, which is then further fragmented to form productions that uniquely identify the metabolic (production scan).

Selectivity can be further enhanced by the quadrupole ion trap, a device that "traps" ions in a space bounded by a series of electrodes. The unique feature of the ion trap is that an MS/MS experiment (or, in fact, multi-step MS experiments) can be performed sequentially in time within a single mass analyzer, yielding a wealth of structural information. Hybrid quadrupole-time-of-flight (Q-TOF) LC/MS/MS systems can also be used for the characterization of metabolite profiles. The configuration of Q-TOF results in high sensitivity in mass resolution and mass accuracy in a variety of scan modes.

Liquid chromatography coupled with nuclear magnetic resonance spectroscopy (LC-NMR) provides a way of confirming absolute molecular configurations. A linear ion-trap mass spectrometer possesses significantly enhanced production-scanning capabilities, while retaining all of the scan functions of a triple quadrupole MS. The ultra-high resolution and sensitivity of Fourier transform ion-cyclotron resonance MS (FI-ICRMS) can be useful for the analysis and characterization of biological mixtures. Data processing and interpretation software packages also enable efficient identification and quantification of metabolites using the tissue-engineered devices of the present invention.

A widely used method to study in vitro drug metabolism is the use of tissue homogenates. The tissues within the three-dimensional systems of the invention can be cultured in the presence of a test agent and harvested to obtain tissue homogenate preparations for use in enzyme analysis. Preparation of tissue homogenates is well known in the art and involves the steps of tissue homogenization and subcellular fractionation to yield two main fractions routinely studied in drug metabolism: the post-mitochondrial supernatant and the endoplasmic reticulum (microsomal) fraction.

The three-dimensional tissue culture devices of the invention can also be used to evaluate a test agent's efficacy. Efficacy can be detected by measuring individual parameters associated with the repair, enhancement, improvement and/ or regeneration of a disease model comprising an injured tissue grown in a three-dimensional system of the invention. In disease models of the invention, the injury can be induced or can be the result of a pre-existing condition in the tissue donor, including conditions relating to inherited genetic abnormalities. Either the induced or pre-existing condition can comprise a weakened state resulting from a previous drug exposure. Test agents, or combinations of test agents, can be analyzed for efficacy in disease models of the invention.

In one embodiment, selected tissues of interest can be treated with agents known in the art to cause cellular damage (e.g., toxins, mutagens, radiation, infectious agents and chemical agents), inducing injury in the tissue. In another embodiment, selected tissues of interest can be altered using standard recombinant techniques to induce a disease state. For example, techniques of homologous recombination can be used to insert a transgene into a cell, or "knock-out" gene expression of a gene of interest. For a review of homologous recombination, see Lewin, B., Genes V, Oxford University Press, New York, 1994, pp. 968-997; and Capecchi, M., (1989) Science 244:1288-1292; Capecchi, M., (1989) Trends Genet. 5 (3):70-76. In another embodiment, the selected tissue of interest is injured as a result of an inherited genetic defect, which can be a single gene defect or a multifactorial defect. For a discussion of inherited disorders, see Thompson, McInnes and Willard, Genetics in Medicine, 5.sup.th Ed., W.B. Saunders Company, 1991.

Tissue engineered systems of the invention can be used to determine the range of effective dosimetry of a test agent. The effect of increasing concentrations of the test agent (i.e., dose) on tissues of interest can be monitored to detect efficacy. A therapeutic effect, when observed can be equated with a measurement of concentration/cells $cm^2$. By calculating the effective concentration according to the distribution of cells in the tissue engineered system, one of skill in the art can extrapolate to the living system, to estimate therapeutic doses in subjects of various weights.

Using methods of the invention, various doses of individual test agents and combinations of test agents will be screened in panels comprised of tissues having diverse genetic backgrounds to determine the pharmacogenetic efficacy profile of the test agents. For example, multiple doses of, or combinations with, test agents will be screened for efficacy, or the lack thereof, specific to one or more genetic backgrounds.

Methods of the invention can be carried out using tissues of any kind. The following description provides specific information relating to three preferred embodiments of the invention, which include the use of the systems/devices of the invention with cells derived from liver, heart, and kidney.

Liver

The liver plays a major role in carbohydrate metabolism by removing glucose from the blood, under the influence of the hormone insulin, and storing it as glycogen. When the level of glucose in the blood falls, the hormone glucagon causes the liver to break down glycogen and release glucose into the blood. The liver also plays an important role in protein metabolism, primarily through deamination of amino acids, as well as the conversion of the resulting toxic ammonia into urea, which can be excreted by the kidneys. In addition, the liver participates in lipid metabolism by storing triglycerides, breaking down fatty acids, and synthesizing lipoproteins. The liver also secretes bile, which helps in the digestion of fats, cholesterol, phospholipids, and lipoproteins.

Analysis of metabolic function will indicate toxicity in liver. Thus, in liver tissue engineered systems of the invention, metabolic assays to detect toxicity of a particular test agent are preferred. Metabolic enzymes, including but not limited to, cytochrome P450, alkaline phosphatase, glycolytic enzymes such as alpha-galactosidase, beta-galactosidase, alpha-glucosidase, beta-glucosidase, alpha-glucuronidase, beta-glucuronidase, and alpha-amylase, NADPH-cytochrome P450 reductase, cytochrome $b_5$, N-demethylase, 0-demethylase, acetylcholinesterase, pseudocholinesterase, among other esterases, epoxide hydrolase, amidases, Uridine diphosphate (UDP)-glucuronosyltransferases, phenol sulfotransferase, alcohol sulfotransferase, steroid sulfotransferase, and arylamine sulfotransferase, UDP-glycosyltransferases, purine phosphoribosyltransferase, N-acetyltransferases, glutathione S-transferase, phenylethanolamine N-methyltransferase, non-specific N-methyltransferase, imidazole N-methyltransferase, catechol-O-methyltransferase, hydroxyindole-O-methyltransferase, and S-methyltransferase, alcohol dehydrogenase, aldehyde dehydrogenase, xanthine oxidase, amine oxidases such as monoamine oxidases, diamine oxidases, flavoprotein N-oxidases, and hydroxylases, aromatases, cysteine conjugate .beta.-lyase, and alkylhydrazine oxidase can be tested for metabolic activity using assays well known in the art (this is described in great detail in other portions of the application). Cytochrome p450 enzymes that can be tested include, but are not limited to, CYP1A1, CYP1A2, CYP2A3, CYP2B6, CYP2B7, CYP2B8, CYP2C8, CYP2C9, CYP2C10, CYP2D6, CYP2D7, CYP2D8, CYP2E1, CYP2F1, CYP3A3, CYP3A4, CYP3A5, and CYP4B1.

In one embodiment, the test agent comprises antiviral activity, most preferably, antiviral activity against hepatitis. Currently, there is a great need for safe and effective treatments for hepatitis (Mutchnick, M. G., et. al., Antiviral Research (1994) 24:245-257). For example, clinical tests on the use of the nucleoside analog fialuridine (FIAU) for treatment of chronic hepatitis B were suspended recently due to drug-related liver failure leading to death in some patients. Test agents demonstrating efficacy against hepatitis can also be screened for acute, subacute and chronic toxicity by monitoring metabolic function, preferably of metabolic function of cytochrome P450 and alkaline phosphatase, following administration.

Test agents can be screened for efficacy in tissue engineered systems of the invention comprising liver cells affected with diseases including, but not limited to, cancer, diabetes, acute hepatitis, fulminant hepatitis, chronic hepatitis, hepatic cirrhosis, fatty liver, alcoholic hepatopathy, drug induced hepatopathy (drug addiction hepatitis), congestive hepatitis, autoimmune hepatitis, primary biliary cirrhosis and hepatic *porphyria*, and pericholangitis, sclerosing cholangitis, hepatic fibrosis and chronic active hepatitis, which have been reported to occur with a high frequency as complications of inflammatory bowel diseases such as ulcerative colitis and Crohn's disease.

Preferably, test agents will be assayed for their ability to reduce or prevent of progress of hepatic necrocytosis and/or accelerate hepatic regeneration. For example, expression levels of Rasp-1, a gene that is upregulated during regeneration of liver tissue, can be monitored following administration of a test agent. Rasp-1 is described in U.S. Pat. No. 6,027,935, the contents of which are incorporated herein by reference for their description of Rasp-1 sequences, antibodies and assays.

In a preferred embodiment, test agents are screened for efficacy in the treatment of hepatitis viral infections, particularly infections of hepatitis B and hepatitis C. Other hepatitis viruses that are significant as agents of human disease include hepatitis A, hepatitis delta, hepatitis E, hepatitis F, and hepatitis G (Coates, J. A. V., et. al., Exp. Opin. Ther. Patents (1995) 5 (8): 747-756). The test agent can comprise, for example, nucleoside analog antivirals, immunomodulators, immunostimulators (e.g., interferons and other cytokines) or other immune system-affecting drug candidates, including, but not limited to, thymic peptides, isoprinosine, steroids, Schiff base-forming salicylaldehyde derivatives such as Tucaresol, levamisol, and the like (Gish, R. G., et al., Exp. Opin. Invest. Drugs (1995) 4 (2):95-115; Coates, J. A. V., et al., Exp. Opin. Ther. Patents (1995) 5 (8):747-765).

Anti-hepatitis efficacy of a test agent can be determined according to methods known in the art. For example, following treatment with a test agent, the amount of hepatitis virus or viral DNA in the culture medium can be determined by PCR analysis (e.g., of sedimented particles). DNA measurements can be correlated with viral replication to assess post-treatment infectivity. Alternatively, viral loads can be measured directly. Other measures of efficacy include measurement of enzyme levels, including but not limited to SGOT, ALT and LDH, histologic analysis and normal production of total liver proteins, such as the clotting factors.

In a preferred embodiment, the efficacy of a test agent is determined in liver tissues infected with the hepatitis C virus. In a preferred embodiment, test agents are screened for efficacy in the treatment of liver cancer. Reduction or elimination of transformed liver cells in response to treatment with a test agent can be detected by measuring decreases in hypercalcaemia and CEA expression. Reduction in proliferation can also be determined by cell counting.

Heart

The toxic effect of a test agent in cardiac tissue engineered systems of the invention can be detected using a variety of assays known in the art. For example, assays to detect toxicity of a particular test agent preferably comprise measurement of QT intervals, changes in electrophysiology (e.g., changes in $K^+/Ca^{2+}$ channels, hERG) and/or arrhythmia by T-wave *alternans* (TWA).

*Alternans* of the electrocardiogram is defined as a change in amplitude and/or morphology of a component of the ECG that occurs on an every-other-beat basis (Walker, M. L. and Rosenbaum, D. S., (2003) Cardiovasc. Res. 57: 599-614). TWA is the beat-to-beat alternation of T-wave amplitude, and is closely linked to electrical instability in the heart. Beat-to-beat microvolt fluctuation of the T wave can be detected using high-resolution electrodes and signal processing techniques (Gold, M. R., and Spencer, W. (2003) Curr. Opin. Cardiol. 18: 1-5). A large number of beats, generally 128, are sampled, and the voltages of multiple corresponding points on the T-wave are computed and averaged. Through fast-Fourier transformation, these consecutive amplitudes are displayed spectrally, yielding several frequency peaks. These peaks correspond to thoracic excursions with respiration, other repetitive body movements, and ambient electrical noise. The peak at 0.5 cycles/beat, if present, is caused by TWA. The *alternans* magnitude, $V_{alt}$, represents the difference between the even or odd beat and the mean amplitude, in microvolts. A threshold of 1.9 uV is used for significance. The *alternans* ratio (k) is another parameter measured and represents the ratio of the *alternans* amplitude to the SD of the background noise. It is required to be greater than 3.0 for significance. Additionally, TWA must be sustained for more than one minute.

Test agents can be screened for efficacy in tissue engineered systems of the invention comprising cardiac cells affected with diseases including, but not limited to, congestive heart failure, coronary artery disease, myocardial infarction, myocardial ischemia, effects of atherosclerosis or hypertension, cardiomyopathy, cardiac arrhythmias, muscular dystrophy, muscle mass abnormalities, muscle degeneration, myasthenia gravis, infective myocarditis, drug- and toxin-induced muscle abnormalities, hypersensitivity myocarditis, autoimmune endocarditis, and congenital heart disease. Preferably, test agents will be assayed for their ability to accelerate cardiac regeneration or improve contractile properties. In general, efficacy can be indicated by detection of improved contractility, electromechanical conduction and/or association, susceptibility to electrical dysfunction, ventricular fibrillation (sudden death), ionotropy, chronotropy, and decreased leakage of enzymes (e.g., CPK and SGOT).

In various embodiments, the devices of the invention can be utilized or coupled together, including, e.g., in series (i.e., in tandem), in parallel or combinations thereof, wherein a first device prepared from a first type of tissue (e.g., hepatic) can be linked in series with a second device prepared from a second type of tissue (e.g., cardiac) in order to study drug effects and interactions with multiple tissues. For example, a plurality of Angiochip or Angiotube systems may be configured in series, whereby a first Angiochip/Angiotube is formed of one type of cell or tissue (e.g., cardiac) and a second "downstream" or "upstream" Angiochip/Angiotube is formed of a second type of cell or tissue (e.g., diseased cardiac, or hepatic). In this manner, the interaction of drugs may be tested in the context of multiple organ or tissue systems. For example, a test agent may be introduced into an Angiochip/Angiotube prepared from hepatic tissue, which may be linked downstream to a second Angiochip/Angiotube prepared from cardiac tissue. In this manner, the drug may first interact with the hepatic tissue, and any metabolic products resulting therefrom may flow downstream to the cardiac tissue Angiochip/Angiotube, thereby facilitating one to test the effect of the drug's metabolism on cardiac function. Thus, the invention contemplates a plurality of devices arranged in a tandem (i.e., in series) manner for use in testing inter-organ drug interactions in the body. Any conceivable combination of tissues could be tested in tandem, for example, cardiac/hepatic or hepatic/cardiac.

Kidney

Pharmaceuticals and biologics are a common source of kidney injury (i.e., nephrotoxicity), causing approximately 20% of acquired episodes of acute renal failure (ARF). The development of acute renal failure (ARF) in a hospitalized patient results in a 5-fold to 8-fold higher risk of death. Although hemodialysis, hemofiltration and peritoneal dialysis treatment with its small solute and fluid clearance function has prevented death from hyperkalemia, volume overload and uremic complications, such as pericarditis, patients with ARF still have mortality rates exceeding 50. It is not a complete renal replacement therapy because it only provides filtration function and does not replace the hemostatic, regulatory, metabolic, and endocrine function. Patients with end stage renal disease on dialysis continue to have major medical, social and economic problems. Most drugs found to cause nephrotoxicity exert toxic effects by one or more common pathogenic mechanisms. These include altered intraglomerular hemodynamics, tubular cell toxicity, inflammation, crystal nephropathy, rhabdomyolysis, and thrombotic microan-giopathy. Knowledge of offending drugs and their particular pathogenic mechanisms of renal injury is critical to recognizing and preventing drug-induced renal impairment. A safer and more effective assay for measuring the potential for nephrotoxicity of drugs and biologics would no doubt significantly help reduce the amount of kidney injury today due to medication. Thus, in certain embodiments the bioreactor systems described herein, including, but not limited to a biowire system, a biotube system, a biorod system, an angiochip system, or an antiotube system, can be used to assess kidney tissue, and in particular, measure or assess nephrotoxic effects of drugs and biologics on the kidney.

The methods and bioreactor systems described herein, including, but not limited a biowire system, a biotube system, a biorod system, an angiochip system, or an antiotube system, can be used to test any drug or biologic of interest. Such agents can include active agents known to be nephrotoxic, such as radiographic contrast media (e.g., "contrast agent" or "dye"), non-steroidal anti-inflammatory drugs (NSAID's), amphotericin, cisplatin, methotrexate, acyclovir, gentamicin, acetylcholinesterase inhibitors, other nephrotoxic drugs, and internally generated substances such as products of tumor lysis and products of rhabdomyolysis and toxins associated with infections or septicemia, and the methods of the present invention may also be used to prevent or mitigate renal damage due to an overdose or other ingestion, absorption or exposure to such nephrotoxic substances.

In various embodiments, the devices of the invention can be utilized or coupled together, including, e.g., in series (i.e., in tandem), in parallel or combinations thereof, wherein a first device prepared from a first type of tissue (e.g., renal) can be linked in series with a second device prepared from a second type of tissue (e.g., cardiac) in order to study drug effects and interactions with multiple tissues. For example, a plurality of Angiochip or Angiotube systems may be configured in series, whereby a first Angiochip/Angiotube is formed of one type of cell or tissue (e.g., cardiac) and a second "downstream" or "upstream" Angiochip/Angiotube is formed of a second type of cell or tissue (e.g., diseased cardiac, or renal). In this manner, the interaction of drugs may be tested in the context of multiple organ or tissue systems. For example, a test agent may be introduced into an Angiochip/Angiotube prepared from hepatic tissue, which may be linked downstream to a second Angiochip/Angiotube prepared from renal tissue. In this manner, the drug may first interact with the hepatic tissue, and any metabolic products resulting therefrom may flow downstream to the renal tissue Angiochip/Angiotube, thereby facilitating one to test the effect of the drug's metabolism on organ function. Thus, the invention contemplates a plurality of devices arranged in a tandem (i.e., in series) manner for use in testing inter-organ drug interactions in the body. Any conceivable combination of tissues could be tested in tandem, for example, renal/hepatic or hepatic/renal.

EXAMPLES

Reference will now be made in detail to exemplary embodiments of the invention. In particular, the following Examples discloses five (5) exemplary embodiments of the present invention which may be referred to as Biowires (Example 1, a single-wire tissue culture embodiment), Biotube (Example 2, a perfusable wire tissue culture embodiment), Biorod/BiowireII (Example 3, a contractile force tissue culture embodiment), Biobranch/Angiochip (Example 4, a vascularized tissue culture embodiment), Angiotube (Example 5, a perfusable contractile force tissue culture embodiment). While the invention will be described in conjunction with the exemplary embodiments, it will be understood that it is not intended to limit the invention to those embodiments. To the contrary, it is intended to cover alternatives, modifications, combinations of embodiments, and equivalents as may be included within the spirit and scope of the invention as defined by the appended claims.

Example 1: Biowire

Structure, Preparation, and Use of an Exemplary Single Wire Embodiment (i.e., Biowire)

In a first embodiment, the invention relates to a bioreactor device for growing a three-dimensional tissue comprising a bioreactor having a well or channel, a longitudinal scaffold or suture supported or suspended over the length of the channel, wherein the bioreactor and channel are configured to receive cells seeded therein sufficient to form a 3D tissue strand around the longitudinal scaffold. In various embodiments, the longitudinal scaffold can be a polymer filament, e.g., POMac (poly(octamethylene maleate (anhydride) citrate) or any other suitable polymer scaffold material.

In embodiments involving cardiac cells (or other electrically-stimulated cells), the bioreactor can be further configured to include electrodes configured to generate an electric field across the channel of the bioreactor. The direction of the electric field can be in any direction, but preferably in a direction that is parallel to the length of the channel (and the resulting tissue strand), or which is perpendicular to the length of the channel (and the resulting tissue strand).

As may be used herein, the first embodiment of the invention may be referred to as "Biowire," which may refer to, but is not limited to, the tissue strand itself (i.e., the cells that grow on a bioreactor device as described herein) or the system comprising the tissue strand and the bioreactor together. Biowire may also be referred to herein as its commercial name of BIOWIRE™. which encompasses both the tissue strand itself, or the system comprising the tissue strand and the bioreactor device in which the tissue strand has grown or has been placed. In this embodiment, the device may be scaled up to a configuration that comprises a plurality of bioreactor channels and longitudinal scaffolds such that a plurality of three-dimensional tissue strands may be grown simultaneously.

This first embodiment also relates to methods for growing the tissue strands in the bioreactor, to the three-dimensional tissue strands themselves, to systems comprising both the bioreactor and grown tissue strands, and to methods for using and/or testing the tissue strands (or systems comprising the tissue strands) in various applications, including, but not limited to, (a) the testing of the efficacy and safety (including toxicity) of experimental pharmacologic agents (including, but not limited to, small molecule drugs, biologics, nucleic acid-based agents), (b) the defining of pharmacokinetics and/or pharmacodynamics of pharmacologic agents (including, but not limited to, small molecule drugs, biologics, nucleic acid-based agents), (c) characterizing the properties and therapeutic effects of pharmacologic agents (including, but not limited to, small molecule drugs, biologics, nucleic acid-based agents) on a subject, (d) screening of new pharmacologic agents, (e) provide implantable engineered tissues for use in regenerative medicine for treating damaged and/or diseased tissues, (e.g., use of the tissue constructs, devices, and/or systems of the disclosure to study cardiac disease states, including patients with electrical conduction defects (iPSC-CM)), and (f) personalized medicine. In this embodiment, the device can be configured at a multi-well plate, such as a 6-well, 12-well, 24-well, 96-well, 384-well, and 1536-well plate.

FIGS. 2a-2b show schematics of an example of the disclosed devices. This example device may be suitable for generating a tissue strand, where the device includes features that may promote cell alignment and elongation in the tissue.

The example device may include a longitudinal bioreactor channel in which cells seeded for a tissue culture may be received. A longitudinal scaffold may be supported (e.g., suspended) over the length of the channel. The scaffold may serve as a support for the seed cells to form a tissue structure along the length of the scaffold. The scaffold and channel configuration may enable cell alignment and elongation during cultivation of the tissue.

FIG. 2a shows an example design of the device as a microfabricated bioreactor. In this example, the device includes, as the scaffold, a suspended suture (e.g., a 6-0 suture) template in the bioreactor channel or well. The device may be manufactured using suitable microfabrication techniques, and may be made of any suitable material, such as poly(dimethylsiloxane) (PDMS). Other materials, including poly(methyl methacrylate) (PMMA), polystyrene or other polyurethanes, such as POMac, may be used. Example dimensions are shown in the figure, although other sizes may be suitable.

FIG. 2b shows example steps in generation of a 3D tissue strand, in this example a cardiomyocyte strand, using the example device. At I, the scaffold (e.g., a surgical suture) was placed in the center of the channel. At II, a cardiomyocyte suspension in collagen type I gel was seeded into the main channel around the suture. At III, a pre-culture of hESC-cardiomyocyte was introduced into the channel and cultured over a determined length of time. A time length of 7 days was found to be suitable to allow cells to remodel the gel and contract around the suture. At IV, the resulting tissue strand may be stable after the determined time and can be removed from the device.

The gel in which the seed cell suspension is provided to the device can be any suitable gel capable of supporting the delivered cells, such as collagen or collagen-derived materials. The gel may also contain various growth factors, cell media components, and/or nutrients, such as, but not limited to, carbohydrates, proteins and/or amino acids, Fibroblast Growth Factor (FGF), Brain-Derived Neurtropic Factor (BDNF), beta-Nerve Growth Factor (BNGF), interleukens (e.g., IL-4, IL-2, IL-6, IL-18, IL-15, IL-1), cytokines, IL-6, Granulocyte Macrophage Colony-Stimulating Factor (GM-CSF), Stem Cell Factor (SCF), Interferon Gamma (IFN-gamma), Epidermal Growth Factor (EGF), Recombinant Human Hepatocyte (RHH), Recombinant Human Insulin (RHI). As will be appreciated by those having ordinary skill in the art, the growth factors can be specific for a particular tissue being cultured in the bioreactor, e.g., cardiac-specific or hepatocyte-specific growth factors. Such factors will be well-known in the art.

The example device may be fabricated using any suitable technique, such as soft lithography techniques. In an example, a two-layer SU-8 (Microchem Corp.) master was used to mold PDMS. Briefly, device features were printed on two film masks (CADART) corresponding to the two-layer design. SU-8 2050 was spun onto 4-inch silicon wafer, baked, and exposed to UV light under the first-layer mask to create the first layer including the suture channel and the chamber with thickness of 185 µm. The second layer, including only the chamber with thickness of 115 µm was spun on top. After additional baking, the second-layer mask was aligned to the features on the first layer and then UV exposed. Finally, the wafer was developed using propylene glycol monomethyl ether acetate (Doe & Ingalls Inc.). PDMS was then cast onto the SU-8 master and baked for 2 hr at 70° C. The device was configured to hold the scaffold, in this example a piece of surgical suture, suspended (e.g., centrally) in the channel to which the cell suspension gel may be added.

Although certain materials, techniques and dimensions are described above, other suitable materials, techniques and dimensions may be used for the example device. Although a surgical silk suture is described, other supports, such as lengths of other materials (e.g., poly(glycerol sebacate), POMac, poly(lactic acid), poly(glycolic acid), poly(ε-caprolactone), various polyurethanes as well as co-polymers thereof), may be used as a scaffold for supporting cultivation of the tissue strand.

B. Experimental Testing of an Exemplary Biowire Tissue Culture System

Mature and beating rat and human cardiac tissues were generated using the device of Example 1A and the generated tissues were assessed for functional and structural properties.

Example Methods and Analyses

Neonatal rat cardiomyocytes were obtained from 2-day old neonatal Sprague-Dawley rats as described previously[21] and according to a protocol approved by the University of Toronto Committee on Animal Care. The culture media contained 10% (v/v) fetal bovine serum, 1% (4-(2-hydroxyethyl)-1-piperazineethanesulfonic acid) (HEPES), 100 U/ml penicillin-streptomycin, 1% Glutamine, and the remainder Dulbecco's modified Eagle's medium.

The cardiomyocytes used were derived from two different human embryonic stem cell lines (hESC, Hes2 and Hes3) and two different hiPSC lines (CDI-MRB and HR-I-2Cr-2R). Both hESC lines and hiPSC line HR-I-2Cr-2R were maintained as described[2,4]. Embryoid bodies (EBs) were differentiated to the cardiovascular lineage as previously described[2,4]. In brief, EBs were generated by culture in StemPro-34 (Invitrogen) media containing BMP4 (1 ng/ml). On day 1, EBs were harvested and suspended in induction medium (StemPro-34, basic fibroblast growth factor (bFGF; 2.5 ng/ml), activin A (6 ng/ml) and BMP4 (10 ng/ml)). On day 4, the EBs were harvested from the induction medium and re-cultured in StemPro-34 supplemented with vascular endothelial growth factor (VEGF; 10 ng/ml) and DKK1 (150 ng/ml). On day 8, the medium was changed again and the EBs were cultured in StemPro-34 containing VEGF (20 ng/ml) and bFGF (10 ng/ml) for the duration of the experiment. Cultures were maintained in hypoxic environment (5% $CO_2$, 5% $O_2$) for the first 12 days and then transferred into a 5% $CO_2$ for the remainder of the culture period. EBs were dissociated for seeding in tissue at day 20 (EBd20) as well as at day 34 (EBd34) and day 40-44 (EBd44) for specific cellular and electrophysiological analyses. CDI-MRB hiPSC-derived cardiomyocytes were purchased from Cellular Dynamics International and used for tissue production immediately after thawing.

Cardiac cells from neonatal rat isolation were first suspended at 200 million/ml (unless specified otherwise) in Collagen Type I based gel (2.5 mg/ml of rat tail collagen type I (BD Biosciences) neutralized by 1N NaOH and 10×M199 media as described by the manufacturer) with the supplements of 4.5 μg/ml glucose, 1% (v/v) HEPES, 10% (v/v) Matrigel (BD Biosciences), and 2 μg/ml $NaHCO_3$. Suspended cardiac cells were then seeded into the cell culture channel of the example device (3 μl per tissue strand). After 30 min incubation at 37° C. to induce the gelation, appropriate media were added. Cardiac tissue strands were kept in culture for up to 14 days with media change every 2-3 days. Cardiac tissue strands starting with different cell densities (100 and 200 million/ml) were seeded to study the effect of the cell seeding density. Collagen-based gel was seeded into the cell culture channel of the example device without loading cardiac cells, to serve as a cell-free control. Ultra-long cardiac tissue strands were generated with an example device having a 5 cm long bioreactor channel fabricated in a similar manner as described above and seeded with neonatal rat cardiomyocytes. After seeding, brightfield images of the tissue strands were taken every day (n=3 per group) using an optical microscope (Olympus CKX41) and the diameters of the tissue strands at five distinct locations were averaged with image analysis.

For human cardiac tissue strands, day 20 EBs generated as described above were incubated in collagenase type I (1 mg/ml; Sigma) and DNAse (1 mg/ml, CalBiochem) in Hank's Balanced Salt Solution (NaCl, 136 mM; $NaHCO_3$, 4.16 mM; $Na_3PO_4$, 0.34 mM; KCl, 5.36 mM; $KH_2PO_4$, 0.44 mM; dextrose, 5.55 mM; HEPES, 5 mM) for 2 hr at 37° C. EBs were centrifuged (800 r.p.m., 5 min), incubated with trypsin (0.25%, Gibco) for 5 min at 37° C. and pipetted gently to dissociate the cells. After dissociation, cells were centrifuged (1,000 r.p.m., 5 min), counted and seeded at $0.5 \times 10^6$ cells/strand of 0.5 cm in length. This ratio was maintained for generation of longer tissue strands. Cells were seeded in collagen type I gels (4 μl/0.5 cm wire length; 2.1 mg/ml of rat tail collagen type I (BD Biosciences) in 24.9 mM Glucose, 23.81 mM $NaHCO_3$, 14.34 mM NaOH, 10 mM HEPES, in 1×M199 media+10% of growth factor reduced Matrigel (BD Biosciences)) by pipetting the cell suspension into the main channel of the example device. CDI-MRB hiPSC-derived cardiomyocytes were thawed, counted and seeded in same concentration as hESC-derived cardiomyocytes. After seeding, cells were kept in culture for 7 days to allow collagen matrix remodeling and assembly around the suture.

Different electrical stimulation conditions were applied to the rat cardiac tissue strands as described previously[2]. Parallel stimulation chambers were fitted with two ¼-inch-diameter carbon rods (Ladd Research Industries) placed 2 cm apart, perpendicular to the tissue strands (such that the electrical field was parallel with the tissue strand long axis), and connected to a stimulator (S88X, Grass) with platinum wires (Ladd Research Industries). The perpendicular stimulation chambers were built with two carbon rods 1 cm apart placed parallel with the tissue strands (i.e. the field was perpendicular to the long axis of the tissue strands). The tissue strands were pre-cultured for 4 days until the tissue strand structures were established and their spontaneous beating was synchronized, and then subjected to the electrical field stimulation (biphasic, rectangular, 1 ms duration, 1.2 Hz, 3.5-4 V/cm) for 4 days with 10 μM ascorbic acid supplemented in the culture media while control tissue strands were cultured without electrical stimulation. At the end of electrical stimulation, the rat cardiac tissue strands were stained against cTnT and Cx-43, or their mechanical properties were measured by atomic force microscopy (AFM).

For human cardiac tissue strands, after preculture for 7 days, tissue strands were transferred to stimulation chambers fitted with two ¼-inch-diameter carbon rods (Ladd Research Industries, Burlington, Vt.) placed 2 cm apart and connected to a cardiac stimulator (Grass s88x) with platinum wires (Ladd Research Industries). Tissue strands were placed perpendicular to the electrodes and were either submitted to electrical stimulation (rectangular, biphasic, 1 ms, 3-4 V/cm) or cultured without electrical stimulation (non-stimulated controls or CTRL) for 7 days. Two electrical filed stimulation protocols were used: (I) where stimulation started at 1 Hz and increased gradually and daily to 3 Hz (1, 1.83, 2.66 and 3 Hz) where it was maintained for the remainder of the week or (II) where stimulation started at 1 Hz and increased gradually to 6 Hz throughout the week (1, 1.83, 2.66, 3.49, 4.82, 5.15 and 6 Hz, daily frequencies). FIG. 3A shows example electrical stimulation regimens applied to the tissue cultivated in the device of Example 1. Pre-cultured tissue strands were submitted to electrical stimulation at 3-4 V/cm for 1 week. Electrical stimulation started at 1 Hz and was progressively increased to 3 Hz where it was kept for the remainder of the week (low frequency ramp-up stimulation regimen or 3 Hz group). In addition, stimulation rate was progressively increased from 1 to 6 Hz (High frequency ramp-up stimulation regimen or 6 Hz group).

Figure 4:
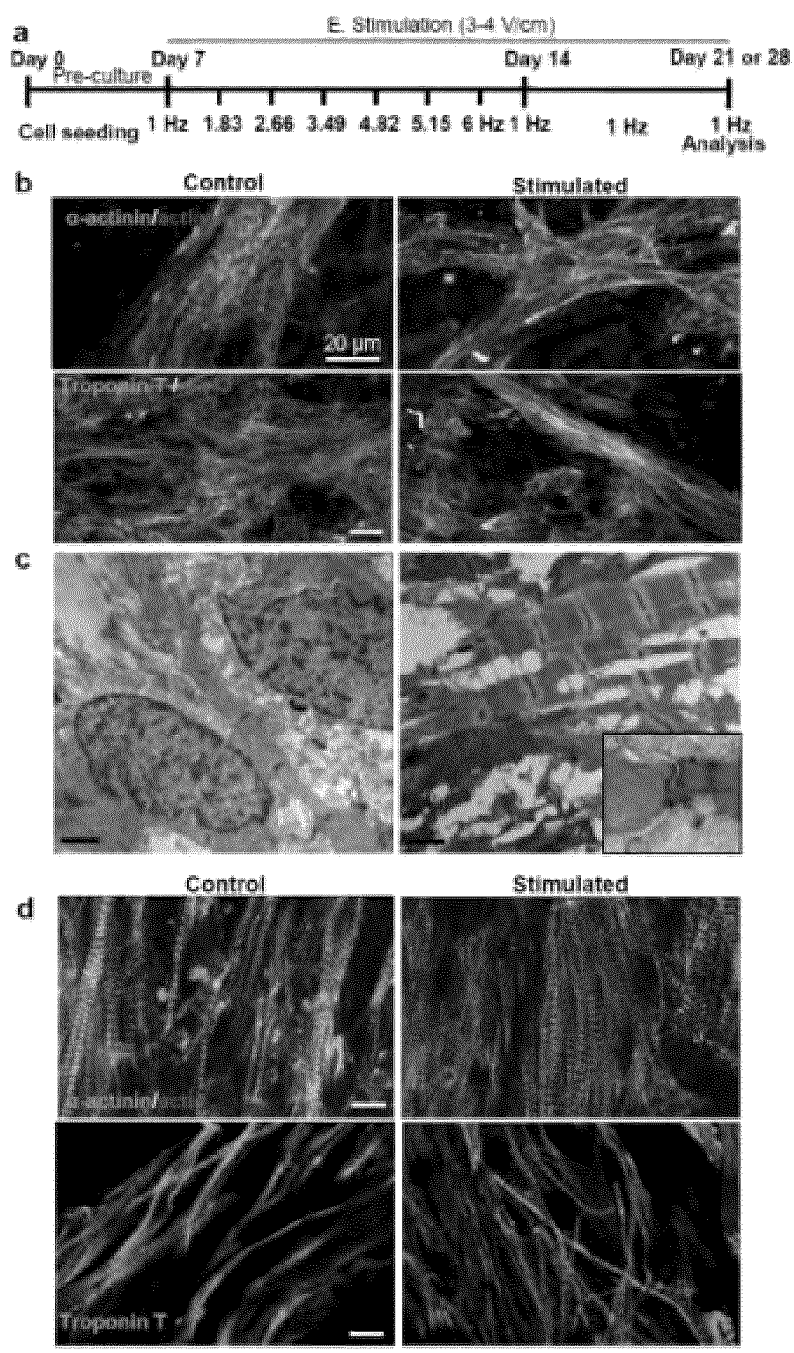
FIGS. 4a-4d show an example protocol for long-term cultivation of cardiac tissue strands and the organization of contractile apparatus of cardiac tissues cultured using an exemplary biowire system of the disclosure.

Since increased time in culture has been shown to affect maturation[11,28], age matched EBs (EBd34) were used as an additional control. For long term stimulation experiments, the tissue strands were precultured for 7 days as described above, followed by 7 days of 6 Hz ramp-up protocol, at which point the frequency was decreased to 1 Hz (to mimic post-natal heart rate decrease) and maintained for additional 14 days. FIG. 4A shows an example electrical stimulation regimen used for this.

To verify that the cultivated cardiomyocyte tissue strands truly exhibited maturation on a single-cell basis, assays were performed in which single cells were used. FIG. 3B illustrates how, at the end of the stimulation regimen, cells from the cultivated tissue strands were isolated to be assessed for functional, ultrastructural, cellular and molecular responses.

The cultivated tissue strands were digested with collagenase type I (1 mg/ml; Sigma) and DNAse (1 mg/ml, Cal-Biochem) in Hank's Balanced Salt Solution (NaCl, 136 mM; $NaHCO_3$, 4.16 mM; $Na_3PO_4$, 0.34 mM; KCl, 5.36 mM; $KH_2PO_4$, 0.44 mM; dextrose, 5.55 mM; HEPES, 5 mM) for 4 hr at 37° C., centrifuged (800 r.p.m., 5 min), incubated with trypsin (0.25%, Gibco) for 5 min at 37° C. and pipetted gently to dissociate the cells. Isolated single cells were seeded on Matrigel- or laminin-coated glass cover slips as described below before area, calcium transient and patch clamp measurements were performed.

The progression of tissue assembly was assessed at various levels after 2 weeks in culture (i.e. 7 days of gel compaction followed by 7 days of stimulation): functional (excitation threshold (ET), maximum capture rate (MCR), conduction velocity, $Ca^{2+}$ handling); ultrastructural (sarcomere development, frequency of desmosomes), cellular (cell size and shape, proliferation, distribution of cardiac proteins: actin, troponin T and α-actinin), electrophysiological (hERG, $I_{K1}$, $I_{Na}$) and molecular (expression levels of cardiac genes and proteins).

Nuclei elongation and alignment were quantified. Cell nuclei within the tissue strands were visualized by DAPI staining and z-stack images were obtained by confocal microscopy with 3 μm interval. Each stack of the confocal images was analyzed in ImageJ 1.45s (National Institutes of Health, USA) with an automated algorithm described by Xu et al[27] with approximately 1000 nuclei analyzed per sample. Nuclei elongations were characterized as nucleus aspect ratios, the ratio of long axis over short axis of the nuclei, and nuclear alignment was characterized by orientation angles. In the control monolayer group, orientation of the nuclei was characterized compared to an arbitrarily defined orientation, while in the tissue strand group, the orientation of the suture templates was set as reference.

Rat cardiac tissue strands were fixed with 4% paraformaldehyde, permeabilized by 0.25% Triton X-100, and blocked by 10% bovine serum albumin (BSA) Immunostaining was performed using the following antibodies: mouse anti-cardiac Troponin T (cTnT) (Abcam; 1:100) and rabbit anti-Connexin 43 (Cx-43) (Abcam; 1:200), goat anti-mouse-Alexa Fluor 488 (Jackson Immuno Research; 1:400) and anti-rabbit-TRITC (Invitrogen; 1:200). Nuclei were counterstained with 4',6-diamidino-2-phenylindole (DAPI) (Biotium; 1:100). Phalloidin-Alexa 660 (Introgen; 1:600) was used to stain F-actin fibers. For confocal microscopy, the stained cardiac tissue strands were visualized under an inverted confocal microscope (Olympus IX81) or an upright confocal microscope (Zeiss LSM 510).

Immunostaining of human cardiac tissue strands was performed using the following antibodies: mouse anti-cTNT (1:100, Thermo Scientific; MS-295-P1), mouse anti-α-actinin (1:200, Abcam, ab9465), anti-mouse-Alexa Fluor 488 (1:400, Invitrogen, A21202), anti-Ki67 (1:250, Millipore, AB9260), anti-rabbit-TRITC (1:400, Invitrogen, 81-6114). DAPI was used to counterstain nuclei. Phalloidin Alexa Fluor 660 (1:1000, Invitrogen, A22285) was used to detect actin fibers. The stained cells were visualized using a fluorescence microscope (Leica CTR6000) and images captured using the Leica Application Suite software. For confocal microscopy cells were visualized using a fluorescence confocal microscope (Zeiss LSM-510).

After application of electrical stimulations for 4 days, rat cardiac tissue strands were tested using a commercial atomic force microscope (AFM) (Bioscope Catalyst; Bruker) mounted on an inverted optical microscope (Nikon Eclipse-Ti). The force-indentation measurements were done with a spherical tip (radius=5-10 μm) at nine distinct spots to evenly cover the center of the cardiac tissue strands with 5 nN trigger force at 1 Hz indentation rate. The cantilever (MLCT-D, Bruker) had a nominal spring constant of 0.03 N/m. The Hertz model was applied to force curves to estimate the Young's modulus and detailed data analysis was described elsewhere[30]. All AFM measurements were done in fluid environment at room temperature.

The tissues were also investigated using transmission electron microscopy (TEM). Tissue strands were fixed with 4% Paraformaldehyde, 1% Glutaraldehyde in 0.1 M PBS for at least 1 hr and washed 3 times with PBS pH 7.2. Post-fixation was done with 1% Osmium Tetraoxide in 0.1 M PBS, pH 7.2 for 1 hr and dehydrated using ethanol series from 25 to 100%. Tissue was infiltrated using Epon resin and polymerized in plastic dishes at 40° C. for 48 hr. Tissue was stained with Uranyl Acetate and Lead Citrate after sectioning. Imaging was performed at Hitachi H-7000 transmission electron microscope.

For optical mapping, tissue strands were incubated with a voltage sensitive dye (Di-4-ANEPPS 5 μM, Invitrogen) for 20 min at 37° C. in warm Tyrode's solution (NaCl 118 mM, KCl, 4.7 mM, $CaCl_2$ 1.25 mM, $MgSO_4$ 0.6 mM, $KH_2PO_4$ 1.2 mM, $NaHCO_3$ 25 mM, glucose 6 mM; oxygenated by bubbling carbogen 95% $O_2$, 5% $CO_2$ for at least 20 minutes shortly before use). Dye fluorescence was recorded on a MVX-10 Olympus fluorescence microscope equipped with a high-speed CMOS camera (Ultima-L, Scimedia)[29-30]. The 1-cm sensor had 100×100 pixel resolution and the spatial resolution varied between 50 to 100 μm/pixel. Imaging was performed at 200 frames/s. The fluorescence was excited using a mercury arc source (X-Cite Exacte) with green filter (Olympus U-MWIG2 filter cube). The constructs were electrically point-stimulated using a bipolar electrode made of two fine wires (AWG#32) inserted in a stainless steel needle, which was mounted on a micromanipulator (World Precision Instruments). For electrical field stimulation, the chamber depicted in FIG. 3 was used. The plate containing the tissue strands was placed on a heated plate (MATS-U55S, Olympus) and temperature was regulated at 38° C. Data analysis was performed using BrainVision software (Scimedia).

Intracellular recordings were also taken. Action potentials were recorded in tissue strands with high-impedance glass microelectrodes (50-70 MΩ, filled with 3 M KCl) at 37±0.5° C. Tissue strands were superfused with Kreb's solution containing (in mM): 118 NaCl, 4.2 KCl, 1.2 $KH_2PO_4$, 1.8 $CaCl_2$, 1.2 $MgSO_4$, 23 $NaHCO_3$, 20 Glucose, 2 Na-Pyruvate, equilibrated with 95% $O_2$ and 5% $CO_2$, final pH was 7.4. The microelectrodes were connected to an Axopatch 200B amplifier (Axon Instrument) current-clamp. Signals were filtered at 1 KHz, sampled at 2 KHz and analyzed with Clampfit 10 (Axon Instrument). Resting potentials were measured at I=0 mode. For some experiments, tissue strands were paced using field stimulation set at twice the excitation threshold.

Patch-clamp recordings were taken. Single cells isolated from cultivated tissue strands or EBs were seeded on laminin-coated glass cover slips (Laminin, Sigma-Aldrich, 10 µg/cm$^2$) overnight before patch-clamp experiments were performed. Whole-cell patch-clamp recordings were made using an Axopatch 200B amplifier at room temperature (23-25° C.). Data were analyzed with Clampfit 8.0 (Axon Instrument). Amplifier was set at I=0 when measuring resting potential of cells. Action potentials were recorded by using the current-clamp mode method. Myocytes were stimulated at 1 Hz and the maximum rate of membrane depolarization, the action potential peak and APD90 of the 10$^{th}$ action potential were measured. The membrane potentials were not corrected for the liquid junction potentials, which were estimated to be 15.9 mV (estimated with Clampfit 8.0) for the solutions used. Na$^+$ current, hERG current and $I_{k1}$ current were also recorded under voltage-clamp conditions with 70-80% series resistances compensation. Na$^+$ current was induced from holding potential of −80 mV by applying a series of test pulses ranging from −120 mV to +30 mV for 500 ms with 10 mV increments followed by a test pulse to −10 mV for 100 ms for steady-state inactivation measurement. Although this protocol simultaneously activates overlapping voltage-dependent Ca$^{2+}$ currents, these Ca$^{2+}$ currents were estimated (using prepulse protocols) to be less than 3% of the evoked Na$^+$ currents. hERG was assessed by measuring tail currents in response to steps to −50 mV (for 500 ms) following depolarization to voltage steps ranging from −45 mV to 60 mV with 15 mV increments for 2,000 ms. The peak amplitude of hERG tail current was measured and compared. $I_{K1}$ current was measured in two ways that were found to be equivalent for these studies. For complete I-V relationships, Ba$^{2+}$-sensitive currents were assessed by subtracting (trace-by-trace for voltage steps ranging from −120 to −10 mV in 10 mV increments from holding potential of −40 mV) the currents measured in the presence of 500 µM Ba$^{2+}$ from the current measured in the absence of Ba$^{2+}$. For the purposes of measuring the $I_{K1}$ density, the background current was subtracted from that measured in the absence of Ba$^{2+}$ at −100 mV.

Patch-clamp recordings were performed in bath solutions containing (in mM): 140 NaCl, 4 KCl, 1 $MgCl_2$, 1.2 $CaCl_2$, 10 HEPES, 10 D-glucose, at the pH 7.35 adjusted with NaOH. Pipette resistance was around 5.5-7.5 MΩ when filled with a solution containing (in mM): 120 potassium aspartate, 20 KCl, 4 NaCl, 1 $MgCl_2$, 5 MgATP, 10 HEPES, 10 EGTA, at the pH 7.2 adjusted with KOH (calculated reversal potential of K$^+$ was −95.6 mV after pH adjustment).

Dofetilide 100 nM[31] and $BaCl_2$ 500 µM[11] were used to block hERG current and $I_{k1}$ respectively.

Calcium transient measurements were taken. Tissue strands were dissociated by incubation with collagenase and trypsin as described in detail above. The dissociated cardiomyocytes were plated onto growth factor free Matrigel (diluted 1:60 in RPMI media)-coated 25-mm microscope glass coverslips overnight. Cells were then incubated with 5 µM of fluo-4 acetoxymethyl ester (fluo-4 AM) in culture media for 2 hours at 37° C. Subsequently, cardiomyocytes were washed twice with dye-free medium and placed back into the incubator for 30 min. A laser scanning confocal microscope (Zeiss LSM 510) was used to measure the fluorescence intensity of fluo-4 AM. The coverslips containing the fluo-4 AM-loaded cardiomyocytes were moved onto a special chamber and tightly secured. Approximately 1.8-1.9 ml of culture medium was added into the chamber, which was placed on a temperature controlled-plate (37° C.) on the microscope. Fluo-4 was excited via an argon laser (488 nm) and emitted fluorescence was collected through a 505 nm emission filter. Changes in fluo-4 AM fluorescence intensity, which indicates transient fluctuation of cytosolic calcium concentration, were recorded in frame and line scan model. The images and fluorescence data were acquired through Zeiss software. The fluorescence data were analyzed with Origin 8.5 software. Fluorescence signals (F) were normalized to baseline fluorescence after loading fluo-4 AM. The rising phase of the signals was fitted by linear model while the decaying phase of the signals was fitted by ExpDecay with Offset model. Caffeine, Verapamil (Sigma) and Thapsigargin (Invitrogen) were directly added into the chamber that contained the cardiomyocytes during imaging at concentrations indicated in the figures. Cells beating at similar average beating frequency (9.4±0.7 bpm for control, 9±0.7 bpm for 3 Hz, and 10±0.8 bpm for 6 Hz regimen) were used for calcium transient measurements in order to ensure that differences in beating rates would not affect the measurements.

Quantitative RT-PCR was performed as previously described[32]. Total RNA was prepared with the High Pure RNA Isolation Kit (Roche) and treated with RNase-free DNase (Roche). RNA was reverse transcribed into cDNA using random hexamers and Oligo (dT) with SuperScript VILO (Invitrogen). RT-qPCR was performed on a LightCycler 480 (Roche) using LightCycler 480 SYBR Green I Master (Roche). Expression levels were normalized to the housekeeping genes TATA box binding protein (TBP) or Glyceraldehyde 3-phosphate dehydrogenase (GAPDH). The oligonucleotide sequences are summarized in Table 3 shown in FIG. 28.

Flow cytometry analysis was performed. Cells were obtained from tissue strands or EBs by dissociation with collagenase and trypsin as described above and fixed with 4% paraformaldehyde for 10 min at room temperature. For intracellular epitopes, cells were permeabilized in PBS containing 5% fetal bovine serum (FBS) and 0.1% Triton X for 10 minutes on ice before a blocking step of 5% FBS in PBS for 30 min. Cells were incubated with the following antibodies in blocking buffer on ice for 1 hour: anti-CD31-PE (1:100), anti-CD90-APC (1:500, BD biosciences, 553373 and 559879, respectively); anti-cTNT (1:100, Thermo Scientific, MS-295-P1); anti-calponin H1 (1:250, Abcam, ab46794); anti-vimentin (1:100, Sigma Aldrich, V6630). Secondary antibodies used were anti-mouse-Alexa Fluor 488 (1:400, Invitrogen, A21202) and anti-rabbit-Cy5 (1:500, Jackson ImmunoResearch, 111-175-144). Due to the intrinsic variability in the percentage of cardiomyocytes in each assay, the percentage of cells positive for each marker (above the secondary antibody only control) was normalized to the starting cell population (EBd20) of each experiment to accurately evaluate if a change in cell population was occurring.

Tissue strands were solubilized in (2×) Novex Tris-Glycine SDS sample buffer (Life technologies) and proteins were separated by electrophoresis in Novex Tris-Glycine gels (Life technologies) and transferred to Biotrace NT (Nitrocellulose, Pall Corp.). Membranes were probed with either anti-myosin heavy chain (total, Abcam, ab15), Phospholamban 1D11 (from Dr. A. Gramolini, University of Toronto) or GAPDH (Millipore, MAB374) antibodies. Secondary antibodies used were peroxidase conjugated (DAKO, P0448 or P0447). Membranes were developed with ECL reagent Luminata Classico Substrate (Millipore).

Statistical analysis was performed using SigmaPlot 12.0. Differences between experimental groups were analyzed by Student's t test or two-way ANOVA. Normality test (Shapiro-Wilk) and pairwise multiple comparison procedures (Holm-Sidak method) were used for two-way ANOVA tests or Chi-square test as appropriate based on normality and variance of data. $P < 0.05$ was considered significant for all statistical tests.

Example Results and Discussion

Generation and Characterization of Rat Cardiac Tissue Strands

Figure 5:
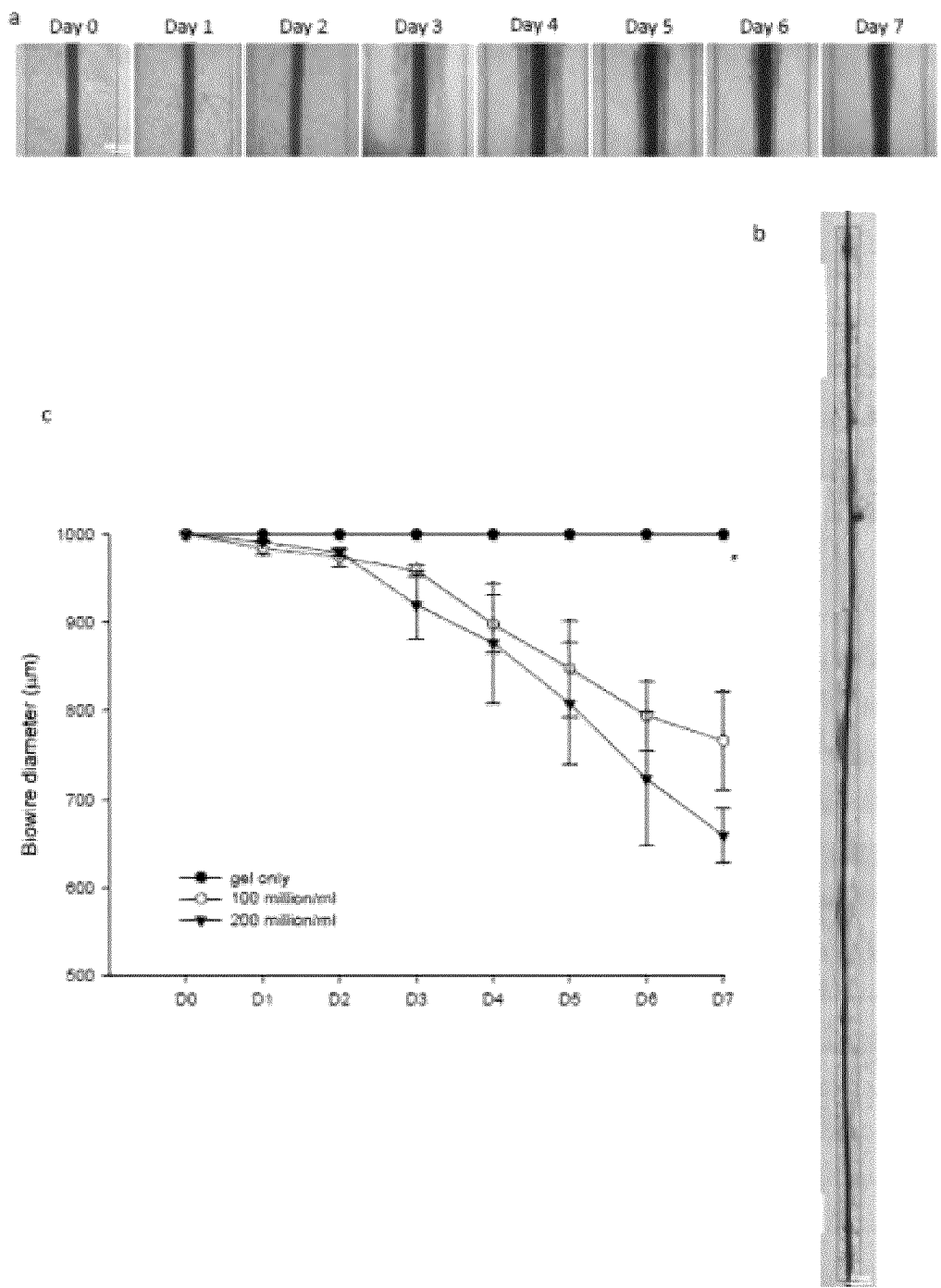
FIGS. 5a-5c show the generation of cardiac tissues over seven days, in accordance with an exemplary biowire system of the disclosure.

The disclosed devices may enable in vitro reproduction of the highly anisotropic structure of the native myocardium. The supporting wire may serve a function similar to the in vivo capillaries that serve as templates around which cardiomyocytes elongate and align. Primary neonatal rat cardiomyocytes were used to generate 3D, self-assembled cardiac tissue strands by seeding within type I collagen-based gel into microfabricated PDMS platforms with suspended templates. Seeded neonatal rat cardiomyocytes (8.75 million cells/ml) remodeled and contracted the collagen gel matrix around the suture templates within a week, to form the tissue strand structure (see FIG. 5a). The gel compaction only occurred with the presence of the seeded cells, as cell-free gels did not compact or degrade during the culture time, and the compaction rate positively correlated with the cell seeding density. Cardiac tissue strands of different dimensions could be generated by customizing the dimensions of the example device. For example, tissue strands as long as 5 cm may be generated, as shown in FIG. 5b. Generation of longer tissue strands may be possible using a device of suitable dimensions.

FIG. 5c shows quantification of gel compaction and its dependence on initial seeding density of cardiomyocytes (mean±SD, n=3). With no cardiomyocytes seeded (gel only), the gel did not compact and form tissue strands structure. Tissue strands with higher seeding density (200 million cells/ml) compacted faster than those with lower seeding density (100 million cells/ml) during the remodeling.

Figure 6:
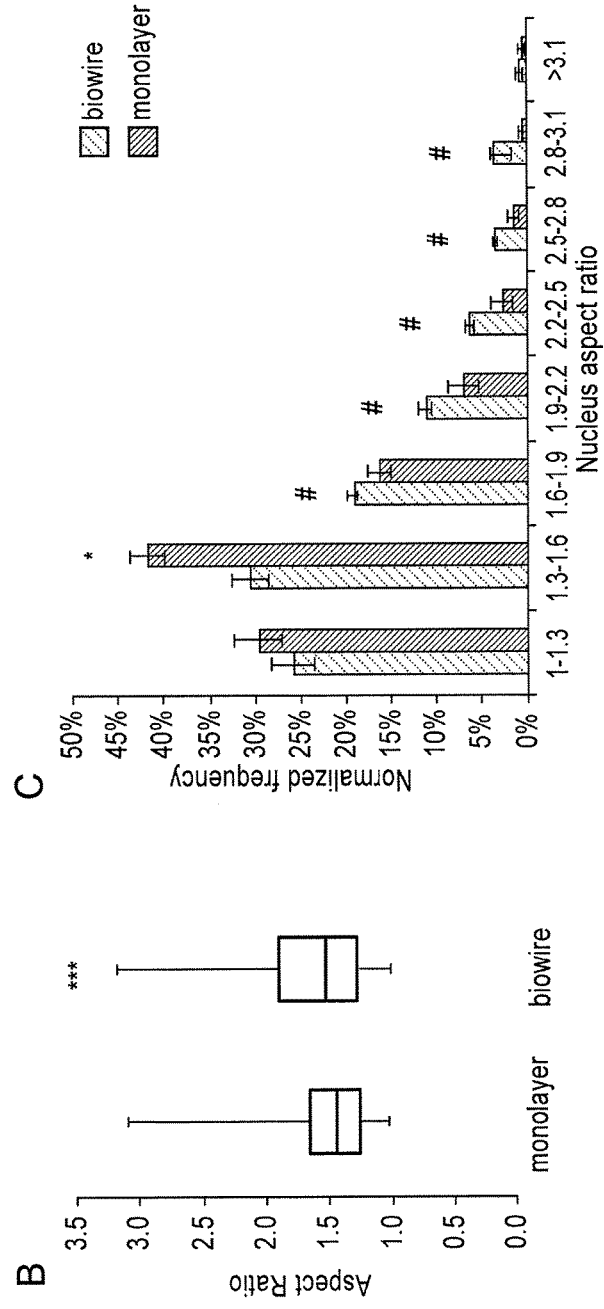
FIGS. 6a-6d show the shapes and orientations of cardiac cells cultured in accordance with an exemplary biowire system of the disclosure, compared with monolayer tissues.
Figure 6:
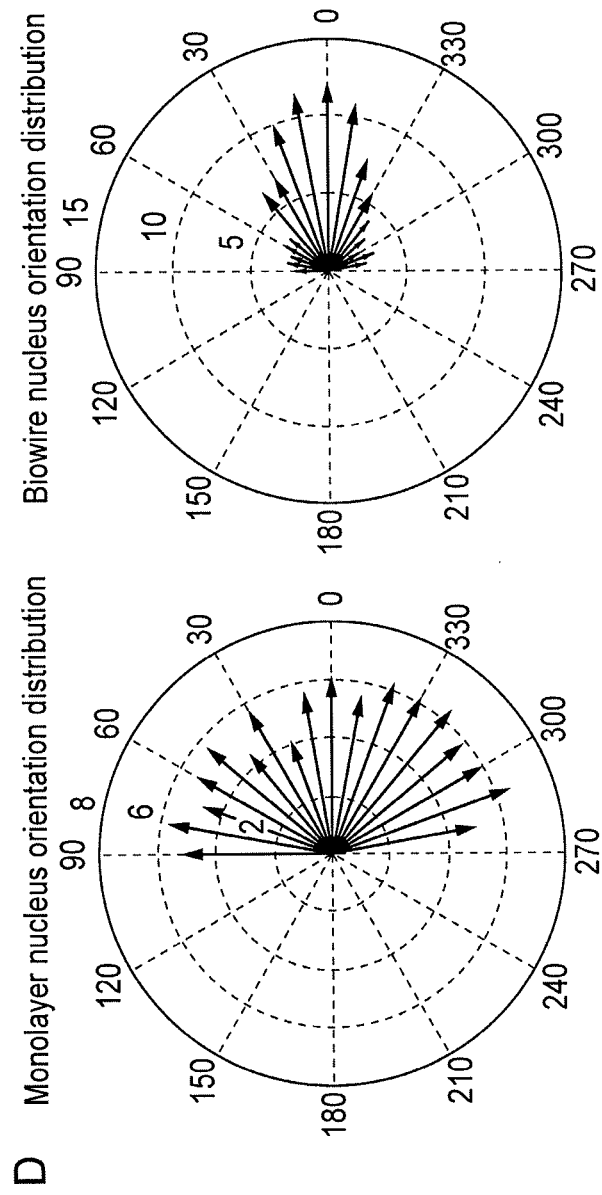

As illustrated in FIG. 6, the suture template may provide topographical cues in the tissue strands for the cardiomyocytes to elongate and align. FIG. 6a shows confocal images of a tissue strand with nuclei counterstained with DAPI (left) and cardiac Troponin-T (cTnT) stained with Alexa 488 (right). Image analysis of the cell nuclei that was counterstained with DAPI revealed nuclei elongation and alignment along the axis of suture template. In FIG. 6b, nuclei aspect ratios (~1000 nuclei characterized per sample) of cardiac cells cultured as monolayer vs. seeded in the tissue strands are shown in box plot showing the $1^{st}$ quartile, median, and $3^{rd}$ quartile with a significant difference between two groups (***, $p < 0.001$). FIG. 6c is a histogram showing the distribution of nuclei aspect ratios of tissue strand group and monolayer group (mean±SD, n=3 per group). There were significantly higher frequencies in the lower aspect ratio range in monolayer group (*, $p < 0.05$) and higher frequencies in higher aspect ratio range in the tissue strand group (#, $p < 0.05$). Characterization of nucleus orientation (see FIG. 6d) also revealed random distribution of nuclei in the monolayer group (random direction as 0°) while cell nuclei in the cultivated tissue strands were oriented along with the axis of the suture template (orientation of suture template as 0°).

Neonatal rat cardiac tissue strands started to beat spontaneously between 3 and 4 days post-seeding and kept beating during gel compaction, demonstrating that the example device allowed for electromechanical coupling of the cells within the hydrogel matrix. The spontaneous beating of tissue strands with higher seeding density (200 million/ml) started earlier and was more prominent than in those with lower seeding density (100 million/ml), which is thought to be a result of the presence of more cardiomyocytes and better coupling. Immunohistochemistry staining showed that the rat cardiac tissue strands expressed the sarcomeric protein, cTnT (see FIG. 6a, right).

Electrical Stimulation of Rat Tissue Strands

Figure 7:
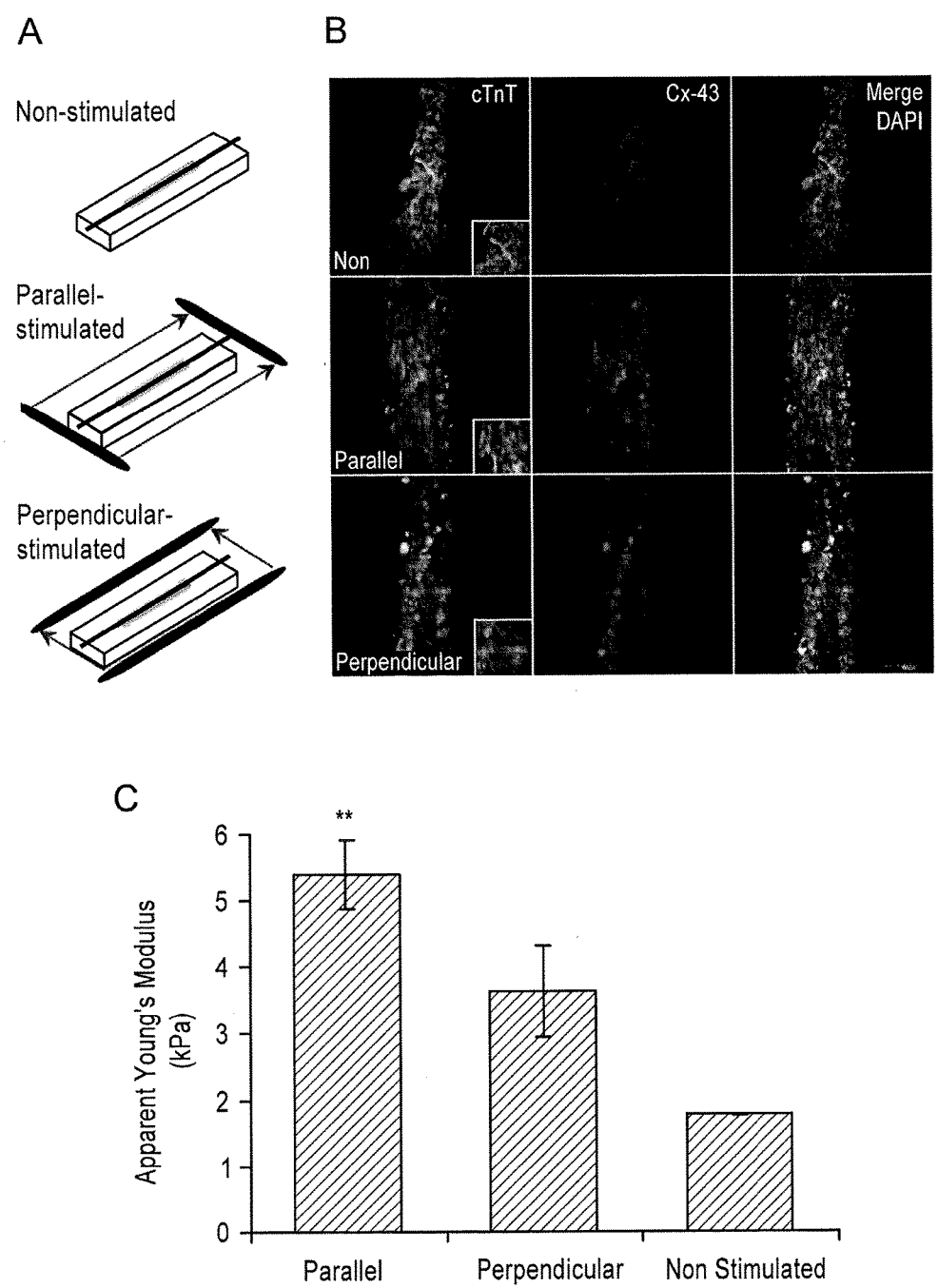
FIGS. 7a-7c show example results from electrical stimulation of rat cardiac cells generated in accordance with an exemplary biowire system of the disclosure.

To demonstrate the versatility of the disclosed Example 1 device, electrical stimulation was applied to further improve the phenotype of cardiomyocytes. FIG. 7a shows experimental set-up of tissue strands under different electrical stimulation conditions. Carbon rods connected to an external stimulator provided either parallel or perpendicular electrical field stimulation on cardiac tissue strands for 4 days starting on Day 4.

Immunohistochemical staining was carried out. FIG. 7b shows representative confocal images of cultivated rat cardiomyocytes tissue strands after application of different electrical stimulation conditions. Parallel-stimulated tissue strands showed more cTnT+ structures oriented along with the suture template (left) and stronger expression of Connexin 43 (Cx-43) (right) compared with non-stimulated (control) and perpendicular-stimulated tissue strands. Cx-43 is a marker for the gap junctions between adjacent cardiomyocytes, indicating better coupling between the cardiomyocytes.

When handling the rat cardiac tissue strands outside the device, it was noticed that the parallel-stimulated tissue strands were stiffer than the non-stimulated control. This was further assessed by AFM analysis (n=3 per group), which revealed significantly (p=0.009) improved mechanical properties of parallel-stimulated tissue strands compared to non-stimulated controls (see FIG. 7c).

Figure 8:
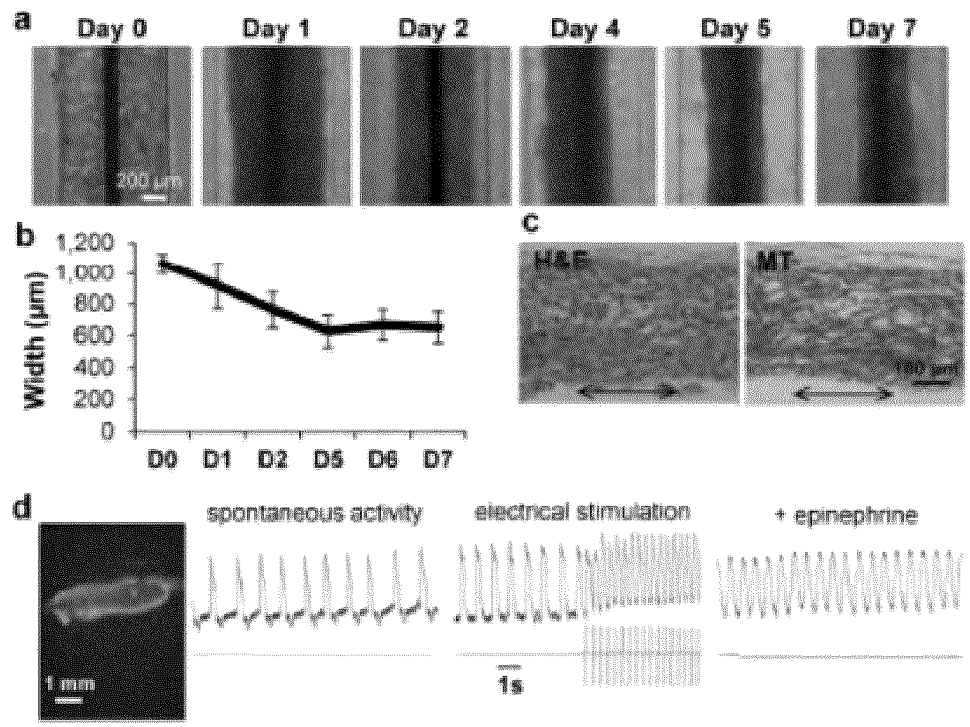
FIGS. 8a-8d show example images and results from generation of human cardiac cells in accordance with an exemplary biowire system of the disclosure.

Engineering of Human Cardiac Tissue Strands hPSC-cardiomyocytes and supporting cells obtained from directed differentiation protocols were used to generate 3D, self-assembled cardiac tissue strands by cell seeding into a template polydimethylsiloxane (PDMS) channel, around a sterile surgical suture in type I collagen gels. FIGS. 8a-d illustrate results obtained with Hes2 hESC-derived cardiomyocytes. FIG. 8a shows example images of pre-culture of hESC-cardiomyocyte in the device template for 7 days. Seeded cells remodeled and contracted the collagen gel matrix during the first week with ~40% gel compaction. FIG. 8b shows quantification of gel compaction on the indicated days of culture (average+/−s.d., n=3 (day 0), n=4

(days 1-7)), showing a final width of ~600 µm. This allowed removal of the cultivated tissue strand from the PDMS template.

Histology revealed cell alignment along the axis of the suture. FIG. 8c shows Hematoxylin and Eosin (H&E) and Masson's Trichrome (MT) staining of tissue strand sections (arrows represent suture axis). Tissue strands were found to beat synchronously and spontaneously between 2 and 3 days post-seeding and kept beating after gel compaction, demonstrating that the setup enabled electromechanical cell coupling. Tissue strands could be electrically paced and responded to physiological agonists such as epinephrine (β-adrenergic stimulation) by increasing spontaneous beating frequency. FIG. 8d shows optical mapping of impulse propagation. A representative picture (left) of a tissue strand being imaged with potentiometric fluorophore (DI-4-ANEPPS) showing the spontaneous electrical activity, with impulse propagation recording (left trace recording), response to electrical stimulation (middle trace recording, stimulation frequency is depicted in red trace below) and increase in frequency of spontaneous response under pharmacological stimulation (epinephrine, right trace recording).

After pre-culture for 1 week, tissue strands were either submitted to electrical field stimulation or cultured without stimulation (non-stimulated controls) for 7 days (as shown in FIG. 3a). Two different protocols were used where stimulation rate was progressively and daily increased from 1 to 3 Hz (see in FIG. 3a, the low frequency ramp-up regimen, referred to as low frequency or 3 Hz from here on) or from 1 to 6 Hz (see FIG. 3a, the high frequency ramp-up regimen, referred to as high frequency or 6 Hz from here on) to assess whether effects were dependent on stimulation rate.

Physiological Hypertrophy in Human Stimulated Tissue Strands

After 2 weeks in culture, immunostaining demonstrated that cells throughout the tissue strands strongly expressed cardiac contractile proteins sarcomeric α-actinin, actin and cardiac Troponin T (see FIGS. 9a, 10, 11 and 12).

Figure 9:
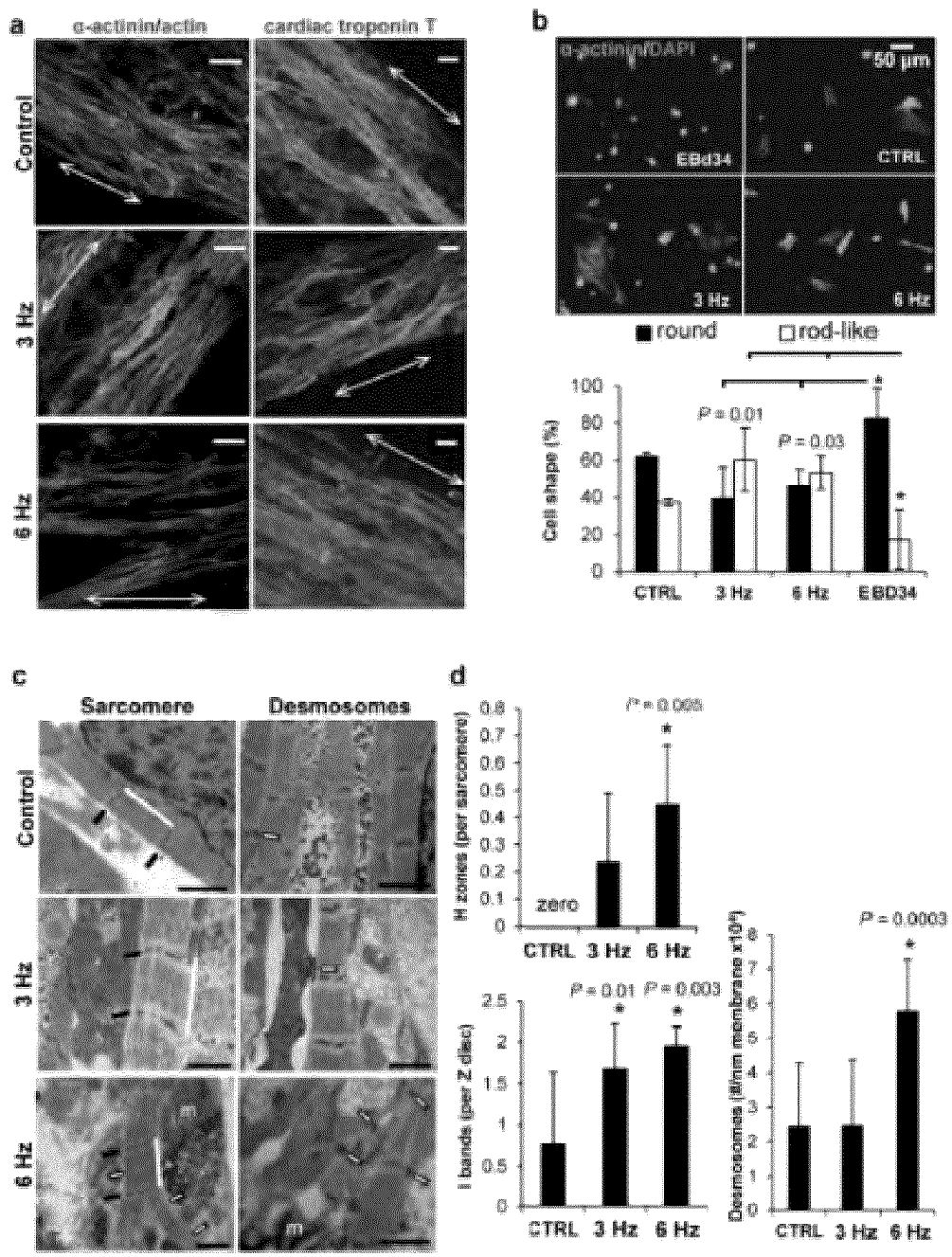
FIG. 9a-9d show examples of cultured tissue strand cells prepared in accordance with an exemplary biowire system of the disclosure which were cultured in combination with electrical stimulation promoted physiological cell hypertrophy and improved cardiomyocyte phenotype.

FIG. 9 shows that cultured tissue strands in combination with electrical stimulation promoted physiological cell hypertrophy and improved cardiomyocyte phenotype. FIG. 9a shows representative confocal images of non-stimulated (control) and electrically stimulated tissue strands (3 and 6 Hz ramp-up) showing cardiomyocyte alignment and frequent Z disks (arrows represent suture axis). Scale bar 20 µm. FIG. 9b shows analysis of cardiomyocyte cell shape in different conditions (average+/−s.d., EBd34 vs. 3 Hz P=0.01 for both rod and round like; EBd34 vs. 6 Hz P=0.03 for both round and rod-like). n=3 per group. FIG. 9c shows representative ultrastructural images of non-stimulated (control) and electrically stimulated tissue strands showing sarcomere structure (Sarcomere panel, white bar; Z disks, black arrow; H zones, white arrows; m, mitochondria) and presence of desmosomes (Desmosomes panel, white arrows). Scale bar 1 µm. FIG. 9d shows morphometric analysis (average+/−s.d.) showing ratio of H zones to sarcomeres (CTRL vs. 6 Hz, P=0.005) ratio of I bands to Z disks (CTRL vs. 3 Hz, P=0.01; CTRL vs. 6 Hz, P=0.003) and number of desmosomes per membrane length (CTRL vs. 6 Hz, P=0.0003). n=4 per condition. * denotes statistically significant difference between group and control. In normal adult cells the ratio of H zones to sarcomeres is 1 and of I bands to Z disks is 2. FIGS. 9a-9d illustrate results with Hes2 hESC-derived cardiomyocytes.

Figure 10:
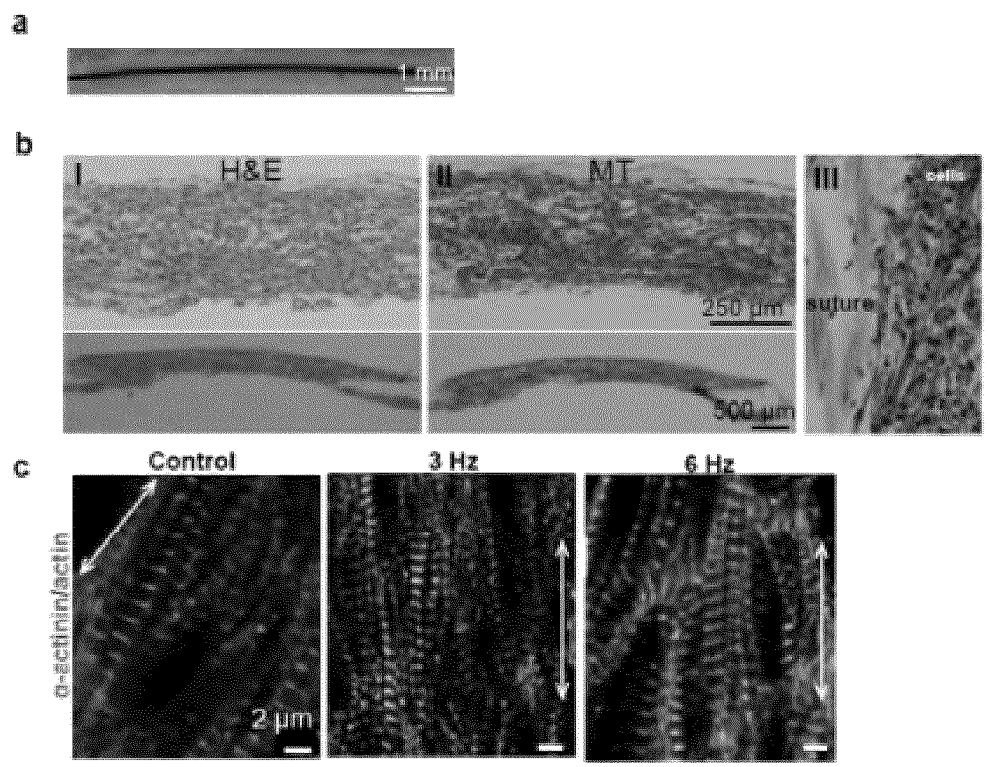
FIGS. 10a-10c show morphology of cultivated tissue strands prepared in accordance with an exemplary biowire system of the disclosure and indicates that the morphology was maintained after removal from PDMS templates.

FIG. 10 illustrates the morphology of the cultivated tissue strands. FIG. 10a shows that tissue strands maintained structure after removal from PDMS templates. FIG. 10b shows lower magnification images of (I) Hematoxylin and Eosin (H&E) and (II) Masson's Trichrome (MT) stained tissue strand sections. (III) High magnification image of MT stained section showing detail of suture/cell-containing gel interface. FIG. 10c shows high magnification confocal images of α-actinin and actin stained tissue strands showing details of sarcomere structure. Arrow represents the suture axis. FIGS. 10a-10c illustrate results with hESC-derived cardiomyocytes obtained from Hes2 cell line.

Figure 11:
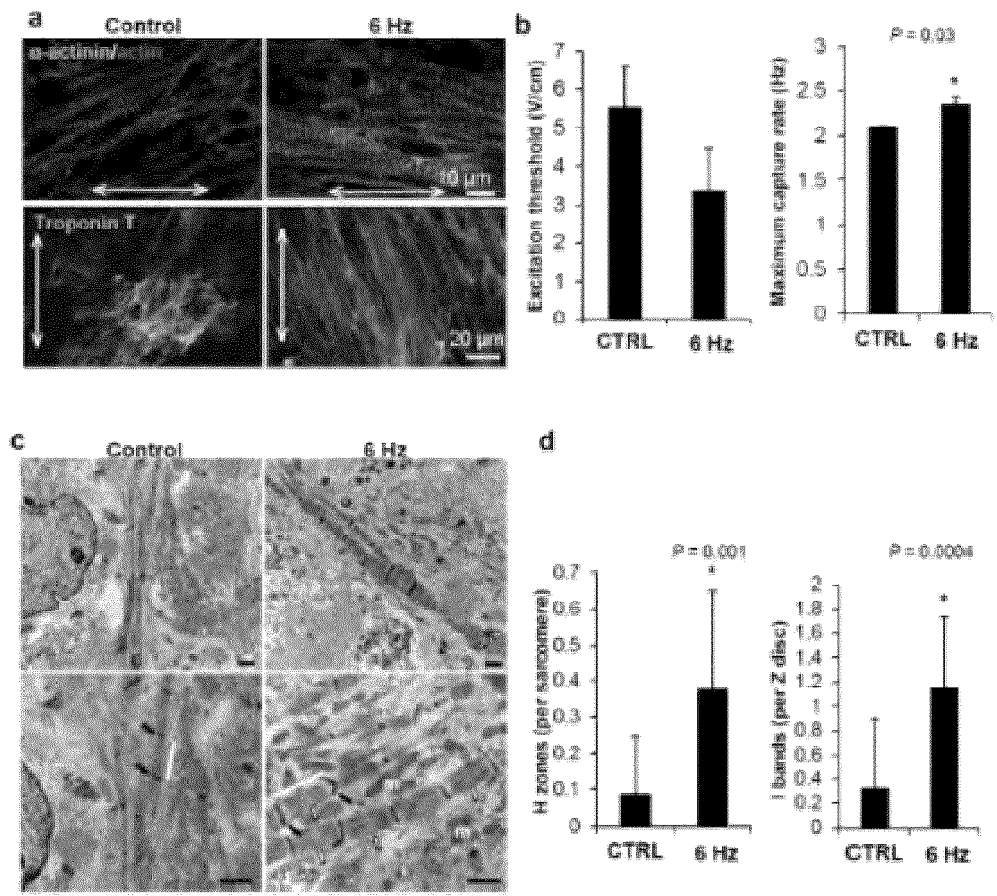
FIGS. 11a-11d show that hiPSC-derived cardiomyocyte tissue strands grown in accordance with an exemplary biowire system of the disclosure displayed signs of maturation when submitted to electrical stimulation.

FIG. 11 illustrates that CDI-MRB line hiPSC-derived cardiomyocyte tissue strands also displayed signs of maturation when submitted to electrical stimulation. FIG. 11a shows representative confocal images of non-stimulated (control) and electrically stimulated tissue strands (6 Hz ramp-up protocol) showing cardiomyocyte alignment and frequent Z disks (arrows represent suture axis). FIG. 11b shows that electrical stimulation improved excitation threshold and tissue interconnectivity (maximum capture rate; CTRL vs. 6 Hz, P=0.03, measured by point stimulation). Ultrastructural analysis demonstrated that electrical stimulation at high frequency (6 Hz ramp-up regimen) induced cardiomyocyte self-organization. FIG. 11c shows representative images of non-stimulated (control) and electrically stimulated tissue strands showing sarcomere structure (Sarcomere, white bar; Z disks, black arrows; H zones, white arrows; m, mitochondria; Nascent intercalated discs, red arrows). Scale bar 1 µm. FIG. 11d shows morphometric analysis (average±s.d.) showing ratio of H zones to sarcomeres (CTRL vs. 6 Hz, P=0.001) and ratio of I bands to Z disks (CTRL vs. 6 Hz, P=0.004). In normal adult cells the ratio of H zones to sarcomeres is 1 and ratio of I to Z disks is 2. n=3-4 per condition.

Figure 12:
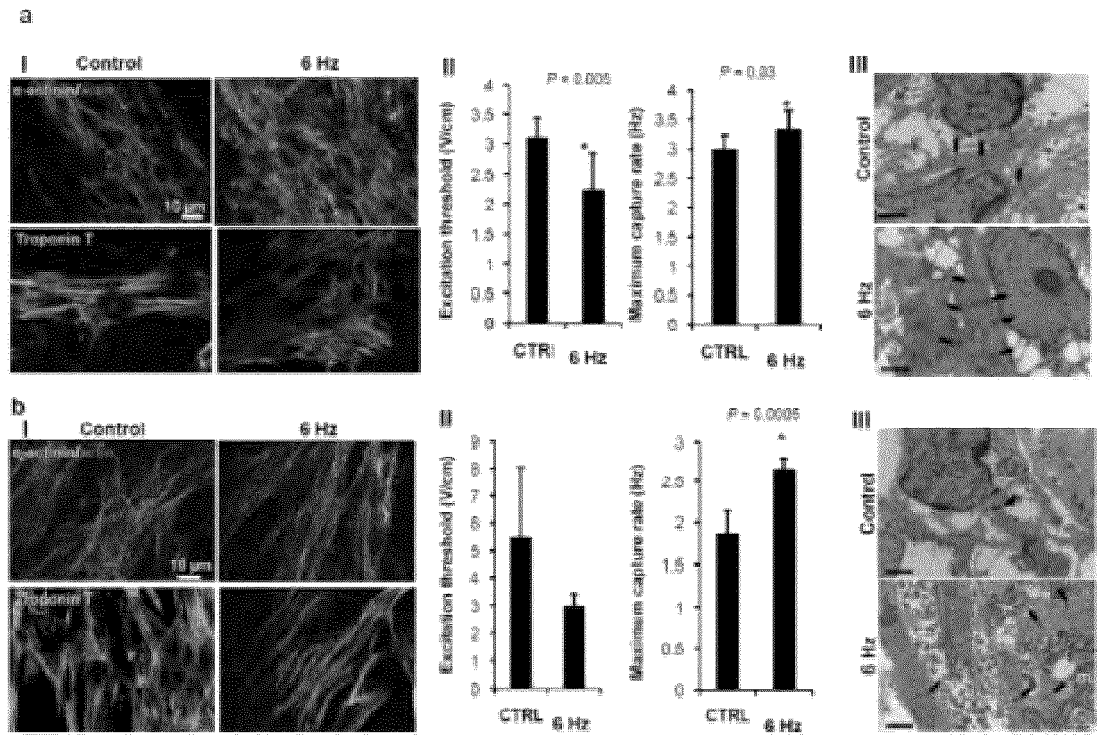
FIGS. 12a-12b show examples of electrical stimulation promoted maturation of other stem cell-derived cardiomyocyte tissue strands grown in accordance with an exemplary biowire system of the disclosure.

FIG. 12 illustrates that electrical stimulation promoted maturation of other hPSC-derived cardiomyocytes. FIG. 12a illustrates results for Hes3 cell line hESC-derived cardiomyocyte tissue strands and FIG. 12b illustrates results for HR-I-2Cr-2R cell line hiPSC-derived cardiomyocyte tissue strands. FIGS. 12a(I) and 12b(I) show representative confocal images of non-stimulated (control) and electrically stimulated tissue strands (6 Hz ramp-up protocol) showing cardiomyocyte alignment and frequent Z disks. FIGS. 12a(II) and 12b(II) show that electrical stimulation improved excitation threshold and tissue interconnectivity (maximum capture rate, measured by point stimulation) of hESC- and iPSC-derived cardiac tissue strands. n=4-7 per condition. Average±s.d., * denotes statistical significance. FIGS. 12a(III) and 12b(III) show ultrastructural analysis of cardiomyocyte tissue strand self-organization (Z disks, black arrows; nascent intercalated discs, red arrow). Scale bar 1 µm.

These example results show that sarcomeric banding of the contractile apparatus (see FIGS. 9a, 11 and 12) and myofibrillar alignment along the suture axis was qualitatively similar to the structure of adult heart[22]. Tissue strands kept in culture for 3 and 4 weeks maintained cell alignment and their contractile apparatus structure as evidenced by confocal and transmission electron microscopy (see FIG. 4).

Early in cardiac development, cardiomyocytes are round shaped cells differentiating into rod-shaped phenotype after birth[33]. Adult human cardiomyocytes display a structurally rigid architecture, retaining a rod-like shape[34] immediately after dissociation while hESC-cardiomyocytes remain round. Age matched EBs (EBd34) and tissue strands were dissociated and the cells were seeded into Matrigel-coated plates. While ~80% of cardiomyocytes from EBd34 displayed a round phenotype, this number was significantly lower (~50% less) in electrically stimulated samples (see FIG. 9b). Percentage of rod-like cardiomyocytes was significantly higher (~4 fold) in electrically stimulated tissue strands (see FIG. 9b) as compared to EBd34.

Figure 13:
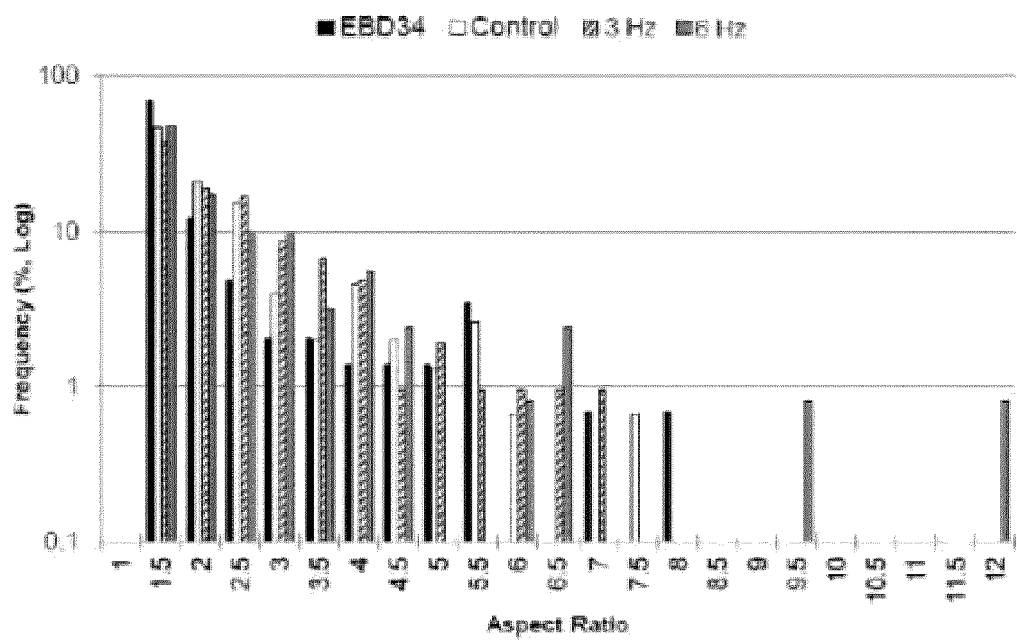
FIG. 13 shows a bar-graph analysis of cell aspect ratio for cells in cultivated tissue strands prepared using an exemplary biowire system of the disclosure confirming a change in shape towards more rod-like in electrically stimulated tissue strands compared to cells from age matched embryoid bodies (EBd34).

FIG. 13 shows an analysis of cell aspect ratio for the cells in the cultivated tissue strands. Analysis confirmed a change in cell shape towards more rod-like, in electrically stimulated tissue strands when compared to cells from age matched embryoid bodies (EBd34). Cardiac cells were plotted according to their aspect ratio in 0.5 bin increments (n=3). Measurements were performed in single cell hESC-derived cardiomyocytes (Hes2 cell line) after dissociation from tissue strands.

During development, cardiomyocytes undergo physiological hypertrophy characterized by increased cell size followed by changes in sarcomere structure and downregulation of fetal genes[35]. There was a significant increase in cardiomyocyte size (area of plated cells) in tissue strand conditions compared to cardiomyocytes from age matched EBs (EBd34) (see Table 1 in FIG. 26, EBd34 vs. CTRL P=0.034; EBd34 vs. 3 Hz P=0.003; EBd34 vs. 6 Hz regimen P=0.01). In Table 1, measurements were performed on single Hes2 hESC derived cardiomyocytes dissociated from tissue strands at the end of cultivation. * denotes statistical significance between group and EBd34. Cell area (µm2), average±s.d., n=3. Atrial natriuretic peptide (NPPA), brain natriuretic peptide (NPPB) and α-myosin heavy chain (MYH6) are molecules highly expressed in fetal cardiomyocytes and upregulated during pathological hypertrophy in diseased adult ventricular cardiomyocytes.

Figure 14:
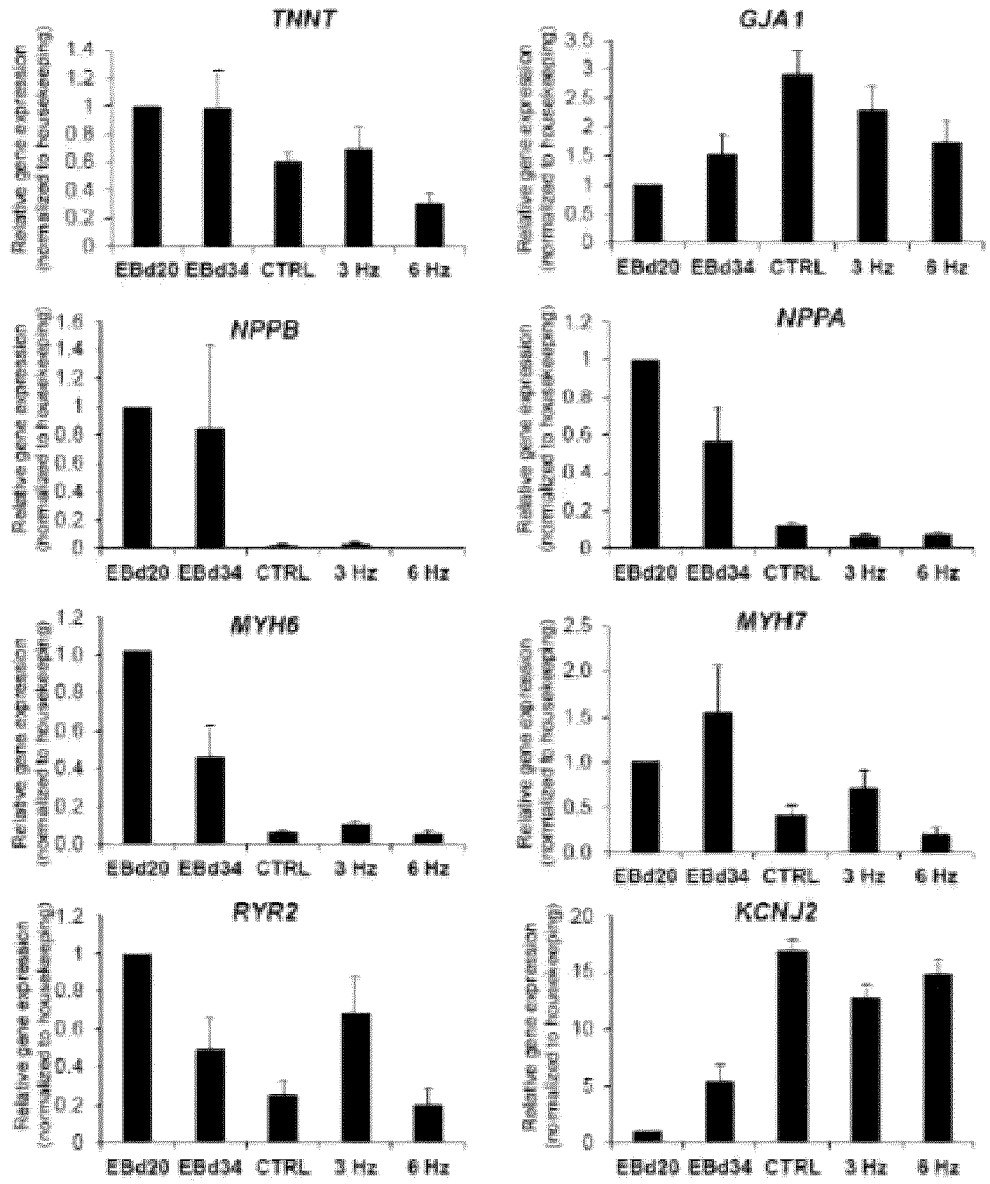
FIG. 14 shows charts of gene expression analysis in various cells from tissue strands grown in accordance with an exemplary biowire system of the disclosure, which demonstrates downregulation of cardiac fetal gene program and upregulation of potassium channel gene.

FIG. 14 shows gene expression analysis of the cultivated tissue strands. Analysis showed downregulation of cardiac fetal gene program and upregulation of potassium channel gene. Cardiac Troponin T (TNNT), Connexin43 (GJA1), Brain natriuretic peptide (NPPB), Atrial natriuretic peptide (NPPA), α-myosin heavy chain (MYH6), β-myosin heavy chain (MYH7), ryanodine receptor 2 (RYR2), potassium inwardly-rectifying channel gene (KCNJ2). Cardiac fetal genes NPPA, NPPB and MYH6 were significantly downregulated in hESC-derived cardiomyocyte tissue strands while KCNJ2 was upregulated compared to age matched EBs (EBd34; average±s.e.m., n=3-6). Hes2 cell line hESC-derived cardiomyocytes.

Figure 15:
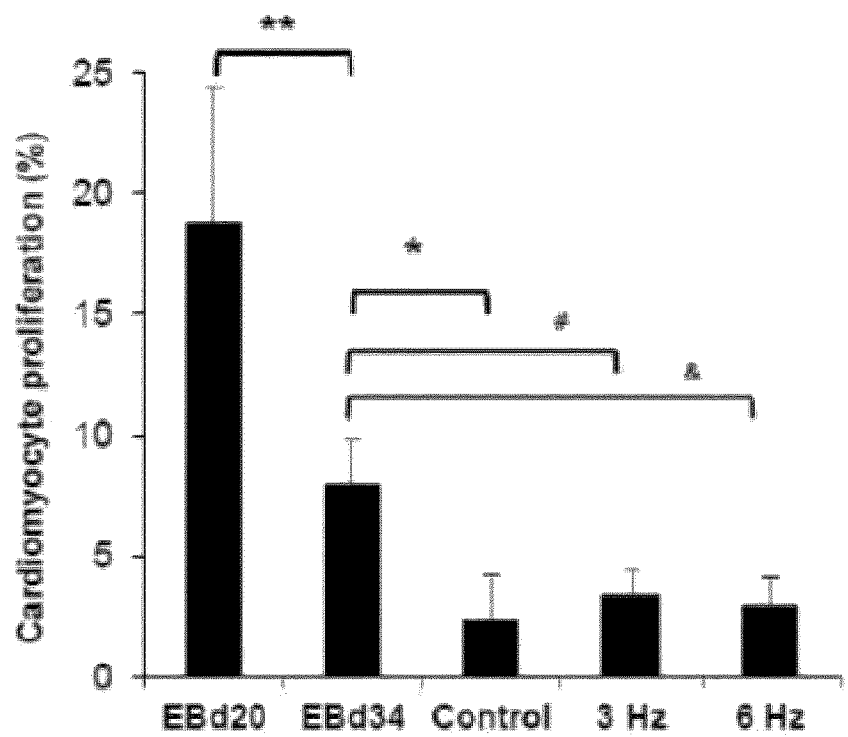
FIG. 15 shows a chart illustrating cardiomyocyte proliferation in tissue strands generated using an exemplary biowire system of the disclosure was lower than in EBs.
Figure 16:
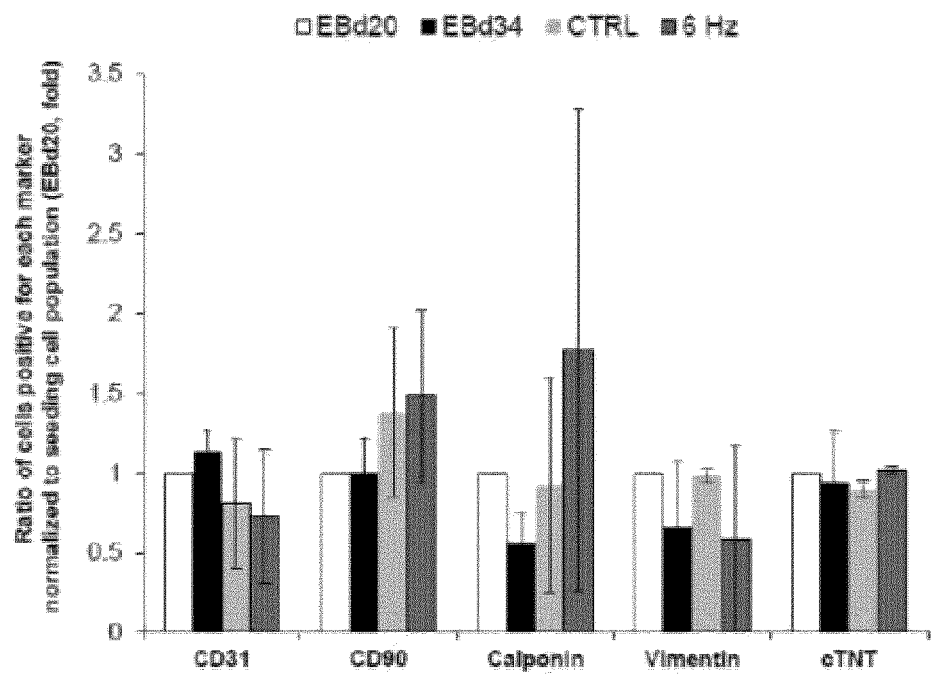
FIG. 16 shows a chart illustrating marker prevalence in tissue strands generated using an exemplary biowire system of the disclosure, demonstrating that the cell population did not vary significantly after cultivation.

Downregulation of the fetal cardiac gene program (NPPA, NPPB, MYH6) in hESC-derived cardiomyocyte tissue strands (see FIG. 14), compared to age matched EBs, in concert with cell size increase, suggested physiological hypertrophy and a more mature phenotype. Potassium inwardly-rectifying channel gene (KCNJ2), that plays important roles in cell excitability and K$^+$ homeostasis[36], was upregulated compared to EBd34.

hESC-cardiomyocytes cultured in tissue strands also displayed lower proliferation rates than those in EBs (see FIG. 15), and the percentage of cardiomyocytes in each condition remained unchanged after culture for 2 weeks (48.2±10.7%, see FIG. 16).

FIG. 15 shows example results demonstrating that cardiomyocyte proliferation in cultivated tissue strands was lower than in EBs. Proliferation was assessed by double staining for sarcomeric α-actinin and Ki67 (n=3-4 per condition, average±s.d.). *, **, # and & represent statistically significant difference compared to EBd34 (EBd20 vs. EBd34, P=0.002; EBd34 vs. CTRL, P=0.019; EBd34 vs. 3 Hz, P=0.016; EBd34 vs. 6 Hz, P=0.015). Measurements were performed on single Hes2 hESC derived cardiomyocytes after dissociation from tissue strands.

FIG. 16 shows example results demonstrating that cell population in the tissue strands did not vary significantly after cultivation. Percentage of cells positive for the different markers normalized to EBd20 (starting population). Cells from EBd20, EBd34 and tissue strands (CTRL and 6 Hz) were stained for CD31 (endothelial cells), CD90 (fibroblasts), calponin (smooth muscle cells), vimentin (all non-myocytes) and cardiac Troponin T (cardiomyocytes), and analyzed by flow cytometry (n=3-6 per condition, average±s.d.). Results with hESC-derived cardiomyocytes Hes2 cell line after dissociation from tissue strands are shown.

Initial percentages of CD31 (2.4±1.5%, endothelial cells[32]), CD90 (34.4±23%, fibroblasts[32]), calponin (35±22%, smooth muscle cells) or vimentin (80±22%, non-myocytes) positive cells in EBd20 population, were largely maintained after tissue strand culture, suggesting that the observed improvements were not related to the induction of a particular cell type.

Maturation of Contractile Apparatus in Cultivated Human Tissue Strands

Cells in non-stimulated tissue strands displayed well-defined Z discs and myofibrils (see FIGS. 9c, 11 and 12) but no signs of Z disc alignment. In contrast, tissue strands stimulated under the high frequency regimen showed signs of maturation, such as organized sarcomeric banding with frequent myofibrils that converged and displayed aligned Z discs (see FIG. 9c, 6 Hz; FIGS. 11 and 12), numerous mitochondria (see FIG. 9c, 6 Hz; FIGS. 11 and 12) and desmosomes (see FIG. 9c). In the 6 Hz condition, mitochondria were positioned closer to the contractile apparatus than in control or 3 Hz conditions (see FIG. 9c, 6 Hz; FIGS. 11 and 12).

Electrically stimulated samples displayed a sarcomeric organization more compatible with mature cells than non-stimulated controls as shown by a significantly higher presence of H-zones per sarcomere (see FIG. 9d, CTRL vs. 6 Hz, P=0.005; FIG. 11d, CTRL vs. 6 Hz, P=0.001) and I-bands per Z disc (see FIG. 11d, CTRL vs. 3 Hz, P=0.01; CTRL vs. 6 Hz, P=0.003; FIG. 11d, CTRL vs. 6 Hz, P=0.0004). Tissue strands stimulated at 6 Hz regimen also displayed a significantly higher number of desmosomes per membrane length than both non-stimulated controls and 3 Hz-stimulated tissue strands (see FIG. 9d, P=0.0003). In hiPSC-derived cardiomyocyte tissue strands, areas with nascent intercalated discs were frequently seen (see FIGS. 11c and 12b).

Functional Assessment of Human Engineered Tissue Strands

Figure 17:
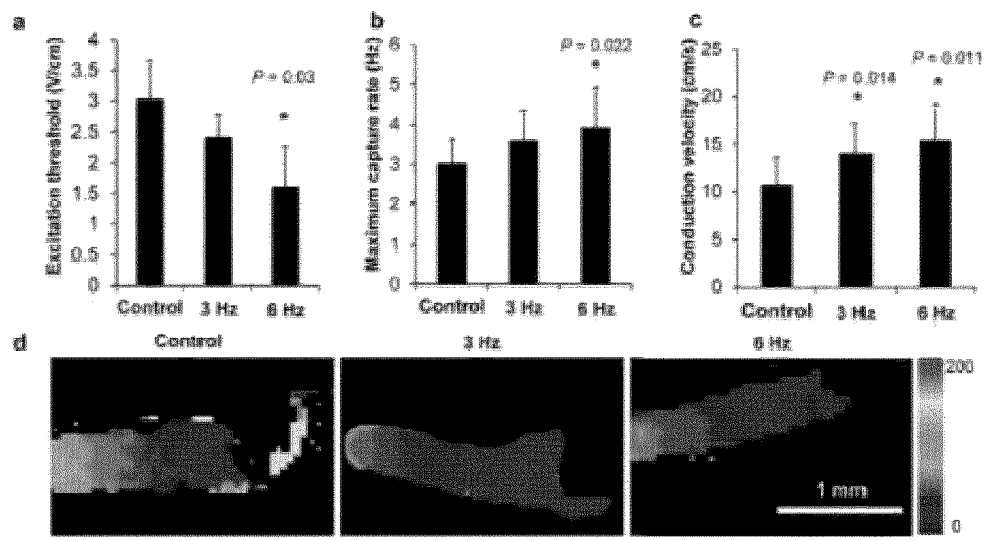
FIGS. 17a-17d shows example results from functional assessment of tissue strands generated in accordance with an exemplary biowire system of the disclosure.

FIG. 17 shows example results from functional assessment of engineered tissue strands. Electrical stimulation was found to improve excitation threshold (FIG. 17a) (CTRL (n=4) vs. 6 Hz (n=3), P=0.03, as measured by field stimulation and videomicroscopy; 3 Hz, n=3), maximum capture rate (FIG. 17b) (CTRL (n=4) vs. 6 Hz (n=4), P=0.022, as measured by point stimulation and optical mapping; 3 Hz, n=3) and electrical impulse propagation rates (FIG. 17c) (CTRL (n=13) vs. 3 Hz (n=10), P=0.014; CTRL vs. 6 Hz (n=5), P=0.011, as measured by point stimulation and optical mapping). Average+/−s.d. FIG. 17d shows representative images of conduction velocity activation maps in tissue strands. * denotes statistically significant difference between group and control. Heat map=0 to 200 ms. FIGS. 17a-17d illustrate results with hESC-derived cardiomyocytes obtained from Hes2 cell line.

Figure 18:
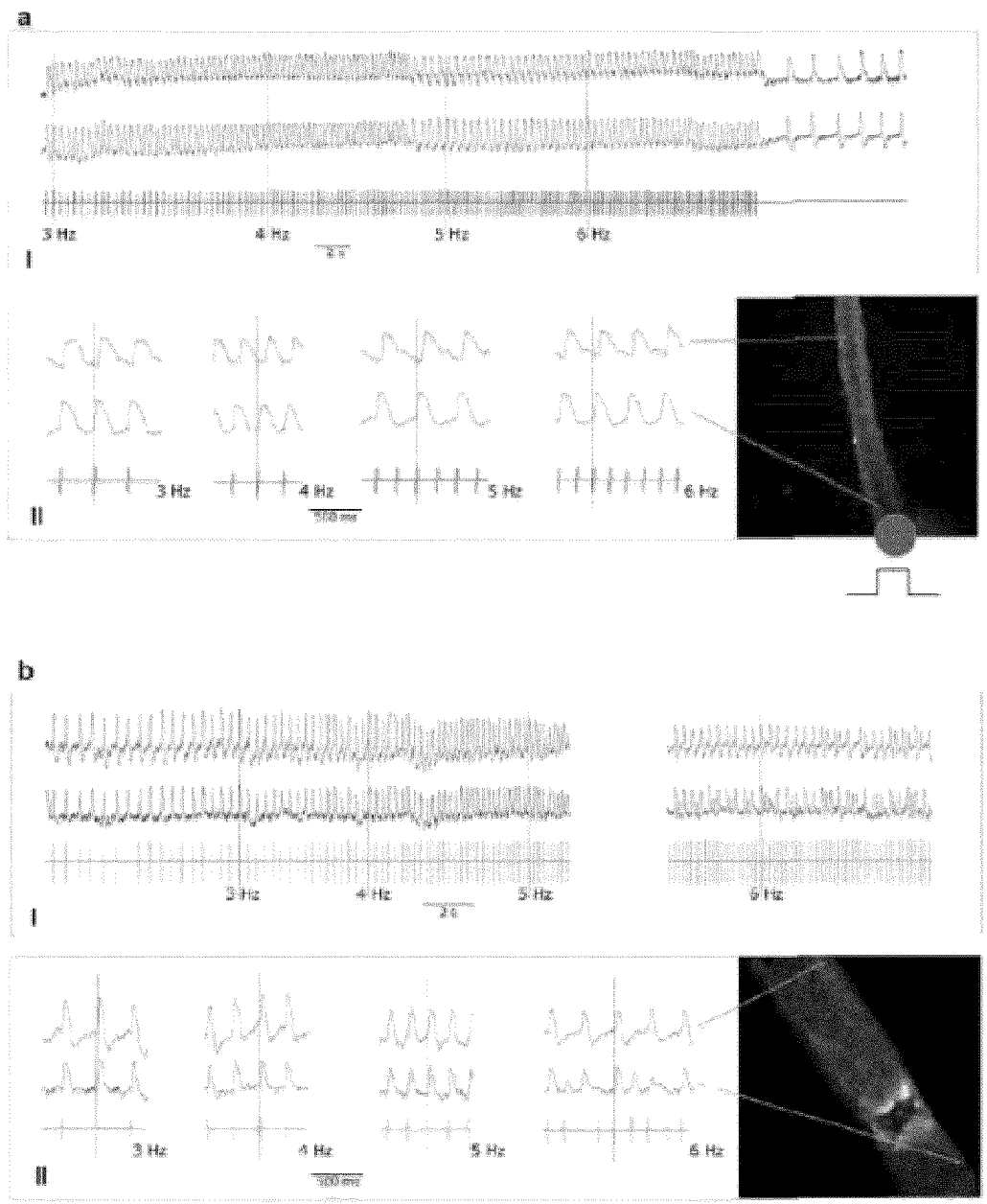
FIGS. 18a-18b show electrical stimulation and capture rate in cardiac cells from tissue strands generated using an exemplary biowire system of the disclosure.

FIG. 18 shows example results demonstrating that maximum capture rate of 6 Hz ramp up stimulated tissue strand was higher with field compared to point stimulation. FIG. 18a shows example electrical point stimulation. In FIG. 18a(I), stimulation frequency is shown in red and capture proximal (bottom tracing) and distal (top tracing) to the stimulation site is shown in black. The time delay between each signal gives an indication of conduction velocity. Consistent capture of the propagation signal in both proximal and distal sites demonstrated absence of functional blockage and good electrical integration in the tissue strands. In FIG. 18a(II), amplification of signals displayed in I at 3, 4, 5 and 6 Hz demonstrated that 1:1 capture was lost above 4 Hz, when capture became 2:1. Propagation between proximal and distal sites remained at 1:1 when stimulated above 4 Hz. Red circle in the image represents site of point stimulation. FIG. 18b shows example electrical field stimulation. In FIG. 18b(I), field stimulation frequency is shown in red tracing and capture at different sites of the tissue strands is shown in black. As expected, no time delay is observed between each signal indicating that cells received the electrical stimulus at approximately the same time. Capture at 1:1 rate was lost above 5.2 Hz when it became intermittent at 6 Hz as shown in FIG. 18b(II). FIGS. 18a-18b illustrate results with hESC-derived cardiomyocytes Hes2 cell line.

Figure 19:
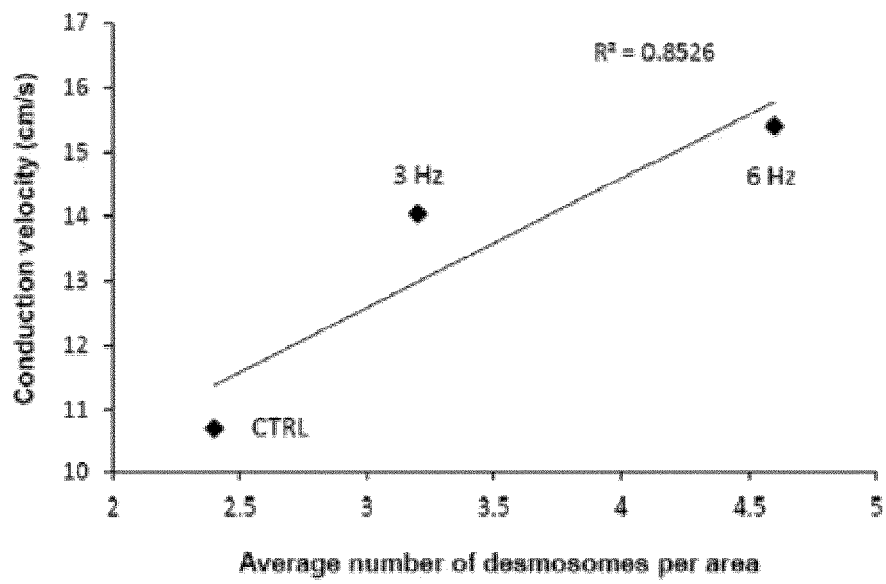
FIG. 19 shows a chart of conduction velocity correlated with the presence of desmosomes in cardiac cells generated using an exemplary biowire system of the disclosure.

FIG. 19 shows example results demonstrating improvement in conduction velocity correlated with the presence of desmosomes. Conduction velocity was in direct correlation with the number of desmosomes, a molecular complex of cell adhesion proteins that links intracellular filaments to cell surface proteins and is responsible for maintaining the integrity of the cardiac muscle during contraction and force transmission ($R^2=0.8526$, CV vs. average number of desmosomes/area). Hes2 cell line hESC-derived cardiomyocytes.

Electrical stimulation with the 6 Hz regimen significantly improved electrical properties of the cultivated tissue strands, leading to a statistically significant reduction in the excitation threshold (see FIG. 19a, CTRL vs. 6 Hz, P=0.03) and an increase in the maximum capture rate (see FIG. 19b, CTRL vs. 6 Hz, P=0.022, FIG. 11, 12) as analyzed by point stimulation at the end of cultivation in conjunction with optical mapping of impulse propagation (see FIG. 18a). Optical mapping demonstrated higher MCR with field stimulation (5.2 Hz) than with point stimulation (4 Hz) (see FIG. 18b, 5.2 Hz capture with intermittent capture at 6 Hz). During field stimulation all cells received the stimulus at the same time and response was not limited by each cell's propagation limitations. Conduction velocity (CV), assessed upon point stimulation at the end of cultivation was ~40 and ~50% higher in the samples electrically stimulated during culture (3 Hz and 6 Hz, respectively), than non-stimulated controls (see FIGS. 17c and 17d, CTRL vs. 3 Hz, P=0.014; CTRL vs. 6 Hz, P=0.011). Improvements in electrical properties (ET, MCR and CV) were more pronounced with the high frequency regimen compared to the low frequency one. Improvement in conduction velocity was found to be in direct correlation with the average number of desmosomes (see FIG. 19, $R^2=0.8526$), a molecular complex of cell-cell adhesion proteins.

Figure 20:
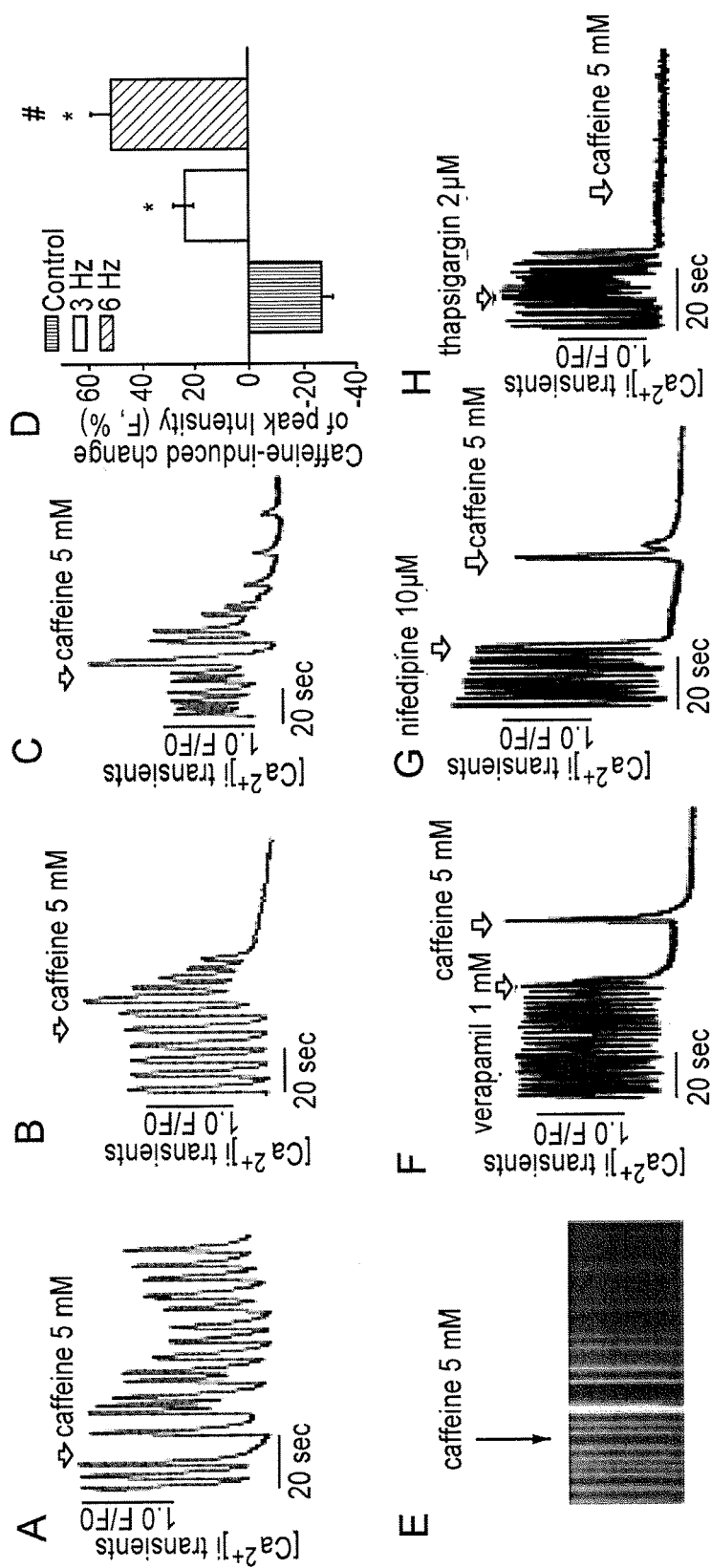
FIGS. 20a-20h show electrical stimulation promoted improvement in $Ca^{2+}$ handling properties in cardiac cells generated using an exemplary biowire system of the disclosure.

Stimulation Improves $Ca^{2+}$ Handling Properties in Cultivated Human Tissue Strands FIG. 20 shows example results demonstrating that electrical stimulation promoted improvement in Ca2+ handling properties. The example results demonstrate Ca2+ release in response to caffeine in non-stimulated control cells (FIG. 20a), 3 Hz ramp-up (FIG. 20b), and 6 Hz ramp-up protocols (FIG. 20c). FIG. 20d shows example results demonstrating caffeine-induced change of peak fluorescent intensity among different experimental groups (mean±s.e.m. after normalizing the peak fluorescence intensity before administration of caffeine) (CTRL vs. 3 Hz, P=1.1×10-6; CTRL vs. 6 Hz, P=2.1×10-7; 3 Hz vs. 6 Hz, P=0.003; n=10 (CTRL), n=8 (3 Hz) and n=9 (6 Hz). FIG. 20e shows representative fluorescence recording of Ca2+ transients before and after administration of caffeine at 5 mM (arrow) in 6 Hz stimulated cells. The example results also demonstrate inhibition of L-type Ca2+ channels with verapamil (FIG. 20f or nifedipine (FIG. 20g) and blockage of SERCA channels with thapsigargin (FIG. 20h) in 6 Hz cells before addition of caffeine. * denotes statistically significant difference between group and control. #denotes statistically significant difference between 3 Hz and 6 Hz group. FIGS. 20a-20h illustrate results with hESC-derived cardiomyocytes obtained from Hes2 cell line and represent measurements performed in single cell cardiomyocytes after dissociation from tissue strands.

Either all[10] or the majority[12] of hESC-cardiomyocytes rely on sarcolemmal $Ca^{2+}$ influx rather than on sarcoplasmic reticulum $Ca^{2+}$ release for contraction, differing markedly from adult myocardium. The effect of caffeine was tested, an opener of sarcoplasmic reticulum Ryanodine channels, on cytosolic $Ca^{2+}$ in single cells isolated from tissue strands. In accordance with previous work[10], none of the hESC-cardiomyocytes in non-stimulated controls were responsive to caffeine (see FIG. 20a), while electrically stimulated cells in both 3 and 6 Hz conditions responded to caffeine by inducing an increase in cytosolic $Ca^{2+}$ (see FIGS. 20b and 20c). Quantification of $Ca^{2+}$ transient amplitudes showed that electrically stimulated cells displayed significantly higher amplitude intensity in response to caffeine than non-stimulated controls, in a stimulation frequency dependent manner (see FIGS. 20d and 20e). Blockage of L-type $Ca^{2+}$ channels in cells from 6 Hz tissue strands with either verapamil (see FIG. 20f or nifedipine (see FIG. 20g) led, as expected in mature cells, to cessation in $Ca^{2+}$ transients. Addition of caffeine post blockage of L-type $Ca^{2+}$ channels led to $Ca^{2+}$ release into the cytosol (see FIGS. 20f and 20g). Blockage of the ion transport activity of sarcoplasmic reticulum $Ca^{2+}$ ATPase (SERCA) by addition of thapsigargin (see FIG. 20h) lead to the cessation of calcium transients with time due to the depletion of $Ca^{2+}$ from sarcoplasmic reticulum. Cardiomyocytes from 6 Hz condition also demonstrated a faster rising slope and time to peak, parameters that represent the kinetics of $Ca^{2+}$ release into the cytosol, and faster τ-decay and time to base, parameters that represent the kinetics of clearance of $Ca^{2+}$ from the cytosol (see Table 2 in FIG. 27). Table 2 shows example results demonstrating that changes in Ca2+ handling properties in cardiomyocytes stimulated with the 6 Hz regimen were compatible with more mature Ca2+ handling properties. Measurements performed on singularized cardiomyocytes dissociated from tissue strands at the end of cultivation. * denotes statistical significance vs. non-stimulated control (mean±s.e.m.).

Taken together, these data indicated that cardiac tissue strands that underwent the 6 Hz stimulation regimen during culture displayed $Ca^{2+}$ handling properties compatible with functional sarcoplasmic reticulum.

Figure 21:
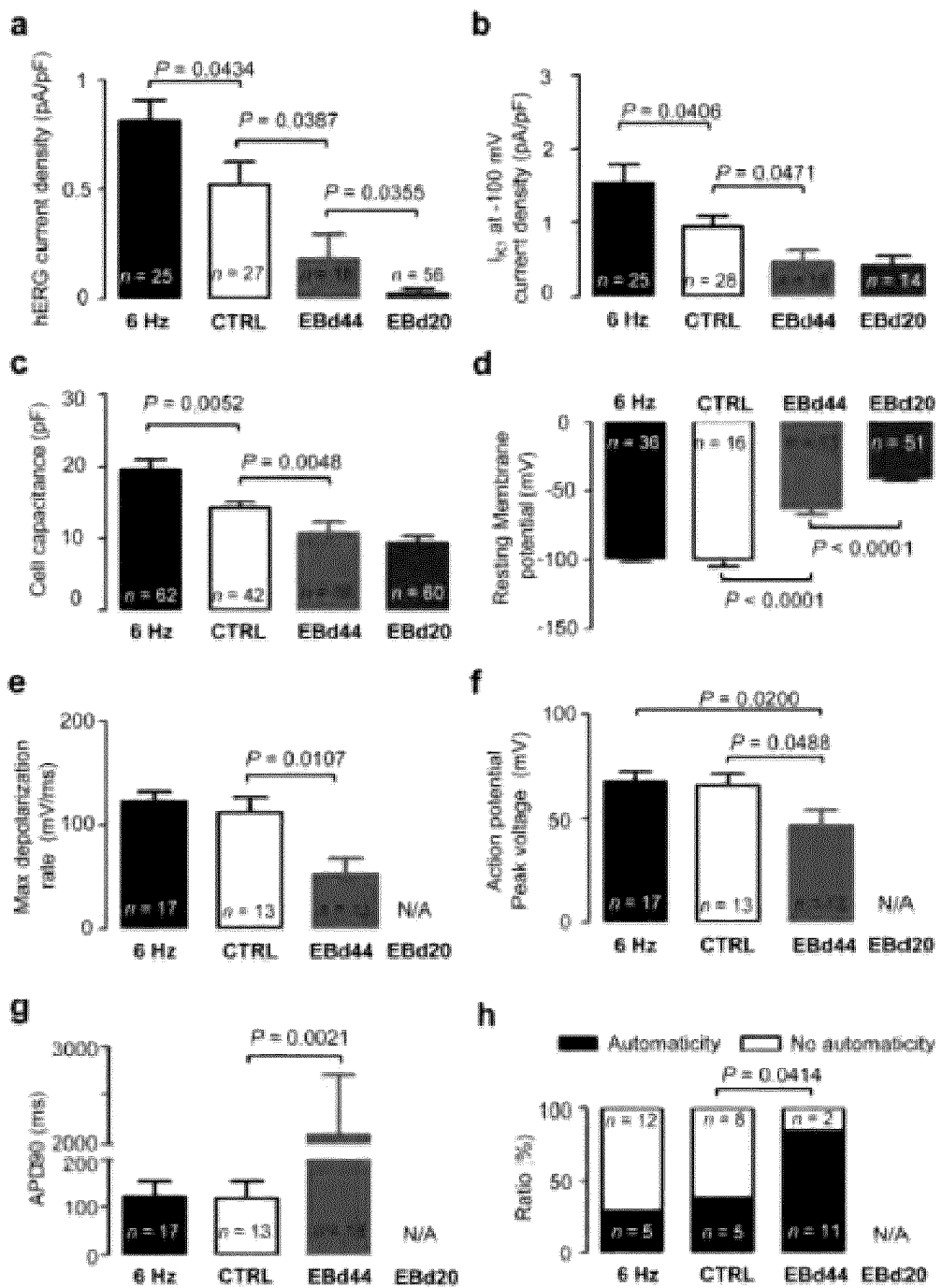
FIGS. 21a-21h show charts illustrating electrophysiological properties in single cell cardiomyocytes isolated from tissue strands generated using an exemplary biowire system of the disclosure, compared with controls.

Stimulation Alters Cultivated Human Tissue Strands Electrophysiological Properties FIG. 21 shows example results demonstrating electrophysiological properties in single cell cardiomyocytes isolated from cultivated tissue strands or embryoid bodies and recorded with patch-clamp. Six Hz stimulated tissue strands (black), control tissue strands (white), EBd44 and EBd20 are shown. The example results show hERG tail current density (FIG. 26a), IK1 current density measured at −100 mV (FIG. 21b), cell capacitance (FIG. 21c), resting membrane potential (FIG. 21d), maximum depolarization rate of action potential (FIG. 21e), action potential peak voltage (FIG. 21f, action potential duration measured at 90% repolarization (FIG. 21g) and ratio of cells displaying spontaneous beating (automaticity) or no spontaneous beating (no automaticity) (FIG. 21h). FIGS. 21a-21h illustrate results with hESC-derived cardiomyocytes obtained from Hes2 cell line. Average±s.e.m.

Figure 22:
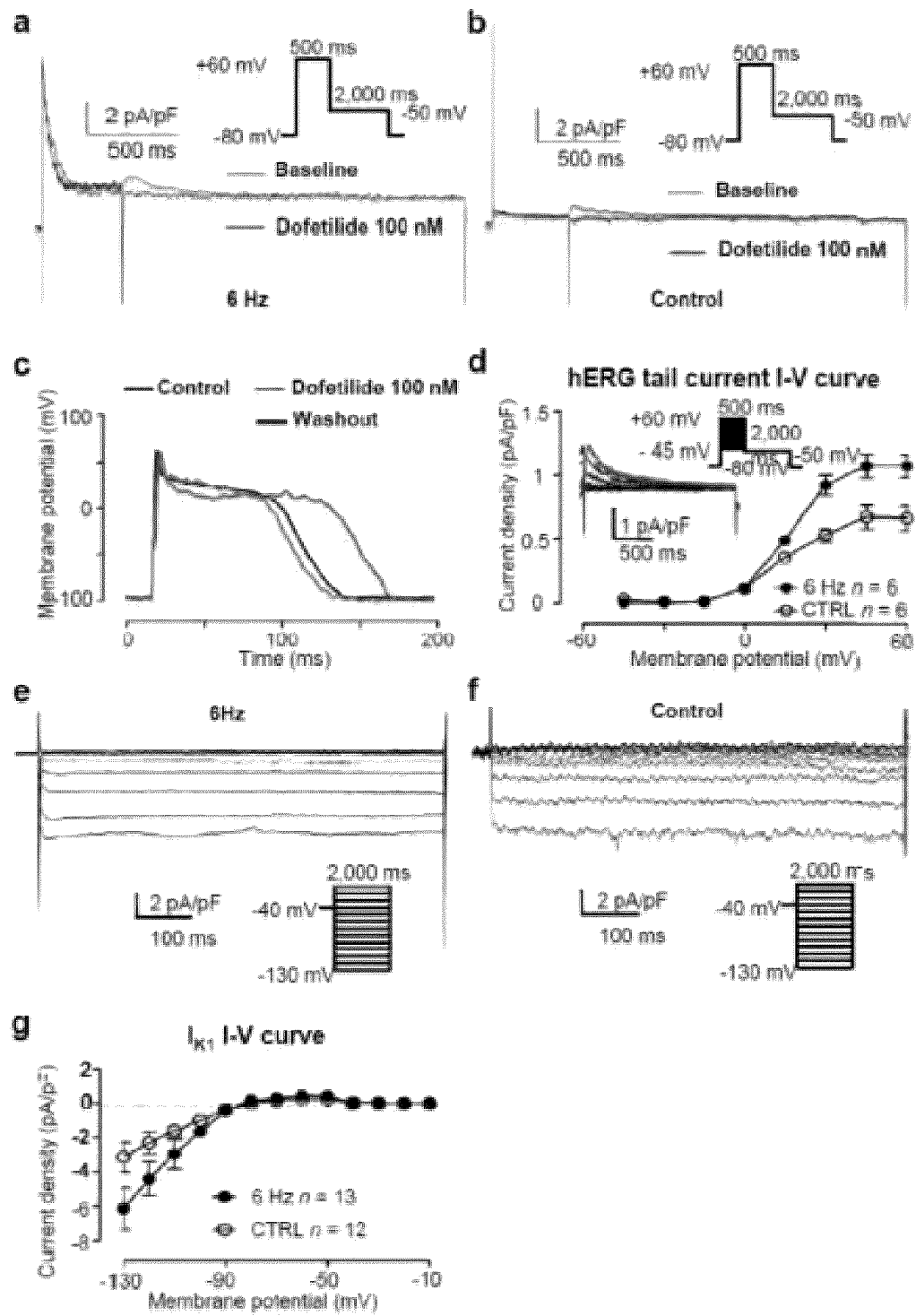
FIGS. 22a-22g show charts illustrating the effects of electrical stimulation on hERG current and IK1 in single cardiomyocytes isolated from tissues generated using an exemplary biowire system of the disclosure.

FIG. 22 shows example results demonstrating the effects of electrical stimulation on hERG current and IK1 in single cardiomyocytes isolated from 6 Hz or control tissue strands. The example results show representative traces of hERG current (FIGS. 22a and 22b), effect of Dofetilide on action potential configuration of cardiomyocytes isolated from the 6 Hz-stimulated tissue strands (FIG. 22c), current density-Voltage relationship of hERG tail current, inset displays expanded view of the tail current part of hERG and recording protocol (FIG. 22d), representative traces of IK1 (FIGS. 22e and 22f), and current density-voltage curve of IK1 (FIG. 22g). FIGS. 22a-22g illustrate results with hESC-derived cardiomyocytes Hes2 cell line after dissociation from tissue strands. Average±s.e.m.

Figure 23:
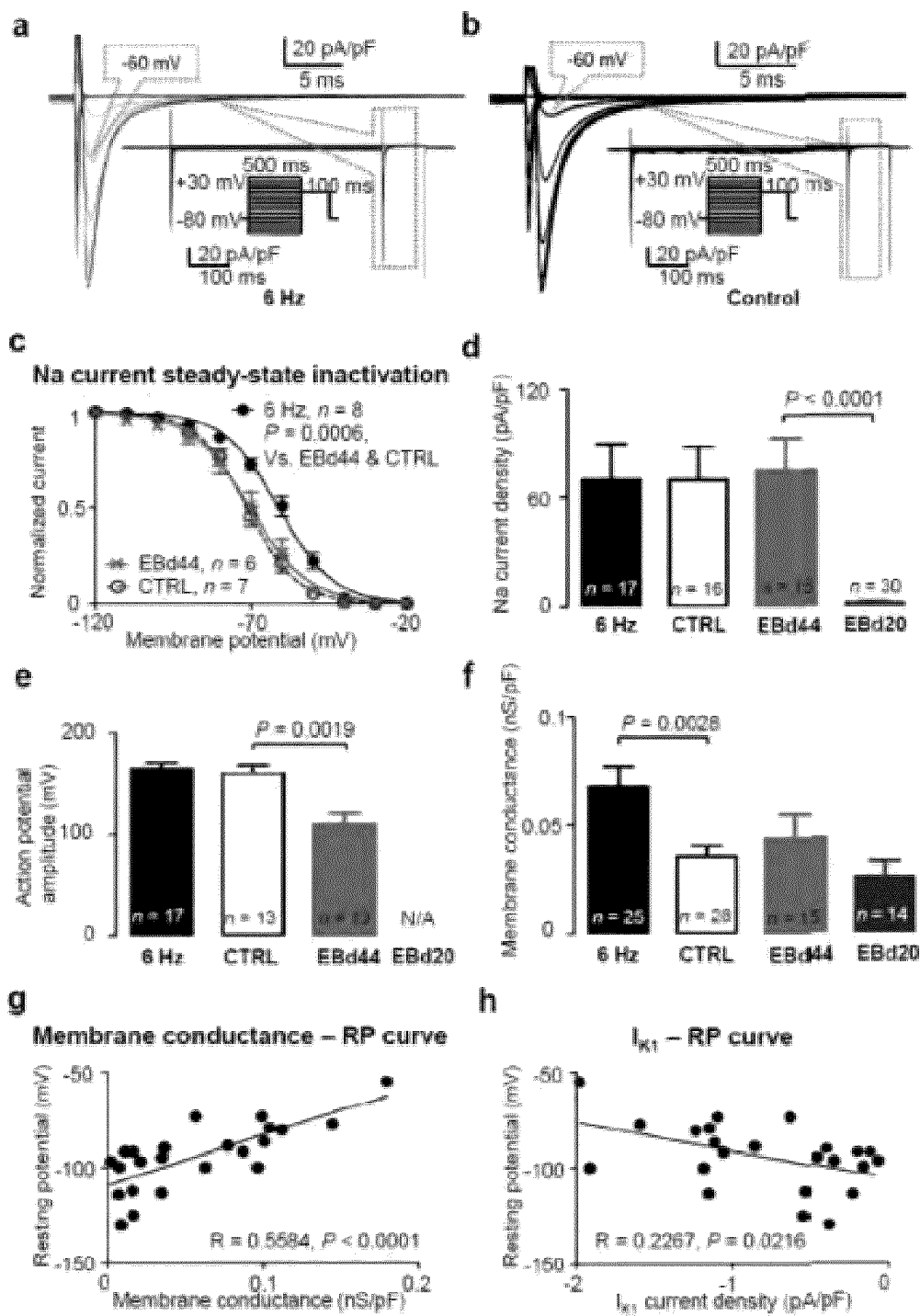
FIGS. 23a-23h show charts illustrating the effects of electrical stimulation on $Na^+$ current, action potential peak, membrane conductance, membrane conductance-resting potential curve and IK1-resting potential curve in single cardiomyocytes isolated from tissues generated using an exemplary biowire system of the disclosure.

FIG. 23 shows example results demonstrating the effects of electrical stimulation on Na+ current, action potential peak, membrane conductance, membrane conductance-resting potential curve and IK1-resting potential curve in single cardiomyocytes isolated from tissue strands. The example results show expanded views of representative Na+ current steady-state inactivation traces recorded from 6 Hz and control tissue strands (FIGS. 23a and 23b, inset figures are full view of the original trace and recording protocol), Na+ current steady-state inactivation curve, 6 Hz group V1/2=−61.06±0.65 mV; control group V1/2=−71.24±0.24 mV and EBd44 group V1/2=−70.35±0.60 mV (FIG. 23c), Na+ current density (FIG. 23d), action potential amplitude (FIG. 23e), membrane conductance at −100 mV (FIG. 23e, membrane conductance-resting potential relationship curve (FIG. 28g), and IK1-resting potential relationship curve (FIG. 23h). FIGS. 23a-23h illustrate results with hESC-derived cardiomyocytes Hes2 cell line. Average±s.e.m.

Figure 24:
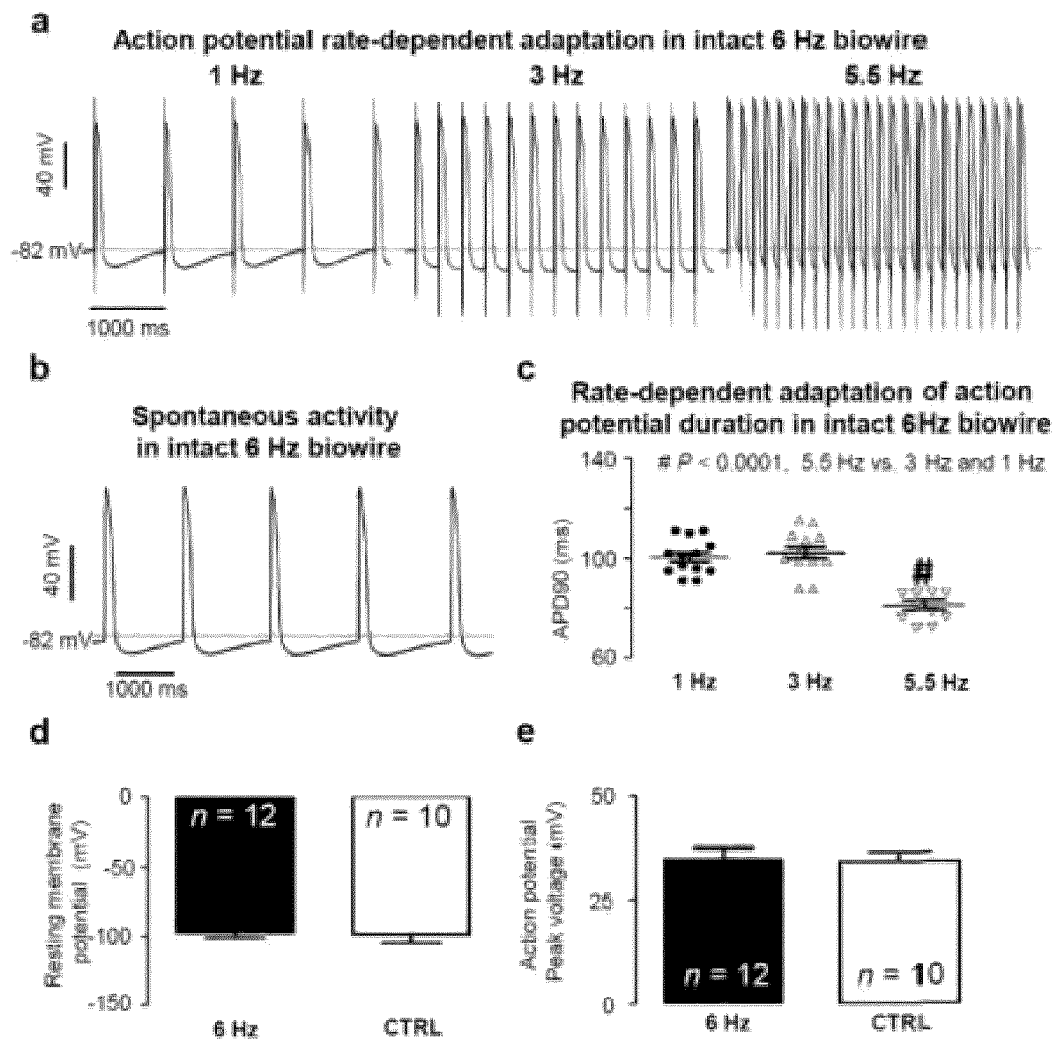
FIGS. 24a-24e show charts illustrating action potential duration rate-dependent adaptation and resting potential in tissues generated using an exemplary biowire system of the disclosure.

FIG. 24 shows example results demonstrating action potential duration rate-dependent adaptation and resting potential in intact 6 Hz tissue strands recorded with high-impedance glass microelectrodes. The example results show action potential of 6 Hz ramp up tissue strands recorded with field stimulation at 1, 3 and 5.5 Hz (FIG. 24a), spontaneous activity in 6 Hz tissue strands (FIG. 24b), rate-dependent adaptation of action potential duration measured at 90% repolarization (APD90) in tissue strands that underwent 6 Hz ramp-up stimulation regimen (FIG. 24c), resting potential (FIG. 24d) and peak voltage of action potential in intact tissue strands (FIG. 24e). FIGS. 24a-24e illustrate results with hESC-derived cardiomyocytes Hes2 cell line. Average±s.e.m.

To assess maturity, action potentials were measured, hERG and $I_{K1}$ currents[11] in cardiomyocytes derived from tissue strands and EBs (see FIG. 21). hERG currents were larger (P=0.0434) in 6 Hz-stimulated tissue strands (0.81±0.09 pA/pF) than non-stimulated controls (0.52±0.10 pA/pF) (see FIG. 21a) without differences in their biophysical properties (see FIG. 22). Cardiomyocytes from both tissue strand groups had higher hERG levels compared to those from EBs day 20 or 44 (see FIG. 21a). Similarly, $I_{K1}$ densities were higher (P=0.0406) in 6 Hz-tissue strands (1.53±0.25 pA/pF, 6 Hz) than in controls (0.94±0.14 pA/pF, CTRL) and $I_{K1}$ levels in both tissue strand groups were higher (P=0.0005) than those recorded in EB-derived cardiomyocytes (see FIG. 21b). Cell capacitance, a measure of cell size, showed higher (P=0.0052) values in the 6 Hz-tissue strands (19.59±1.41 pF; 6 Hz) compared to control tissue strands (14.23±0.90 pF; CTRL) and smaller (P=0.0041) capacitance in EB-derived cardiomyocytes (see FIG. 21c). Resting membrane potentials ($V_{rest}$) of the cardiomyocytes from tissue strands were more negative (P<0.0001) than in EB-cardiomyocytes (see FIG. 21d). Interestingly, after correcting for the liquid junction potential which was ~16 mV, the values of $V_{rest}$ recorded in tissue strand cardiomyocytes with the patch-clamp method were well below the equilibrium potential for Nernst potential for $K^+$ ($E_K$=−96 mV) suggesting that hyperpolarizing currents, possibly those generated by the $Na^+$ pump[37-38], strongly influenced $V_{rest}$. Consistently, it was found that the cardiomyocytes from tissue strands had a very low resting membrane conductance, which correlated (R=0.5584, P<0.0001) with $V_{rest}$, while $I_{K1}$ currents exhibited negative correlations with $V_{rest}$=0.2267, P=0.0216, see FIG. 23). Maximum depolarization rates (see FIG. 21e) and peak voltages of the action potentials (see FIG. 21f) did not differ between the two tissue strand groups. However, both properties were improved compared to EBs (P=0.5248 and P=0.0488, respectively). Action potential durations were longer (P=0.0021) with greater variation in EB-derived cardiomyocytes than tissue strand-derived cardiomyocytes (see FIGS. 21g and 24), suggesting less electrophysiological diversity and more maturation in tissue strands. Automaticity was greater (P=0.0414) in EB-derived cardiomyocytes compared to control tissue strands (see FIG. 21h), which was comparable to 6 Hz-stimulated tissue strands. Taken together, these results support the conclusion that tissue strands and electrical stimulation at the 6 Hz regimen promoted electrophysiological maturation.

Electrophysiological Measurements in Cultivated Human Tissue Strands

The presence of the suture prevented both direct measurements of active force and mechanical stimulation since the suture was stiffer than the surrounding cardiac tissue. This limitation can be overcome in future studies by the use of biodegradable sutures. Therefore, the presented electrophysiological measurements (see FIG. 21), were used to gauge the functional maturation of the conditioned cells. All of the measurements, hERG current, $I_{K1}$ current, cell capacitance, resting membrane potentials, maximum depolarization rate, peak voltage of the action potential, action potential duration and automaticity, exhibited improvements in cardiomyocytes cultivated in tissue strands, compared to those cultivated in EB controls. While electrical stimulation of tissue strands enhanced hERG, $I_{K1}$ and cell capacitance (see FIGS. 21a-21b), there were no differences between stimulated and non-stimulated tissue strands according to the other measures. Specifically, the maximum rate of membrane depolarization during an action potential did not differ (P=0.5248) between 6 Hz and control tissue strands (see FIG. 21e, 122.5±9.30 mV/ms; 6 Hz vs. 111.8±14.67 mV/ms; CTRL), an observation that correlated with the lack of differences in $Na^+$ current densities between the tissue strand groups (see FIG. 23d). $V_{rest}$ did not differ (P=0.88) between the tissue strand groups when using either patch-clamp recordings of single isolated myocytes (−98.58±2.87 mV; 6 Hz vs. −99.44±5.37 mV; CTRL) or sharp microelectrode recordings in intact tissue strands (−97.08±3.95 mV; 6 Hz vs. −98.5±6.09 mV; CTRL, P=0.8425, see FIG. 24). Tissue strands stimulated at 6 Hz, also exhibited a rate-dependent adaptation of action potential duration with the duration of the action potential decreasing with the increase in stimulation frequency from 1 Hz to 5.5 Hz (see FIG. 24).

Cell capacitance measurements were consistent with size measurements in Table 1 (see FIG. 26) in 6 Hz-stimulation regimen compared to the non-stimulated controls suggesting that electrical stimulation induced maturation of cardiomyocytes in tissue strands. While the capacitance measurements illustrated improvements in cell size of 6 Hz stimulated hESC-cardiomyocyte tissue strands compared to EBs, the values clearly indicated that sizes consistent with adult human ventricular myocytes were not achieved. Capacitance of freshly isolated healthy adult human ventricular cardiomyocytes was reported to be in the range from 179-227 pF[39]; that of freshly isolated adult human atrial cardiomyocytes was reported to be 66 pF. Interestingly, after 1 day in culture on 2D substrates capacitance of adult atrial cardiomyocytes declined to 23 pF[40], suggesting that removal of cardiomyocytes from their 3D environment may dramatically affect cell capacitance. The capacitance values reported here were smaller than those reported by others for iPSC-cardiomyocytes derived by engineering blasticidin-resistance gene expression controlled from the cardiac-specific endogenous MYH6 promoter (15.8-88.7 pF)[4] but were similar to other hESC-cardiomyocyte (21.6±1.3 pF, range from 7 to 40 pF) and human fetal cardiomyocyte reports (at age of 90-110 days, 20.3±4.6 pF)[41-42]. Since the differentiated progeny of hPSCs were described to be reflective of very early human development (<6 weeks)[43], it is likely that electrical stimulation rates required for maturation in vitro may differ from in vivo embryo development. Regardless, the remarkable maturation of the in vitro cardiac tissue strands obtained with progressively higher electrical stimulation rates provided an important tool to generate more mature contractile cardiac tissues in vitro.

Figure 25:
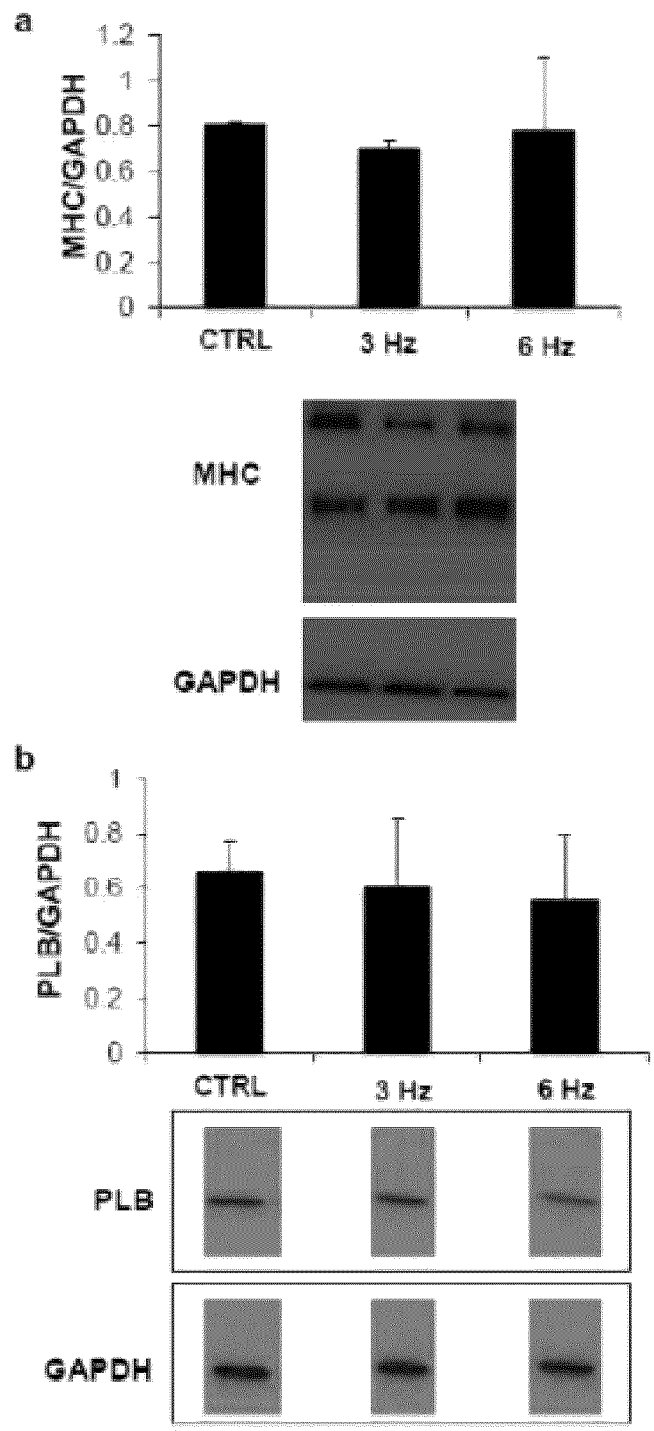
FIGS. 25a-25b show expression of selected cardiac proteins in tissue strands generated using an exemplary biowire system of the disclosure.

Cultivated Tissue Strands Displayed Expression of Myosin Heavy Chain and Phospholamban at Similar Levels FIG. 25 shows example results demonstrating expression of selected cardiac proteins in tissue strands was similar in different conditions. The example results show total cardiac myosin heavy chain expression (FIG. 25a) and phospholamban expression (FIG. 25b) assessed by western blotting of tissue strand lysates (n=3). FIGS. 25a-25b illustrate results with hESC-derived cardiomyocytes Hes2 cell line.

To interrogate whether changes in cardiomyocytes myofibril ultrastructure were associated with changes in contractile protein expression, the expression of total myosin heavy chain (MHC) was analyzed in tissue strands (see FIG. 25a) by western blotting and found that total MHC was expressed at similar levels in electrically stimulated (3 and 6 Hz) and non-stimulated (CTRL) cardiac tissue strands. In addition, also investigated was the expression of phospholamban, a sarcoplasmic reticulum molecule involved in the regulation of $Ca^{2+}$ uptake and previously described as absent in hESC-cardiomyocytes that do not display functional sarcoplasmic reticulum[10]. It was found that phospholamban was, in fact, present in hESC-cardiomyocyte tissue strands at similar levels (see FIG. 25b).

It was reported that a possible cause for lack of functional sarcoplasmic reticulum in hESC-cardiomyocyte was the lack of phospholamban expression[10]. It was possible to detect phospholamban expression in the cells in the present study in all conditions at similar levels, suggesting this was not the cause of improved $Ca^{2+}$ handling properties by electrical stimulation. Differences in phospholamban expression between the cells in the present study and the a in previous[10] study might be explained by the fact that the present study utilized a directed differentiation protocol while others[10] used cardiomyocytes from serum-based spontaneous differentiation.

Although electrical field stimulation was used previously with cells from primary sources and animal tissues[22-23], it is shown here for the first time that the combination of geometric control of 3D tissue assembly and electrical stimulation of hPSC-derived cardiomyocytes and supporting cells improved electrical and ultrastructural properties of human cardiac tissue, resulting in cell maturation. The tissue strand suture remained anchored to the device platform during matrix remodeling, generating tension that resulted in cell alignment along the suture axis.

Normal human fetal heart rate varies significantly, being maintained at ~3 Hz for most of the time[44] while the adult resting heart rate is ~1 Hz[44]. The rate change is associated with changes in contractile protein expression and suggests a possible dependence of cardiac maturation on stimulation rate. The fact that the progressive increase from 1 to 6 Hz was the best condition tested, was surprising since 3 Hz is the average fetal heart rate[44]. This could be a compensatory mechanism for the lack of other important cells types and cell-cell developmental guidance in the in vitro setting. Since field stimulation frequency was gradually increased over 7 days in culture, the 6 Hz group might only lose capture (exceed the rate of 5.2 Hz) at the very last day of stimulation. Therefore, it may be the stimulation at the highest possible rate, and not the rate per se, that is the governing cue for cardiomyocyte maturation in vitro.

Improved cell and myofilament structure in stimulated conditions, with clearly visible Z discs, H zones and I bands, correlated with better electrical properties of stimulated tissue strands such as lower ET, higher MCR, higher conduction velocity, improved electrophysiological and $Ca^{2+}$ handling properties, and upregulation of potassium inwardly-rectifying channel gene (KCNJ2). Lack of M-lines and T-tubules, consistent with previous reports[45-46], indicated absence of terminal differentiation. Although there was a downregulation of structural proteins mRNA in tissue strands compared to EBs, no changes were observed in protein levels. Mechanical stimulation was reported to lead to a robust induction of structural proteins such as myosin heavy chain and induce proliferation of hPSC-derived cardiomyocytes[14,47], suggesting that electrical stimulation of tissue strands at 6 Hz did not simply provide a better mechanical stimulation environment. Previously, mechanical stimulation did not lead to electrophysiological maturation[47]. The use of electrical stimulation in conjunction with stretch as a mimic of cardiac load[14], concurrently or sequentially, might be required to induce terminal differentiation in hPSC-derived cardiomyocytes and upregulate the expression of myofilament proteins. Other strategies might include cultivation in the presence of T3 thyroid hormone[48], insulin like growth factor-I[49], addition of laminin or native decellularized heart ECM into the hydrogel mixture[50] and cultivation on stiffer substrates[51,52].

It is well accepted that some human stem cell lines are more cardiomyogenic than others[12,16] and these differences could also be related to the maturity of the produced cells. In previous reports[10-11,53], many and usually most cells were irresponsive to caffeine at the end of differentiation. Therefore, differences in $Ca^{2+}$ handling properties could also be due to cell line variability. Here, it is demonstrated that within a given cell line, culture in tissue strands and electrical field stimulation enhanced $Ca^{2+}$ handling properties of cardiomyocytes consistent with a functional sarcoplasmic reticulum.

Tissue strand cardiomyocytes were clearly more mature than cardiomyocytes obtained from EBd20 or EBd44, which showed a greater propensity for automaticity, more depolarized membrane potentials, reduced cell capacitance and less hERG and $I_{K1}$ currents. The electrophysiological measurements of the EBd20 cardiomyocytes represented the cell properties prior to their incorporation into tissue strands, while EBd44 cardiomyocytes were cultured for periods slightly longer than the tissue strand culture time allowing assessment of the independent effect of culture time on maturation[54,11]. It is intriguing to consider that the combination of low membrane conductance with $V_{test}$ below $E_K$ may represent an "intermediate" phenotype as cardiomyocytes undergo maturation from the embryonic state.

Correlating the properties of hPSC-cardiomyocytes in tissue strands with mouse or human development could be helpful to gauge maturation stage, however rodent cardiomyocytes are physiologically distinct and age-defined healthy human heart samples are scarce. Additionally, in vitro maturation might not be compatible with embryo development. The small size (radius of ~300 µm) of tissue strand upon gel compaction was selected to be close to the diffusional limitations for oxygen supply to ensure that the tissue strands can be maintained in culture without perfusion. Addition of vascular cells will be imperative for improving survival and promoting integration with the host tissue in future in vivo studies[14]. Thus, the device of Example 1A may provide a unique platform that enables generation of human cardiac tissues of graded levels of maturation that can be used to determine, in future in vivo studies, the optimal maturation level that will result in the highest ability of cells to survive and integrate in adult hearts with the lowest side effects (e.g. arrhythmias).

Example 2: Biotube

A. Structure, Preparation, and Use of a Exemplary Hollow/Perfusable Wire Embodiment (i.e., Biotube)

In a second embodiment, the invention relates to a bioreactor device for growing a three-dimensional tissue that comprises a perfusable lumen comprising a bioreactor having a well or channel, a longitudinal scaffold comprising a lumen which is supported or suspended over the length of the channel, wherein the bioreactor and channel are configured to receive cells seeded therein sufficient to form a tissue strand comprising a lumen. In embodiments involving cardiac cells (or other electrically-stimulated cells), the bioreactor can be further configured to include electrodes configured to generate an electric field across the channel of the bioreactor. The direction of the electric field can be in any direction, but preferably in a direction that is parallel to the length of the channel (and the resulting tissue strand), or which is perpendicular to the length of the channel (and the resulting tissue strand). As may be used herein, the second embodiment of the invention may be referred to as "biotube," which may refer to, but is not limited to, the tissue strand itself (i.e., the cells that grow on a bioreactor device as described herein) or the system comprising the tissue strand and the bioreactor together. Biotube may also be referred to herein as its commercial name of BIOTUBE™, which encompasses both the tissue strand itself, or the system comprising the tissue strand and the bioreactor device in which the tissue strand has grown or has been placed. In this embodiment, the device may be scaled up to a configuration that comprises a plurality of bioreactor channels and longitudinal scaffolds such that a plurality of three-dimensional tissue strands comprising lumens may be grown simultaneously. This second embodiment also relates to methods for growing the tissue strands in the bioreactor, to the three-dimensional tissue strands themselves, to systems comprising both the bioreactor and grown tissue strands, and to methods for using and/or testing the tissue strands (or systems comprising the tissue strands) in various applications, including, but not limited to, (a) the testing of the efficacy and safety (including toxicity) of experimental pharmacologic agents (including, but not limited to, small molecule drugs, biologics, nucleic acid-based agents), (b) the defining of pharmacokinetics and/or pharmacodynamics of pharmacologic agents (including, but not limited to, small molecule drugs, biologics, nucleic acid-based agents), (c) characterizing the properties and therapeutic effects of pharmacologic agents (including, but not limited to, small molecule drugs, biologics, nucleic acid-based agents) on a subject, (d) screening of new pharmacologic agents, (e) provide implantable engineered tissues for use in regenerative medicine for treating damaged and/or diseased tissues, (e.g., use of the tissue constructs, devices, and/or systems of the disclosure to study cardiac disease states, including patients with electrical conduction defects (iPSC-CM)), and (f) personalized medicine. In this embodiment, the device can be configured at a multi-well plate, such as a 6-well, 12-well, 24-well, 96-well, 384-well, and 1536-well plate.

Figure 29:
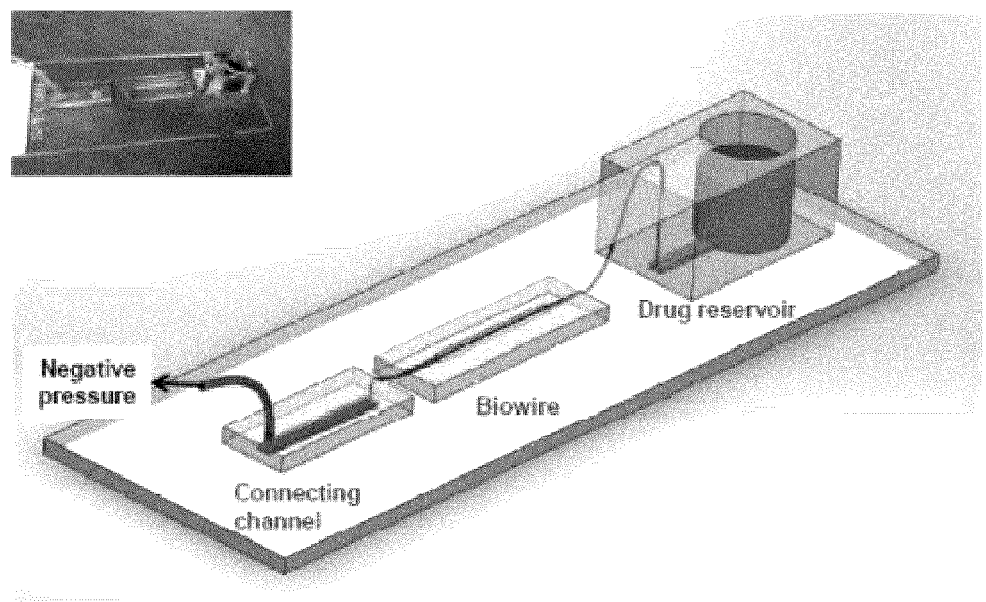
FIG. 29 provides a photograph and schematic depicting a second embodiment of the invention which comprises a perfusable longitudinal element providing a lumen, i.e., the perfusable single-wire 3D tissue culture embodiment (e.g., biotube).

FIG. 29 shows a schematic and an image of an example device suitable for cultivation of a perfusable tissue strand. The device of Biotube may be similar to the device of the Biowire of Example 1, with added features to enable perfusion of the cultivated tissue strand.

The example device may include a longitudinal bioreactor channel in which seed cells for a tissue culture may be received. A longitudinal scaffold may be supported (e.g., suspended) over the length of the bioreactor channel. The scaffold may serve as a support for the seed cells to form a tissue structure along the length of the scaffold. The scaffold may also have a lumen and may enable perfusion of the cultivated tissue strand via the lumen.

In this embodiment, there may be additionally a fluid reservoir (e.g., a drug reservoir) in fluid communication with an inlet at one end of the bioreactor channel. The outlet at an opposing end of the bioreactor channel may be in fluid communication (e.g., via a connecting channel) to an external positive or negative pressure source. Use of negative or positive pressure may help to promote fluid flow and/or perfusion through the lumen of the scaffold. The fluid reservoir and/or the connecting channel may be part of the example device, or these may be separate components connectible to the device. These components may all be supported by and bonded on a substrate, such as a glass slide. An actual image is shown at the top-left corner of FIG. 29.

The example device may include a microfabricated bioreactor channel or chamber, and may include: a microfabricated platform (e.g., made of PDMS) and a scaffold in the form of a suspended tubular template (e.g., made of Polytetrafluoroethylene (PTFE) micro-tubing). By cultivating tissue using a scaffold having a lumen (e.g., a tubular template), the resulting tissue may be provided with a lumen enabling perfusion of the tissue.

The Biotube embodiment may be fabricated in a manner similar to that of the Biowire device of Example 1. In an example, to fabricate the PDMS platform, standard soft lithography technique was used to make a two-layer SU-8 (Microchem Corp., Newton, Mass.) master[20]. The first layer included the template channel and the cell culture chamber, while a second layer included only the cell culture chamber.

Then PDMS was cast onto the SU-8 master and baked for 2 hr at 70° C. A tubular template was then anchored to the two ends of the PDMS platform followed by the bioreactor sterilization in 70% ethanol and overnight UV irradiation. In order to provide perfusion through the tubing template, two microfabricated modules, a drug reservoir and a connecting channel, were added to the example bioreactor device. Both modules were fabricated by first molding PDMS with a single-layer SU-8 master (length×width×height=10×1×0.3 mm). The drug reservoir was created by cutting through the PDMS using a 8 mm biopsy punch (Sklar). The bioreactor channel was connected to the drug reservoir and connecting channel with the PTFE tubing (inner diameter (ID)=0.002 inch, outer diameter (OD)=0.006 inch, Zeus). Tygon tubing (ID=0.01 inch, OD=0.03 inch, Thomas Scientific) connected the perfusion system to external negative pressure generated by a peristaltic pump. The perfusion rate was characterized by the liquid volume collected at the outlet from the peristaltic pump. All the connecting points were secured by epoxy glue and three microfabricated modules were plasma bonded to a glass slide.

Although certain materials, techniques and dimensions are described above, other suitable materials, techniques and dimensions may be used for the example device. Examples of other suitable materials include, without limitation, poly (glycerol sebacate), POMac, poly(lactic acid), poly(glycolic acid), poly(ε-caprolactone), various polyurethanes as well as co-polymers thereof. Although certain types of tubing and connections are described, other means of fluid communication may be used. For example, the reservoir, bioreactor channel and connecting channel may all be microfabricated together, rather than being separate components.

B. Experimental Testing of an Exemplary Biotube Embodiment

Example Methods and Analyses

Neonatal rat cardiomyocytes or human ESC-derived cardiomyocytes were obtained as described above, for investigation of the Example 1 device. Alternatively, NKX2-5-eGFP reporter human embryonic stem cell (hESC) line[22] that contains the eGFP cDNA inserted into the NKX2-5 locus of HES3 hESCs was maintained as described[23]. Before cardiac differentiation, cells were passed to single cells using TrypLE Express (Gibco) and plated at a density of 260,000 cells/cm$^2$ on a thin layer of reduced growth factor Matrigel (BD Biosciences) and cultured with mouse embryonic fibroblast conditioned medium (MEF-CM). To induce cardiac differentiation, the matrix sandwich protocol was used as described[24] using Activin A between 50-100 ng/mL and BMP4 between 7-10 ng/mL. The resulting cardiomyocyte monolayer cultures were digested on day 19 as previously described[19].

Tissue strands were fixed with 4% paraformaldehyde, permeabilized by 0.25% Triton X-100, and blocked by 10% bovine serum albumin (BSA) Immunostaining was performed using the following antibodies: mouse anti-cardiac Troponin T (cTnT) (Abcam; 1:100), mouse anti-α-actinin (Abcam; 1:200) and anti-rabbit-TRITC (Invitrogen; 1:200), anti-mouse-TRITC (Jackson Immuno Research; 1:200). Nuclei were counterstained with 4',6-diamidino-2-phenylindole (DAPI) (Biotium; 1:100). Phalloidin-Alexa 660 (Introgen; 1:600) was used to stain F-actin fibers. For confocal microscopy, the stained cardiac tissue strands were visualized under an inverted confocal microscope (Olympus IX81) or an upright confocal microscope (Zeiss LSM 510).

Neonatal rat cardiac cells were seeded into the example perfusable bioreactor devices with tubing template. After cultivation for 7 days, the cultivated cardiac tissue strands were sectioned and visualized under environmental SEM (Hitachi S-3400 N). The tissue strands were imaged under variable pressure mode at 70 Pa and 15 kV and the chamber temperature was −20° C.

To visualize the cross-section, perfusable cardiac tissue strands were stained with cTnT antibody and then TRITC. Stained tissue strands were then cryo-sectioned into 500 μm thick sections using a cryostat (Leica CM3050S) and mounted to Superfrost Plus glass slide (VWR). Images of the cross-sectioned tissue strands were acquired by Olympus fluorescent microscope (IX81).

To demonstrate the feasibility of the example device, FITC-labeled polystyrene beads (Spherotech Inc.) were added into the drug reservoir and perfused through the rat cardiac tissue strand, while it beat spontaneously on day 8. Bright-field and fluorescent videos and images were acquired with a fluorescence microscope (Olympus IX81).

Quantification of NO perfusion was carried out. Sodium nitroprusside (SNP) (Sigma) was dissolved in distilled water to make 200 mM SNP solution and then added to the drug reservoir. Perfusion through the tubing template was driven by the external peristaltic pump. Once the SNP solution perfused through the tubing, the peristaltic pump was stopped and the entire perfusion system was kept in cell culture incubator. NO amount in the cell culture channel (outside the PTFE tubing) was quantified with a fluorometric Nitric Oxide Assay Kit (Calbiochem, 482655). In brief, samples collected from the cell culture channels (8 μl, n=3) at different time points (0.5 hr, 6 hr, and 24 hr) were converted to nitrite by nitrate reductase and then developed into a fluorescent compound 1-H-naphthothiazole. The fluorescent signals were quantified by a plate reader (Apollo LB 911, Berthold Technologies) and compared to the nitrate standard.

NO treatment of human cardiac tissue strands was carried out. On day 7, the NO treatment of human cardiac tissue strand was initiated by perfusing the 200 mM SNP solution and the peristaltic pump was stopped once the SNP solution was perfused through the tubing. The beating activities of the human cardiac tissue strands were recorded at 16.67 frames/second before treatment and 24 hr post-treatment by Olympus IX81 while the tissue strands were kept at 37° C. The beating activities of the human cardiac tissue strands were quantified by the image analysis method described by Sage et al[28]. In brief, the movements of one spot at the same location on the human cardiac tissue strand before and after the NO treatment were characterized.

Electrical stimulation and perfusion were carried out. For the human perfusable cardiac tissue strand, only parallel electrical stimulation was applied as described above. Starting on day 4, electrical field stimulations (biphasic, rectangular, 1 ms duration, 1 Hz, 3.5-4 V/cm) were applied for 4 days while control tissue strands were cultured without electrical stimulation. Both stimulated and control tissue strands were perfused with culture medium at a flow rate of 2 μl/min within the PTFE tubing driven by an external syringe pump (PHD Ultra; Harvard Apparatus). At the end of electrical stimulation, the electrical properties of the stimulated and control human cardiac tissue strands were characterized in terms of excitation threshold (ET) and maximum capture rate (MCR) under external field pacing as previously described[29].

Statistical analysis was performed using SigmaPlot 11.0. Differences between experimental groups were analyzed using t-test or one-way ANOVA with significant difference considered as $p<0.05$.

Example Results and Discussion

Generation and Characterization of Perfusable Cardiac Tissue Strands

Primary neonatal rat and hESC-derived cardiomyocytes were used to generate perfusable cardiac tissue strands.

Figure 30:
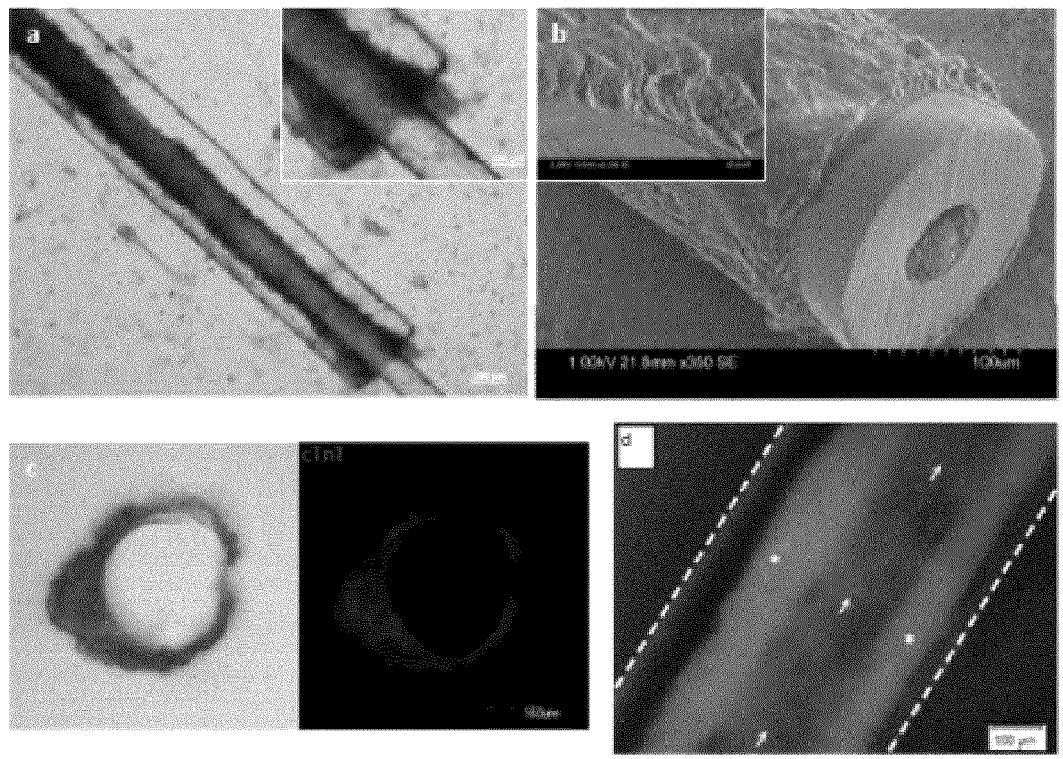
FIGS. 30a-30d are images illustrating the generation of perfusable cardiac tissue strands, generated in accordance with an exemplary biotube system of the disclosure.

FIG. 30 shows example images of cultivated perfusable cardiac tissue strands. FIG. 30a shows that neonatal rat cardiomyocytes (200 million cells/ml) remodeled the gel and compacted around the tubing template (ID=50.8 µm, OD=152.4 µm). A close-up view showing the tubing lumen at the end of the tissue strand is given at top-right. FIG. 30b shows SEM images demonstrating that the cardiac tissue attached to the tubing surface and formed a uniform-thick layer after remodelling FIG. 30c shows representative phase contrast image (left) and confocal image (right) showing the circular morphology of the cross section of the perfusable cardiac tissue strand with the expression of cardiac Troponin-T (cTnT). FIG. 30d shows the tubing-templated tissue strand perfused with FITC-labeled polystyrene beads (1 µm in diameter). Dash lines illustrate the wall of the cell culture channel FITC-labeled beads were indicated by arrows. Asterisks indicate the auto fluorescence from the cardiomyocytes within the cardiac tissue strand. This image was over-exposed to better visualize the fluorescent beads.

Both cell types were able to form the cardiac tissue strands and beat spontaneously (see FIG. 30a). As shown in SEM images, cells attached to the smooth surface of the PTFE tubing after self-remodeling (see FIG. 30b). Cross sections of these perfusable tissue strands showed that self-remodeled cells encircled the tubing template and expressed cTnT (see FIG. 30c).

The feasibility of the example device for cultivating perfusable tissue strands was demonstrated by perfusion with FITC-labeled fluorescent beads. Perfusion rate driven by the peristaltic pump was quantified to be 2±0.16 µl/min (n=3). Bright field video showed both spontaneous beating activity of the rat cardiac tissue strand and the perfusion of the fluorescent beads. The movement of the beads was better visualized under fluorescent view. A snapshot of the video (see FIG. 30d) was overexposed to provide better visualization of the fluorescent beads. The cardiac tissue strand was also visible in this image due to the auto-fluorescence of cardiomyocytes.

NO Treatment of Cultivated Human Cardiac Tissue Strands by Perfusion

Figure 31:
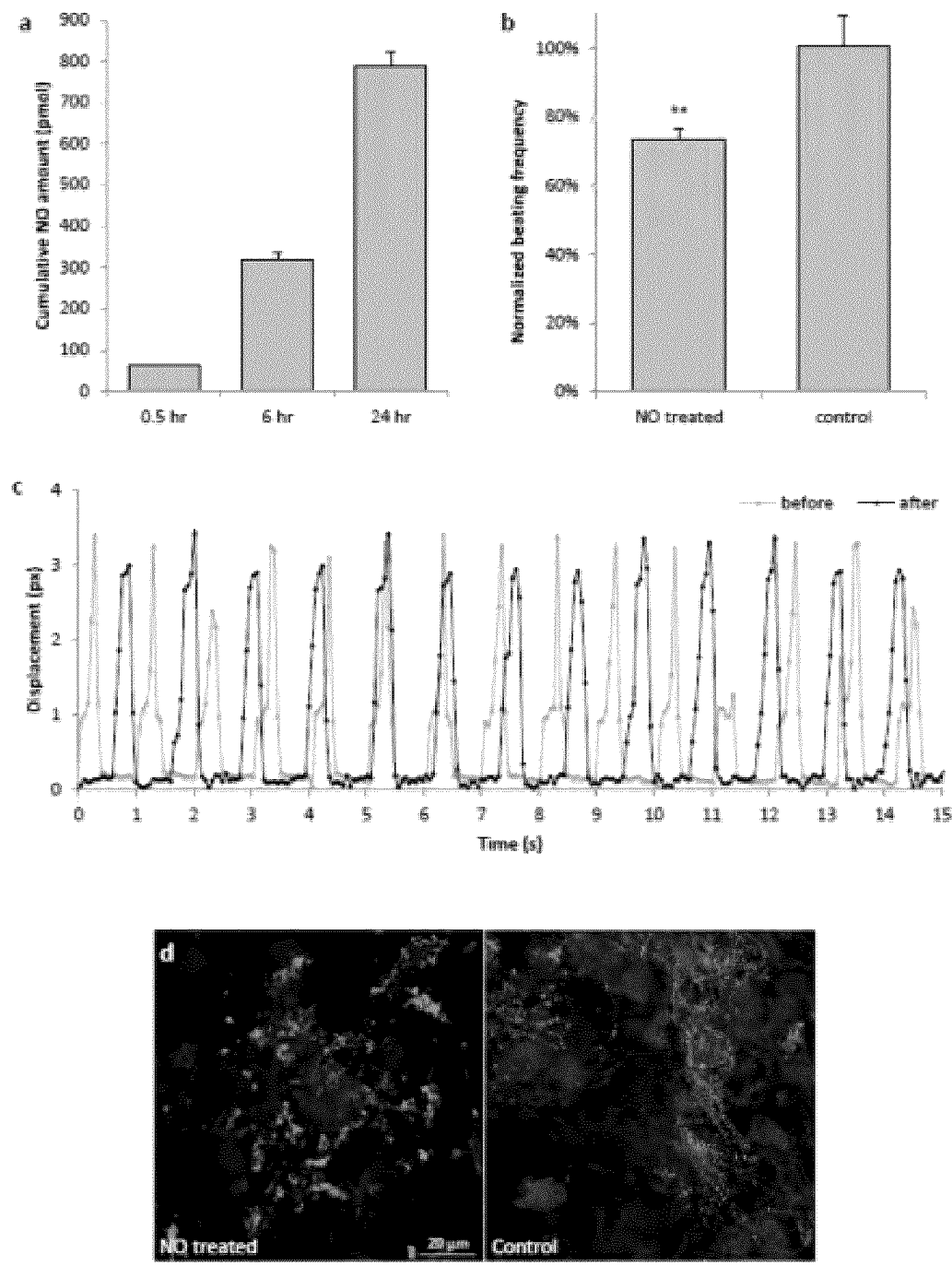
FIGS. 31a-31d illustrate nitric oxide (NO) treatment on human tubing-templated tissues generated in accordance with an exemplary biotube system of the disclosure.

FIG. 31 shows example results of nitric oxide (NO) treatment on human tubing-templated tissue strands. FIG. 31a shows quantification of NO amount passing through the tubing wall after perfusing SNP (200 mM) for 0.5 hr, 6 hr, and 24 hr. FIG. 31b shows that 24 hr NO treatment significantly slowed down the beating of tissue strands compared to the basal levels while there was no significant change in the non-treated tissue strands (n=3 per group, p<0.01). FIG. 31c shows quantification by image analysis, demonstrating that the beating rate of a tissue strand after 24 hr NO treatment was less frequent compared to the basal level. FIG. 31d shows confocal images showing the disrupted α-actinin structure within the NO-treated tissue strand (left) compared to the control (right).

To demonstrate feasibility of drug testing in the perfusable cardiac tissue strand, a pharmacological agent, NO donor SNP, was applied to the culture media that was perfused through the tubing lumen. As NO was generated in the tubing lumen, it diffused through the tubing wall reaching the cell culture outer channel where the total amount of NO was quantified. The amount of NO released from 200 mM SNP was quantified by a fluorometric assay which validated the persistence of the NO release from SNP solution over several hours (see FIG. 31a). The cumulative NO amount in the cell culture channel was 100 µM (800 pmol in 8 µl), which exceeded the physiological levels of NO in vivo[31].

Upon gel compaction, the hESC-derived cardiomyocytes within the tissue strands started spontaneous beating. After NO treatment for 24 hr, performed by perfusion of NO-donor SNP through the tubing lumen, the spontaneous beating of human cardiac tissue strands slowed down and this was further characterized by image analysis (see FIGS. 31b and 31c). In order to compare beating frequency changes between different tissue strands, the frequencies after 24 hr NO treatment were normalized to the basal level (before treatment). The beating frequencies after NO treatment were significantly lower than the basal level (74±3%, n=3) while the control tissue strands remained the same (100±9%, n=3).

The degradation of cytoskeleton of cardiomyocytes within the tissue strands based on hESC derived cardiomyocytes caused by NO treatment through perfusion was characterized using confocal microscopy with immunostaining for α-actinin (see FIG. 31d). It was possible to clearly discern the striated pattern of sarcomeric Z-discs labeled with α-actinin in the control tissue strands, while the NO treated tissue strands showed an overall punctuate pattern. It was also noticed that the Alexa 488 labeled α-actinin staining can be distinguished from the green fluorescent protein (GFP) genetically marked on NKX2-5.

Electrical Stimulation and Perfusion of Cultivated Cardiac Tissue Strands

Figure 32:
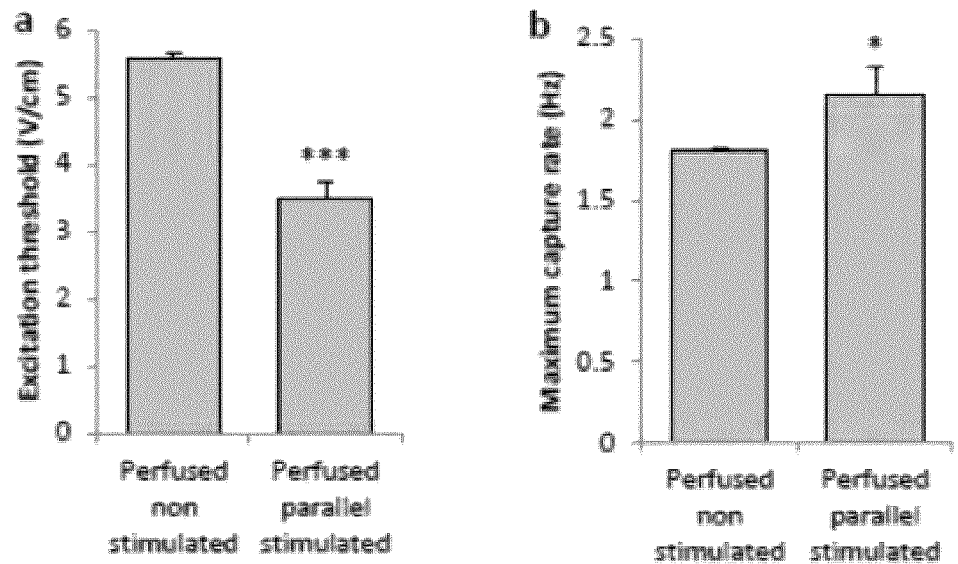
FIGS. 32a-32b show charts illustrating functional properties of tissues generated using perfusion and electrical stimulation, generated in accordance with an exemplary biotube system of the disclosure.

FIG. 32 shows example results demonstrating functional properties of tissue strands cultivated with perfusion and electrical stimulation. FIG. 32a demonstrates that electrically stimulated perfused tissue strands based on hESC derived cardiomyocytes had lower excitation threshold compared to the non-stimulated controls (***, p<0.001). FIG. 32b demonstrates that the electrically stimulated perfused tissue strands based on hESC derived cardiomyocytes had higher maximum capture rate compared to the non-stimulated controls (*, p<0.05).

The perfusable human cardiac tissue strands that underwent medium perfusion through the tubing and parallel electrical stimulation at the same time showed improved electrical properties compared to the non-stimulated controls as assessed by ET and MCR under electrical field stimulation. The ET is the minimum electrical field voltage required for inducing synchronous contractions and the decreased ET of the stimulated tissue strands (see FIG. 32a) indicated better electrical excitability. The MCR is the maximum beating frequency attainable while maintaining synchronous contractions and the increased MCR (see FIG. 32b) of the stimulated tissue strands indicated improved cell alignment and interconnectivity.

The native myocardium consists of spatially well-defined cardiac bundles with supporting vasculature (see FIG. 1a) and the cardiomyocytes within the cardiac bundles are highly anisotropic (see FIG. 1b). The present disclosure, in the device of Example 2A, provides a microfabricated bioreactor to generate cardiac tissue strands in vitro recapitulating the structure and function of native cardiac bundles. This is the first study to examine the drug effects on cardiomyocytes by perfusion within cardiac bundle model, which better mimics native myocardium mass transfer properties compared to other engineered heart tissues. This example device provided topographical cues for the cardiac cells to elongate and align, and was also integrated with other cues, e.g. electrical stimulation.

Gel compaction has been widely applied in tissue engineering to create 3D microtissue constructs for in vivo implantation[32] and in vitro models[16,33]. Compared to scaffold-based constructs, the self-assembled constructs from gel compaction produce increased force of contraction due to the higher cell density after the compaction[34]. Moreover, there is increasing interest in microtissue constructs made by gel compaction as microarrays for drug testing because they provide much higher throughput than conventional models[16,33,35,36]. In this study, type I collagen was chosen as the main gel matrix as it is one of the main ECM components of native myocardium. Previous in vitro collagen-based models only stayed intact for several days due to their poor mechanical properties[33]. In the present example microfabricated device, with the mechanical support provided by the suspended templates, the cardiac tissue strands remained stable in the bioreactor for weeks. It was possible to generate cardiac tissues in larger scale (up to 5 cm long) compared to other in vitro models and the dimensions of the cell culture channel could be easily customized, which could render additional control over the morphology of the cardiac tissue strands. The cell culture channels were initially designed to be 300 μm in height considering the limitations for oxygen and nutrient supply[37]. Moreover, the presence of the templates enabled easy disassembly of the tissue strand from the bioreactor device and facile handling of the cardiac tissue strands at the end of cultivation for further characterization.

In some examples, the microfabricated bioreactor device was also able to generate cardiac tissue strands that are 5 cm long, which is comparable to the height of the human heart. The feasibility of handling individual cardiac tissue strands together with the ability to create macro-scale tissue strands raise up the prospect of investigating the alignment of multiple cardiac tissue strands by bundling or weaving them together to generate thicker structures, using similar methods as described by Onoe et al[38]. To characterize the force generated by the cardiac tissue strands or cardiac tissue strand bundles, degradable sutures could be used to generate template-free cardiac tissue strands.

To validate the example microfabricated bioreactor device, neonatal rat cardiomyocytes were used in preliminary studies. Only when seeded at higher cell density (>5×10$^7$ cells/ml), which is comparable to the cell density in native rat myocardium (~10$^8$ cells/ml)[39], the cardiac tissue strands started spontaneous beating on day 3-4. The template provided contact guidance for the cells to elongate and align along with, recapitulating the anisotropic properties of cardiomyocytes in the native myocardium. The image analysis was done on cell nuclei due to the difficulty of defining cell membranes within 3D tissue. However, nuclear alignment is a sufficient indication of cell alignment and also one of the hallmarks of native myocardium (see FIG. 1c).

To further develop the example device, PTFE tubing was used as the template instead of the 6-0 silk suture. The commercially available PTFE tubing was chosen because it is biocompatible (USP Class VI), extremely non-absorbent, and micro-scale in dimension (ID=50 μm, OD=150 μm), on the order of post-capillary venules in size[54], although other materials and dimensions may be suitable. Due to the small size of the inner lumen, negative pressure was used to drive the perfusion instead of positive pressure. Two microfabricated modules were added to the example system to enable long-term perfusion and incubation of the tissue strand. Indicated by the shortening of tissue strand during self-remodeling, the cell attachment on PTFE tubing was not as strong as that on silk suture, mainly because of the smoothness of the PTFE tubing surface (see FIG. 30b). However, the cell-gel composite was still able to assemble itself around the tubing with a circular cross-section.

In this study, NO was chosen as a model drug because of following reasons: (1) NO is produced by endothelial cells in native myocardium, and then transported in the radial direction to cardiomyocytes[40], the scenario the example device aims to recapitulate; (2) NO plays a critical role in regulating myocardial function, through both vascular-dependent and -independent effects[40]; (3) there is increasing evidence showing that NO is directly implicated in cardiomyocyte disease development and prevention, such as in ischemia-reperfusion injury[41]; (4) NO is a small gas molecular, which can readily pass the tubing wall. SNP was chosen as the NO donor because it is a common NO donor used in clinical studies[42,43]. Moreover, SNP aqueous solution was reported to release NO at a constant rate over several hours in vitro[44].

For the NO treatment testing, human cardiac tissue strands were generated from hESC-derived cardiomyocytes. The human cardiac tissue strand started spontaneous beating as early as day 1 and the beating was synchronized within 7 days. After 24 hr of NO treatment, the beating frequencies of the human cardiac tissue strands significantly slowed down compared to their basal level. This result corresponds with the vasodilator effect of NO in vivo[45] and might be caused by degradation of myofibrillar cytoskeleton, which has been seen by Chiusa et al[46]. However, NO shows bi-polar inotropic effect at lower concentrations with diverse intracellular mechanisms and there were discrepancies between studies due to the lack of standardization for in vitro models[40]. Therefore the example microfabricated bioreactor device could serve as a platform to uncover the effects of NO on cardiomyocytes at the tissue level.

To demonstrate the versatility of the disclosed device, electrical stimulation was integrated with the system as it has been reported to improve the phenotypes of cardiomyocytes[2,20]. Because the cells in the cardiac tissue strands were anisotropic, both parallel- and perpendicular-field electrical stimulations were studied on the rat tissue strands. The higher tissue stiffness under parallel electrical stimulation, which was closer to the isolated neonatal rat cardiac myofibrils (61 kPa)[47], were attributed to more organized electrical contractile apparatus as characterized by immunohistochemical staining. The perfusable human cardiac tissue strands were electrically stimulated and perfused at the same time and this brings the prospect to study the interaction between electrical stimulation and pharmaceutical agents delivered in a physiological manner. A more detailed study on electrical stimulation alone of tissue strands based on human pluripotent cardiomyocytes has been done and indicated that electrical stimulation of progressive frequency increase markedly improved the maturation of hPSC-derived cardiomyocytes in terms of myofibril structure and electrical properties[19].

Medium perfusion has been recognized to improve the viability and functionality of cardiomyocytes within cardiac constructs in vitro since perfusion significantly improves oxygen and nutrient supply[48]. In most of previous studies, bioreactors provided medium perfusion by sandwiching cell-laden porous scaffold, while exposing the cardiomyocytes directly to the flow[48-50]. This does not exactly recapitulate the native myocardium where the blood supply flows through a dense vascular network that minimizes transport distances but also protects cardiomyocytes from shear[51]. More recently, bioreactors were developed to provide the electrical stimulation and medium perfusion simultaneously and it was shown that perfusion and stimulation had a synergistic effect on improving the contractile functionality of the cardiac constructs[52,51]. However, the cardiac constructs in these systems were based on isotropic porous scaffolds and therefore unable to provide the information about the effect of electrical stimulation on anisotropic cardiac tissue.

Previous studies describe the design of perfusion bioreactors that enable high-throughput in vitro drug testing on cardiac constructs[53,50]. Kaneko et al designed a microchamber array chip to evaluate single cell level interactions for drug testing[53]. Agarwal et al designed a bioreactor composed of a microarray of cantilevers that was able to characterize diastolic and systolic stresses generated by anisotropic cardiac microtissue in real-time and the bioreactor could provide electrical stimulation on these cardiac microtissues[50]. These two studies characterized cardiac function on either single cell or monolayer level, which might be insufficient to provide accurate information of cardiac disease as in the complex natural system. Moreover, the drugs investigated in these studies were directly applied to the cells, instead to the blood compartment, and the presence of flow generated shear stress on cardiomyocytes, both of which contributed to the generation of an unphysiological environment compared to that cardiomyocytes experience in the native heart.

The disclosed devices may provide one or more advantages, including one or more of: (1) they are a better mimic of the native cardiac bundle structure with anisotropic alignment; (2) the presence of the template enables easier handling for later characterization and keeps the entire structure stable for weeks; (3) the device could be easily customized and applicable for high-throughput drug screening; (4) the device provides topographical stimulation by itself; (5) the device is versatile and could be integrated with other stimuli as well (e.g. mechanical stimulation); (6) the perfusable example system is the first platform to study pharmacological agents applied to cardiomyocytes by perfusion through cardiac bundle mimic and could provide valuable knowledge on cardiac disease development and therapeutics.

The permeability of the commercially available PTFE tubing may render limitations on the drug candidates that can be tested, as only small molecules can diffuse appreciably through the tubing wall and proteins cannot. However, other materials may be used, for example tubing materials should be microporous for better permeability. Further studies may be carried out to investigate other relevant pharmacological agents and seeding endothelial cells in the tubing lumen to study the interaction between endothelial cells and cardiomyocytes.

In conclusion, cultivation in the example device may provide one or more of the following: 1) improved hESC-cardiomyocyte architecture and induced physiological hypertrophy, 2) induced sarcomere maturation and 3) improved electrophysiological properties in a stimulation frequency dependent manner, representing a first step towards obtaining adult-like human cardiomyocytes.

Example 3: Biorod

Figure 33:
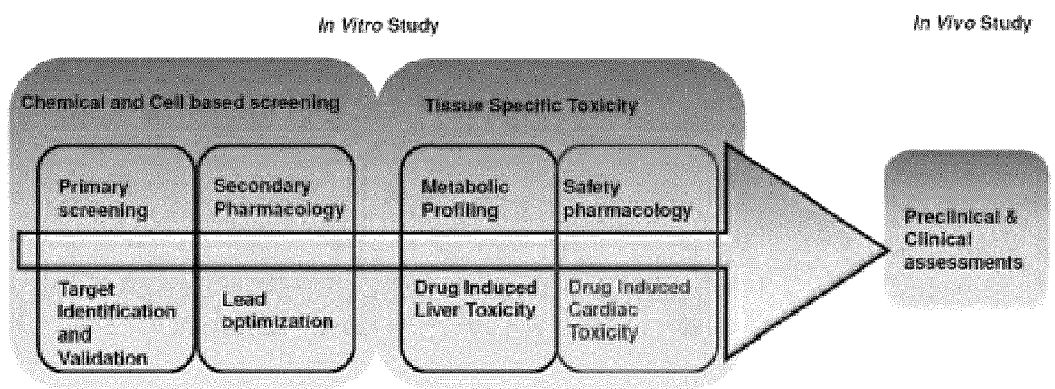
FIG. 33a-b provides (a) a schematic of standard drug screening processes from in vitro studies through clinical in vivo assessments and (b) solutions provided by the invention with respect to various problems with traditional drug screening processes.

FIG. 33 depicts a typical scenario of the drug discovery pathway. As will be appreciated, drug discovery and development consists of an arduous testing process, beginning with the demonstration of pharmacological effects in in vitro experimental cell and animal models and ending with drug safety and efficacy, clinical and pre-clinical studies. It is estimated that only a very small number of compounds receives FDA approval as a safe and effective new medicine. Approximately 25% of compounds are eliminated in pre-clinical toxicological studies. Thus, a significant number of drug candidates in pre-clinical development fail to progress out of this stage due to unacceptable levels of toxicity in test systems. Many of the failures related to cardiotoxic effects caused by the drugs which are difficult to assess using current method and techniques.

While technological advances in cell, molecular, and biochemical assays have made significant strides, a number of significant problems still exist with currently available techniques for evaluating drug toxicity effects. First, in vitro assays using purified or recombinant enzymes and cell cultures provide the first step in determining pharmacologic and toxicologic parameters to be used thereafter in animal models, but are often too simplistic to account for the multifactorial events that occur during drug metabolism in a native human tissue or system. Second, data obtained in animal models cannot be reliably extrapolated to human systems. Third, many drugs used to treat chronic diseases such as HIV infection or Alzheimer's disease necessitate dosing regimens that are applied over long periods of time, and in some cases, over the lifetime of an individual. Currently, development of chronic toxicity is most practically observed during long-term patient use.

Given the high failure rate of drug candidates, particularly with respect to cardiac toxicity, new and improved methods for determining, measuring, evaluating, and otherwise detecting toxicity, and in particular, cardiac toxicity, are highly desired.

A. Structure, Preparation, and Use of an Exemplary Dual-Wire Contractile Force Tissue Culture Embodiment (i.e., Biorod or Biowire II)

In a third embodiment, the invention relates to a bioreactor device for growing a three-dimensional tissue that is suitable for measuring contractile forces.

Figure 34:
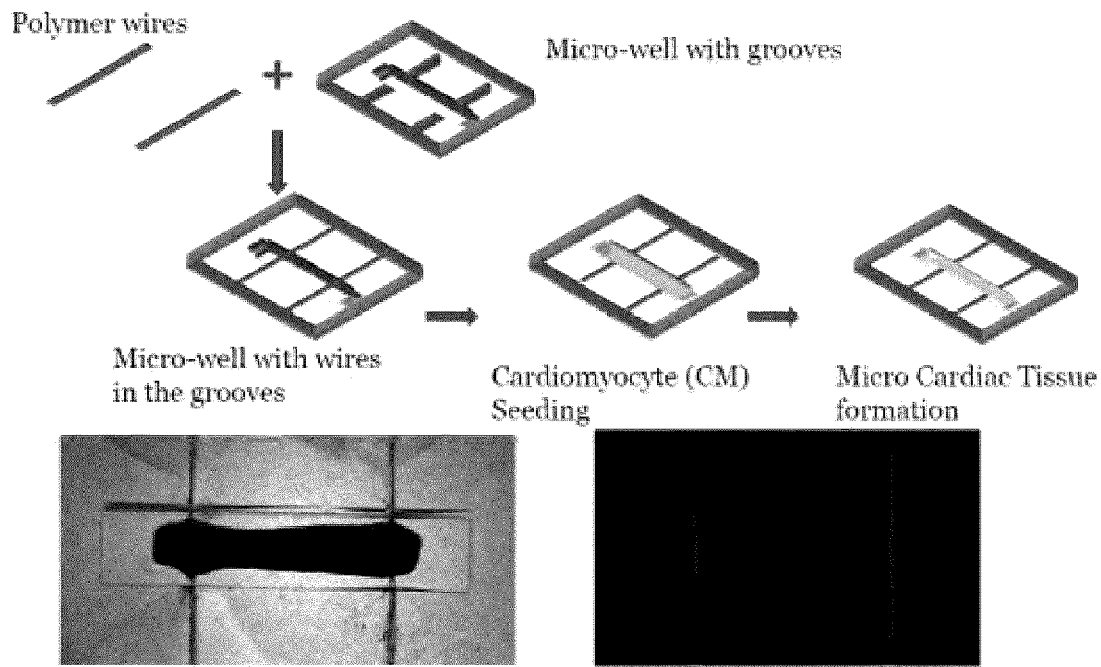
FIG. 34 provides a schematic showing the various components of exemplary Biorod/Biowire II systems of the disclosure (e.g., biorod), including polymer wires affixed to a micro-well across the groove. Seeded cells (e.g., cardiomyocytes) with time form three-dimensional tissue strands which affix to and stretch between the polymer wires at each end of the grooved growth chamber. The polymer wires in certain embodiments (e.g., POMac) fluoresce under UV illumination.
Figure 35:
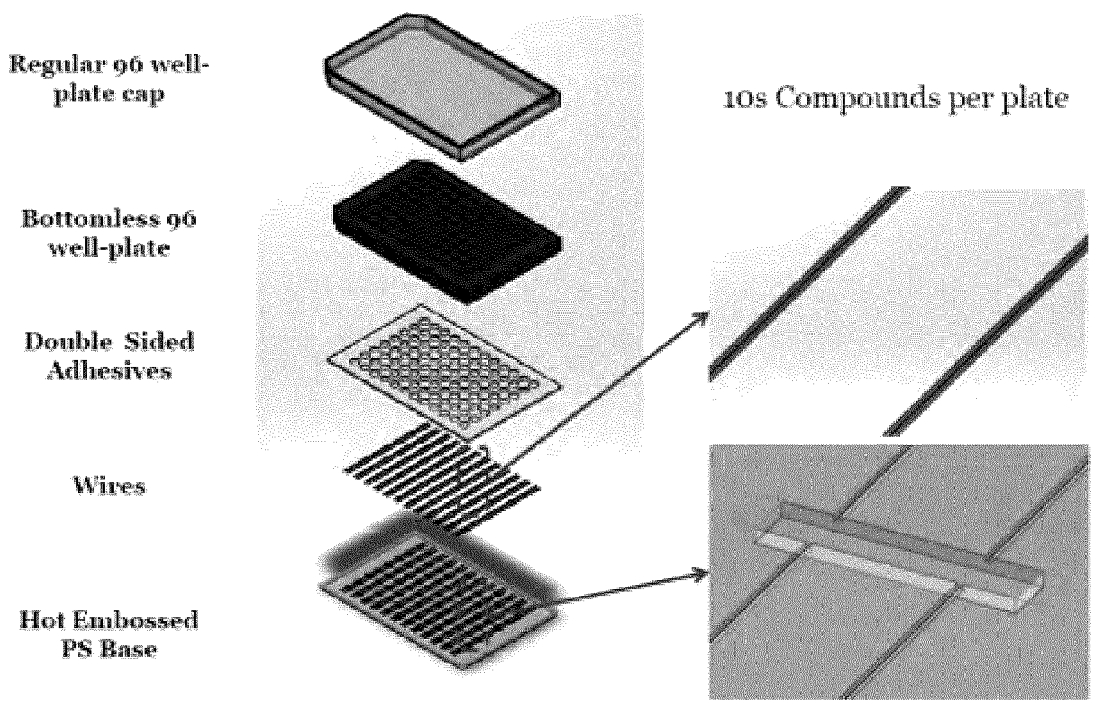
FIG. 35 provides a schematic showing the configuration of an exemplary biorod system of the disclosure in a 96-well format.

FIG. 34 provides a schematic of the design of a dual-wire contractile force tissue culture embodiment of the invention, which may be referred to as "Biorod" or "Biowire II" herein. As shown in the schematic, the Biorod embodiment comprises a macrowell or macrochamber in which is formed a microwell or microchamber and a pair of grooves that intersect the microchamber in a generally perpendicular arrangement. The microchamber is adapted for growing cells and/or tissue and may be seeded with cells of a desired tissue. The grooves are adapted for receiving a pair of polymer wires such that the polymer wires when placed in the grooves traverse the open space of the microchamber. The orientation of the polymer wires/grooves relative to the microchamber is not limited to a perpendicular configuration, but may be any suitable angle so long as the resulting 3D tissue strand that forms in the channel and attaches at each end to the polymer wires such that the cells form an interconnection or cellular bridge or strand between the polymer wires. Preferably the polymer wires are positioned generally parallel to one another and generally perpendicular with the microchannels. However, any suitable configuration is contemplated. For example, the polymer wires and grooves may be arranged generally parallel to one another, and generally perpendicular to the general orientation of the microchannel. In other embodiments, the polymer wires and grooves may be arranged at different angles with respect to the general orientation of the microchannel. In addition, while the polymer wires are depicted in a generally straight configuration, the wires may also be configured having curves and/or otherwise non-straight portions. The polymer wires can preferably be deflectable, deformable, bendable, or the like, which can further configured to allow the measurement of contractile forces exerted by the tissue strand on the polymer wires. The Biorod embodiment may also be configured such that the polymer wires have different properties which together facilitate the measurement of contractile forces. For example, the biorod may be configured where one of the wires is deflectable, deformable, bendable, or the like and another wire is rigid. In this manner, contractile activity can be monitored and/or measure based on the movement of the flexible wire. Any suitable configuration of wires is envisioned and can be used so long as contractile force of a tissue strand may be measured. The Biorod embodiment may also be configured in accordance with FIG. 35 as an array of individual Biorod growth chambers, each comprising the macrowell and a microchamber and the polymer wires.

Figure 36:
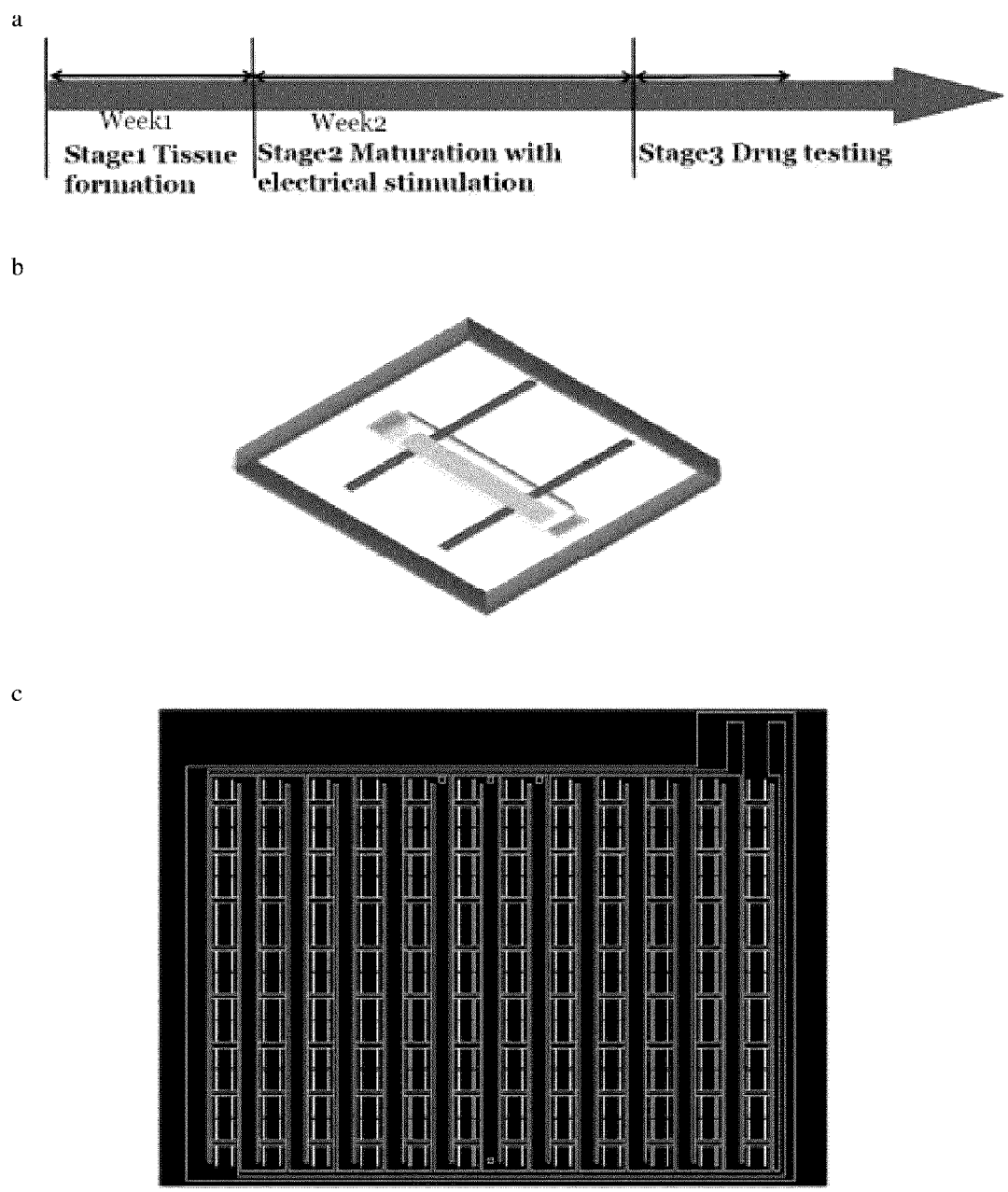
FIG. 36 provides a schematic depicting the timeline in operating an exemplary biorod system of the disclosure, including Stage 1 (tissue formation wherein the well is seeded and cell grow), Stage 2 (wherein cells are maturated with electrical stimulation), and Stage 3 (drug testing stage).

As shown in FIG. 36, the microwells may be configured with two electrodes (at the terminal ends of the microchannel) for stimulating cardiac cells. FIG. 36 also depicts a typical timeframe required for testing drugs using the Biorod system, which includes "Stage 1" (tissue strand formation), "Stage 2" (maturation of tissues using electrical stimulation), and "Stage 3" (the testing stage). In more detail, as a drug screening application, engineered cardiac tissue should mimic healthy adult cardiac tissue as much as possible to provide strong data. To have a high fidelity cardiac tissue, this embodiment can be incorporated with electrical stimulation. By comparison, current technologies of cardiac differentiation are only able to provide immature cardiac muscle cells. Electrical stimulation has been found to significantly enhance the degree of maturation of cardiac tissues. Therefore, the first week of culture is focused on tissue formation, the second week introduces electrical stimulation to mature the tissue, and the third week and on can be used for short and long term drug testing. However, this particular protocol is not meant to be limiting and other electrical stimulation protocols are envisioned and contemplated here. One may make adjustments to the protocol parameters in any suitable way, such as the duration of electrical stimulation and the pacing frequencies.

Figure 37:
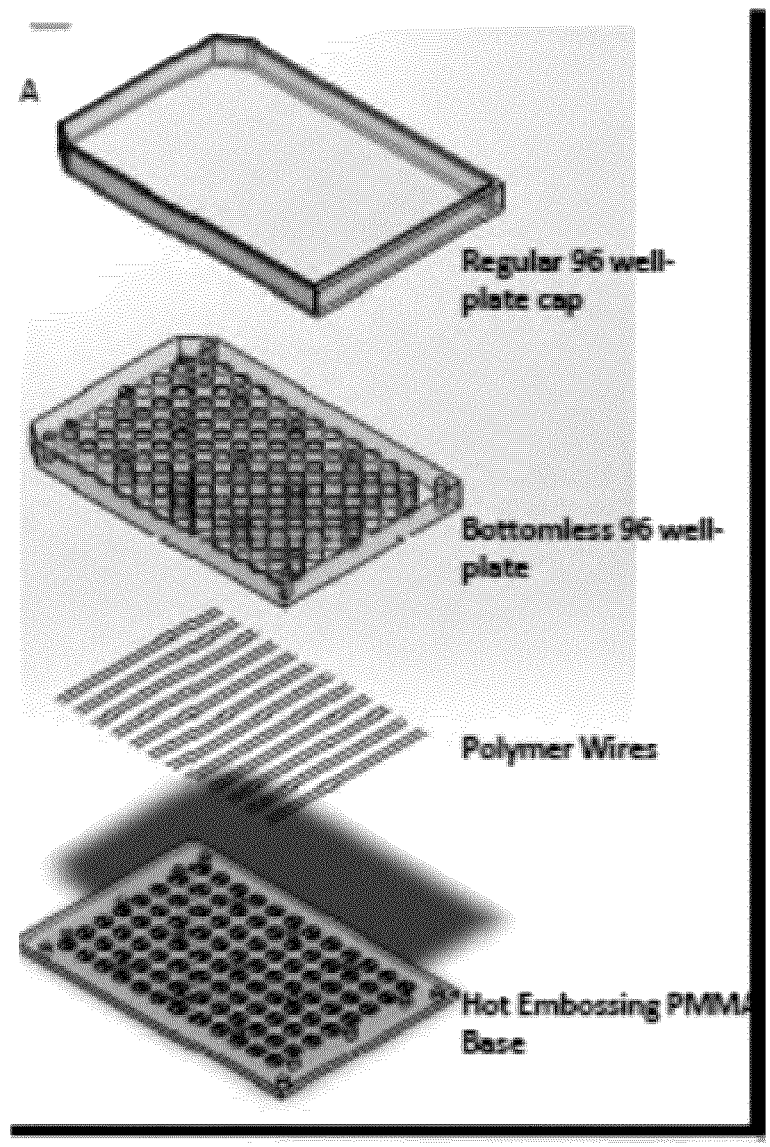
FIG. 37 provides photographs and schematics depicting an exemplary biorod system of the disclosure which enables the measurement of contractile forces on the tissue strand, i.e., the contractile force tissue culture embodiment. (a)-(c) depict an exemplary fabrication process for the device depicted in (d1-d3). In particular, (a) depicts a 96-well format, including a hot embossing PMMA base, polymer wires affixed thereon, a bottomless 96-well plate overlay, and a plate cap. Schematic (b) depicts the formation of the PMMA base, and includes images of an actual PMMA base. Schematic (c) depicts the formation of the polymer (e.g. POMac) wires. Schematic (d) depicts the arrangement of the polymer wires over the well/growth chambers.
Figure 37:
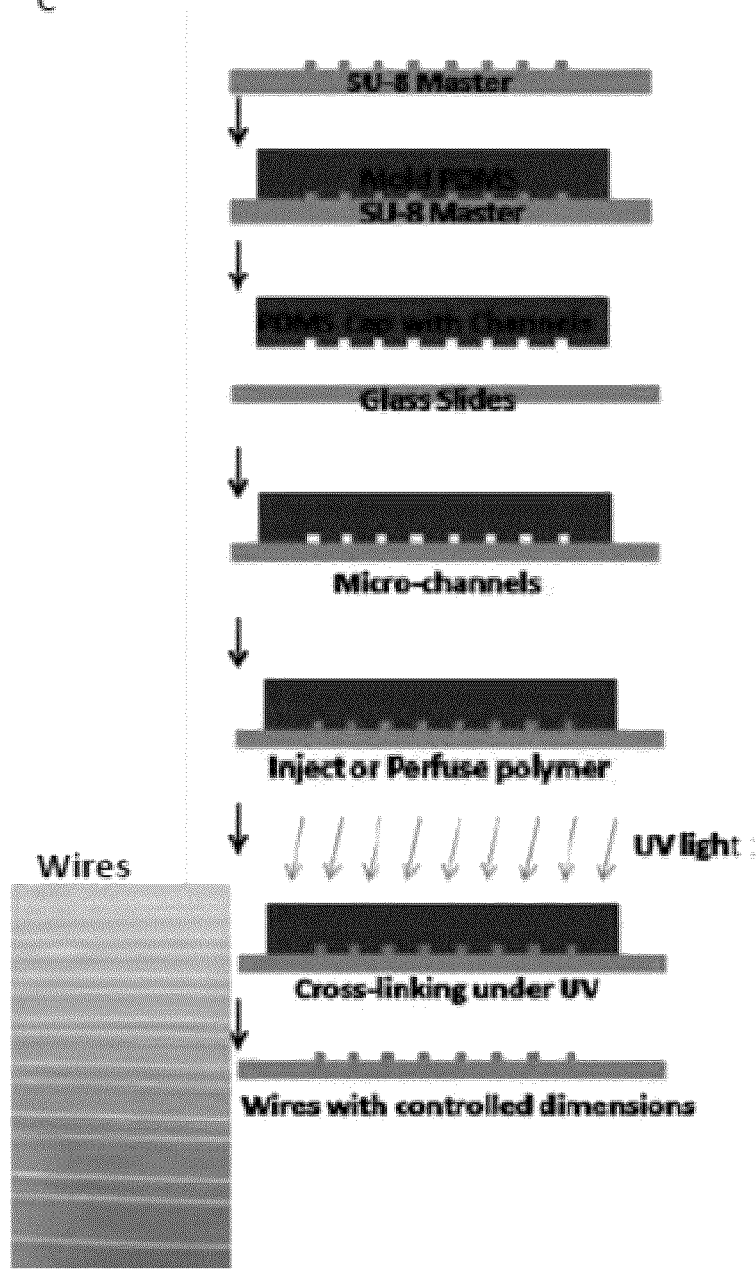

As depicted in FIG. 37, the Biorod embodiment of the invention can comprise a bioreactor having a well or channel and a scaffold comprising two longitudinal elements (e.g., wires or sutures) oriented generally perpendicular to the longitudinal dimension of the bioreactor channel and disposed over the width the channel at or near opposing ends of the channel. The longitudinal elements may function as anchors or support for the seeding of cells in the bioreactor channel to form a tissue strand that comprises both elements therein.

The longitudinal elements can preferably be deflectable, deformable, bendable, or the like, which are further configured to allow the measurement of contractile forces exerted by the tissue strand on the longitudinal elements. The bioreactor can be further configured to include electrodes configured to generate an electric field across the channel of the bioreactor. The direction of the electric field can be in any direction, but preferably in a direction that is parallel to the length of the channel (and the resulting tissue strand), or which is perpendicular to the length of the channel (and the resulting tissue strand).

As may be used herein, the term "Biorod" may refer to, but is not limited to, the tissue strand itself (i.e., the cells that grow on a bioreactor device as described herein) or the system comprising the tissue strand and the bioreactor together. Biorod may also be referred to herein as its commercial name of BIOROD™, which encompasses both the tissue strand itself, or the system comprising the tissue strand and the bioreactor device in which the tissue strand has grown or has been placed.

The Biorod embodiment may be scaled up to a configuration that comprises a plurality of bioreactor channels and longitudinal scaffolds such that a plurality of three-dimensional tissue strands for measuring contractile force may be grown simultaneously, e.g., on a 96-well plate format as shown in FIG. 37A.

The Biorod embodiment also relates to methods for growing the tissue strands in the bioreactor, to the three-dimensional tissue strands themselves, to systems comprising both the bioreactor and grown tissue strands, and to methods for using and/or testing the tissue strands (or systems comprising the tissue strands) in various applications, including, but not limited to, (a) the testing of the efficacy and safety (including toxicity) of experimental pharmacologic agents (including, but not limited to, small molecule drugs, biologics, nucleic acid-based agents), (b) the defining of pharmacokinetics and/or pharmacodynamics of pharmacologic agents (including, but not limited to, small molecule drugs, biologics, nucleic acid-based agents), (c) characterizing the properties and therapeutic effects of pharmacologic agents (including, but not limited to, small molecule drugs, biologics, nucleic acid-based agents) on a subject, (d) screening of new pharmacologic agents, (e) providing implantable engineered tissues for use in regenerative medicine for treating damaged and/or diseased tissues, and (f) measuring the contractile force exerted by the tissue strand on the longitudinal elements, for example, in response to the administering of a test agent to the tissue strand. In this embodiment, the device can be configured at a multi-well plate, such as a 6-well, 12-well, 24-well, 96-well, 384-well, and 1536-well plate.

Figure 38:
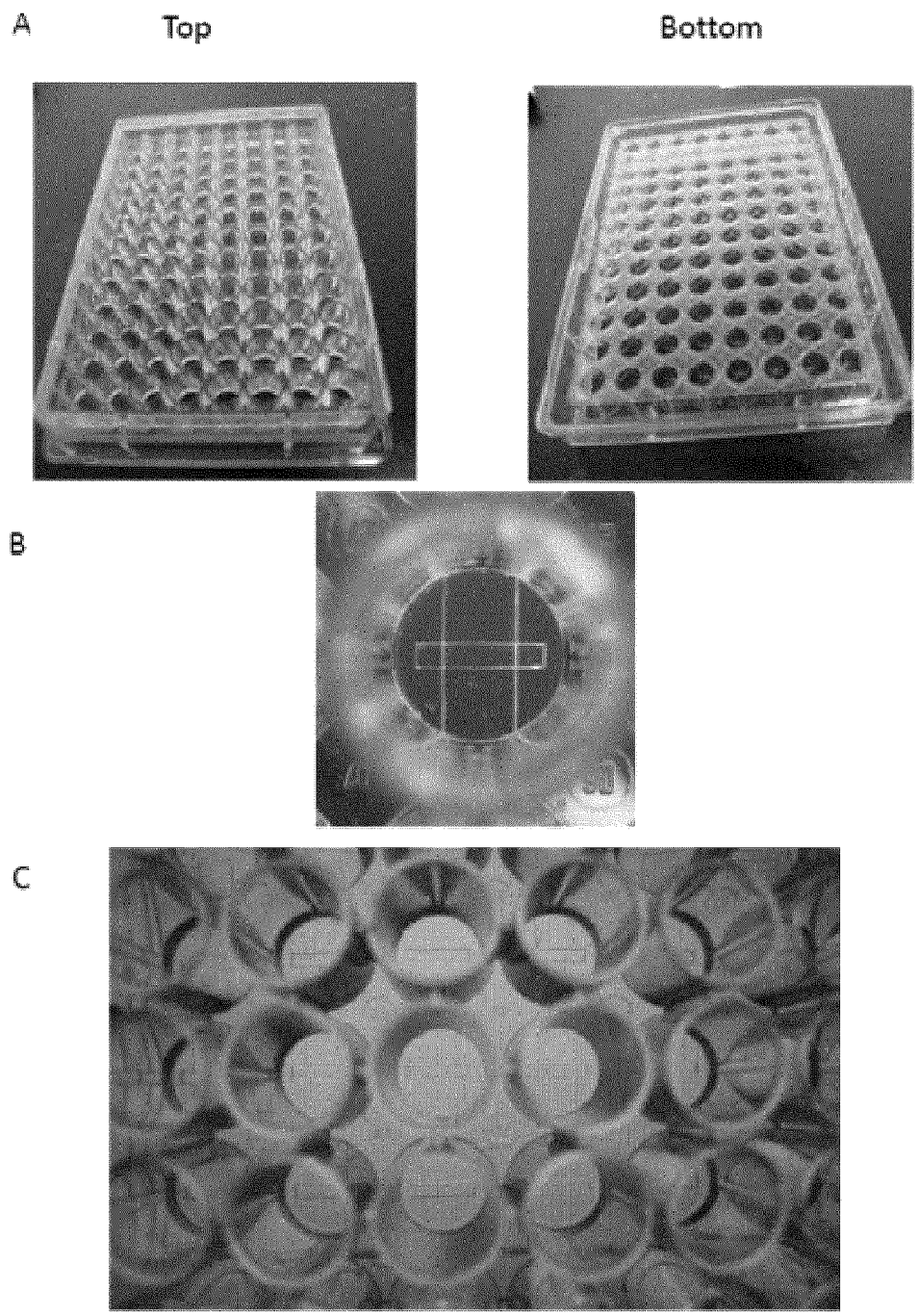
FIG. 38 provides photographs of an example of the disclosed devices fabricated according to the process of FIGS. 37a-37d.

FIGS. 37 and 38 show schematics and images of an example Biorod device suitable for cultivation of tissues that may be suitable for measurement of contractile force. In this example, the device may be scaled up to a plate configuration having multiple wells, for the simultaneous cultivation of multiple tissue strands. However, in other examples the device may be configured for cultivating a single tissue strand (e.g., having a single well).

The example device may include a longitudinal bioreactor channel in which seed cells for a tissue culture may be received. A scaffold including two wires oriented perpendicular to the bioreactor channel may be supported (e.g., suspended) over the width of the bioreactor channel near opposing ends of the bioreactor channel. The wires may serve as anchors for the seed cells to form a tissue structure along the length of the bioreactor channel. The wires may be deflectable. The device may enable measurement of contractile forces exerted by the tissue strand.

In some examples, the device may be a multi-well device having a plurality of bioreactor wells, each well comprising a bioreactor channel and scaffold as described above.

As shown in FIG. 37a, the device, when configured as a multi-well plate, may include four components: a base layer, supports (e.g., wires), a well-plate (e.g., defining 96 wells) and a plate cap. In examples where there are less wells, the device may be microfabricated on using less layers (e.g., a well-plate may not be needed where there is only one well). Proportional changes of the dimensions of wells and/or wires can be used in a scale-up (e.g., to 384 well plate format) or scale-down of the device, as appropriate. For example, proportional changes of the dimensions of the wells and/or wires may be used to create other multi-well plate configurations such as 6-well, 12-well and 24-well plates. Any suitable technique may be used to fabricate the example device, including techniques used for fabrication of the devices of Example 1 and Example 2, as well as hot-embossing and injection-molding techniques, among others.

Figure 1:
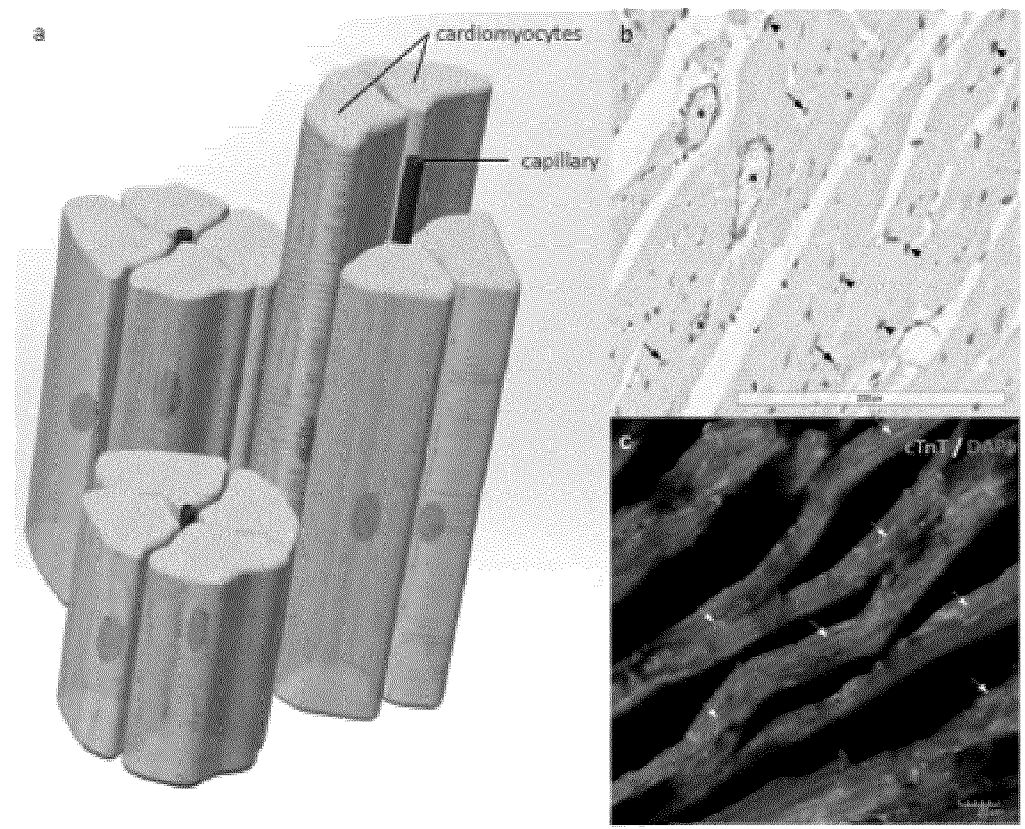
FIGS. 1a-1c show examples of cardiac bundles in native myocardium.
Figure 2:
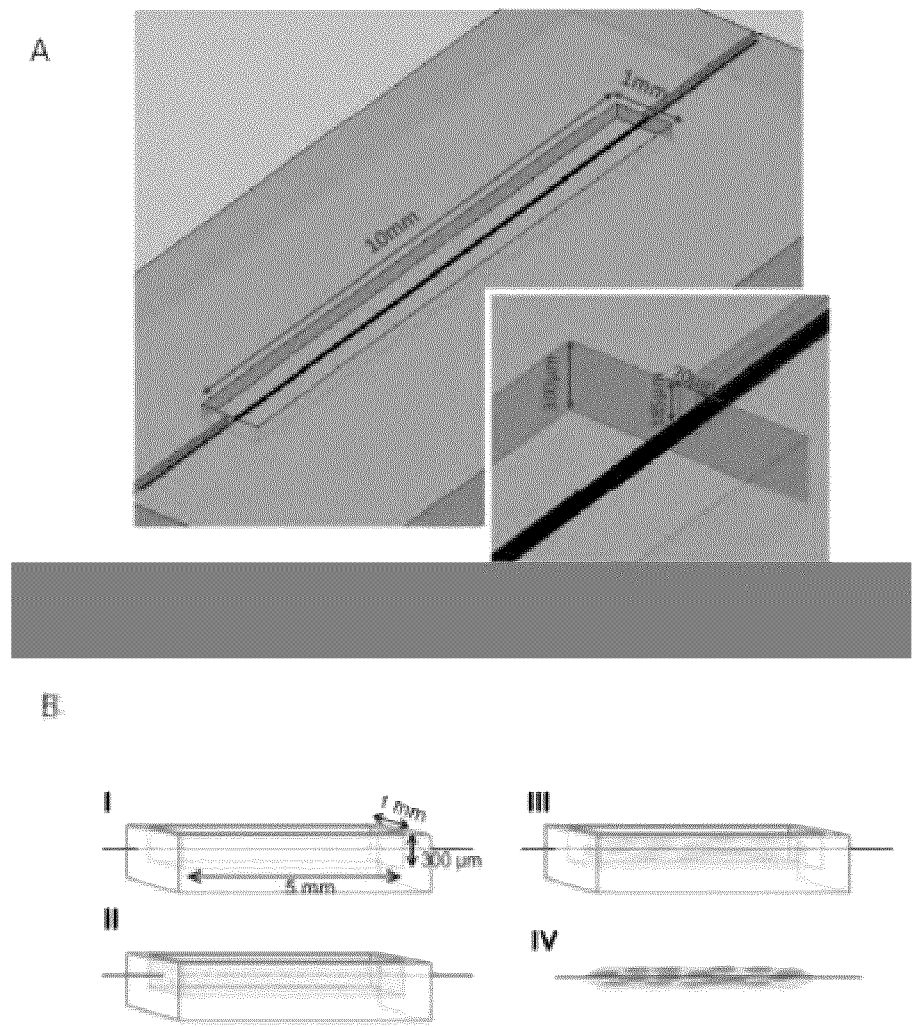
FIGS. 2a-2b provides schematics depicting a first embodiment of the invention, i.e., the single-wire 3D tissue culture embodiment (e.g., biowire systems). Section B depicts the progression of tissue culturing in the growth chamber, resulting with time in part IV as a three-dimensional (3D) tissue strand which is formed around the wire.
Figure 3:
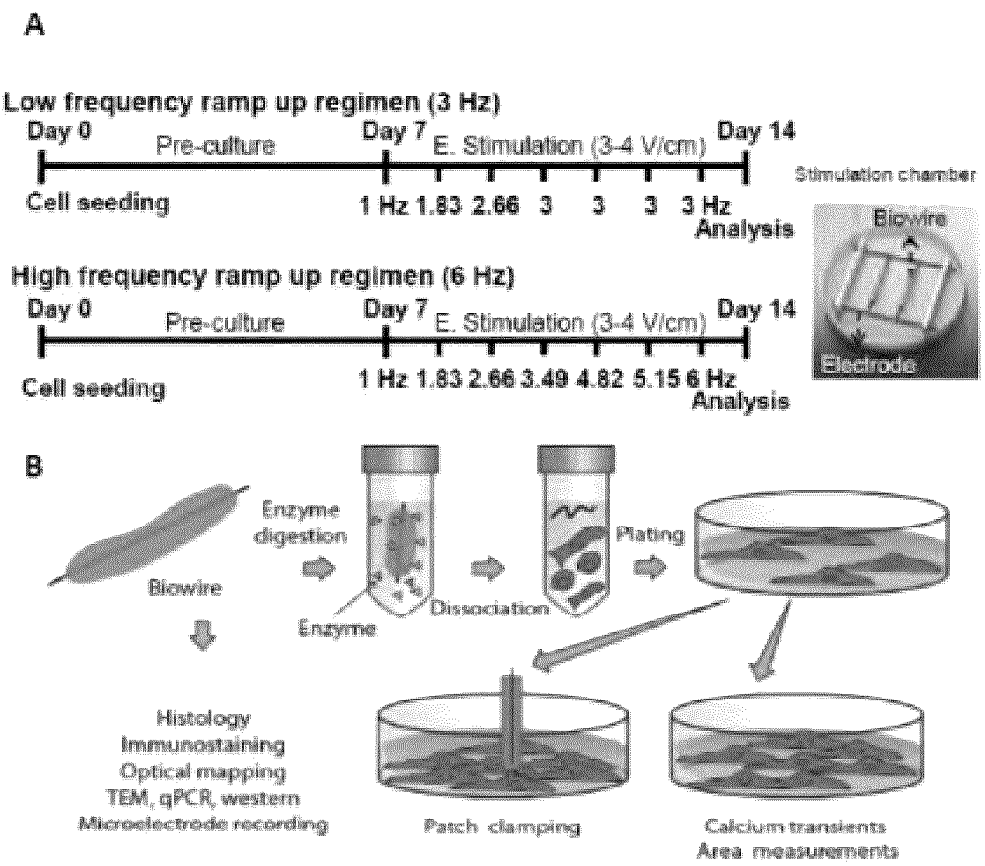
FIGS. 3a-3b show example electrical stimulation regimens suitable for generating cardiac tissues using an exemplary biowire system of the disclosure, and isolation of cardiac cells from the generated tissues.

FIG. 37B1 schematically shows an example fabrication process to generate a poly(methyl methacrylate) PMMA base using hot embossing techniques. FIG. 37B2 shows the SU-8 master and PMMA base after hot embossing with a closer view of individual well dimensions. FIG. 37C is an illustration of wire fabrication process (right) and wires after fabrication (Left). FIG. 37D1 is a schematic illustration of a 96 well-plate based PMMA base with the installed wires. FIG. 37D2 is a detailed view of a single well of the plate. FIG. 37D3 is an image of a fabricated PMMA base with the wire installed in one row of wells and closer top view of a single well with wires.

In an example, the base layer pattern was pre-designed in AutoCAD and translated to SU-8 masters via standard soft lithography techniques. SU-8 master was then transferred into a hot embossing master and used to generate an array of micro-wells within PMMA using suitable hot embossing techniques (see FIG. 37B1). Alternatively, tissue culture polystyrene could also be used or any number of biologically inert castable polymers, such as polycarbonate. One bioreactor micro-well was located in the center of a single well of a 96 well plate. The dimensions of the micro-well were 5 mm in length by 1 mm in width by 300 µm in depth. Other dimensions may be used for different tissue types. Two universal grooves throughout every column of micro-wells were placed 1 mm from both short sides of the micro-wells (see FIG. 37B2). The grooves were 100 µm in width by 100 µm in depth. Other groove dimensions may be suitable for different tissues. The grooves were used to house the scaffold (e.g., wires) for cell assembly. However, the grooves are optional and not required for function as the wires can be attached at the tops of the microwells.

In the example shown, polymer wires were used as supports for cultivating tissue in the bioreactor micro-wells. The wires with controlled dimensions (100 µm by 100 µm in cross-section) were made of poly(octamethylene maleate (anhydride) citrate) (POMaC) (see FIG. 37C). To prepare poly(octamethylene maleate (anhydride) citrate) (POMaC) prepolymer, 1,8-octandiol, citrate acid, and maleic anhydride were mixed at 5:1:4 molar ratio and melted at 160° C. under nitrogen purge. The temperature was then dropped to 140° C. and the mixture was stirred for three hours. The resultant pre-polymer solution was then dissolved in 1,6-dioxane and purified via drop-wise precipitation in distilled water. Precipitated polymer was lyophilized for 2 days and then mixed with 5% w/w UV initiator (Irgacure 2959). To fabricate wires, PDMS cap with micro-channels was generated using a SU-8 master with standard soft lithography. Then PDMS cap was lightly pressed on a glass slide. Prepolymer solution of POMaC was then perfused into these micro-channels by syringe pump or simply by a capillary effect. After the prepolymer went through the entire channel, it was cross-linked under a UV lamp for 45 mins. Other suitable curing times are also possible to achieve the desired mechanical properties, i.e., tunability. The PDMS cap was peeled and wires remained on the glass slide. The wires were released from the PDMS micro-channels due to POMaC's higher affinity to glass than PDMS. These wires were then placed into grooves on the PMMA base layer (see FIGS. 37D1-D3).

After assembly, every micro-well included a scaffold of two supports, in this example auto-fluorescent and flexible wires, positioned at the edges of the well. Commercially available 96 bottomless well-plates and cap were used to complete the assembly of the plates. Specifically, bottomless 96 well-plates were placed on top of the PMMA base layer to secure the wires in place and create independent wells without cross-contamination.

FIGS. 38a-38c show actual images of an example device fabricated as described above. One bioreactor well is located in each well of a 96 well plate. Wires placed on the side of the bioreactor well enable force of contraction measurements. FIG. 38a shows top and bottom views. FIG. 38b shows a close-up view of a single well. FIG. 38c shows a view of multiple wells of the 96 well plate.

Although certain materials, techniques and dimensions are described above, other suitable materials (e.g., polystyrene and/or polyurethanes, among others), techniques and dimensions may be used for the example device. Although a polymer wire is described as being used, other supports may be suitable, including lengths of other materials. For example, wires may be made out of poly(glycerol sebacate), POMac, poly(lactic acid), poly(glycolic acid), poly(ε-caprolactone), various polyurethanes as well as co-polymers thereof, silk, microstructured, nanofabricated materials, and/or materials doped with nanostructures such as nanorods or quantum dots, among others.

B. Experimental Testing of an Exemplary Biorod/Biowire II Embodiment

Example Methods and Analyses

Cardiomyocytes were derived from human embryonic stem cell lines (hESC, Hes2). Embryoid bodies (EBs) were differentiated to the cardiovascular lineage and disassociated as previously described in Device 1 Methods. Before cell seeding, micro-well surface was rinsed with 5% (w/v) Pluronic Acid (Sigma P2443) and then air dried in the bio-safety cabinet. hESC derived cardiomyocytes were suspended at 200 million/ml (unless specified otherwise) in Collagen Type I based gel (3.0 mg/ml of rat tail collagen type I (BD Biosciences) neutralized by 1N NaOH and 10×M199 media as described by the manufacturer) with the supplements of 0.45 g/ml glucose, 1% (v/v) HEPES, 10% (v/v) Matrigel (BD Biosciences), and 0.2 g/ml $NaHCO_3$. Suspended cardiomyocytes were then seeded into the cell culture channel (2.5 µl per well). After 30 min incubation at 37° C. to induce the gelation, appropriate media were added. After seeding, cells were kept in culture for 7 days to allow collagen matrix remodeling and assembly around the wires. Cardiac tissue strands were kept in culture for up to 21 days with media change every 2-3 days. Preferably, the tissue strands should be kept in culture for at least 2 weeks to allow for maturation; however there is no limitation on the maximum culture duration. Cardiac tissue strands were seeded to observe the stability and reproducibility of tissue in long term culture. After seeding, brightfield images (see FIG. 39A for an example) of the tissue strands were taken every day (n=3 per group) using optical microscope (Olympus CKX41) and the diameters of the tissue strands at four distinct locations were analyzed with imageJ (see FIG. 39B for an example). Tissue strand lengths were also analyzed with same method.

Figure 39:
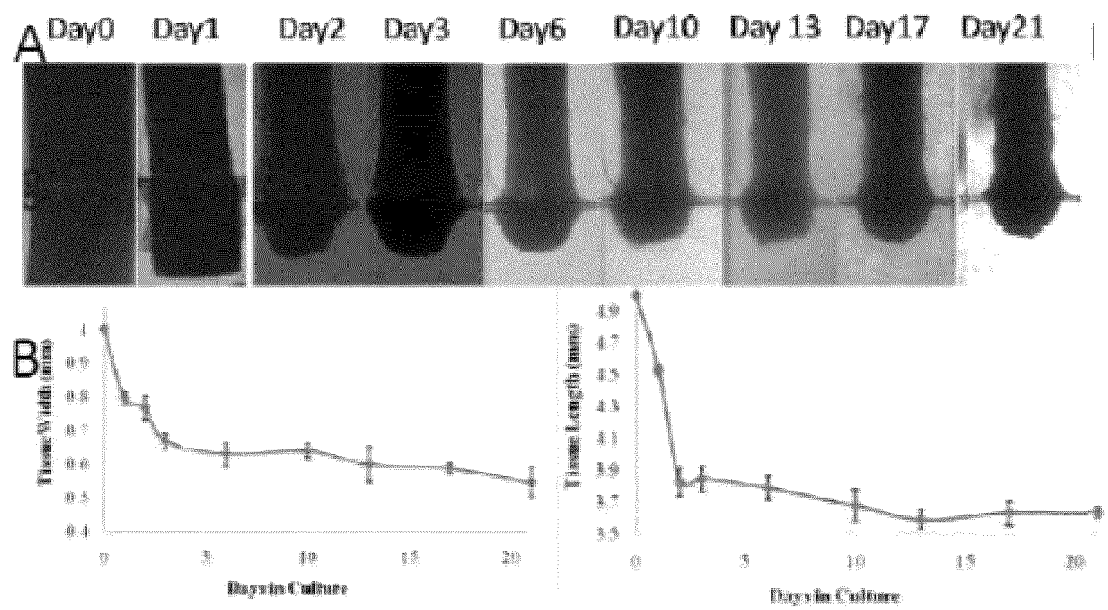
FIGS. 39a-e illustrates tissue compaction and force measurement in tissues generated in accordance with an exemplary biorod system of the disclosure.
Figure 39:
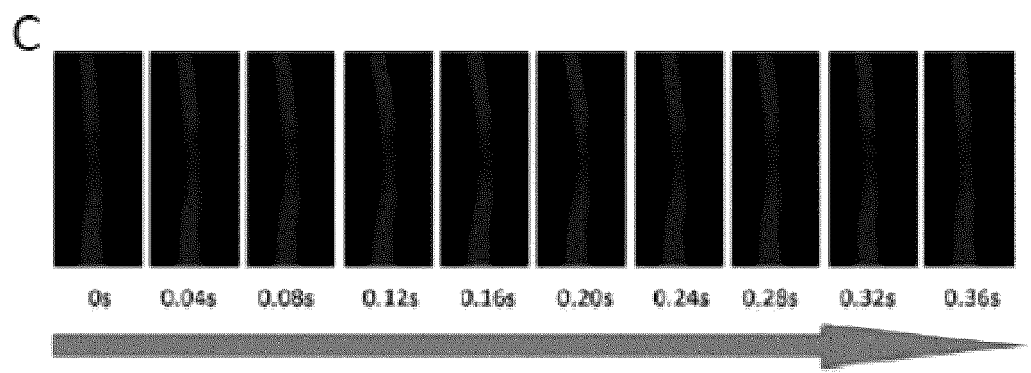
Figure 39:
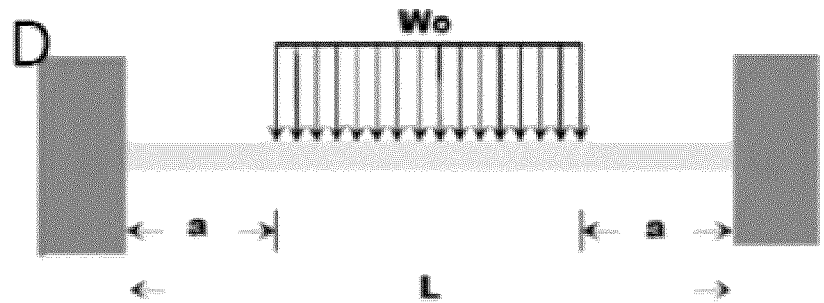

FIG. 39 shows example results demonstrating tissue compaction and force measurement in the disclosed devices having multi-well plate configurations. Human embryonic stem cell (hESC) derived cardiomyocytes were used as a cell source. FIG. 39A shows cardiac tissue formation and stabilization starting from seeding (day 0), via gel compaction (day 1 to day 6) and a stable period (day 6 to day 21). FIG. 39B shows qualification of tissue widths and lengths during compaction and tissue remodelling during 3 weeks of continuous culture, (mean±SD, n=3). Both width and length significantly changed within the first week, and remained stable for the next two weeks of culture.

For validation of electrical stimulation in tissue strands cultivated using the device of Example 3, PDMS micro-well with same dimensions was used for convenience. Electrical stimulation was applied to tissue using similar setup as in the investigation of the device of Example 1. Two ¼-inch-diameter carbon rods (Ladd Research Industries) were placed 2 cm apart from inner edges. Tissues were placed perpendicular to the carbon rod and were on the same height as center of carbon rod. Two carbon rods were connected to external electrical stimulator (Grass S88X) with platinum wires (Ladd Research Industries). After 7 days of cell compaction, tissues were introduced to electrical stimulation in a stimulation chamber. The pacing frequency started at 1 Hz and increased gradually and daily to 6 Hz throughout the week (1, 1.83, 2.66, 3.49, 4.82, 5.15 and 6 Hz, daily frequencies) as described in the investigation of the device of Example 1. Additional 1 week of culture with 1 Hz electrical pacing was continued to leave enough time for tissue maturation and short or long term drug testing experiment.

For PMMA plate, gold electrodes will be printed at both short ends of micro-well (see FIG. 37D2) and extending to the edge of plate to connect with external electrical stimulator (Grass S88x) for field stimulation. The dimension is 0.2 mm by 1 mm by 0.1 mm height in this example.

Figure 39E:
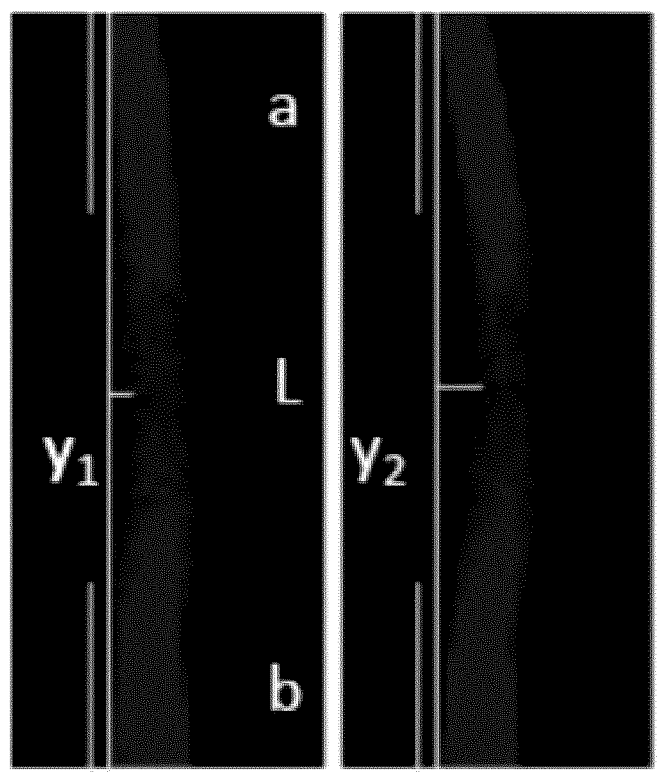

Tissue contractile behavior tracing and measurement was carried out. POMac is auto-fluorescent at a wide range of wavelengths; therefore the wires were imaged with a fluorescence microscope under DAPI channel (e.g. 461 nm wavelength) to trace the bending movements of the wires. The POMac is auto-fluorescent at a wide range of wavelengths, including under FITC and Trite channels. Images were taken at 25 frames per second (fps) (see FIG. 39C). Image sequences were analyzed with ImageJ software using tracking plugin. To calculate the forces originated from cardiac tissues, beam deflection formula with uniformly distributed load in the middle section was used here. FIG. 39C shows bending behaviour of single wire due to contractile behaviour of the engineered cardiac tissue in a time course. The engineered cardiac tissues were paced at 2 Hz frequency. From this image sequence, contraction and relaxation time of beating can be estimated. FIG. 39D shows an illustration of beam deflection scenario with two fixed ends. Tissue stretching wires can be considered uniformly distributed Load, Wo (Load per force bearing length), which can be calculated with displacement of center point of wires in image sequence, and F can be calculated as well. FIG. 39E shows static tension F1 (due to cell compaction and remodeling) and dynamic tension F2 (due to contraction of tissue) and a procedure to decouple both forces. Briefly, entire beam length was L. Section of wire with tissue wrapping around it was experiencing load. Here, the load was assumed to be evenly distributed throughout this section, and Wo was load per length. Because of the pluronic acid coating, tissue formations were very symmetrical and perpendicular to the wires. The distance between side of the tissue and a well wall is a, which was assumed equal for both sides. The deflection at center point was y.

According to the formula in FIG. 39D, with image analysis, deflection at a center point can be easily obtained. In this case, Wo and force per cross-section area were calculated (stress at mid-point of tissue). Deflection of wires depended on two different tensions. One tension was generated by gel compaction and cell assembly process. This tension is F1 which is static during short time frame (e.g. hours) calculated from y1 when tissue is at relax state (see FIG. 39E). The total deflection y2 was caused by two tensions, F1, and F2. Tension F2 was dynamic, and subjected to contraction behavior of the tissue. The tension F2 was a target of the measurements. In order to measure the accurate contractile force F2, compaction tension F1 needed to be decoupled.

Force measurement validation was carried out. All direct force measurements were conducted by Biograf force transducer (Kent Scientific). Due to the small sizes of tissues and wires, a scale up of well with wires was setup, using geometric similarity rules.

Figure 40:
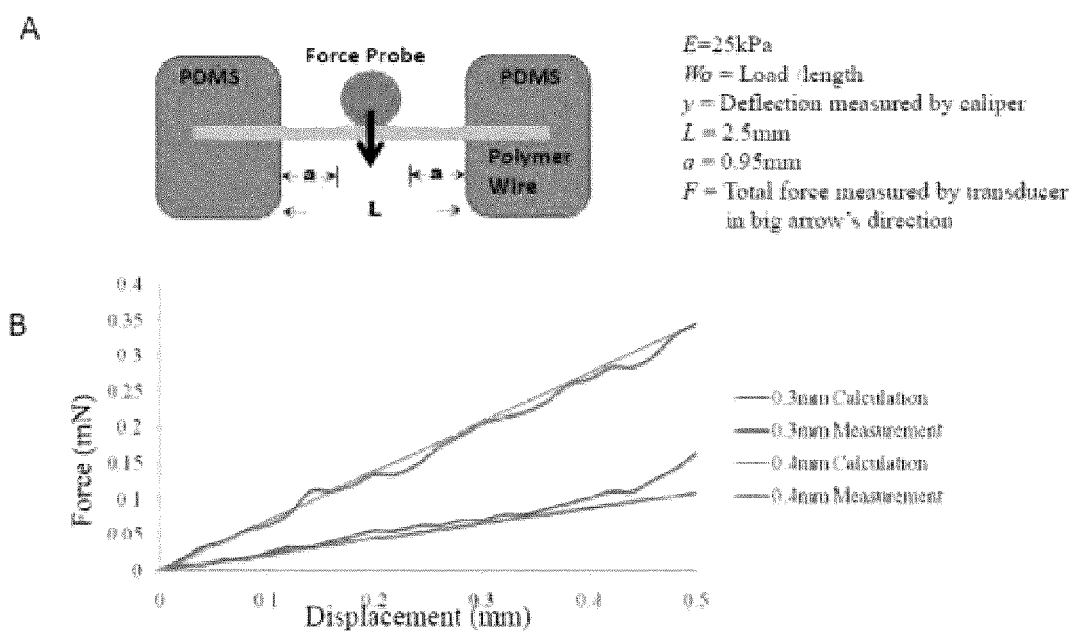
FIGS. 40a-40b illustrate force measurement validation of tissues generated in accordance with an exemplary biorod system of the disclosure.

FIG. 40 illustrates the force measurement validation. To validate the equation, scaled-up setup was necessary due to the sensitivity of force transducer. FIG. 40A shows a schematic illustration of a scaled-up setup to compare calculated force and measured force. The force is calculated by substituting deflection y, wire length L and distance from the wire fixed ends and edge of force probe, a, into the formula presented in FIG. 40D. The measured force was obtained using a Biograf apparatus (Kent Scientifics). Two different wire cross-sections were used to validate the formula. From FIG. 40B, measurements and calculation data from the same samples coincide up to 0.5 mm of wire deflection. In this case, force calculations were not considered accurate when the deflection exceeded 20% of wire length. (n=3).

Well width L was 2.5 mm, force transducer probe diameter was 0.6 mm, therefore, when probe was placed at center point, a=0.95 mm. Elastic modulus of POMaC was calculated by stress-strain curve with stretching along its longitude. During the test, force probe was moving against POMac wire at the center point (see FIG. 40A). Force reading and displacement were recorded simultaneously. Cross-sections of two different wire sizes were 0.3 mm by 0.3 mm and 0.4 mm and 0.4 mm. The forces calculated from formula using displacement, elastic modulus and cross-section area were compared with the force reading from transducer.

On day 21, the electrical properties of the stimulated and control human cardiac tissue strands were characterized in terms of excitation threshold (ET) and maximum capture rate (MCR) under external field pacing as described above for the investigation of the device of Example 1.

Figure 41:
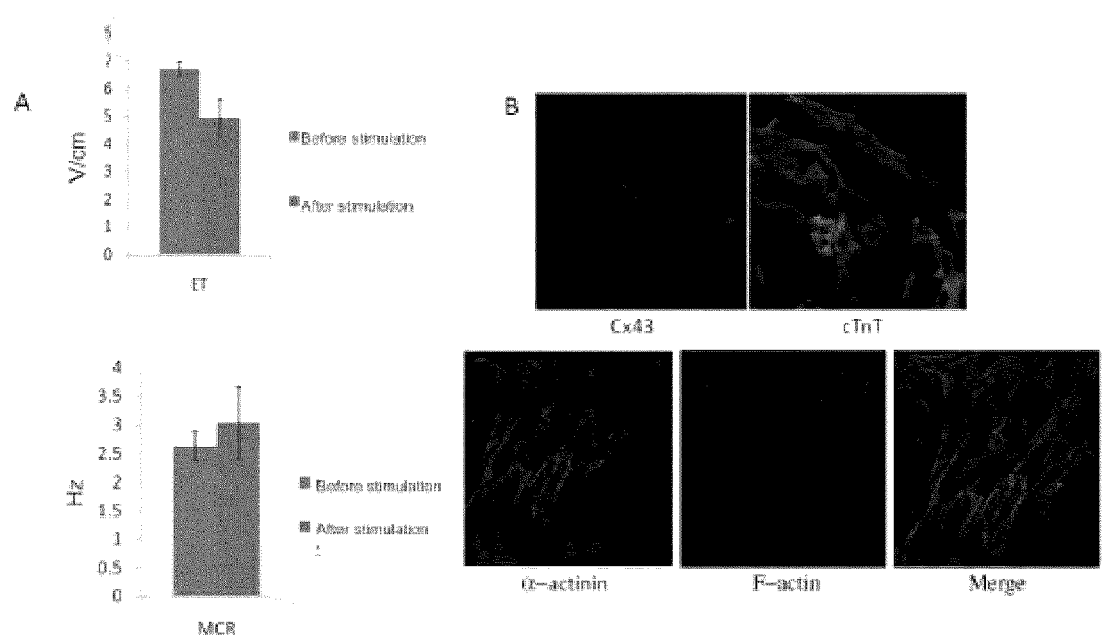
FIGS. 41a-41b show functional assessment of tissues generated in accordance with an exemplary biorod system of the disclosure.
Figure 42:
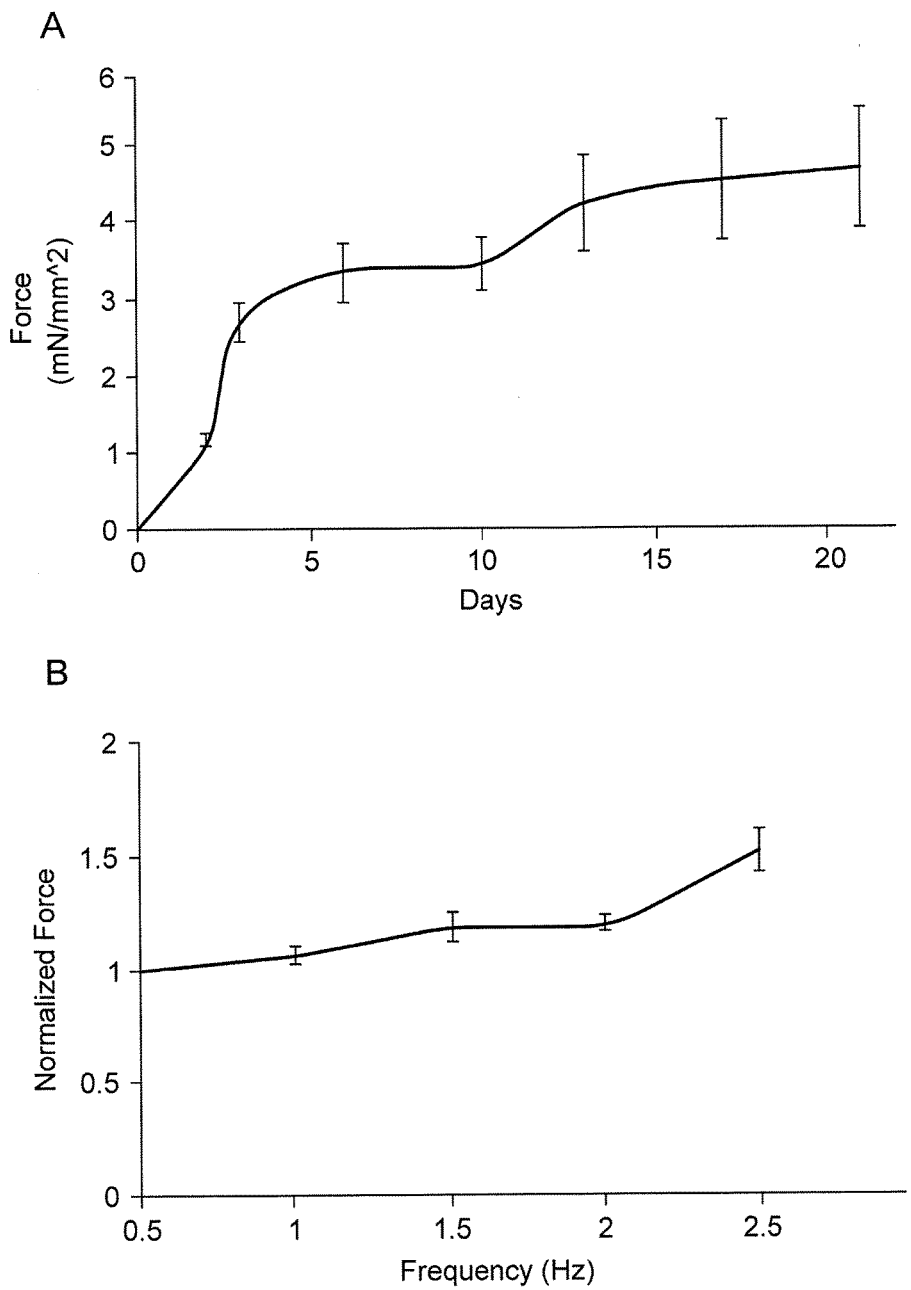
FIGS. 42a-42b. Tissue contractility assessment in accordance with an exemplary biorod system of the disclosure.

Immunostaining and confocal microscopy was carried out for characterization of the cardiac tissue cultivated in the device of Example 3. Example results are shown in FIG. 41. FIG. 41A shows assessment of electrical properties with excitation threshold and maximum capture rate on day 21 as end point measurements, (mean±SD, n=3). FIG. 41B shows fluorescence images on cellular protein expression on day 21 after seeding (end point assessment): Gap junction protein, connexin 43 (Cx43)); sarcomere protein Cardiac troponin T (cTnT) and F-actin (Infrared Red); alpha-actinin. Staining for f-actin and alpha-actinin showed co-localized unique striation structures. FIG. 42A shows results from video taken at day 2, 3, 6, 10, 13, 17, 21 to quantify contraction forces of the spontaneous beating. Contractile forces increased rapidly in the first week and approached a plateau in the second and third week. FIG. 42B shows force per cross-section calculated from deflection at day 21 (end point assessment) with pacing frequency from 0.5 Hz to 3 Hz.

After normalizing to forces generated at 0.5 Hz, FIG. 42B showed positive force-frequency relationship, (mean±SD, n=3).

At the end of 3 weeks, tissue strands were stained for cTnT, Connexin 43, F-actin and alpha-actinin Tissue strands were fixed with 4% paraformaldehyde, permeabilized by 0.25% Triton X-100, and blocked by 5% fetal bovine serum (FBS) Immunostaining was performed using the following antibodies: mouse anti-cardiac Troponin T (cTnT) (Abeam; 1:200), rabbit anti-Connexin 43 (Cx-43) (Abeam; 1:200), mouse anti-α-actinin (Abeam; 1:200), goat anti-mouse-Alexa Fluor 488 (Jackson Immuno Research; 1:400), anti-rabbit-TRITC (Invitrogen; 1:200), anti-mouse-TRITC (Jackson Immuno Research; 1:200) Phalloidin-Alexa 660 (Invitrogen; 1:200) was used to stain F-actin fibers. For confocal microscopy, the stained cardiac tissue strands were visualized under an upright confocal microscope (Zeiss LSM 510) (see FIG. 41B).

At seven different time points (2, 3, 6, 10, 13, 17, 21 days after seeding), the contractile behavior of spontaneous beating was assessed. For assessments at different time points, used exactly the same setting on the fluorescence microscope and located the same position of tissue to ensure a good comparison.

Drug testing was carried out. To demonstrate the potential of these tissue strands for studying responses to pharmacologic agents, the study examined whether the tissues responded appropriately to well-known cardiac compounds, including norepinephrine, E-4301 and isoproterenol.

Example Results and Discussion

Despite great efforts and expenses put in pharmaceutical development, there are still many drugs entering the market that result in the withdrawal due to cardiac-related side effects. Many research groups are now focused on cardiac tissue specific in vitro screening of drug candidates to weed out unqualified drug candidates before clinical trials are initiated[55-59]. In order to design a successful platform for this application, various criteria may be considered. First of all, it may be useful for materials used in the device to not influence drug concentrations in the well. Therefore, the entire platform may be fabricated using inert, non-absorbing materials. PDMS is a very popular material that can be easily manipulated and fabricated into fine features. Therefore many groups are using PDMS to construct microdevices for cardiac drug testing[60-61]. However, PDMS is highly drug absorbable and has been approved to use as drug delivery vehicle[62-65] due to hydrophobicity of the majority of drug candidates that result in ample and easy drug absorption into this material. In this case, PDMS and other drug absorbable polymers cannot be used in contact with drugs while testing in the device.

Secondly, it may be useful for engineered cardiac tissues (ECT) to be easily reproduced and maintained in culture stable for at least 3 weeks to allow proper cell maturation and investigation of drug effects. The observation during these 3 week cultures should be completed without destroying the tissue. Post deflection characterization is a well-accepted way to characterize tissue contractile behaviours[55, 58,60-61,66-68]. In this approach, cardiac micro-tissues are generated in a microwell containing a pair of cylindrical posts. The tissues assemble around the posts and the post deflection allows measurements of the contraction force. However, this process is often difficult to control. Tissues often slip off the posts due to posts' significant deformation. This may cause the loss of specimens during the culture process. The fabrication process becomes significantly more difficult if a cap is to be added on top of the post to prevent sample loss. Moreover, the force measurement of post deflection design significantly relies on location of tissue on the posts. The tissue commonly moves upward during long term culture and the measurement is not easily conducted accurately by microscopy. In fact, to determine the exact position of the tissue on the post, the well needs to be cut and the tissue needs to be imaged from a side.

The example device described above may serve as a high throughput drug testing device, which may satisfy one or more of the above useful criteria. The example device of Example 3 may overcome one or more of the above limitations. The supporting wires around which the cells self-assemble may be all located at the same level, thus the tissue may always end up at the same place. The supporting wires may be firmly fitted within the well and there may be no free ends, thus the tissue may not slip off the wire. In addition, wire deflection may allow for the accurate measurement of the contraction force as well as the decoupling of the passive from the active tension.

In this example device, PMMA and POMaC were used as materials contacting medium and tissues in the culture. POMaC is less hydrophobic[69] comparing to PDMS and therefore may reduce the chance of drug absorption. In addition, minimal volumes of POMaC may be used since the device well is constructed from the inert PMMA. POMaC wires in the example have elastic modulus of 25 kPa which is close to mechanical properties of native and engineered cardiac tissues[47] which is capable of providing physiological relevant micro-environment. Different pre-load can be simulated with tunable mechanical properties of PoMAC wire using various UV curing energy. Therefore, the obtained data may be more clinically relevant for both physiological and pathological cases. In addition, force measurement can be more sensitive with softer materials like POMaC compared to stiffer materials such as PDMS. This may be beneficial to a high throughput design with miniaturized tissue size. The fabrication process can be scaled-up to commercial manufacturing using hot embossing technology, as disclosed in the examples herein (see FIG. 38).

The example device of Example 3 may be able to reduce or eliminate the need for height assessment of the cultivated tissue. Because the seeding volume and cell density are defined and the wires are all placed at the same and constant position, the engineered cardiac tissue may always be at the same position during the entire culture period. The parameters for force calculation can be easily retrieved in the deflection tracking image sequences. Without a free-end such as the one found in posts, ECTs may have no way of slipping off and causing sample loss. FIG. 39C is a sample of a time-course of fluorescence images illustrating how the wires bended during tissue contraction. Cardiac tissues started beating the second day after seeding and kept beating throughout the entire culture period. This demonstrated high level of electromechanical coupling of the cells within the hydrogel matrix. Further, after 21 days of culture with electrical stimulation, FIG. 39B showed that tissue dimensions were quickly changed during first week and reached a plateau at the beginning of the second week maintaining the dimensions during the entire cultivation period. The results confirmed that human cardiac tissues finished the gel compaction and self-assembly in the first week Small standard deviation suggests the tissues are highly reproducible.

The validation experiments have two aspects, force measurement validation and tissue characterization. The validation test on force measurement in FIG. 40 confirmed that calculation using formula in FIG. 39D is precise when deflection is within 20% of wire length. Larger deflection may require use of other formulas. The electrical properties of ECT were improved after electrical stimulation, specifically excitation threshold (ET) was significantly reduced in stimulated samples. Whereas maximum capture rates (MCR) did not change significantly, the trend was considered to show improvement (see FIG. 41A) Immunostaining of Connexin 43 indicated gap junction proteins were expressed at cell surfaces. cTnT staining confirmed the presence of sarcomeric protein in the cells. Sarcomeric-α-actinin and f-actin structures of the cardiomyocytes were also presented and localized together to indicate cell elongation in the ECT (see FIG. 41B).

FIG. 42A shows the changes of contractile forces within 3 weeks of culture. At seven different time points (2, 3, 6, 10, 13, 17, 21 days after seeding), the contractile behavior of spontaneous beating was assessed. The contractile force increased significantly in the first week due to elevated electrical coupling of the cells in hydrogel. The second and the third week of culture showed no significant improvement on contractile forces. Force-frequency relationship presented in FIG. 42B suggests ECT resembles native cardiac tissue with Bowditch staircase phenomenon up till 2.5 Hz of electrical stimulation.

Figure 43:
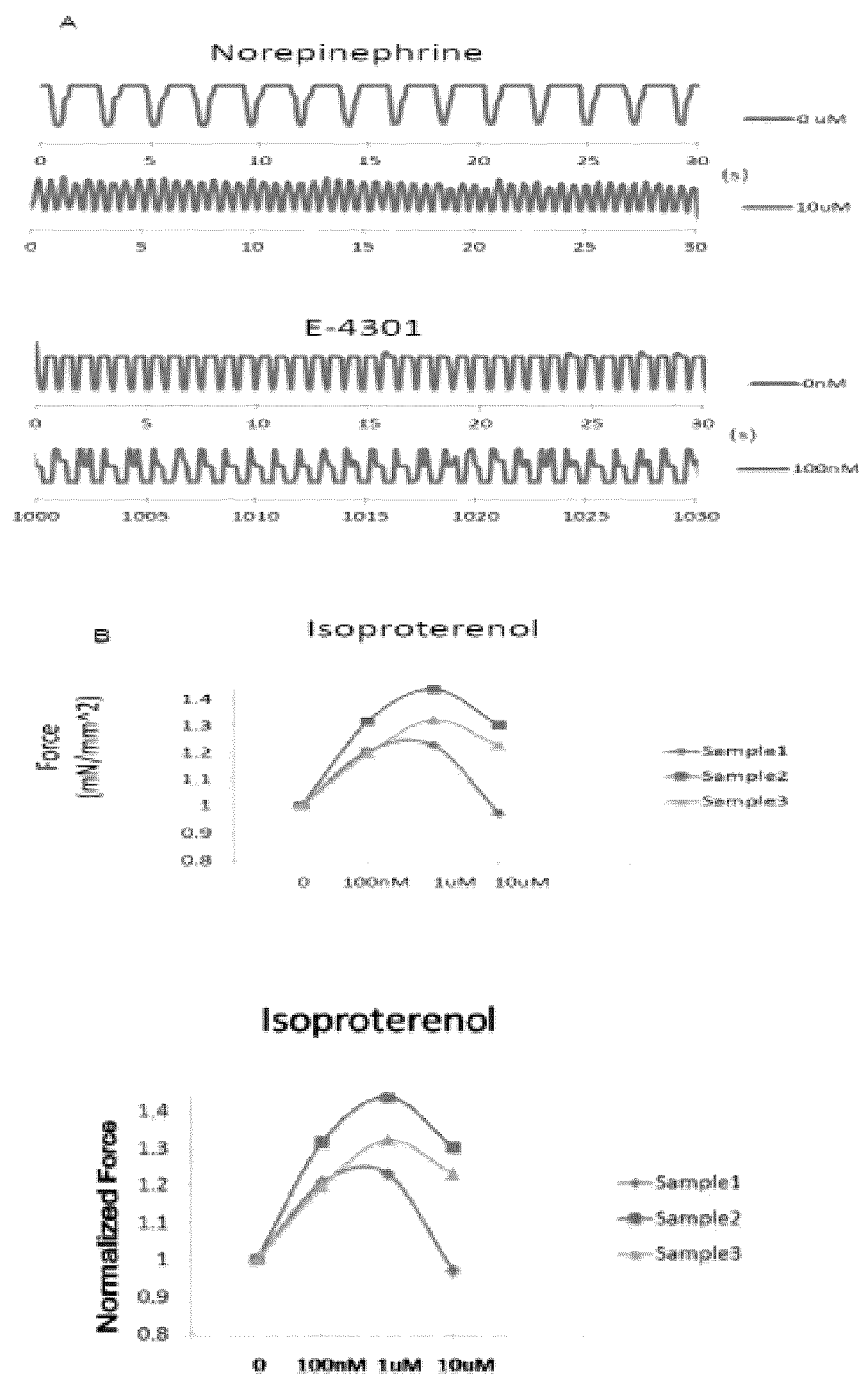
FIG. 43a-43b show results of drug testing on tissues generated in accordance with an exemplary biorod system of the disclosure.

FIG. 43 shows example results from drug testing. Norepinephrine is a stress hormone acting in the fight-or-flight response, by directly increasing heart rate[72]. FIG. 43A shows a representative tissue beating pattern at a given concentration of drugs in comparison with the control. The addition of Norepinephrine at 10 μM resulted in significant increased beating frequency. E4301 works as a blocking agent for human $I_{kr}$ cardiac ion channel, blockage of which can result in after-depolarization and dangerous arrhythmias[56]. E4301 addition at 100 nM resulted in prolonged relaxation and occasional after beat, which clearly represent the function of this agent. Isoproterenol is a non-selective beta-adrenergic agonist that increases cardiac output. High dosage can desensitize the tissue and cause reverse effect[73]. FIG. 43B showed a dose responsive trend of tissue contractile forces normalized to forces before drug addition. Tissue had positive inotropic action (increase in contractility) at 100 nM and 1 μM, and a slight negative inotropic effect (decrease in contractility) at 10 μM.

FIG. 43 shows example results from drug testing. Norepinephrine is a stress hormone acting in the fight-or-flight response, by directly increasing heart rate[72]. FIG. 43A shows a representative tissue beating pattern at a given concentration of drugs in comparison with the control. The addition of Norepinephrine at 10 μM resulted in significant increased beating frequency. E4301 works as a blocking agent for human $I_{kr}$ cardiac ion channel, blockage of which can result in after-depolarization and dangerous arrhythmias[56]. E4301 addition at 100 nM resulted in prolonged relaxation and occasional after beat, which clearly represent the function of this agent. Isoproterenol is a non-selective beta-adrenergic agonist that increases cardiac output. High dosage can desensitize the tissue and cause reverse effect[73]. FIG. 43B showed a dose responsive trend of tissue contractile forces normalized to forces before drug addition. Tissue had positive inotropic action (increase in contractility) at 100 nM and 1 μM, and a slight negative inotropic effect (decrease in contractility) at 10 μM.

In summary, this example device may generate at least partially matured human cardiac tissues in a high throughput manner. The design may reduce or eliminate the use of PDMS and it was fully compatible with commonly used 96 well-plate format. The miniaturization and automation measurements of force and other key aspects of contractile properties, such as beating frequency, contraction and relaxation time, can be successfully carried out. Human cardiac tissues also responded appropriately to well-known drugs: norepinephrine, E-4301 and isoproterenol.

The example device may be versatile and subjected to various modifications. For example, because two support wires are installed onto one well, the material of one wire can be changed to facilitate other purposes. For example, one wire can be changed into platinum wire or other electrical conductive polymer to conduct point electrical stimulation. With wire made of magnetic materials (polymer), an external magnetic field can facilitate electrical and mechanical stimulation in conjunction as a mimic of cardiac load[74]. This setup might help push the maturation of ECT further.

Figure 44:
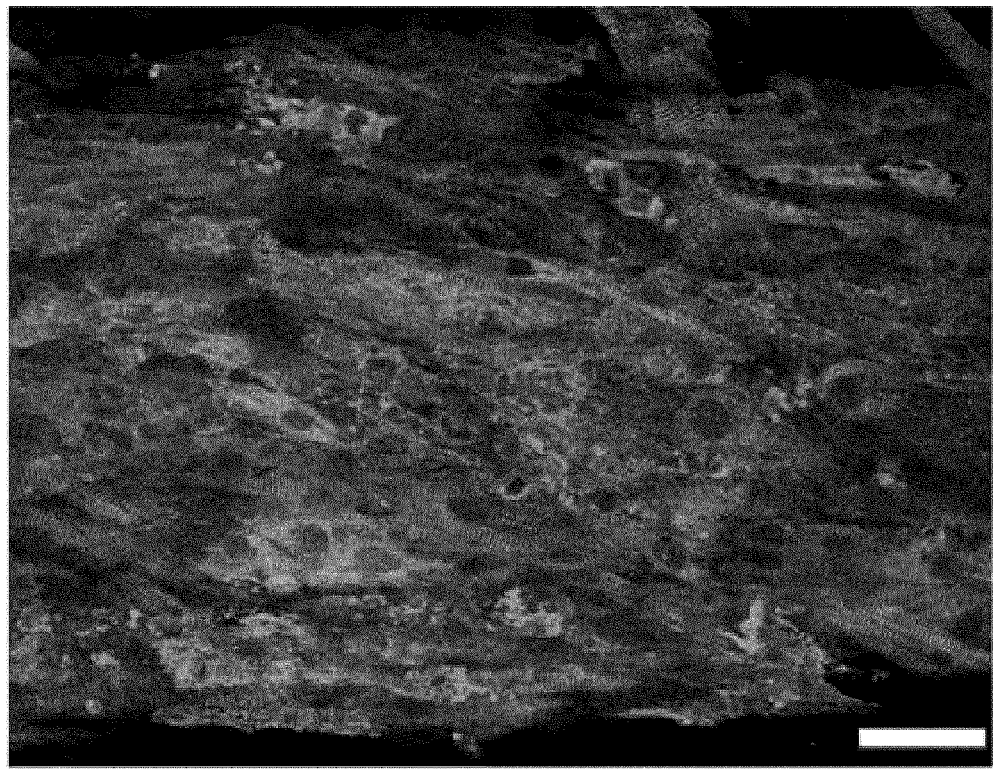
FIG. 44 is a fluorescence microscopy image of cells of the tissue strand of an exemplary biorod system of the disclosure stained for alpha-actinin (cytoskeletal stain) and DAPI (to indicate the nucleus).

FIG. 44 provides a fluorescence microscopy image of cells of the tissue strand of the Biorod embodiment stained for alpha-actinin (cytoskeletal stain) and DAPI (to indicate the nucleus). Clear sacromere structure can be seen with fully elongated cells having a high degree of cell alignment in the tissue, each of which is indicative of highly matured cardiac tissue as a result of electrical stimulation.

Figure 45:
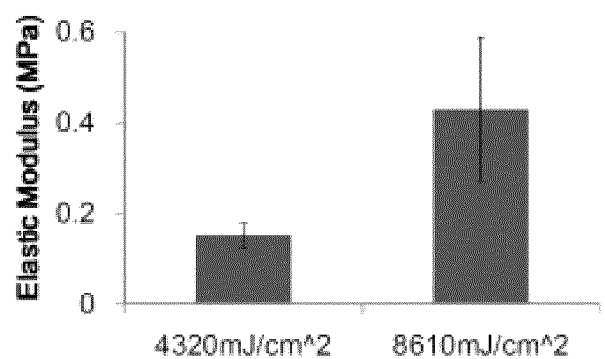
FIG. 45 provides experimental results demonstrating that tissue strand of an exemplary biorod system of the disclosure simulates human myocardium with respect to elasticity.

FIG. 45 provides experimental results demonstrating that tissue strands of the Biorod embodiment simulate human myocardium with respect to elasticity. Human myocardium ranges in tissue elasticity from about 20 kPa to 0.5 MPa. When implanting replacement cardiac tissue, it is crucial to ensure that the implanted tissue anchor point has similar mechanical properties of the native tissue in order to simulate a physiological environment that is native, which is ideal for both in vitro and in vivo applications. In preferable aspects, the mechanical properties of the polymer of the Biorod device is tunable by controlling the polymerization using different crosslinking energy. Tunability can also be controlled by the ratio of the mixtures of polymer units during the polymerization reaction. The bar graph shows distinct elastic modulus when the POMac polymer wires/bendable elements of the Biorod device are crosslinked at two different energy levels. The elastic modulus at both energies (4320 mJ/cm$^2$ and 8610 mJ/cm$^2$) fall right into the range of adult myocardium, but the elastic modulus is lower with lower curing energies. The mechanical properties of the polymer wires can also be increased using increased curing energy in order to create a particular pathological condition.

Figure 46:
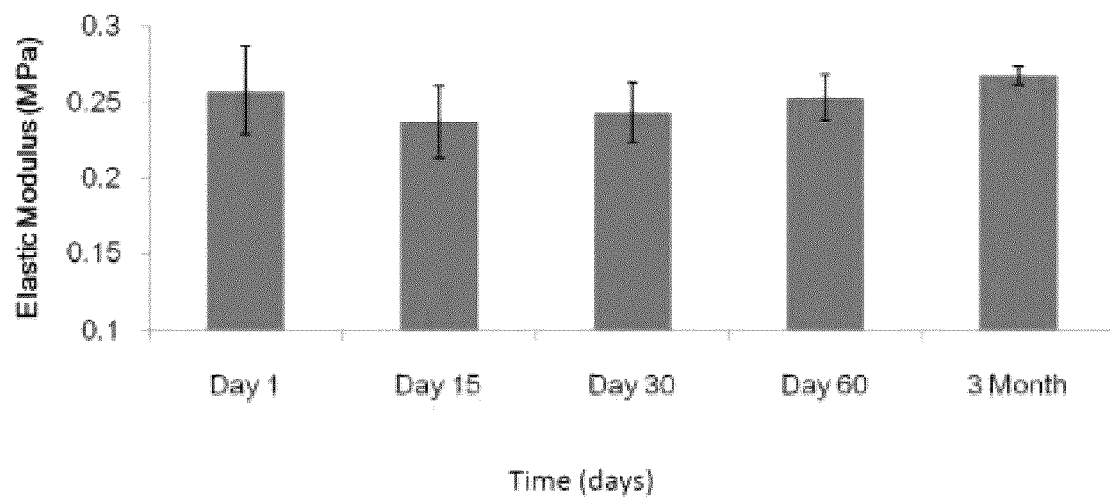
FIG. 46 provides a bar chart demonstrating the stability (in terms of elastic modulus) of the POMac polymer wires of an exemplary biorod system of the disclosure over 3 months.

FIG. 46 provides a bar chart demonstrating the stability (in terms of elastic modulus) of the POMac polymer wires of the Biorod embodiment over a period of 3 months. The data indicate that even after a period of 3 months, the elastic modulus remains relatively constant, demonstrating that the POMac wires are substantially stable with time.

Figure 47:
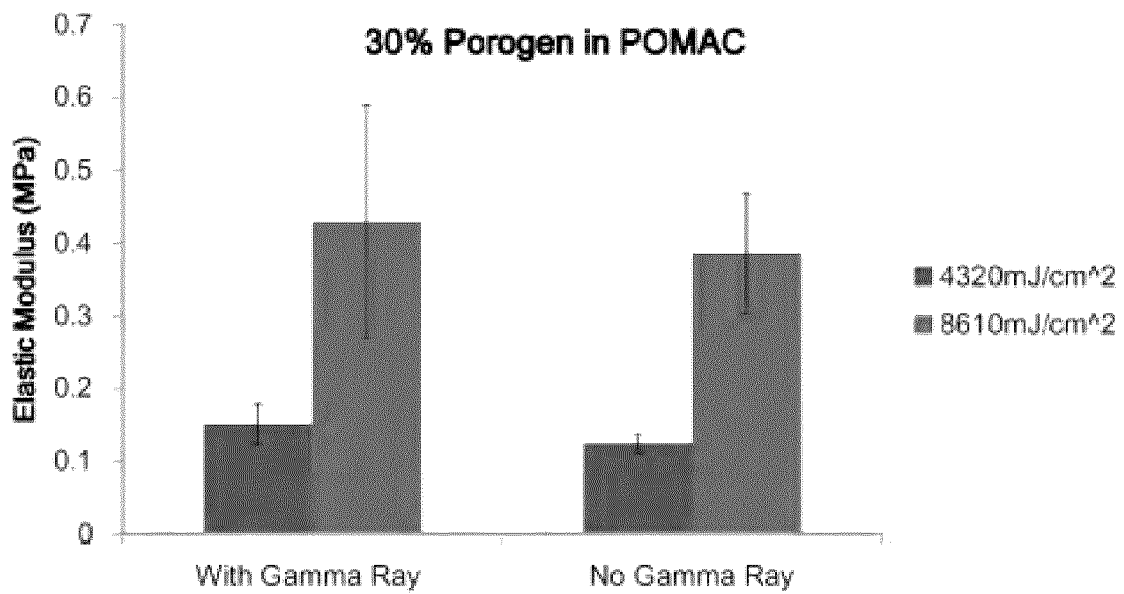
FIG. 47 provides data demonstrating that the POMac polymer wires of an exemplary biorod system of the disclosure may be sterilized by gamma irradiation without any influence in elastic modulus.

FIG. 47 provides data demonstrating that the POMac polymer wires of the Biorod embodiment may be sterilized by gamma irradiation without any influence in elastic modulus, even at two different curing energies.

Figure 48:
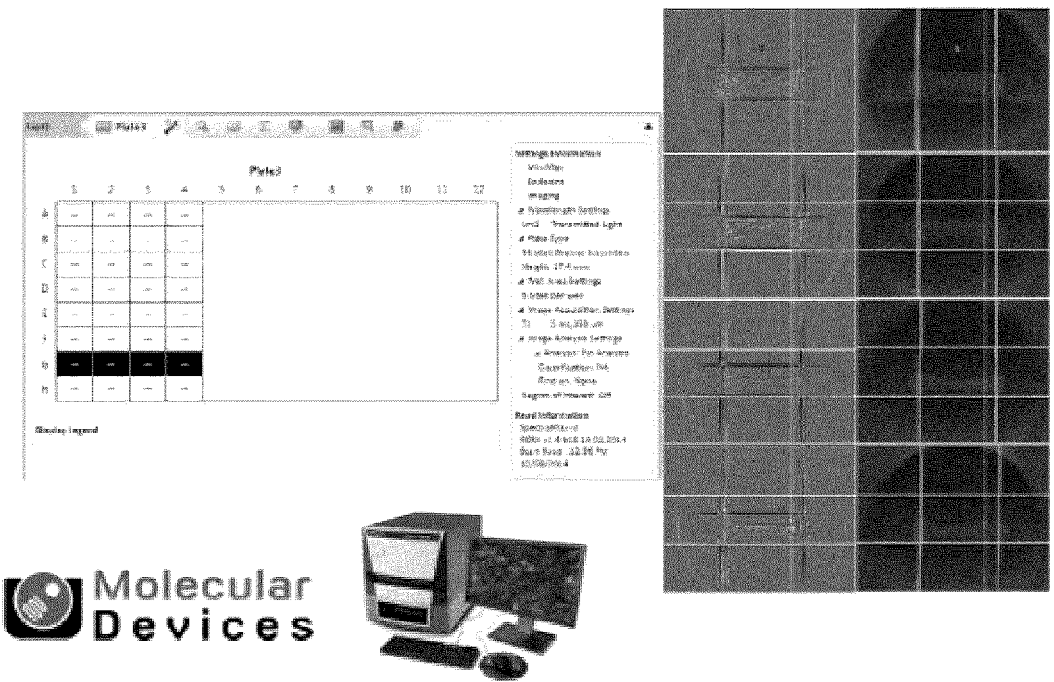
FIG. 48 provides a schematic demonstrating one manner by which batch images of an exemplary biorod system of the disclosure may be acquired using commercially available instrumentation (e.g., Molecular Devices).

FIG. 48 provides a schematic demonstrating one manner by which batch images of the Biorod plates may be acquired using commercially available instrumentation (e.g., Molecular Devices). The commercially available Spectramax device from Molecular Devices is used in our lab to take pictures in batch for gel compaction and passive tension created by tissue compaction.

Figure 49:
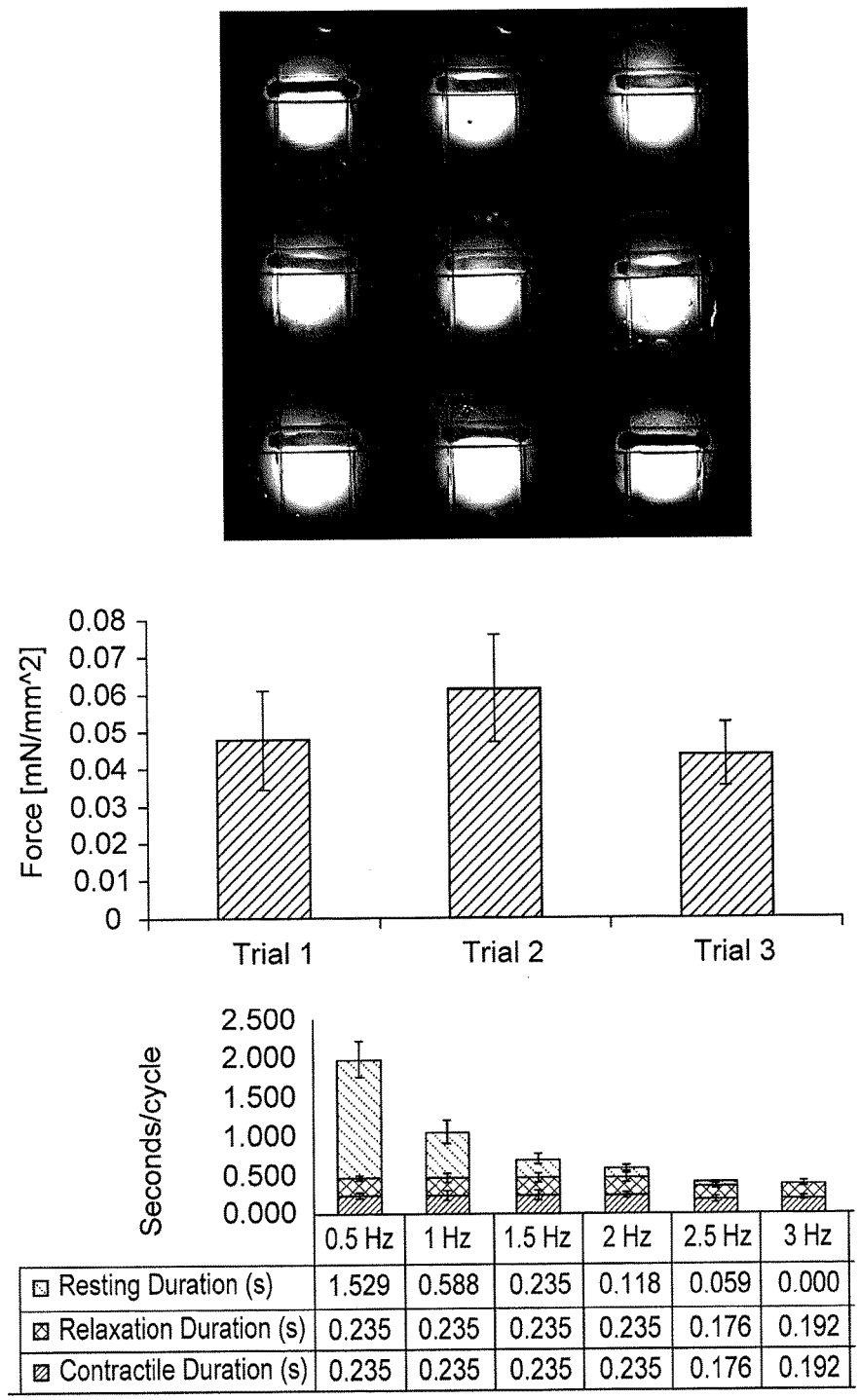
FIG. 49 provides data demonstrating that the tissue strands yield consistent and highly reproducible data within a single 96-well plate in accordance with an exemplary biorod system of the disclosure.
Figure 50:
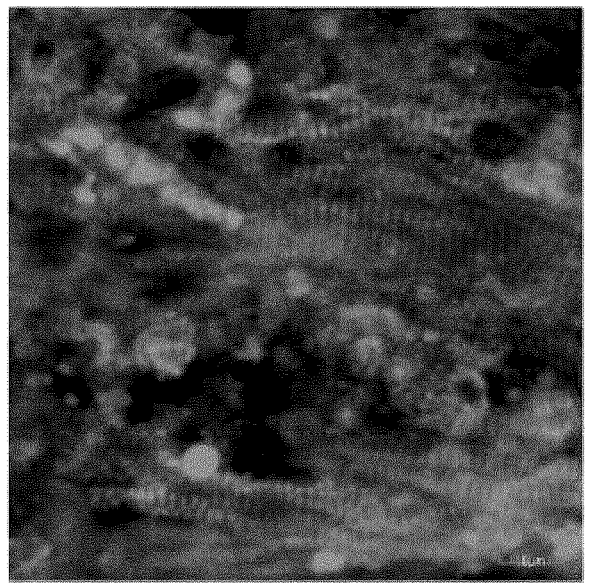
FIG. 50 provides a fluorescence microscopy image of cells of an exemplary biorod system of the disclosure stained with alpha-actinin to show that orientation of the cells.

FIG. 49 provides data demonstrating that the tissue strands yield consistent and highly reproducible data within a single 96-well plate using rat neonatal cell sources. The forces of samples from different trials were compared. Also, as shown in the bar graph at the lower right of FIG. 49, parameters including tissue contraction, relaxation, and resting time under same beating frequency have little variances. These evidences show high level of reproducibility of the tissue strands in the Biorod device. FIG. 50 is an in situ alpha-actinin immunofluorescence image of a Biorod tissue strand in a 96 well-plate showing the elongated cell structure, consistent orientation, and the subcellular structure.

The Biorod embodiment, as supported by the above experimental testing, has numerous advantages and features, the least of which include:

Allows for easy handling and long term observation.

Provides a high throughput platform in tissue engineering field.

Provides a complete drug inert environment for drug testing.

Free of PDMS.

High fidelity cardiac tissue.

Incorporate electrical stimulation to push maturation.

Controlled (i.e., tunable) mechanical properties of polymer wires (i.e., bendable elements) by polymerization of polymer using different curing energies, and polymer unit compositions/ratios In-situ long term and end point assessment Calcium transient measurement IHC staining Possibly alter one side of wire into other material to allow various applications Point electrical stimulation using Pt wires Mechanical stretching with magnetic field Example 4: Biobranch/Angiochip A. Structure, Preparation, and Use of an Exemplary Vascularized Tissue Culture Embodiment (i.e., Biobranch/Angiochip)

In a fourth embodiment, the invention relates to a bioreactor device for growing a three-dimensional tissue comprising a three-dimensional branched tissue having one or more internal luminal passageways (e.g., mimicking a vascularized three-dimensional tissue structure). This embodiment of the invention can comprise a bioreactor having a three-dimensional shaped scaffold or extracellular matrix unit that contains a first portion for growing seeded cells and a second portion for providing interconnected channels that pass through the first portion. The bioreactor may be configured to mimic a biological vasculature. The scaffold may serve as a support for seeded cells to form a tissue structure in which a network of channels, preferably perfusable channels, are formed. The network of channels may also include micro-holes (10-20 um in diameter) on the channel wall to enhance channel permeability as well as facilitate migration of cell (e.g. monocytes). The bioreactor can be further configured to include electrodes configured to generate an electric field across the bioreactor. The direction of the electric field can be in any direction, but preferably in a direction that is generally parallel with the longitudinal axis of the scaffold. In another embodiment, the direction of the electric field can be generally perpendicular with the longitudinal axis of the scaffold. As may be used herein, the fourth embodiment of the invention may be referred to as "biobranch," which may refer to, but is not limited to, the three-dimensional tissue formation itself (i.e., the cells that grow on a bioreactor device as described herein) or the system comprising the tissue formation and the bioreactor together. Biobranch may also be referred to herein as its commercial name of BIOBRANCH™, which encompasses both the tissue formation itself, or the system comprising the tissue formation and the bioreactor device in which the tissue has grown or has been placed. This fourth embodiment also relates to methods for growing the tissue in the branched bioreactor, to the three-dimensional tissue itself, to systems comprising both the bioreactor and grown tissue (i.e., integrated bioreactor), and to methods for using and/or testing the tissue strands (or systems comprising the tissue strands) in various applications, including, but not limited to, (a) the testing of the efficacy and safety (including toxicity) of experimental pharmacologic agents (including, but not limited to, small molecule drugs, biologics, nucleic acid-based agents), (b) the defining of pharmacokinetics and/or pharmacodynamics of pharmacologic agents (including, but not limited to, small molecule drugs, biologics, nucleic acid-based agents), (c) characterizing the properties and therapeutic effects of pharmacologic agents (including, but not limited to, small molecule drugs, biologics, nucleic acid-based agents) on a subject, (d) screening of new pharmacologic agents, (e) provide implantable engineered tissues for use in regenerative medicine for treating damaged and/or diseased tissues, (e.g., use of the tissue constructs, devices, and/or systems of the disclosure to study cardiac disease states, including patients with electrical conduction defects (iPSC-CM)), and (f) personalized medicine.

Figure 51:
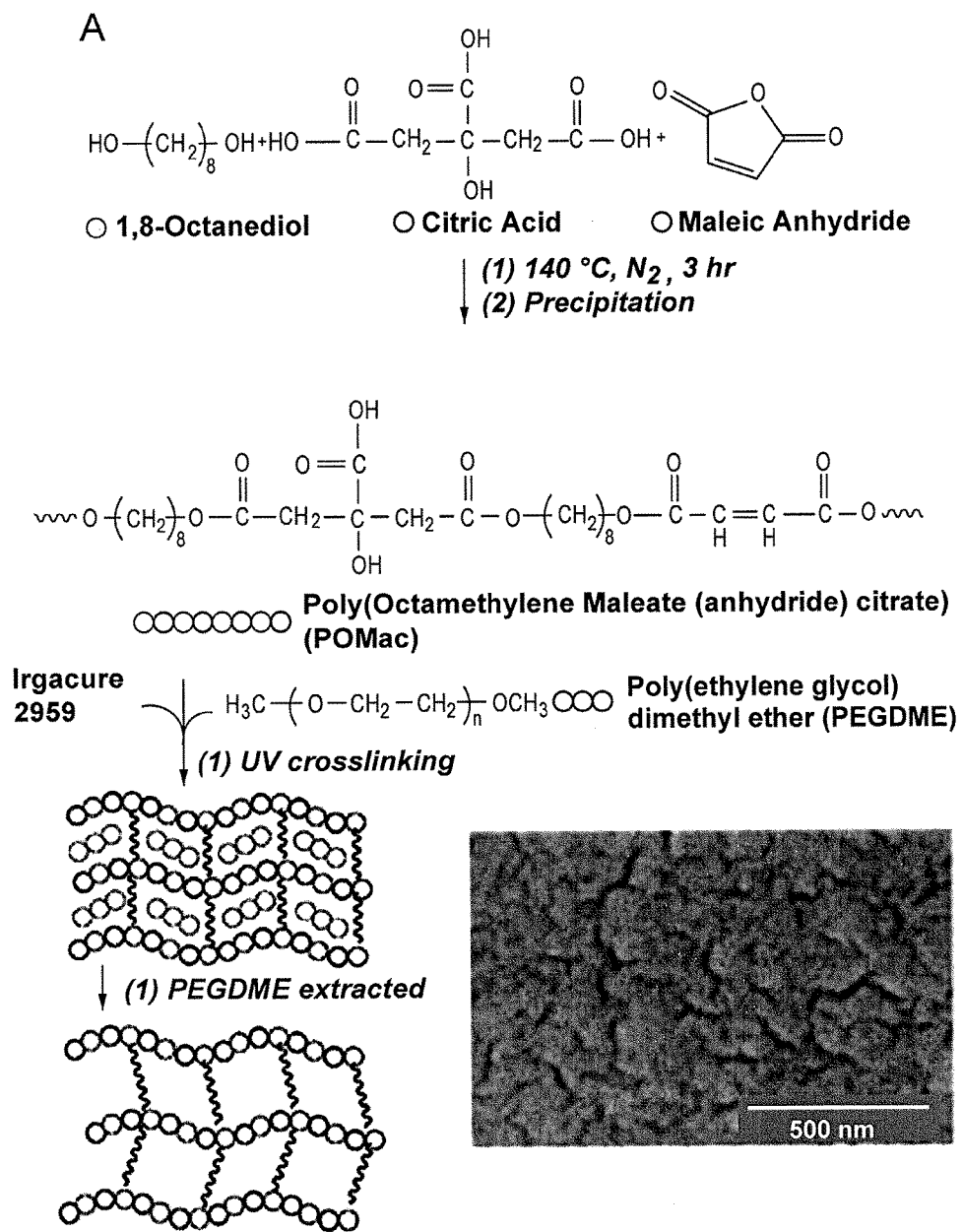
FIG. 51 provides (a) schematic depicting the synthesis of POMac (a biodegradable elastomer, poly(octamethylene maleate (anhydride) citrate) pre-polymer solution, a UV-polymerizable polymer which can be used for rapid assembly under mild conditions and which degrades by hydrolysis. POMac is synthesized from non-toxic monomers (citric acid, maleic anhydride, 1,8-octandiol). The inset shows an SEM of the AngioChip scaffold surface, revealing wrinkle-shaped nano-pores. The PEGME porogen was leached in PBS for 1 day. Scale bar: 500 nm.
Figure 51:
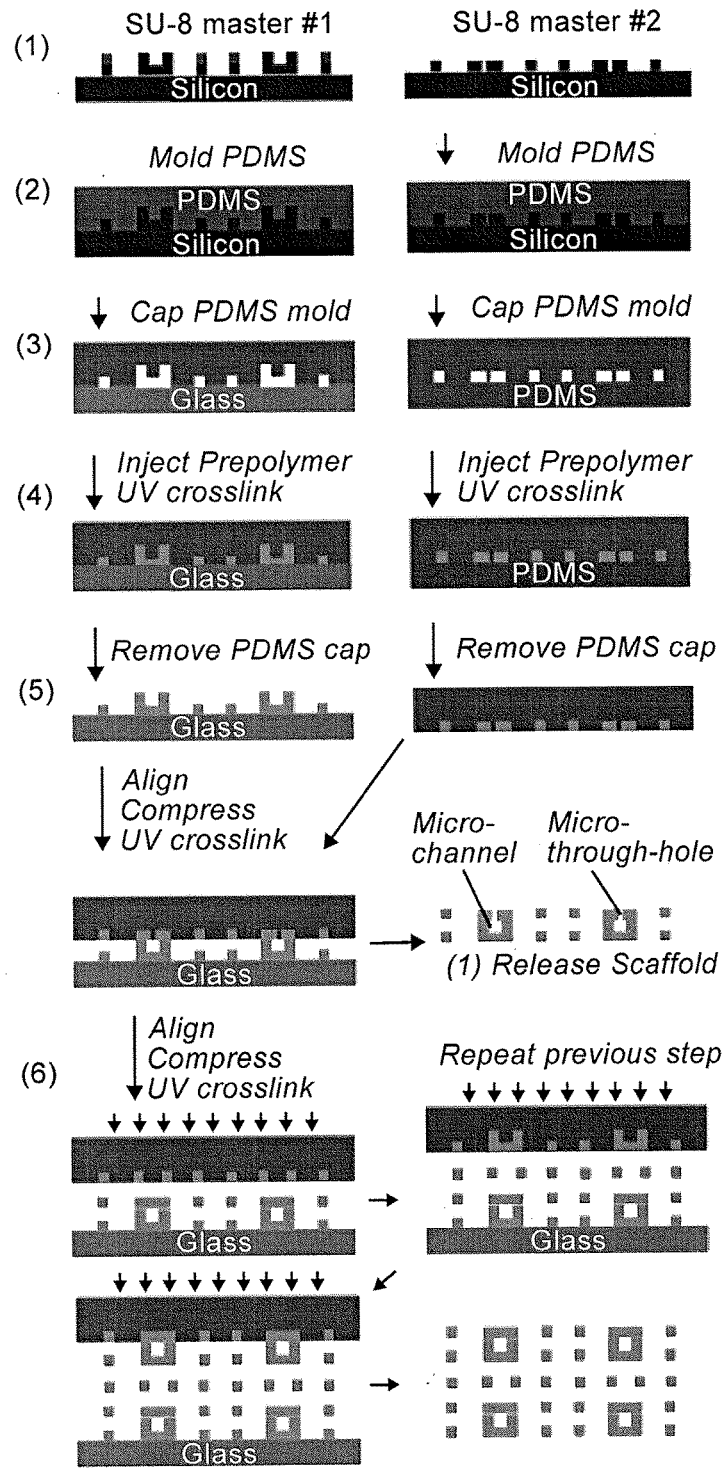
Figure 51:
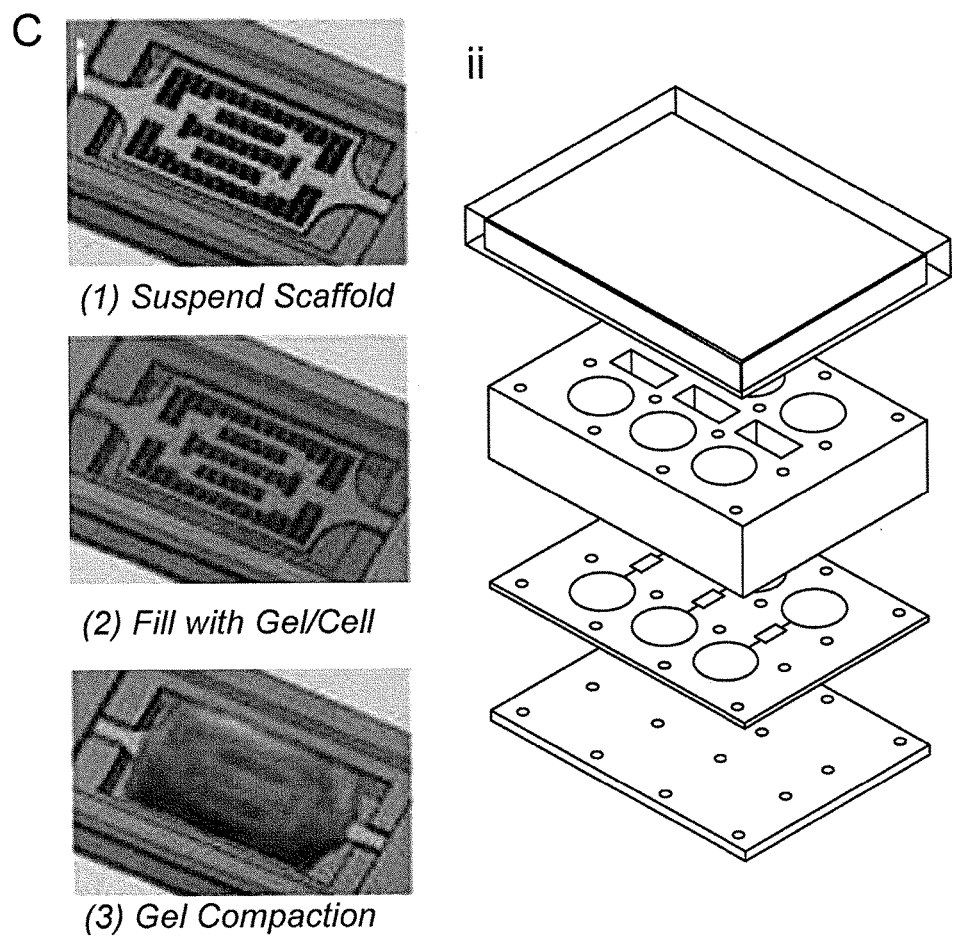
Figure 51:
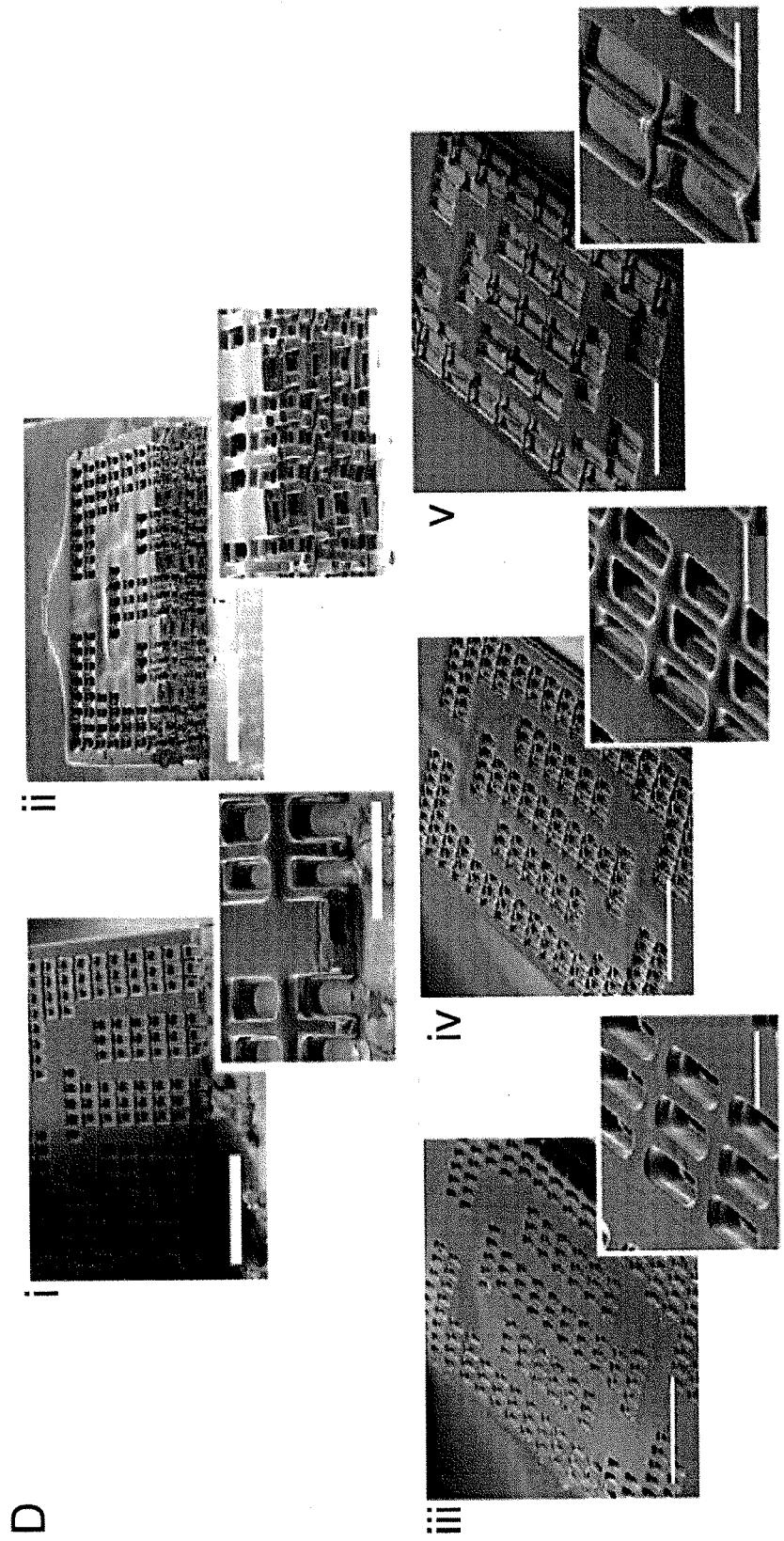
Figure 51:
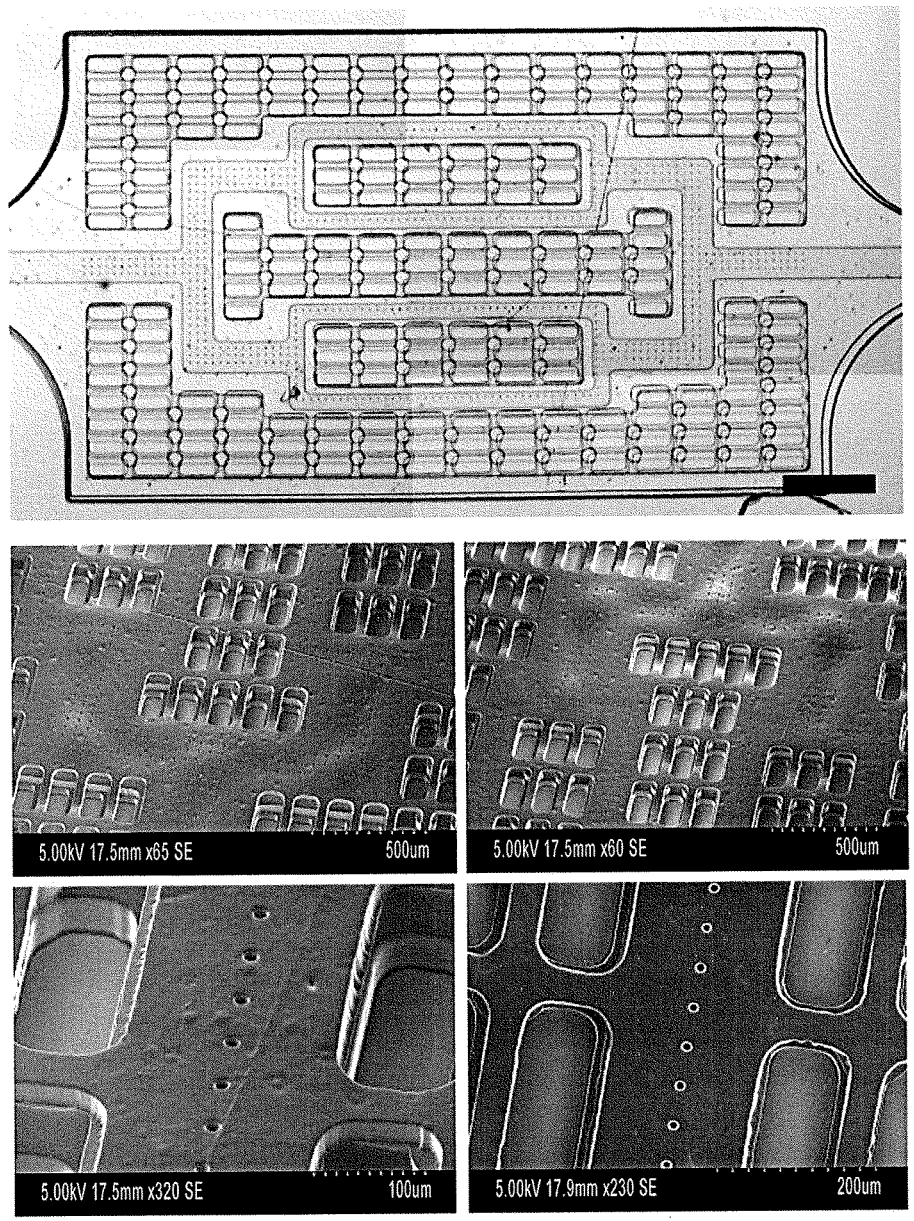
Figure 51:
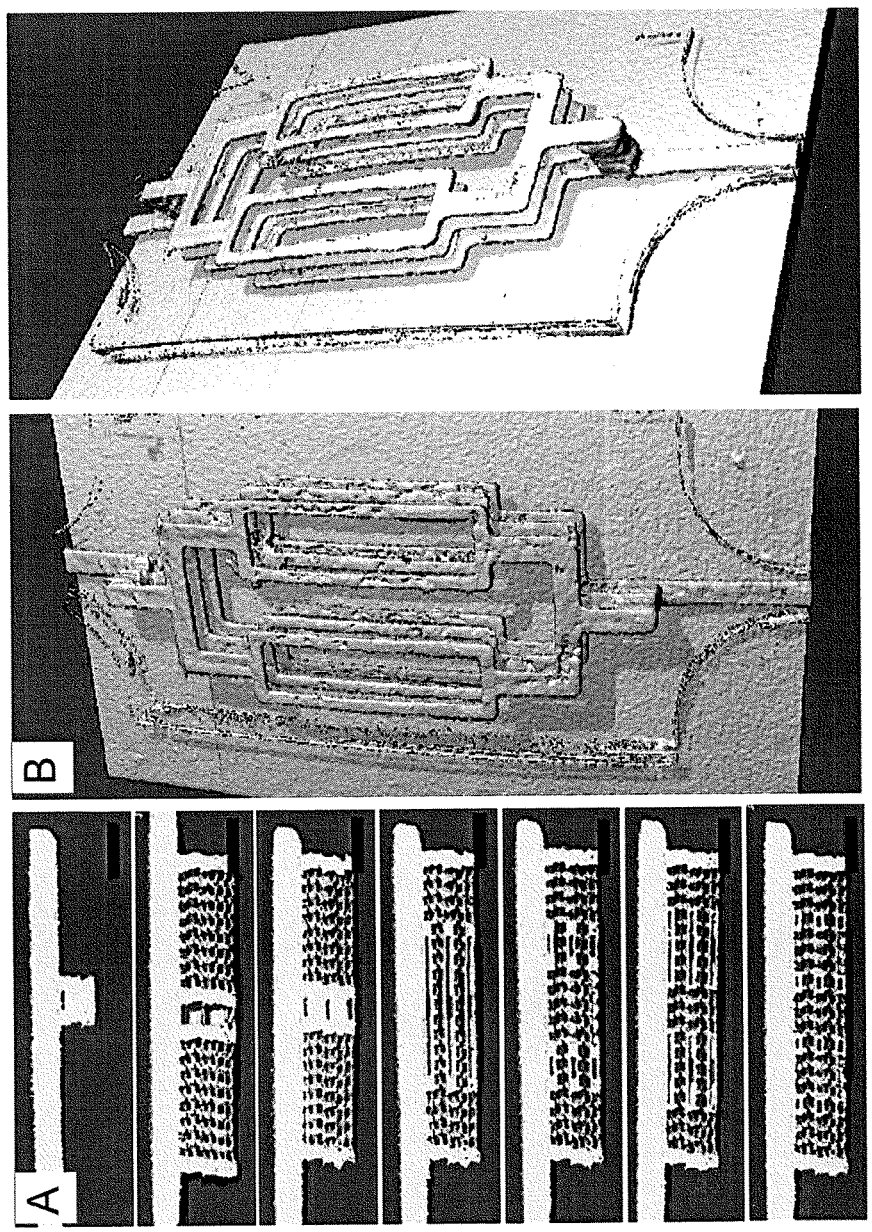
Figure 51:
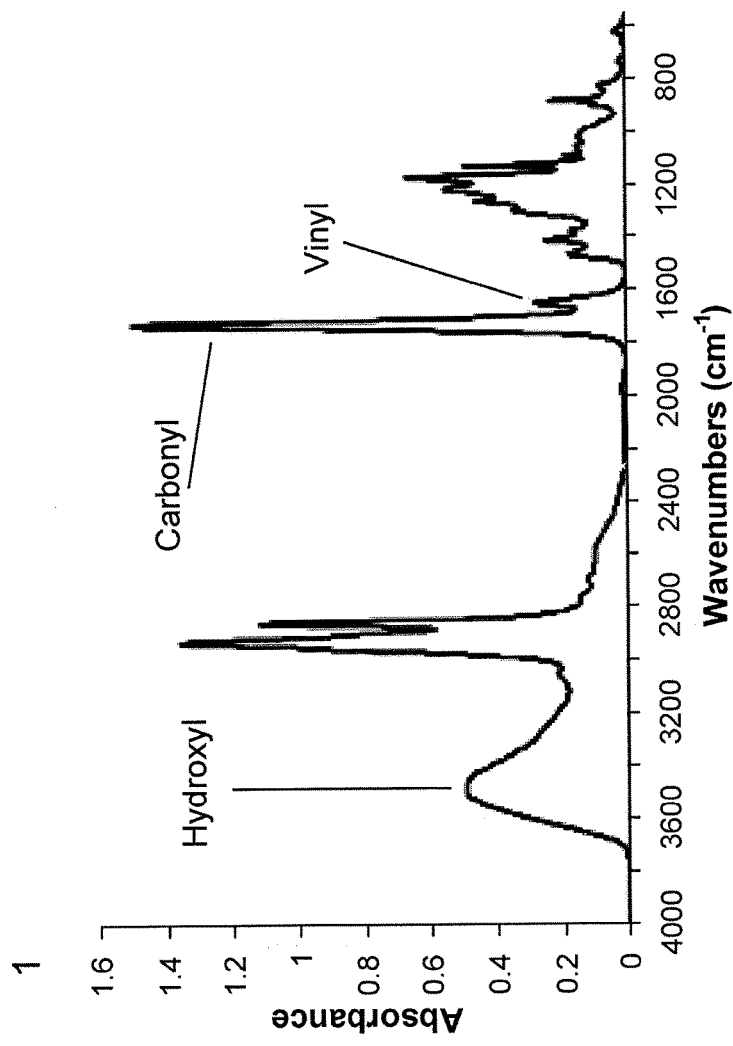
Figure 51:
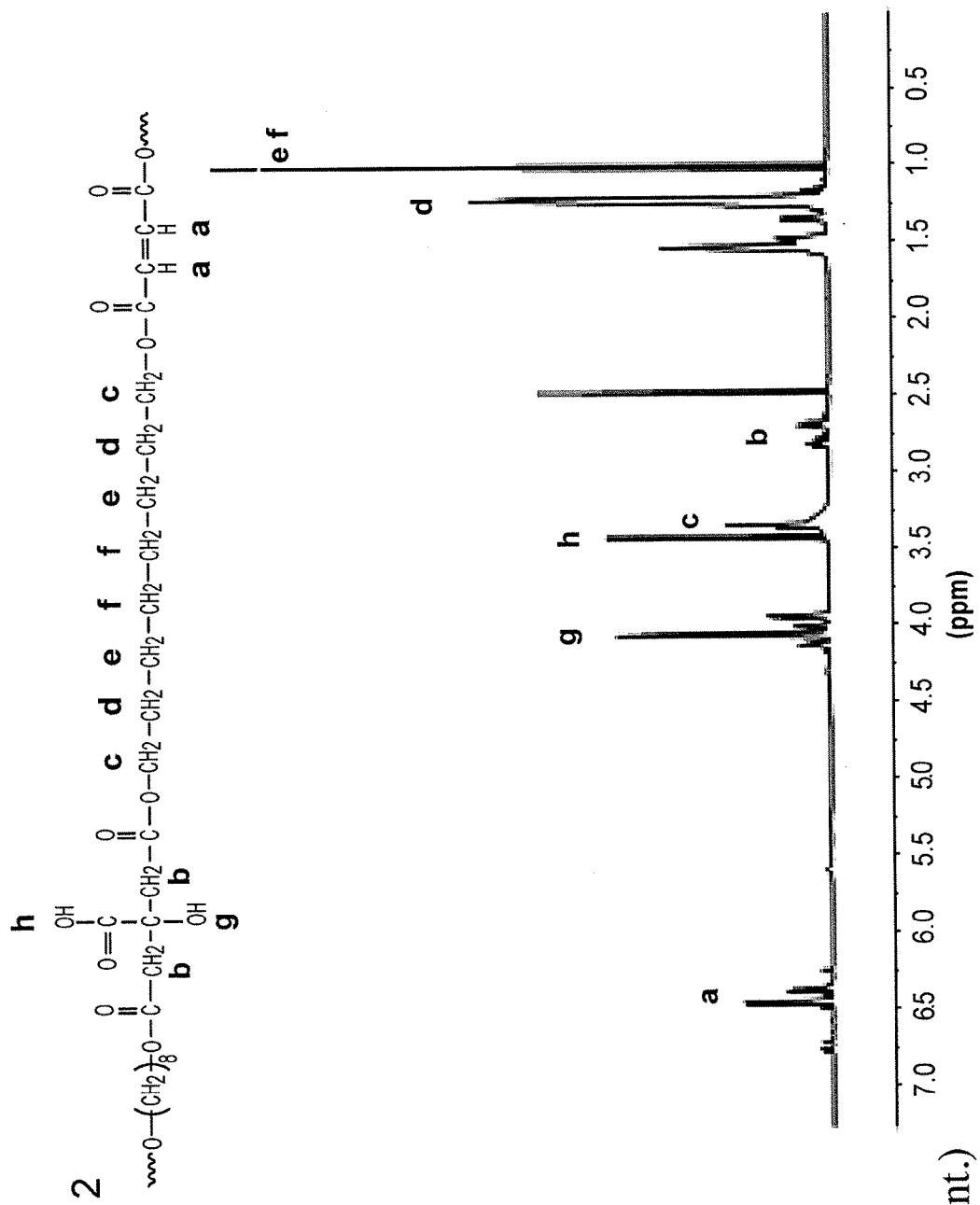
Figure 52:
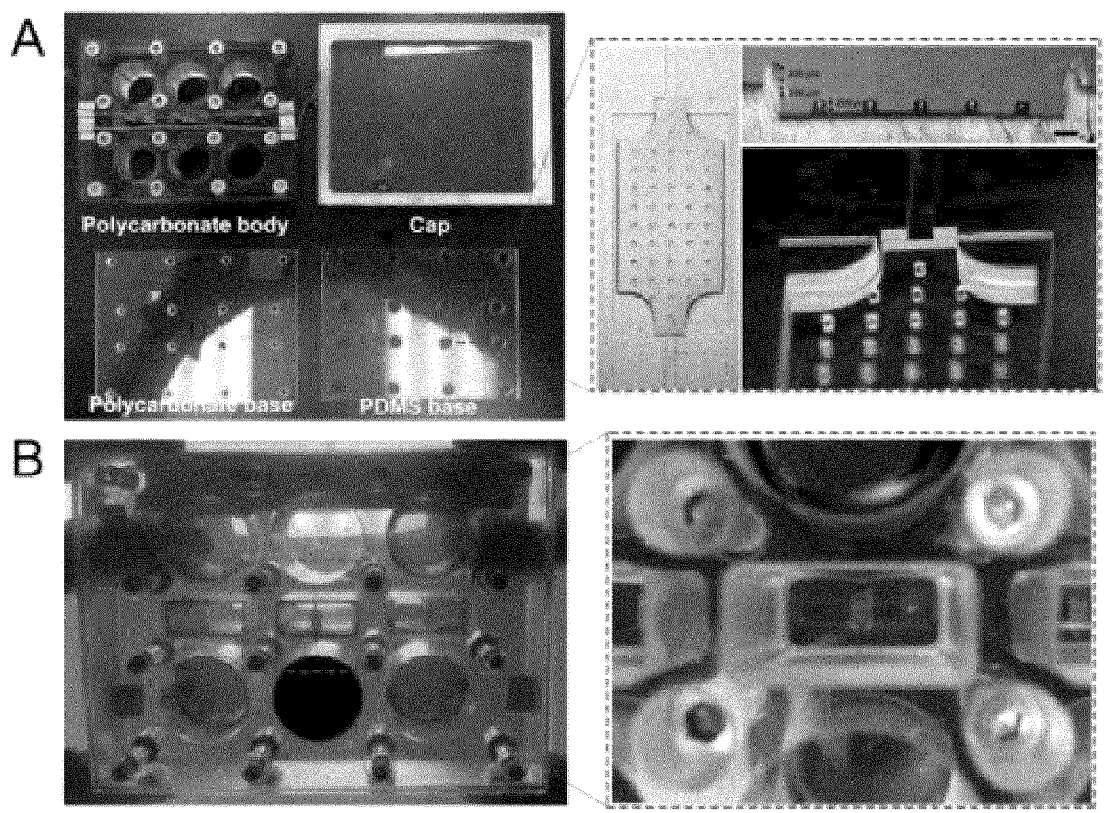
FIG. 52 Bioreactor assembly. (A) Image of the four components (cap, polycarbonate body, PDMS base, and polycarbonate base) of the bioreactor. (Inset) Image of the trench structure on the PDMS base where the AngioChip scaffold was placed. An array of micro-posts was used to lift the AngioChip scaffold up ~200 μm from the base so that cells could wrap around the scaffold from the bottom. The total height of the PDMS trench is 700 μm. Cell/gel suspension was cast into the trench where the scaffolds were installed and filled to the top. (B) Image of the assembled bioreactor with three cardiac tissues perfused with color dye. (inset) Magnified image of a perfused cardiac tissue in the main well.
Figure 53:
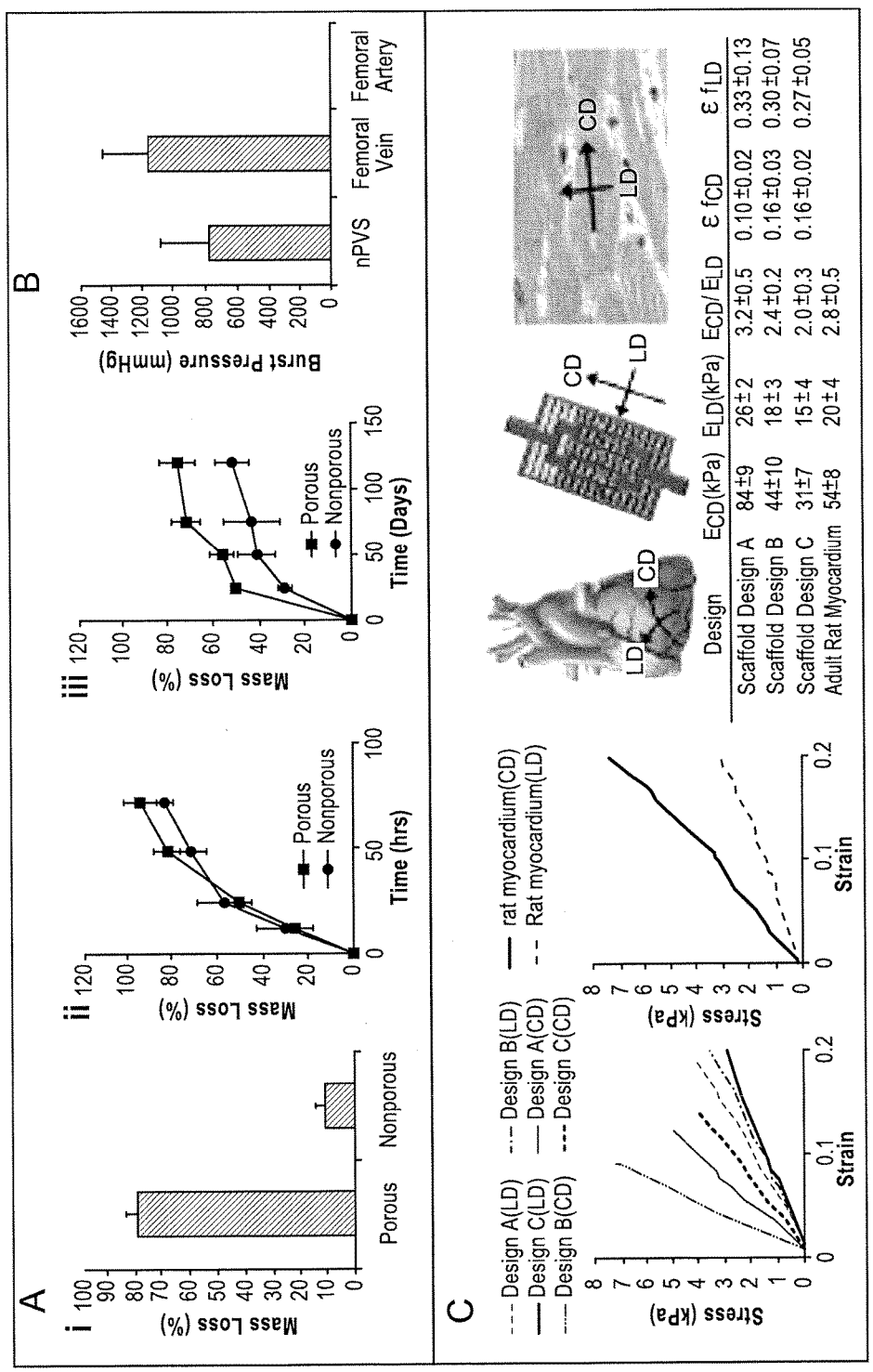
FIGS. 53a-53d show results of assessment of the physical properties of the AngioChip scaffold.
Figure 53:
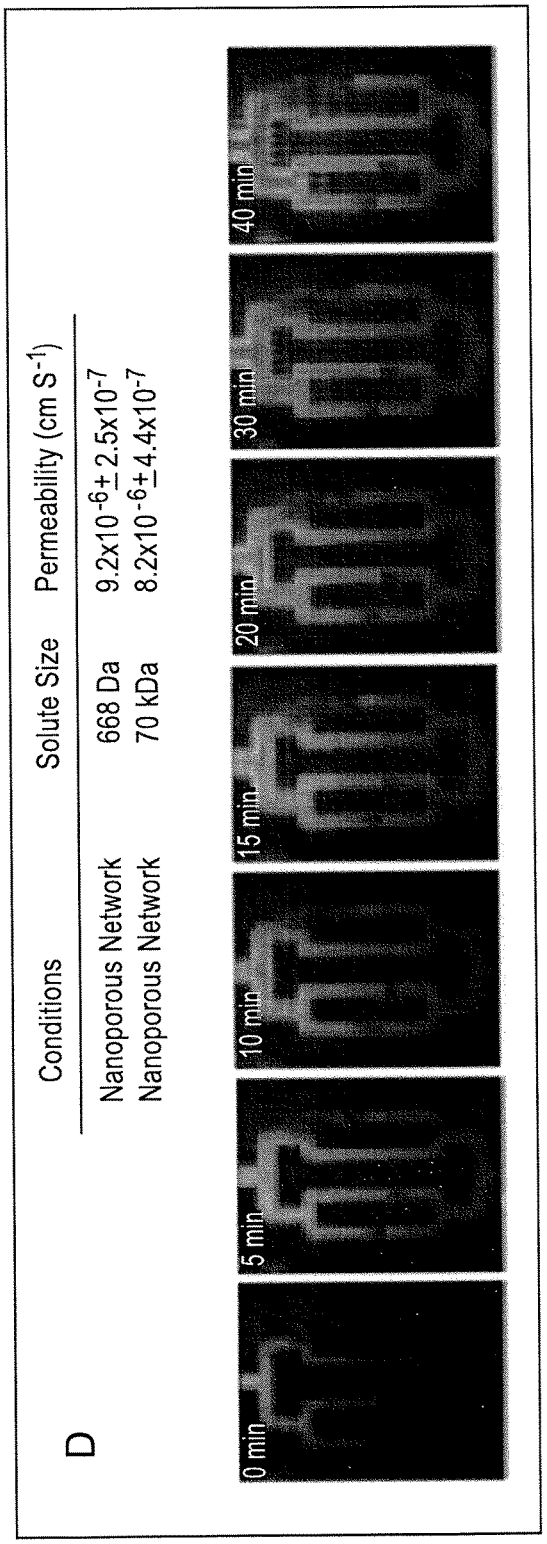
Figure 54:
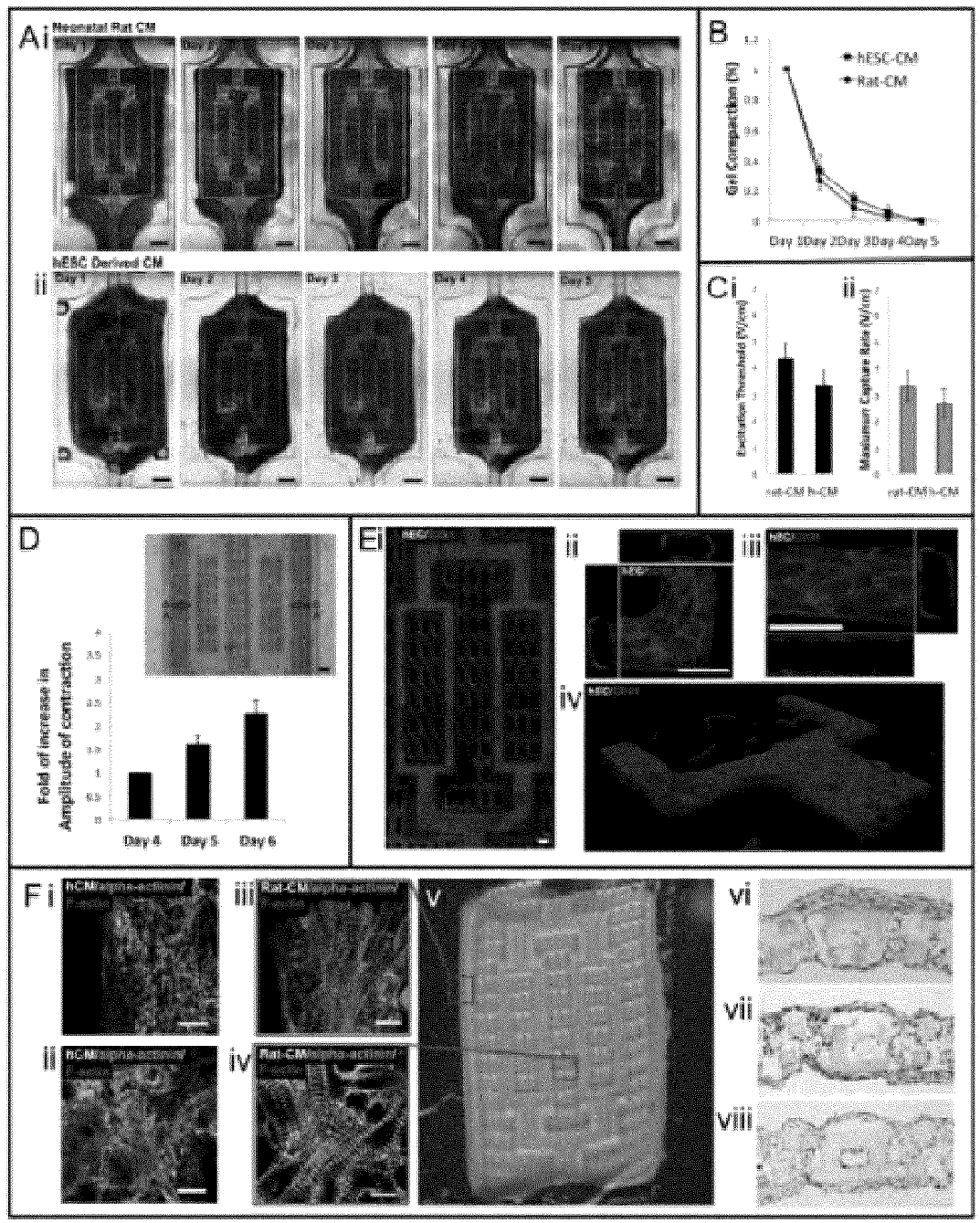
FIGS. 54a-54f illustrate formation and vascularization of tissues generated in accordance with the AngioChip embodiment.
Figure 55:
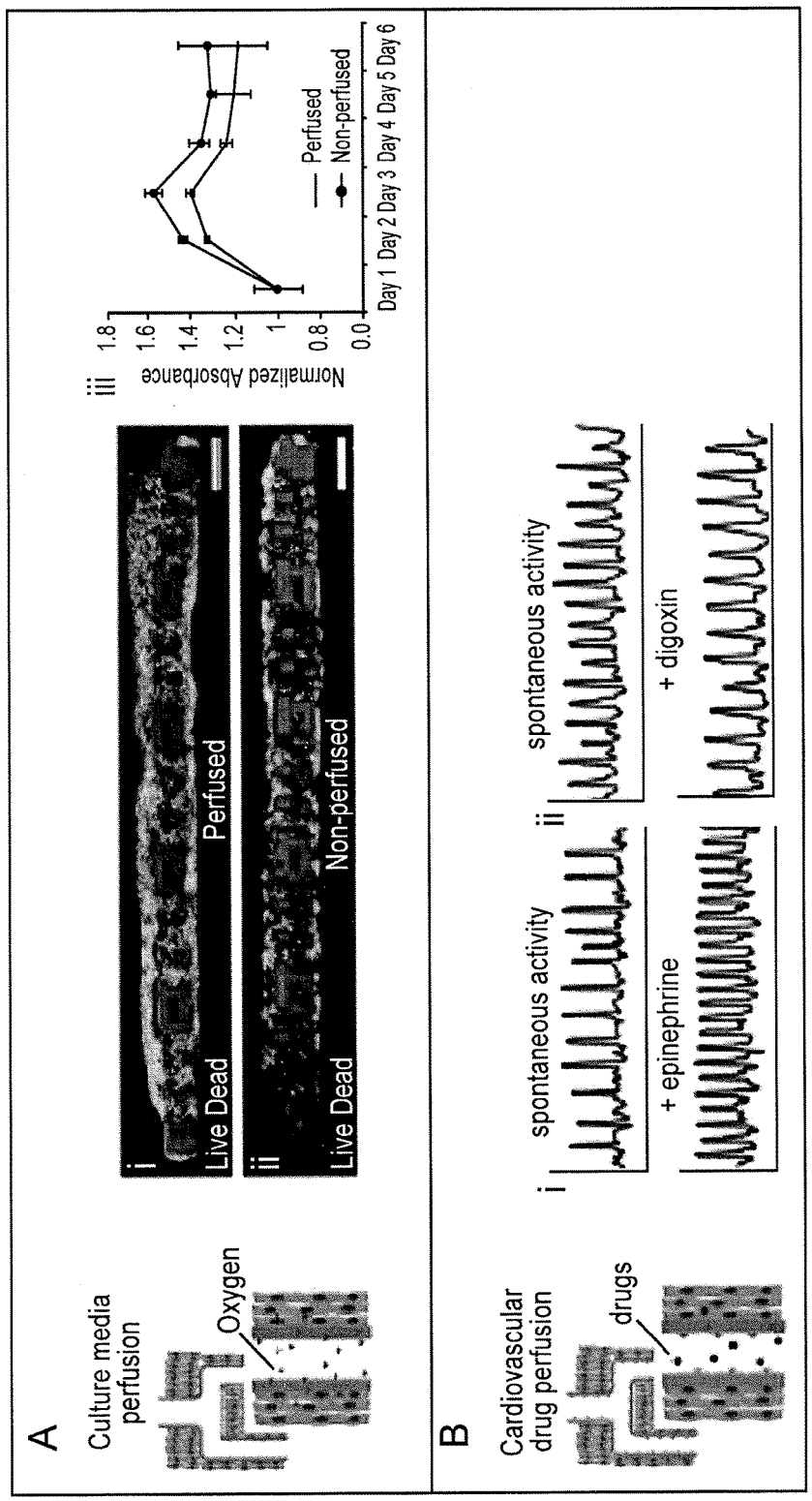
FIGS. 55a-55d illustrate validation of vascularized cardiac tissues generated in accordance with the biobranch embodiment.
Figure 55:
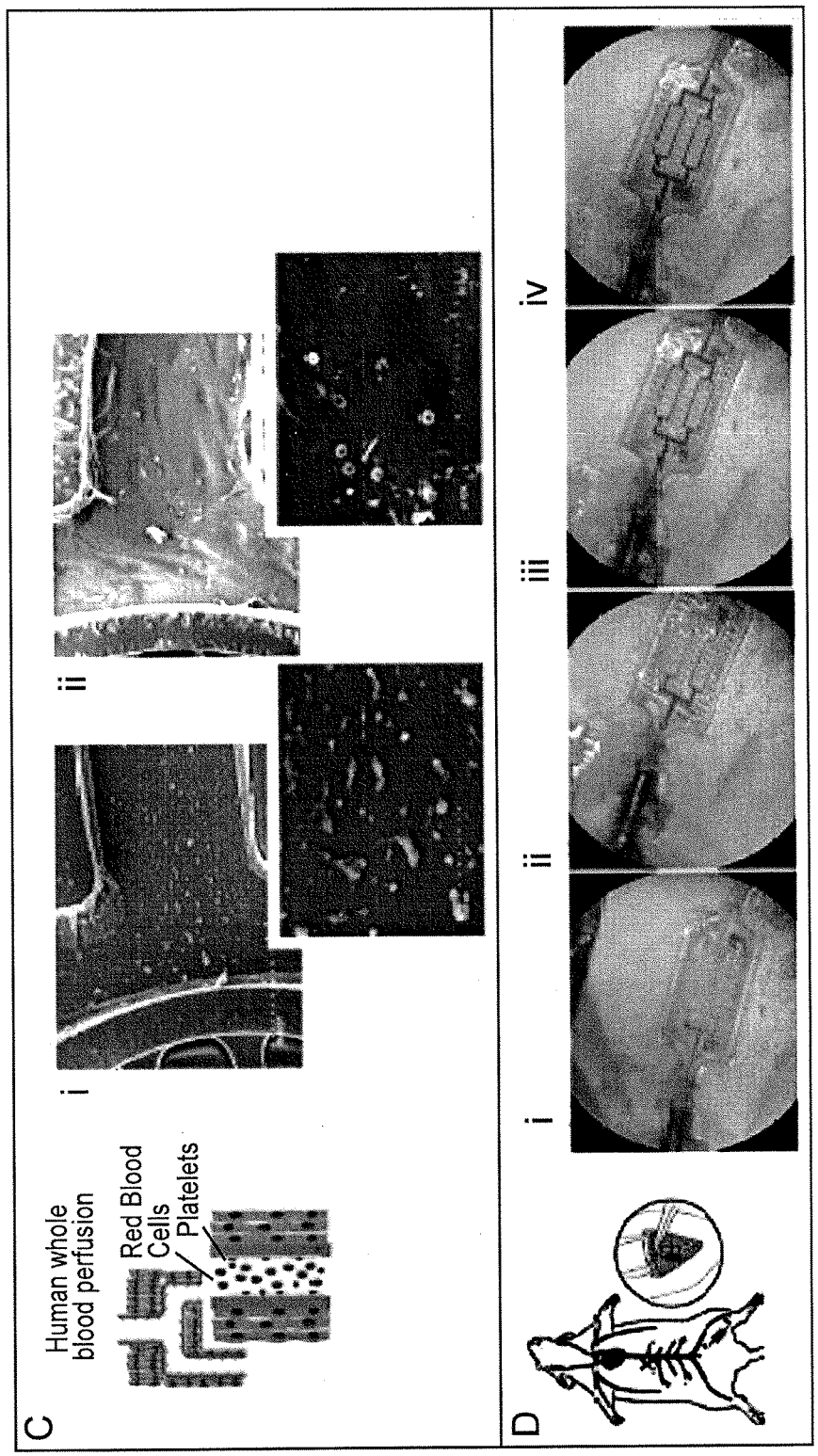

FIGS. 51 and 52 show an example device suitable for cultivation of branched tissues that may include branched vasculature. The device of Example 4 may be similar to the device of Example 1, however instead of a single channel the device in Example 4 may have three-dimensional branched channels. An example method for fabrication of the device of Example 4 is described below.

The example device may include a bioreactor chamber in which seed cells for a tissue culture may be received. A scaffold may be received in the bioreactor chamber. The bioreactor chamber may include protrusions (e.g., posts) to support the scaffold over the base. This may enable the cultivated tissue to encapsulate the scaffold. The scaffold may include a three-dimensional network of struts and perfusion channels. The scaffold may be configured to mimic a biological vasculature. The scaffold may serve as a support for the seed cells to form a tissue structure about the three-dimensional network, enabling generation of a tissue structure with three-dimensionally branched vasculature.

The present disclosure provides a method for fabricating scaffolds suitable for cultivating a branched tissue structure. The scaffold may include internal cavities (e.g., a tube, 2D branched micro-channel network, or 3-D branched micro-channel network) and/or a suspended structure (e.g., a mesh or lattice matrix) and may be formed of biodegradable materials (or POMaC).

The example fabrication method uses a 3-D stamping method to fabricate 3-D structures with internal cavities and/or suspended structures. The 3-D structures in this example may be fabricated in a layer-by-layer process, involving aligning, stacking and bonding two or multiple patterned polymer sheets together. A 3-D scaffold having two or more layers, and having internal cavities and/or suspended structures defined by its layers may thus be fabricated.

The microfabrication method may use a mold formed of a material that has a first adhesion strength to the scaffold material (e.g., a biopolymer material or biodegradable material, such as POMaC as shown in FIG. 51(*a*)). The mold may be provided on a substrate that has a second adhesion strength to the scaffold material. The second adhesion strength may be greater than the first adhesion strength, such that, after molding a layer in the mold, the layer may be released from the mold while remaining adhered to the substrate. The present disclosure has found that forming the mold using PDMS and using a glass slide as the substrate achieves suitable differential adhesion strength with POMaC as the scaffold material.

A pre-polymer of the scaffold material may be introduced into and cured in the mold, forming a first layer of the scaffold supported by the substrate. Because the scaffold material has greater adhesion strength to the substrate than to the mold, the layer may be released from the mold while maintaining adherence to the substrate. This may allow the scaffold to be more easily manipulated while it is being built up layer-by-layer.

Additional layer(s) may be formed for the scaffold. Additional layer(s) may be formed using the same mold or a different mold. For example, an additional layer may be formed using a different second mold that is formed of the same mold material, and that is supported by a mold base formed of the same mold material. The additional layer, after it has been cured in the second mold, may be released from the mold base while remaining adhered to the second mold. This may allow each additional layer to be more easily manipulated, thus enabling more precise alignment, stacking and bonding as the scaffold is built up layer-by-layer. After the additional layer is properly bonded to the first layer or the previously-bonded layer, the additional layer may be released from the second mold, thus being ready to receive the next additional layer.

When all layers of the scaffold have been thus bonded and the scaffold is complete, the scaffold may be released from the substrate.

In an example of the fabrication method (as shown in FIG. 51(b)), a PDMS mold is fabricated for each individual layer of the scaffold structure with standard soft lithography. One mold may be created for the base layer (bottom first layer) and multiple molds for all other subsequent upper layers. The PDMS mold for the base layer may be capped onto a substrate, such as a glass slide, non-permanently. The PDMS molds for all subsequent upper layers may then be capped onto another flat PDMS sheet non-permanently.

The polymer mixture may then be injected into the mold. The mold with the polymer mixture may be exposed to UV light and partially cross-linked and solidified. The PDMS mold for the base layer with the glass slide cap may be then un-capped from the glass slide. The injected polymer, once cross-linked, may exhibit stronger attachment to the glass slide than to the PDMS mold, and therefore can be released from the PDMS mold while remaining attached to the glass slide.

The PDMS mold for all subsequent upper layers with the PDMS sheet cap may be then un-capped from the PDMS Sheet. The PDMS mold has more surface area in contact with the polymer than the PDMS. Therefore the polymer may be more strongly attached onto the PDMS mold than the PDMS sheet and hence may not be released from the PDMS mold.

Each polymerized polymer within the PDMS mold for the upper layers can then be manipulated relatively easily with the PDMS mold and aligned, stacked, and bonded to the base layer polymer on the glass slide with additional UV crosslinking. After UV crosslinking, all stacked polymer layers may be permanently bonded to each other.

The glass slide may adhere more strongly to the polymer scaffold than the PDMS mold currently holding the upper polymer layer. So the polymer scaffold may detach from the PDMS mold and remain attached on to the glass slide when the PDMS mold is removed.

More molds with the patterned polymers for the upper scaffold layers can be transferred, stacked, and bonded on to the current scaffold in the same way, in order to create a thicker scaffold.

Since the polymer scaffold may not attach to the glass slide permanently, the entire scaffold may be released from the glass slide simply by soaking the scaffold in water or buffer solution.

This example fabrication method may overcome one or more disadvantages of conventional 3-D fabrication techniques. For example, a limitation with conventional 3-D polymer scaffold fabrication includes the lack of an easy and practical way to transfer thin patterned polymer sheets and stack them together. If a polymer sheet is completely released from its mold, then the thin sheet cannot be handled easily and accurately, and thus precise alignment is typically difficult or impossible. Without precise alignment it would be difficult or impossible to create accurate internal cavities (such as micro-channels with precise and thin channel walls) and suspended structures.

POMaC displays differential non-permanent adhesion strength to glass (stronger adhesion) and PDMS (weaker adhesion). The disclosed fabrication method uses this property to capture and release thin POMaC polymer sheets with the PDMS mold, as well as to align and bond to other patterned sheets with greater control and precision.

Although the disclosed fabrication method is described using a POMaC material, other materials may also be used. The disclosed fabrication method may be expected to work for any material where there is such a pair of substrates (such as glass and PDMS) that can be molded and that shows differential non-permanent adhesion strength to the material.

The present disclosure provides a fabrication method using a biodegradable material that can be transferred easily and precisely with just glass slide and PDMS, which has not been achieved conventionally. For example, similar biodegradable materials such as PGS stick to PDMS completely and therefore cannot be used in the same way. The present disclosure has found a material that is suitable for this fabrication method and has demonstrated the technique.

Compared to 3-D printing, the disclosed fabrication method may allow creation of a suspended structure as well as internal cavities in a biomaterial scaffold, without sacrificial material. With 3-D printing it is typically difficult to find a sacrificial material that is compatible with the printed biomaterials. If no sacrificial material is used, then to create suspended structure, the material must be printed in mid-air, which is extremely challenging with biomaterial. The disclosed method may allow pre-patterning of each individual polymer sheet, then the sheets may be simply stacked together and each layer released, to create suspended structures relatively easily. However, despite the currently 3D printing limitations, the present invention does not preclude the use of 3D printing methodologies so long as the described microstructures can be formed, including the branched networks, macropores, and micropores.

The disclosed method can be used to make various 1-D, 2-D and 3-D structures, including wire, tube, 2-D branched network, 3-D branched network, and mesh structures, among others. The disclosed method may be particularly useful for creating structures with internal cavities, such as tube, 2-D, 3-D branched network and mesh structures.

The 2-D and 3-D micro-channel network scaffold and fabrication thereof as disclosed herein may be advantageous over conventional techniques in various ways, such as the design of the scaffold, the inclusion of a built-in microchannel network in the scaffold, as well as the ability to fabricate such a scaffold precisely, using suitable biomaterials.

In an example, the device was fabricated using a pre-polymer solution. FIG. 51(a) shows a schematic illustration of the chemical synthesis of an example pre-polymer solution, as well as polymer photo-crosslinking mechanism and nano-pores formation. The inset in FIG. 51(a(shows a SEM image of an example resulting scaffold surface revealing nano-scale wrinkle-shaped pores. (Scale bar: 500 nm).

In an example, to prepare poly(octamethylene maleate (anhydride) citrate) (POMac) prepolymer, 1,8-octandiol, citrate acid, and maleic anhydride were mixed at 5:1:4 molar ratio and melted at 160° C. under nitrogen purge. The temperature was then dropped to 140° C. and the mixture was stirred for three hours. The resultant pre-polymer solution was then dissolved in 1,6 dioxane and purified via drop-wise precipitation in distilled water. Precipitated polymer was lyophilized for 2 days and then mixed with poly (ethylene glycol) dimethyl ether (PEGDM, Mw~500, Sigma) at 60% w/w and 5% w/w UV initiator (Irgacure 2959).

The ratio of the prepolymer components may be changed to adjust the physical properties of the resultant polymer.

The scaffold pattern was pre-designed in AutoCAD and translated to SU-8 masters via standard soft lithography techniques as described previously. A silicone elastomer [poly(dimethylsiloxane), PDMS] was molded against the SU-8 master and cured at room temperature for 2 days.

Patterned PDMS for the first layer and other layers of the scaffold was then temporally bonded to glass slides and flat PDMS respectively to form closed channels via static adhesion. Pre-polymer solutions were then injected into the patterned channels and left overnight at room temperature. Next, injected polymer solution was cross-linked under a UV lamp for 5 mins and then the PDMS mold was delaminated to release the patterned polymer structure such that the first layer will adhere to the glass slides and detach from the patterned PDMS while the other layers will adhere to the patterned PDMS and detach from the flat PDMS. All patterned layers were aligned to and compressed against the first layer or previous layer with a UV aligner (Q2001, Quintel Co., San Jose, Calif.) followed by additional UV exposure for 1 min to permanently bond the layers together. Fabricated scaffolds were lastly immersed in PBS overnight to leach out PEGDM porogen. In this example, 4 scaffolds could be fabricated at a time.

FIG. 51(b)(1-5) is a schematic diagram of example vascular scaffold layer-by-layer molding and bonding procedures for a single layer vascular network fabrication. The inset shows a SEM image of cross section of channel lumen. (Scale bar: 100 µm). FIG. 51(b)(6) is a schematic showing an example of multi-layer vascular network fabrication.

The example device may serve as a bioreactor for co-culture of endothelial cells and cardiomyocytes onto the scaffold under medium perfusion. In this example, the device included four components: the cap, the reservoirs, the PDMS slab, and the base (see FIG. 51(c)(ii)). The device in this example was designed to culture three scaffolds in separate culturing chambers at a time. The reservoir piece (2.5 cm thick) includes 6 wells for placing endothelial growth medium that perfuses through the scaffold network and supplies oxygen and nutrients to the cultivating tissues from within and 3 wells which contain cardiomyocyte growth medium that provides nutrients to the tissue surface. The PDMS slab (2 mm thick) includes three trenches where the scaffolds can sit. The trenches have base layers where micro-posts were included to help lift the scaffold up from the bottom so that cells/gel can encapsulate the entire scaffold. The trench also includes an open inlet and outlet channel where the inlet and outlet of the scaffold precisely fit.

FIG. 52 shows an example holder for the device of Example 4. In this example, the holder incorporates trenches and posts that are designed to keep the tissue suspended to help enable gel infiltration and more efficient remodelling. Example dimensions of the trench are shown in the figure.

After the scaffolds are positioned onto the trench, the PDMS slab can be sandwiched between the base component and the reservoir component so that the PDMS open inlet and outlet channels were capped by the reservoir component, hence anchoring the scaffolds. The three components were secured with stainless steel screws and capped. Endothelial cell medium was perfused from the top wells to the capped channel through the scaffold network which exited into the bottom wells driven by the pressure head differences between the two wells.

FIG. 51(c)(i) illustrates an example process of cardiac cell seeding/tissue formation using the example device showing gel compaction.

FIG. 51(d) shows SEM images showing the cross sectional view of (i) a 2-D vascular scaffold, and (ii) 3-D vascular scaffold. SEM images showing the top view the single-layer vascular scaffolds with different lattice matrix design are shown in FIG. 51D(iii) illustrating a single mesh layer design, FIG. 51D(iv) illustrating a design having two dense mesh layers supported by posts, and FIG. 51D(v) illustrating a design with two loose mesh layers supported by posts.

FIG. 51(e) provides SEM images of AngioChip scaffolds with 10 micron micro-holes. (A) provides image of an AngioChip scaffold with 10 micron through-holes patterned throughout its network wall. Scale bar: 600 microns. Image was stitched from multiple images. (B) SEM of an AngioChip scaffold with 10 micron through-holes viewed from different angles. Scale bars are shown in images.

FIG. 51(f) provides microCT of 3-D AngioChip scaffolds. (A) MicroCT scans of the cross-section of a 3-D AngioChip scaffold from its inlet to the branches along the long-edge direction of the scaffold. Scale bar: 400 microns. (B) MicroCT of the internal network of an AngioChip view from different angles. The scaffold was perfused with barium sulfate solution through its internal network hence increasing its density for improved visualization. The thickness of the scaffold network wall was 50 µm. The inlet, outlet, and the first order branch had an inner luminal dimension of 50 µm by 200 µm. The second order branch had an inner luminal dimension of 50 µm by 100 µm. The network was designed so that the endothelial cells in the first and second order branches experienced the same level of shear stress. The networks on each layer were connected through a vertical channel and were 300 µm apart in z-axis. The scaffold mesh was made of 50 µm struts. The struts were spaced 250 µm apart in the long-edge direction, 100 µm apart in the short-edge direction, and 50 µm apart in the z-axis.

FIG. 51(g) provides the molecular structural characterization of POMac polymer solution. (A) Fourier transform infrared (FT IR) spectroscopy. (B) Nuclear magnetic resonance (NMR) spectroscopy.

Although certain materials, techniques and dimensions are described above, other suitable materials, techniques and dimensions may be used for the example device. The device may be designed with different channel and layer configurations, to enable cultivation of tissues with different branch configurations, for example.

The disclosed devices may be formed of any suitable materials using any suitable techniques. For example, the device may be formed using a polymer material, such as poly(dimethysiloxane) (PDMS) or poly(methyl methacrylate) (PMMA) material. In some examples, portions of the device that is expected to come into contact with cells, tissues and/or culture medium (e.g., the bioreactor channel or chamber and the scaffold) may be substantially free of poly(dimethysiloxane) (PDMS). The scaffold may be made of a biodegradable material. Other suitable materials may include poly(glycerol sebacate), POMac without citric acid, poly(lactic acid), poly(glycolic acid), poly($\varepsilon$-caprolactone), various polyurethanes as well as co-polymers thereof, silk, microstructured, nanofabricated materials, and/or materials doped with nanostructures such as nanorods or quantum dots, among others.

The disclosed devices may be useful for various applications including, in vitro drug testing, direct anastomosis in an animal or human patient, or implantation in an animal or human patient, among others. The disclosed devices may also be provided in the form of a microfabricated chip.

The present disclosure also provides methods for cultivating tissues using the disclosed devices. Example methods are discussed further below. The method may include introducing seed cells into the bioreactor channel or bioreactor chamber of the device (e.g., introducing a gel in which seed cells are embedded). The seed cells may then be cultured in the bioreactor channel or bioreactor chamber. During culture, electrical stimulation may be provided to the cells according to a defined regimen, which defines specific frequency of stimulation at specific times.

The disclosed devices and methods may be used for cultivation of human or animal tissue, including muscle cells (e.g., cardiomyocytes, skeletal muscle cells, or smooth muscle cells), excitable cells (e.g., neurons) or cells requiring vasculature (e.g., hepatocytes). Other cells may be cultured together also. For example, epithelial cells, endothelial cells, smooth muscle cells, and various types of stem cells, such as pluripotent stem cells, mesenchymal stem cells, cord blood derived stem cells, and the differentiated progeny of these cell types, among others, may be cultured as well.

To enable greater appreciation and understanding of the disclosed devices, examples of tissue cultivation using example devices are described below. Example studies were also carried out to investigate tissues generated using examples of the disclosed devices. These example studies may help to validate use of the disclosed devices for generating biologically-relevant tissues, which may be suitable for various applications including drug-testing in vitro, for building a human-on-a-chip with several different compartments as well as for direct anastomosis and implantation into an animal or a human patient, among other applications.

B. AngioChip: a biodegradable scaffold with built-in vasculature for organ-on-a-chip engineering and direct surgical anastomosis Using a new 3-D stamping technique, this Example teaches an AngioChip scaffold manufactured from a synthetic biodegradable elastomer (poly(octamethylene maleate (anhydride) citrate—POMac). The AngioChip contains an internal 3-D, perfusable, branched micro-channel network coated with endothelial cells, embedded into a lattice matrix, with tunable mechanical properties, supporting assembly of different types of parenchymal cells. Tunability can be achieved at least by adjusting the amount of crosslinking energy and/or the ratio of different polymer units during the polymer reaction. For example, in the case of POMac, one could reduce the amount of citric acid to make a more hydrophobic polymer which has stiffer properties. The design enabled us to effectively decouple the material choice for the engineered vessel network from the material choice for the cell seeding in the parenchyma, enabling extensive remodelling while maintaining open channels. Incorporation of nano-pores and micro-holes in the vessel walls enhanced vessel permeability, permitted inter-cellular crosstalk, and extravasation of model inflammatory cells. Vascularized hepatic tissues and cardiac tissues, engineered using AngioChips, were shown to process clinically relevant drugs delivered through their internal vasculature. AngioChip cardiac tissues were also implanted via direct surgical anastomoses to the femoral vessels of rat hindlimbs, establishing immediate blood perfusion.

Introduction

Successful engineering of multi-cellular interfaces on-a-chip has primarily focused on the vascular interface of different organs (e.g. lung, gut) in a closed 2-D microfluidic platform. However, for solid organs (e.g. myocardium, liver) the formation of tissue-level organizational structures involves a 3-D environment. For example, macroscopic contraction and physiological maturation of cardiac muscle relies on the formation of aligned tissue bundles with elongated cells. Hepatic tissue requires the 3-D aggregation of hepatocytes. Current 3-D micro-tissues composed of parenchymal cells have been studied in the absence of a vasculature, whereas vasculature-on-a-chip has primarily been studied separately from parenchymal cells. Therefore, incorporating essential vascular interfaces within a 3-D functional tissue environment is a critical step towards high-fidelity organ-on-a-chip models.

A similar vascularization challenge has been experienced on the macro-scale. Numerous tissue types have been successfully engineered in vitro, but clinical translation has been achieved only for thin tissues or those with a low metabolic demand (e.g. skin, cartilage and bladder). Large solid tissues (e.g. myocardium, liver) are highly sensitive to oxygen levels and become vulnerable within hours without oxygen supply. These solid tissues would benefit greatly from rapid vascularization in vitro and direct vascular integration in vivo. So far, surgical anastomosis of vascularized tissues has only been demonstrated using vascular explants, requiring multiple surgeries to harvest the vascular bed.

Vascular networks can be engineered with subtractive fabrication by embedding a sacrificial carbohydrate-glass lattice, Pluronic F127, dry alginate fibers, or gelatin in hydrogels. However, the soft hydrogel provides only a temporary structural support for the fragile hollow network and does not permit extensive tissue remodeling, which inevitably alters the hydrogel structure and collapses the embedded network. Synthetic biodegradable polymers could provide sufficient structural support to the engineered vessels, but their low permeability prevents biomolecule exchange and cell migration between the vessels and the parenchymal space. Furthermore, current fabrication techniques can only create layered channel networks with physical barriers that prevent seeded parenchymal cells from forming interconnected tissue in 3-D.

To accommodate these two opposing material criteria, this provides the AngioChip, a stable biodegradable scaffold with a built-in branching micro-channel network that contained two unique features realized by our new 3-D stamping technique. First, the synthetic built-in vascular walls were thin and flexible, yet strong enough to mechanically support a perfusable vasculature in a contracting tissue and enable direct surgical anastomosis. Second, to allow efficient molecular exchange and cell migration, nano-pores and micro-holes were incorporated into the vascular walls. By establishing a stable, permeable, vessel network within AngioChips, material constraints were limited, which allowed use of any soft natural extracellular matrix (e.g. collagen, Matrigel) embedded with cells in the parenchymal space permitting the extensive tissue remodelling. To structurally reinforce the remodeled tissue, the AngioChip parenchymal space structure can also be fine-tuned to mimic the anisotropic mechanical properties of native tissues (e.g., myocardium), which would otherwise be difficult to achieve with a homogeneous hydrogel. Based on this methodology, a functional and vascularized cardiac and hepatic tissue for both micro-scale organ-on-a-chip models and tissue replacements was created.

Results

The AngioChip scaffolds were constructed with a new 3-D stamping technique using a biodegradable elastomer, poly(octamethylene maleate (anhydride) citrate) (POMaC) (FIG. 51A). POMaC is UV-polymerizable, allowing rapid assembly under mild conditions, degrades by hydrolysis, and is synthesized from non-toxic monomers (citric acid, maleic anhydride, 1,8-octandiol) (FIG. 51A). With 3-D stamping, thin POMaC sheets were pre-patterned, in a scalable manner (FIG. 51B), under UV illumination and stamped onto each other, layer-by-layer, to form complex suspended structures, and internal cavities, with precise alignment down to several microns. POMaC exhibited non-permanent and differential adhesion to glass (strong) and polydimethylsiloxane (PDMS) (weak) after photo-cross-linking, due to oxygen-induced inhibition of free radical polymerization on the surface of the PDMS, which leaves a non-polymerized POMaC layer at the interface. Utilizing this characteristic, patterned POMaC sheets were robustly transferred, aligned and released from one substrate (PDMS) then bound to the POMaC structures supported by a glass substrate (FIG. 51B). This method circumvented the challenge of printing biomaterials in mid-air, as with conventional 3-D printing, and avoided the use of sacrificial materials. 3-D stamping enabled patterning of POMaC into various intricate structures from a 1-D tube (FIG. 56e) to 2-D bifurcating conduits (FIG. 56f or a 3-D branching network (FIG. 56g) mimicking a vascular bed within a lattice matrix, tailored to support the parenchymal cells (FIG. f, g, h and FIG. 51b).

Figure 56:
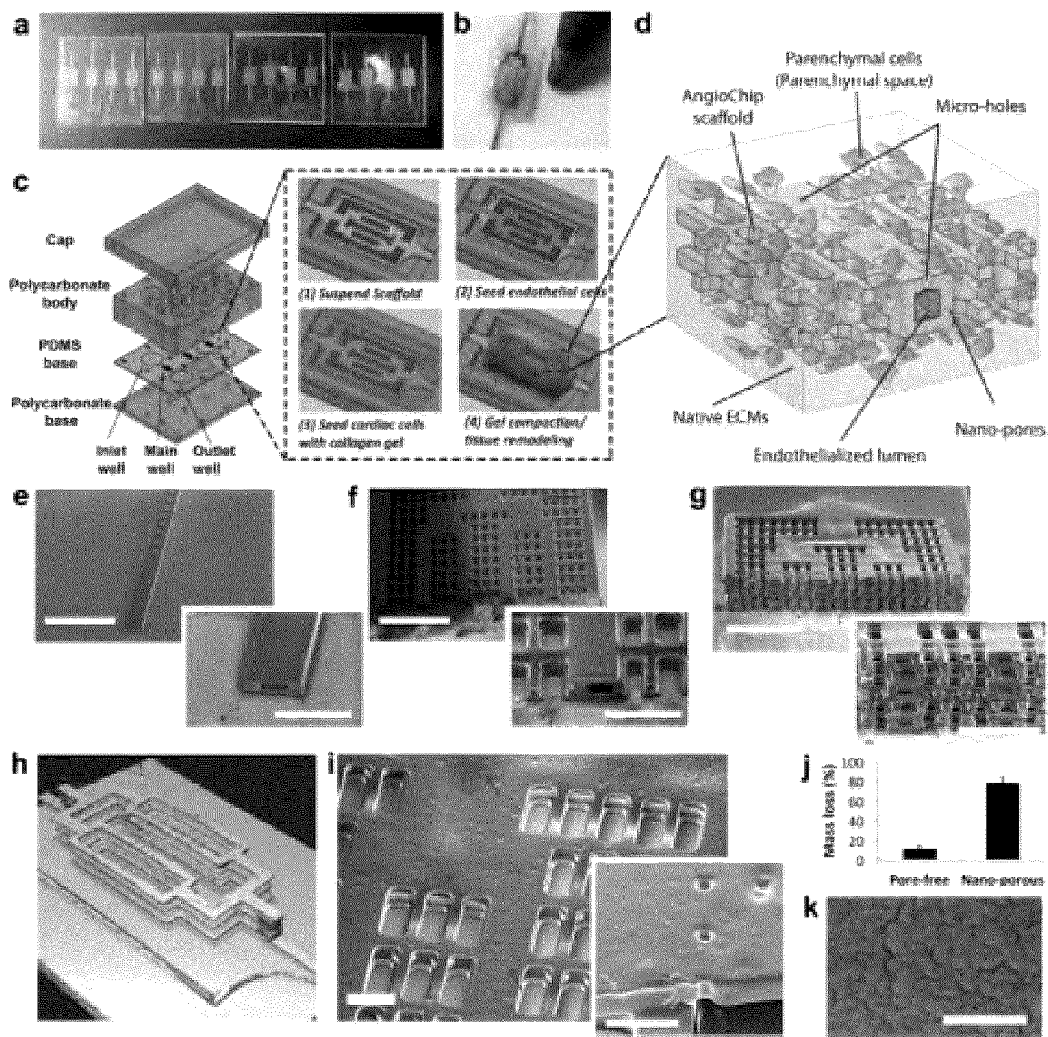
FIG. 56 exemplary AngioChip scaffold fabrication and visualization. (a) Image of multiple AngioChip scaffolds patterned in parallel on glass slides. (b) Image of an AngioChip hepatic tissue, perfused with a color dye, besides a tip of a ballpoint pen for scale. (c) Schematic of the assembly of the bioreactor and the assembly of vascularized tissue. (d) Schematic of a part of an AngioChip tissue. (e-g), SEM of (e) a 1-D tube (scale bar: 1.5 mm and 500 μm), (e) a 2-D AngioChip scaffold (scale bar: 1 mm and 300 μm) and (g) a 3-D AngioChip scaffold (scale bar: 1 mm and 500 μm) created using the 3-D stamping technique. (h), MicroCT image of the internal 3-D network of a 3-D AngioChip scaffold perfused with barium sulphate solution. (i), SEM of an AngioChip scaffold with 10 μm micro-holes on the channel walls. Scale bar: 200 μm. (inset) SEM of the cross-section of a 10 μm micro-hole. Red arrows point to the micro-holes. Scale bar: 50 μm. (j), Mass loss in 1 day from porogen leaching for pore-free and nano-porous AngioChip scaffolds (average±s.d., n=3). Pore-free and nano-porous corresponds to scaffolds fabricated without or with the use of porogen, respectively. (k), SEM of the surface of AngioChip scaffold after porogen leaching. Scale bar: 500 nm.

Interconnected internal network branched in the x-y as well as y-z planes and was perfusable through a single inlet and outlet (FIG. 56h, 51f). The smallest micro-channel in the network was 100 μm by 50 μm, with wall thickness of 25-50 μm. To improve the exchange of biomolecules and cell migration across the channel wall, 10 μm micro-holes were patterned in the upper channel walls (FIG. 56i, FIG. 51e). To further enhance oxygen and nutrient exchange, nano-pores were incorporated into the bulk POMaC polymer material by embedding and subsequently leaching out a porogen, confirmed by mass reduction (FIG. 56j) and resulting in wrinkled nano-pores, as described (FIG. 56k).

For perfusion culture, the AngioChip scaffolds were installed in the main well between the inlet and outlet well of a customized bioreactor (FIG. 56c). Culture medium or endothelial cell (EC) suspension was perfused through the internal network driven by the liquid pressure head differences between the inlet and outlet well (FIG. 56c, FIG. 52, FIG. 62). This design removed the need for bulky external pumps; hence preserving an open configuration allowing access to both the tissue parenchymal space and the internal vasculature using simple tools (e.g. micropipettes), and enabling facile tissue removal (FIG. 56b). ECs were cultured within the internal network while the parenchymal cells were cultured within the lattice matrix with native extracellular matrices (ECMs) allowing tissue remodelling (FIG. 56d).

Figure 57:
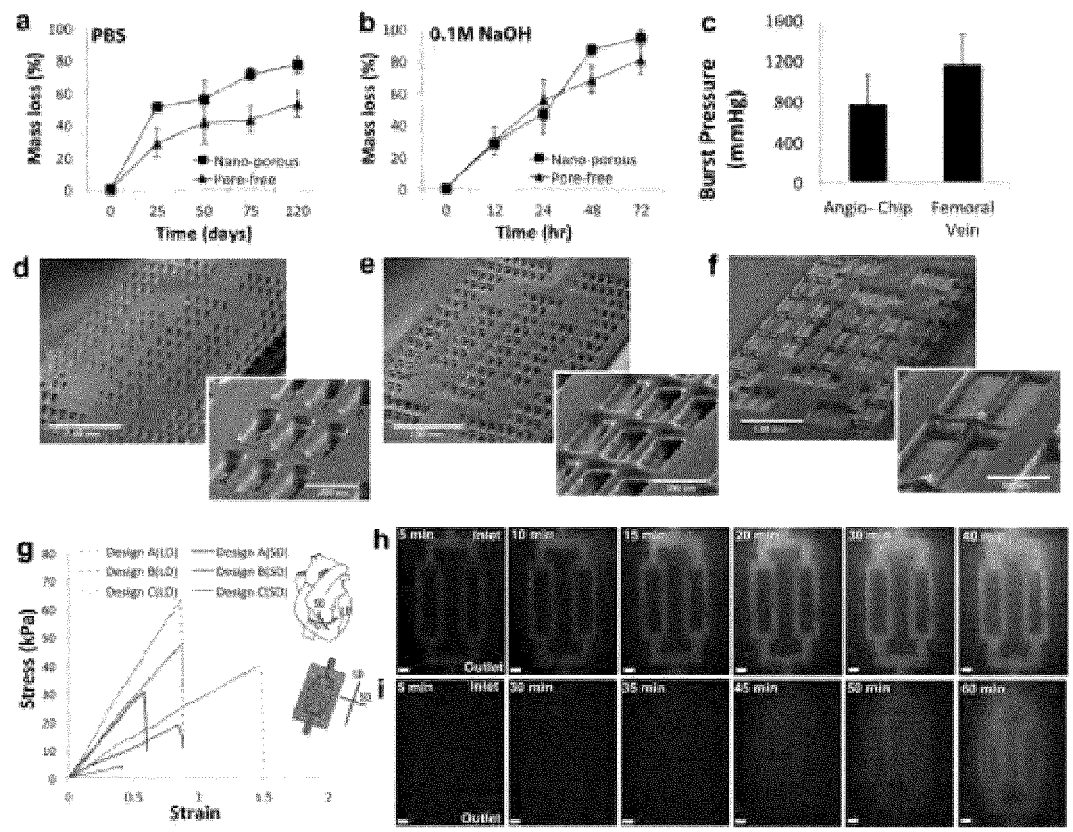
FIG. 57 Physical characterization of the AngioChip scaffolds. (a-b), Mass loss of AngioChip scaffolds with or without nano-pores in (a) PBS and (b) 0.1M NaOH solution (average±s.d., n=3). (c), Burst pressure of the AngioChip scaffolds (average±s.d., n=4) and rat femoral veins (average±s.d., n=6). (d-f), SEM of the AngioChip scaffolds with lattice matrix of increasing macro-porosity: (d) design A (scale bar: 1 mm and 200 μm), (e) design B (scale bar: 1 mm and 200 μm), and (f) design C (scale bar: 1 mm and 300 μm). (g), Representative uniaxial tensile stress-strain plots of the AngioChip scaffolds with the three different lattice matrix designs. Long-edge direction (LD) and short-edge direction (SD) correspond to the circumferential and longitudinal axes of the heart, respectively. (h), Time-lapse fluorescent images of 332 Da FITC diffusing from the built-in network of an AngioChip scaffold with 10 μm through-holes to the surrounding lattice matrix. Scale bar: 300 μm. Final Images were stitched from multiple images. (i), Time-lapse images of carboxyfluorescein diacetate (CFDA, 557 Da) diffusing from the built-in internal network to the surrounding cardiac tissue where it is cleaved by the viable cells. Scale bar: 300 μm.

The AngioChip scaffolds degraded gradually in phosphate buffered saline (PBS) over months and to completion in 4 days under alkaline conditions (0.1M NaOH) (FIG. 57a, b). The AngioChip burst pressure was comparable to that of the rat femoral vein (FIG. 57c) and nearly 7 fold higher than the normal systolic blood pressure in a rat (130 mmHg) or a human (120 mmHg), indicating the network will be sufficient to withstand blood perfusion in the peripheral circulation.

The scaffold lattice, intended to support parenchymal cells, was composed of multiple layers of meshes connected by vertical posts (50 μm diameter). This unique feature cannot be achieved with other fabrication methods (e.g. laser microablation) and provides 100% interconnectivity within the lattice, facilitating cell seeding in thick constructs and allowing parenchymal cells to form interconnected tissues in both the x-y and y-z plane. The geometry and density of the lattice were varied in three different designs to fine-tune the scaffold mechanical properties to resemble the anisotropic stiffness of the adult rat ventricular myocardium as in design B (FIG. 57d-f, FIG. 64, FIG. 65, FIG. 62). Anisotropy was enabled by the rectangular shape of the mesh, with the spatial density of the struts higher in the long-edge direction (LD) than the short-edge direction (SD) (FIG. 57g). Both the effective stiffness (E) and the ultimate tensile strength (UTS) increased with increasing lattice density. Further design iterations can yield scaffolds with mechanical properties tailored for specific applications (e.g. human myocardium or human liver).

The limited permeability of synthetic polymers limits the success of other biodegradable microfluidic scaffolds. It was found that the cell-free AngioChip scaffold network with 10 μm micro-holes was two times more permeable for small molecules (332 Da FITC, permeability of $(4.4\pm0.1)\times10^6$ cm $s^{-1}$ n=3, FIG. 57h) and four times more permeable for large molecules (70 kDa TRITC-dextran, permeability of $(3.7\pm1.5)\times10^6$ cm s n=3) than the one without micro-holes (permeability of $(2.0\pm0.2)\times10^6$ cm s and permeability of $(0.9\pm0.03)\times10^6$ cm $s^{-1}$, respectively, n=3). In both cases, the permeability of the scaffold network was higher than the permeability of mammalian venules in vivo $((0.15\pm0.05)\times 10^6$ cm $s^{-1})$ for 70 kDa FITC-Dextran. High permeability of the cell-free network allowed the EC coating to be the dominating factor in determining the final permeability of the microfluidic vessels, similar to how the ECs govern the permeability of blood vessels in vivo. To verify the distribution and the metabolic conversion of diffused biomolecules in the parenchymal space, the live cell tracker dye, carboxyfluorescein diacetate (CFDA, 557 Da), was perfused through the scaffold network surrounded by cardiac cells, staining the live cells in the parenchyma (FIG. 57i), consistent with metabolic conversion and molecular dispersion within a dense tissue.

Figure 58:
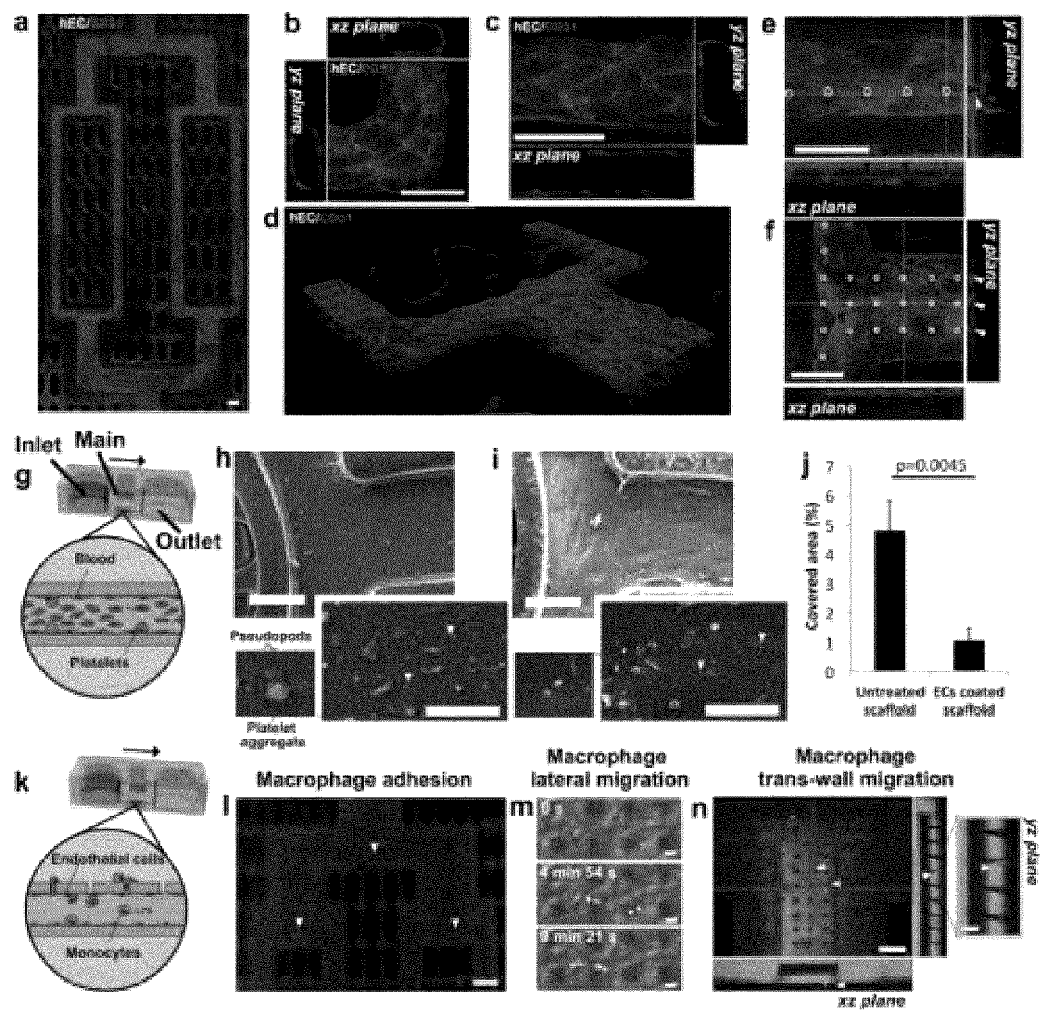
FIG. 58 Endothelialization of an exemplary AngioChip network. (a-f), Immunostaining (CD31) of the internal vasculature of an Angiochip scaffold with (a) a view of the entire network (scale bar: 100 μm. Image was stitched from multiple images), (b) a view of a corner (scale bar: 100 μm), and (c) a straight segment (scale bar: 100 μm), and (d) a branch. Immunostaining (CD31) of the vasculature with 10 μm micro-holes in (e) a straight segment (scale bar: 100 μm), and (f) a branch (scale bar: 100 μm). White circles indicate the location of the micro-holes. White arrows indicate the locations of the micro-holes from the cross-sectional view. g, Schematics of the human whole blood perfusion through the endothelialized AngioChip network. The AngioChip scaffold is located in the main well.

Upon endothelialization with human umbilical vein ECs (HUVECs), CD31 immuno-staining revealed a confluent endothelium on the luminal surface of the built-in network (day 2, FIG. 58a-d) with VE-cadherin expressed at the cell-cell junctions (FIG. 66). The ECs physically covered the micro-holes on the vessel wall (FIG. 58e, f; FIG. 66), conformaly and confluently coating the vessel walls even at the branch points of the 3-D network. To evaluate blood compatibility, human whole blood was perfused through the AngioChip network with or without EC coating at 15 dynes/cm² (~5 µL/min; Re, 0.023) (FIG. 58g). The AngioChip network was designed so that the Ecs in the first and second order branches experienced the same shear stress. Without an EC coating, significantly more platelets bound to the network surface (FIG. 58j FIG. 67) and became activated, as indicated by their extended pseudopodal morphology (FIG. 58h, i). Attached platelets exhibited a trend to spread according to the blood flow pattern and accumulated more at the stagnation regions of branches and turns (FIG. 38h; FIG. 67). Perfused Raw264.7 macrophages exhibited some accumulation and adhesion at the branch points (FIG. 58k, l), migration along the endothelialized surface (FIG. 58m) and trans-migration through the micro-holes on the vessel walls, into the parenchymal space (FIG. 58n). This extravasation between the built-in vasculature and the parenchymal space is a distinctive feature of the AngioChip scaffold and was observed on day 1 independent of scaffold degradation.

To create 3D vascularized hepatic tissue, primary rat hepatocytes mixed with 10% rat primary fibroblasts (to facilitate ECM remodelling and gel compaction) were seeded into the parenchymal space of an endothelialized AngioChip scaffold, resulting in the aggregation of viable cells around the network (FIG. 59a-d). Histology cross-sections illustrated hepatocytes (albumin stained) distributed throughout the lattice and around the vessel network, while ECs (CD31 stained) coated the inner lumen of the network (FIG. 59e-g). Secretion of urea in the outlet wells was maintained in the endothelialized AngioChip tissues but declined overtime without endothelialization FIG. 58h, i), indicated sustained paracrine signalling from the ECs maintained the health of the hepatocytes as described. The higher concentration of urea in the outlet well compared to the main well may suggest the polarization of hepatocytes to direct the secretion towards the built-in vasculature. Hepatic tissues were challenged with terfenadine, an antihistamine withdrawn from the market due to cardio-toxicity (FIG. 59h). Terfenadine is generally metabolized in the liver, to non-cardio-toxic fexofenadine, by the enzyme cytochrome P450 CYP3A4 isoform. Liquid chromatography-mass spectrometry (LC-MS) revealed the presence of fexofenadine in the outlet well, indicating that the perfused drug was delivered to the hepatic tissue from the built-in vasculature, metabolized, and then released back into the vasculature (FIG. 59j).

Cardiac tissues were created from either neonatal rat or human embryonic stem cell (hESC) derived cardiomyocytes that compacted around the vascular network forming a condensed tissue within 5 days (FIG. 60a, b). Synchronous macroscopic contractions were observed as early as day 4 and the electrical excitability parameters of both human and rat tissues fell within the standard range (FIG. 60c, d). Contracting tissues compressed the scaffold at each beat and the amplitude of contraction increased over time, indicating increasing contraction-forces as the tissue matured (FIG. 60e). The built-in mechanically stable vasculature allowed the cardiac tissue to spontaneously contract while being perfused (FIG. 60j). The contractile protein sarcomeric-α-actinin and the structural protein F-actin were visible in the elongated cells (FIG. 60f-i). Histology cross-sections at day 7 showed ECs coated the vessel lumen, while cardiomyocytes distributed throughout the lattice and densely packed around the vessels (FIG. 60k-m) even in 1 mm-thick multilayer AngioChip scaffolds (FIG. 60n). Human cardiac tissue (31±6% cardiomyocytes, n=9, FIG. 68) showed propagation of $Ca^{2+}$ waves across the entire tissue (3.5±2.6 cm $s^{-1}$, n=5), without conduction block (FIG. 60o). Conduction velocity can be further improved by enriching the cardiomyocyte population prior to tissue assembly and applying electromechanical stimulation. Epinephrine (10 µM) and digoxin (10 µM) were perfused through the built-in vasculature to stimulate the cardiac tissues. Within 30 min, the tissues showed the expected positive chronotropic response to epinephrine (FIG. 60p) and negative chronotropic response to digoxin (FIG. 60q). To evaluate the importance of flow, the rat cardiac tissues were cultured with or without medium perfusion. Viability was higher within the perfused tissue compared to the non-perfused tissue which developed a necrotic core at day 7 (FIG. 60r). The most cell death (i.e. lactate dehydrogenase release) occurred within the first 3 days, where medium perfusion helped mitigate cell death (FIG. 60s) on day 2 and 3.

AngioChip scaffolds enabled direct anastomoses of rat cardiac tissues to the femoral vessels on the hindlimbs of adult Lewis rats (FIG. 61). Similar citric acid based polymers have been shown to be antithrombotic in vascular grafts and to support EC growth in vivo. For this proof-of-concept study a worst-case scenario was examined: the animals were only heparinized during surgery and ECs were not used. The inlet and outlet (inner dimension of 100 µm by 200 µm and outer dimension of 200 µm by 300 µm) of AngioChip tissues were connected in two configurations: artery-to-artery graft (FIG. 61a) or artery-to-vein graft (FIG. 61b). In both configurations, blood perfusion through the built-in network was established immediately after the surgery. Blood pulsation was also observed, more noticeably in the artery-to-artery configuration. After 1 week in vivo, no histological signs of rejection were observed, with cells densely wrapping the AngioChips (FIG. 61c-n; FIG. 69-73). Erythrocytes were only observed in the networks of tissues implanted with direct anastomoses (FIG. 61i, j, o). Native angiogenesis also took place as seen from the presence of blood vessels around the implants (FIG. 61f, l). The presence of cardiomyocytes was confirmed with troponin T immunostaining, showing elongated cardiomyocytes intertwining within the lattice of the AngioChips (FIG. 61h, n). The presence of smooth muscle actin (SMA) positive cells was merely 2% in the isolated neonatal rat heart cells; the significant SMA staining (FIG. 61g, m) suggested the penetration of mural cells or myofibroblasts into the implanted tissues consistent with the healing response. The widespread cell infiltration, important to host remodelling, is credited to the open porous structure of the AngioChip parenchymal-space. Implants with direct anastomosis showed significantly higher cell infiltration than the controls, suggesting a greater extent of tissue remodelling was induced (FIG. 61p).

Discussion

In AngioChip scaffold design, we effectively decoupled the material choice for the engineered vessel network from the material choice for the parenchymal-space, allowing us to control the initial architecture of the vasculature and establish immediate perfusion in vitro and in vivo while sustaining the physiological remodelling of parenchymal cells. This micro-engineering approach provided no delay for tissue vascularization, as AngioChip scaffolds had a built-in perfusable vessel network that was fully endothelialized within one day, prior to the assembly of parenchymal cells. The new 3-D stamping technique allowed us to handle polymer sheets as thin as 25 µm with 10 µm holes to create a vessel wall that is merely 2-3 cells thick, thus sustaining paracrine signalling between the ECs and the parenchymal space, that usually decays significantly within a very short distance (~10 cells). The thin channel walls in combination with the nano-pores and micro-holes were the key features that allowed the effective molecular exchange, previously only achievable with hydrogel systems. This design enabled cell extravasation in a vascularized 3-D tissue model, and physiologically relevant mode for delivery of test drugs by convection-diffusion. To further fine-tune the vessel permeability to match the unique environment in different organs, organ specific ECs should be used.

The AngioChip platform enables facile integration of different tissues (e.g., hepatic and cardiac) on a single device by linking multiple AngioChips in series to recapitulate organ-level interactions (FIG. 74). Conventional microfluidics requires bulky external setups that make integration difficult. Closed configuration of conventional chips is incompatible with the current practices in biological laboratories and pharmaceutical industry, which rely heavily on open well for liquid dispensing with micro-pipetting. Our platform, resembling a standard multi-well plate, maintains an open configuration so that both the parenchymal space and the internal vasculature can be easily accessed with simple pipetting and allows different media to be used in each compartment for each type of tissues, thus obviating the need to optimize the co-culture conditions.

As a macro-scale tissue replacement, the AngioChip scaffold manufacturing method is scalable and can be automated for moving towards larger organ fabrication. This is the first engineered vessel network that has shown adequate mechanical stability for surgical anastomosis and improved vessel permeability at the same time. It also enables fine-tuning of the tissues stiffness using rectangular (for anisotropic) or square (for isotropic) lattice in the parenchymal-space, difficult to achieve with hydrogels. The AngioChip scaffolds can also be chemically modified by covalently immobilizing heparin with existing methods to reduce thrombogenicity. Appropriate scaffold degradation rate is critical to host remodelling after mural cells are effectively recruited. Therefore, long-term degradation of the AngioChip in vivo should be examined in the future and fine-tuned for a specific application, by adjusting the citric acid content on the polymer-chain to enable native mural cells and ECM to gradually take over the role of the synthetic polymer vessel wall.

In summary, the AngioChip was used to generate both in vitro cardiac and hepatic tissue models with defined vasculature and in vivo implants with direct surgical anastomoses. Uniquely, this platform could enable direct and rapid translation of in vitro testing results to in vivo validation and development of effective regenerative strategies.

Methods

POMaC Synthesis.

To prepare poly(octamethylene maleate (anhydride) citrate) (POMaC) prepolymer, 1,8-octandiol, citric acid, and maleic anhydride were mixed at 5:1:4 molar ratio and melted at 160° C. under nitrogen purge. After mixing, the temperature was dropped to 140° C. and the mixture was stirred for 2-3 hr. The resultant pre-polymer solution was then dissolved in 1,6 dioxane and purified via drop-wise precipitation in deionized distill water produced from a Direct-Q 5 Water Purification System (Millipore, Billerica, Mass.). Precipitated polymer was collected and lyophilized for 2 days. Prior to photo-crosslinking, POMaC prepolymer was mixed with 5% (w/w) UV initiator (Irgacure 2959, Sigma). To make nano-porous scaffold, POMaC polymer was also mixed with a porogen poly(ethylene glycol) dimethyl ether (PEGDM, Mw~500, Sigma) at 60% (w/w) (FIG. 51a). Pore-free scaffolds were made without adding PEGDM.

Nuclear Magnetic Resonance (NMR) Spectroscopy and Fourier Transform Infrared Spectroscopy (FT IR).

1D 1H CPMGT2 spectrum was acquired at 25° C. on an Agilent DD2 spectrometer operating at 699.806 MHz for 1H (Agilent, Walnut Creek, Calif.). The spectrometer was equipped with a 5 mm HFCN Cold Probe. The spectrum was acquired over a 11160.7 Hz spectral window with 100446 points, a 10 s recycle delay, 2 steady state scans, and 16 transients using a 200 ms CPMGT2 filter. NMR processing was carried out using MNova software (v. 9.0.0, Santiago de Compostela, Spain). Briefly, the spectrum was Fourier transformed, phased, and baseline corrected prior to analysis. Transmission spectra were obtained using an ATR top-plate accessory coupled to a Spectrum One FTIR spectrometer with a fast recovery deuterated triglycine sulfate detector (PerkinElmer, Inc., Waltham, Mass.). The spectra were recorded in the region between 4000 and 650 $cm^{-1}$.

AngioChip Fabrication.

Each layer of the AngioChip scaffold was first generated in AutoCAD and translated to individual SU-8 masters via standard soft lithography techniques as described previously. Silicone elastomer (poly(dimethylsiloxane), PDMS) was moulded against the SU-8 masters and cured at room temperature for 2 days (FIG. 51b). Patterned PDMS moulds for the base layer and upper layers of the 3-D scaffold were capped to glass slides and flat PDMS sheets, respectively. The POMaC solution was then injected into the patterned network through an inlet and outlet and left overnight at room temperature. Injection was achieved by applying a drop of POMaC solution on top of the inlet holes to apply a gentle positive pressure. Overnight, the POMaC solution filled the entire PDMS moulding including the vertical column extending out from the main mesh network. The gentle positive pressure at the inlet pushed out any trapped air inside the mould since the PDMS was porous and allowed air to escape. Next, injected POMaC solution was cross-linked under UV light at an intensity of 10 $mJ/cm^2$ s for 4 min, for the polymer mixed with the porogen, 60% (w/w) PEGDM/POMaC solution, or 10 min if no PEGDM was added. Afterwards, the PDMS moulds were uncapped and the patterned polymer structures were exposed. The patterned POMaC sheets for the first layer were attached onto the glass slides while the patterned POMaC sheets for the following layers were attached onto the PDMS moulds. The exposed POMaC sheets on the PDMS moulds were then aligned to and pressed against the patterned POMaC sheets on the glass slides with a customized UV mask aligner (Q2001, Quintel Co., CA). To bond the layers together, the samples were then exposure to UV at an intensity of 10 $mJ/cm^2$ s for 4 min or 10 min if no PEGDM was added. After the UV exposure, the PDMS moulds were then released, leaving the two patterned POMaC sheets bonded together and attached to the glass slides. This process was repeated to bond additional patterned POMaC sheets to the established base structure. Lastly, fabricated scaffolds were immersed in PBS to release them from the glass slides and incubated overnight at room temperature to leach out the PEGDM porogen. Multiple scaffolds were patterned in parallel on a single glass slide in a single process (FIG. 56a).

Scanning Electron Microscopy.

To illustrate the structure of the AngioChip, AngioChip scaffolds were imaged with Hitachi SEM S-3400 prior to porogen leaching. Cutting the scaffold transversely revealed the cross section. To image the nano-pores of the scaffolds, after porogen leaching in PBS, the scaffolds were first dehydrated in ethanol and then prepared with supercritical point drying hence preventing the collapsing of the nano-pores structure prior to imaging. MicroCT. To visualize the internal architecture of the AngioChip scaffolds, μCT40 (Scanco medical) was used to scan the scaffolds that were anchored onto a polystyrene slide. The program μCT Ray V40 was used to apply a threshold to the acquired images to eliminate background and reconstruct the scaffold in 3-D. To visualize the internal built-in network of the scaffold, the network was filled with barium sulphate suspension (105% w/v, Polibar plus, Therapex) mixed with 2% (w/v) gelatin in PBS (porcine skin, type A, Sigma) at 1:1 (v/v) ratio. The injected solution was allowed to gel at room temperature and imaged with μCT, where a threshold was applied to the acquired image to reveal the built-in network against the other structure of the scaffold.

Scaffold Degradation.

To prepare the nano-porous scaffold samples, a scaffold (3 mm×10 mm×200 μm) with 60% porogen content was first UV cross-linked for 4 min at an intensity of 10 mJ/cm$^2$ s, and then washed in distilled water to leach out the porogen. To prepare the pore-free scaffold samples, scaffolds (3 mm×10 mm×200 μm) with 0% porogen content were UV cross-linked for 10 min at an intensity of 10 mJ/cm$^2$ s. The degradation rates of the scaffolds were determined by tracking the scaffold mass loss over time in PBS (pH 7.4, 37° C.) or in 0.1 M NaOH. After each incubation period, the samples were first thoroughly washed with distilled water and then dried. The mass loss was calculated by comparing the initial mass with the mass measured at the specific time point.

Burst Pressure.

To determine the burst pressure of the AngioChip scaffolds, the inlet of the scaffold was connected to a nitrogen tank with a pressure gauge using a Tygon tubing, while the outlet of the scaffold was sealed with epoxy glue. Pressure was increased gradually until a leak was observed from the scaffold network and the peak pressure was recorded as the burst pressure. If a leak from the junctions at the inlet or the outlet was observed first, the recording was discarded.

Mechanical Testing.

The mechanical properties of the AngioChip scaffold were measured in PBS with a Myograph (Kent Scientific) in the circumferential (along the long edge) and longitude direction (along the short edge) of the AngioChip scaffolds. The slope of the uniaxial tensile stress-strain curve from strain of 0 to 0.1 was used to calculate the effective stiffness of the entire AngioChip scaffold (FIG. 64, FIG. 65). Strain-to-failure values were determined from the strain at the breaking point along the curves. The mechanical stiffness of the adult rat myocardium was measured from the adult hearts of Lewis rats, sacrificed according to a protocol approved by the University of Toronto Animal Care Committee. The adult rat myocardium was sliced into 7 mm long strips with width of 2-4 mm and thickness of 2-4 mm along the circumferential direction or longitudinal direction of the heart. The uniaxial mechanical stiffness of the myocardium was determined from the slope of the tensile stress-strain curve from strain of 0 to 0.1. Anisotropic ratio was determined by dividing the effective stiffness in the circumferential direction with the effective stiffness in the longitudinal direction. The three different scaffold designs had different lattice structures but the same built-in network with a wall thickness of 50 μm, an inner luminal dimension of 50 μm by 200 μm for the inlet, outlet and first order branch, and an inner luminal dimension of 50 μm by 100 μm for the second order branch. The scaffold lattice was made of 50 μm struts. In design A, the struts were spaced 250 μm apart in the long-edge direction, 100 μm apart in the short-edge direction, and no space apart in the z-axis. In design B, the struts were spaced 250 μm apart in the long-edge direction, 100 μm apart in the short-edge direction, and 50 μm apart in the z-axis. In design C, the struts were spaced 550 μm apart in the long-edge direction, 175 μm apart in the short-edge direction, and 50 μm apart in the z-axis.

Permeability.

The permeability of large and small molecules from the built-in network to the surrounding aqueous solution was measured with fluorescent dyes: TRITC-Dextran (~70 kDa, Sigma) and FITC (~400 Da, Sigma), respectively. TRITC-Dextran and FITC solutions were perfused at 0.7 μL/min through the network with inlet concentrations of 10 or 100 μM for 20 hr. After 20 hr, the solution in the middle wells was collected and the concentrations of fluorescent molecules were correlated to a standard curve determined with a fluorescence plate-reader. The channel permeability of the entire AngioChip scaffold to small and large molecules was determined from the net rate of diffusion (total accumulated fluorescent molecules in the middle chamber/time) and the luminal surface area of the network, using Fick's Law with the assumption that the average concentration of fluorescent molecules inside the network is the same to that at the inlet.

Bioreactor Design.

A bioreactor was customized to allow fluid perfusion through the inlet and outlet of the AngioChip scaffolds as well as to facilitate tissue assembly. The bioreactor was composed of four components: a cap, a polycarbonate body, a PDMS base, and a polycarbonate base (FIG. 56c). The bioreactor was designed to accommodate three scaffolds in separate chambers at a time. The polycarbonate body (2.5 cm thick) included 9 wells positioned in three rows: the top row encompassed the inlet wells, the middle row encompassed the main wells, where the AngioChip scaffolds were positioned, and the bottom row encompassed the outlet wells. The PDMS slab (1 mm thick) included three trenches (700 μm deep) where the AngioChip scaffolds were situated. At the bottom of the trenches, micro-posts (200 μm tall) were patterned to lift the AngioChip scaffolds up from the base so that cells/gel can penetrate underneath the scaffolds and encapsulate the entire scaffolds. The trench also included an open inlet and outlet channel where the inlet and outlet of the AngioChip scaffolds could precisely fit. After the AngioChip scaffolds were positioned, the PDMS base was then sandwiched between the polycarbonate base and the polycarbonate body so that the open inlet and outlet channels on the PDMS base were capped with the inlet and outlet of the AngioChip fitted within. The three components were secured with stainless steel screws. Solution and/or cell suspensions were perfused from the inlet wells through the built-in networks of the AngioChip scaffolds to the outlet wells driven by a pressure-head difference between the inlet and outlet wells (FIG. 63). The bioreactor was disassembled in sterile condition to remove the AngioChip tissues for implantation or analysis.

Endothelial Cell Culture.

Human umbilical vein endothelial cells (HUVECs) were purchased from Lonza and cultured with endothelial growth medium (EGM, Lonza) according to the manufacturer's instructions. Passage 3 HUVECs were used for all experiments.

Endothelialization and Tissue Assembly.

To enhance cell attachment onto the AngioChip scaffolds as well as within the internal network, the scaffolds were coated with 0.2% w/v gelatin (from porcine skin, Type A, Sigma) in phosphate buffered saline (PBS) for 2 hr prior to assembly. To prevent cell attachment onto the PDMS base, the PDMS base was coated with 5% w/v Pluronic F-127 (Sigma) in PBS for 2 hr prior to assembly. After the AngioChip scaffolds were placed in the bioreactor, endothelial cells were first seeded into the built-in network of scaffolds by perfusing 20 μL of concentrated endothelial cell suspension (25 million cells/mL) in endothelial cell media into the network for 1 min. The flow was then stopped to allow the cells to attach under static conditions for 2 hr. Unattached cells were flushed by adding 1 mL of endothelial cell media to the inlet wells thus initiating perfusion through AngioChip scaffolds under a flow rate less than 0.7 μL/min (0.62 dynes/cm$^2$, Re, 0.01) to apply minimal stress to the cells while feeding the cells with sufficient media. Within the network, the endothelial cells were allowed to proliferate and form a confluent network overnight. On day 1, to create a hepatic tissue, primary adult rat hepatocytes were seeded at 100 million cells/mL with 15 μL Matrigel (BD Biosciences) onto the AngioChip scaffolds. To create a cardiac tissue, cardiomyocytes isolated from either neonatal rats or derived from human embryonic stem cells (hESCs) were seeded with 15 μL (single layer network) or 40 μL (triple layer network) collagen/Matrigel mixture at 100 million cells/mL onto each AngioChip scaffold. The composition of the collagen/Matrigel mixture was as follows: 2.5 mg ml$^{-1}$ of rat tail collagen type I (BD Biosciences) neutralized by 1 N NaOH and 10×M199 media as described by the manufacturer, supplemented with 4.5 μg ml$^{-1}$ glucose, 1% HEPES, 10% (v/v) Matrigel (BD Biosciences), and 2 μg ml$^{-1}$ NaHCO$_3$. After 30 min gelation at 37° C., 1 mL of cardiomyocyte media or hepatocyte media were added to the middle well. After the seeding of parenchymal cells, additional 4 mL of endothelial cell media were also added to the inlet wells increasing media perfusion rate to 0.7 μL/min (0.62 dynes/cm$^2$, Re, 0.01).

Whole Blood Perfusion.

Human whole blood was collected from three donors according to the University of Toronto institutional guidelines and under an approved Research Ethics Board protocol. Whole blood was treated with 1% (v/v) heparin to prevent clotting during handling[45]. Whole blood was perfused through the endothelialized scaffold or the non-endothelialized scaffold at 15 dynes/cm$^2$ for 30 min at 37° C. The high shear stress perfusion was achieved with a modified bioreactor with extended pressure columns attached to the inlet wells (FIG. 63). The extended columns were filled with blood up to a height of 0.25 m to generate a flow rate of 5 μL/min (15 dynes/cm$^2$ Re, 0.023) within the AngioChip scaffold network. Since the blood perfusion lasted only 30 min, only ~150 μL of blood was perfused, which did not significantly change the height of the column and the flow rate over the 30 min period. After perfusion, the network was flushed with saline and fixed in 2% (v/v) glutaraldehyde in PBS for 48 hr at 4° C. Fixed scaffolds were frozen sectioned to reveal the inner luminal surface of the network and imaged with SEM. The area of platelets were quantified manually by outlining each cell cluster with Adobe Photoshop. The analysis was performed blindly.

Macrophage Adhesion and Migration.

Raw264.7 macrophages were cultured in Dulbecco's Modified Eagle Medium (DMEM, Gibco, Canada) containing 4.5 g/L glucose, with 10% (v/v) fetal bovine serum (FBS, Gibco, Canada), 1% (v/v) HEPES (100 units/mL, Gibco Canada) and penicillin-streptomycin (100 mg/mL, Gibco, Canada). Raw264.7 macrophages were used at passage 10. Prior to the experiment, the macrophages were labeled with either CellTrackerαRed CMPTX (Molecular Probes) or CellTrackerαGreen (Molecular Probes). Endothelialized scaffolds on day 2 were perfused with macrophage suspension with 10 million cells/mL for 1 hr at 37° C. at a flow rate of 0.7 μL/min (0.62 dynes/cm$^2$, Re, 0.01). Macrophage lateral migration on the endothelialized channel luminal surface was captured during the 1 hr perfusion. Macrophage adhesion images were captured at the end of the 1 hr perfusion with a fluorescent microscope. After the 1 hr perfusion, the scaffolds were incubated again at 37° C. overnight. Afterwards the scaffolds were fixed in 4% paraformaldehyde and imaged with the Olympus FV5-PSU confocal microscope to look for macrophage migration through the 10 μm holes.

Hepatocytes Isolation and Culture.

Primary rat hepatocytes were isolated using a modified two step isolation procedure from 8 week old male Sprague Dawley rats according to a protocol approved by the University Toronto Animal Care Committee. Briefly, the rat was heparinized and then anesthetised with isoflurane. Under anesthesia, the abdominal cavity was opened and the liver was isolated from the vascular system by ligating the vena cava and the descending aorta. The liver was then cannulated using PE-50 tubing and perfused. First, the liver was perfused with 250 mL of wash buffer (Hank's Balanced Salt Solution, HBSS (Gibco) containing 12.5 mM 4-(2-hydroxyethyl)-1-piperazineethanesulfonic acid (HEPES) and 0.5 mM ethylene glycol tetraacetic acid (EGTA)), then 250 mL of digestion buffer (HBSS containing 4 mM CaCl$_2$ and 0.1% collagenase type 2 (Worthington)). The liver was removed and manually disassociated in Krebs-Henseleit Buffer (Sigma-Aldrich, K3753) into a cell suspension. Insoluble debris was removed by passing the cell suspension through cotton gauze and a 100 μm filter. The hepatocytes were purified by a series of centrifugation steps starting at 300×g and decreasing to 50×g. The hepatocyte cell suspensions used were determined to be greater than 90% viable and greater than 95% pure. The hepatocytes were either used immediately or frozen for later use. The hepatocytes were cultured in a 50:50 blend of DMEM (Gibco) and MCDB-131 complete (Vec Tech Inc) media plus 10% (v/v) fetal bovine serum (FBS), 1% (v/v) Penicillin Streptomycin and 1× Insulin-Transferrin-Selenium-X (Gibco).

Neonatal Rat Cardiomyocytes Isolation and Culture.

Neonatal rat cardiomyocytes and fibroblasts were isolated by digesting neonatal rat hearts as described previously according to a protocol approved by the University of Toronto Animal Care Committee. Neonatal (1-2 day old) Sprague-Dawley rats were used for in vitro experiments while neonatal (1-2 day old) Lewis rats were used for in vivo experiments. Briefly, the neonatal rats were first euthanized. The hearts were removed and quartered. Quartered hearts were digested in 0.06% (w/v) solution of trypsin (Sigma, Canada) in Ca$^{2+}$ and Mg$^{2+}$ free buffer (HBSS (Gibco)) overnight at 4° C. Then, collagenase II (Worthington, USA 220 units/mL) in HBSS was used to further digest the quartered hearts at 37° C. in series of five 4-8 min digestions. After the collagenase digestion, cells were pre-plated for 40 mins. The non-adherent cells, enriched for cardiomycoytes, were collected and used or plated again and cultured overnight before use. Rat cardiomyocytes were cultured in Dulbecco's Modified Eagle Medium (DMEM, Gibco, Canada) containing 4.5 g/L glucose, with 10% (v/v) fetal bovine serum (FBS, Gibco, Canada), 1% HEPES (100 units/mL, Gibco Canada) and penicillin-streptomycin (100 mg/mL, Gibco, Canada).

hESCs-Derived CM Differentiation and Culture.

HES-3 NKX2-5 GFP positive cells were cultured with previously described techniques. Cells were maintained in hESC media consisting of DMEM/F12 (50/50 (v/v), Mediatech) supplemented with 20% knock-out serum replacement, 100 μM nonessential amino acids, 2 mM glutamine, 50 U/mL penicillin, 50 μg/mL streptomycin (Invitrogen), 10-4 M β-mercaptoethanol (Sigma), and 20 ng/mL hbFGF (R&D Systems) in 6-well tissue culture plates on Mitomyocin C mitotically inactivated mouse embryonic fibroblasts (MEFs). Once confluent, cells were dissociated to single cells at room temperature using Tryple E Express (Life Technologies) and transferred onto ES quality Matrigel (BD Sciences) coated plates at concentrations ranging from 0.13-0.33 million cells/cm$^2$ in conditioned medium[48]. Previously collected conditioned medium from MEFs was supplemented with h-bFGF and changed daily until induction of differentiation. Cells were washed before induction in RPMI/B27 (Life Technologies) and media replaced with RPMI/B27 supplemented with ranges of 6-12 μM CHIR 99021 (Stemgent) to induce differentiation. Exactly 24 hr after induction, media were replaced with fresh RPMI/B27. At 72 hr after induction, 1 mL of media in each well was mixed with 1 mL fresh RPMI/B27 with 5 μM Wnt inhibitor IWP-4 (Stemgent). Media was replaced on day 5, changed on day 7 to RPMI/B27 with insulin (Life Technologies) and then replaced every 3 days thereafter until dissociation. Cell monolayers were dissociated using Collagenase type II (1 mg/ml) on day 20-30, for 120 min in 37° C. and 5% $CO_2$ incubator and then further dissociated in Triple E Express in 37° C. water bath for 5 min. Cellular analysis was accomplished with FACScalibur (BD Sciences) to determine final CM concentration as determined by NKX2-5 GFP reporter.

Histology and Immunofluorescent Staining.

Immuno-fluorescent staining was performed to assess the morphology of cultivated AngioChip tissues. The tissues were first fixed in 4% (w/v) paraformaldehyde in PBS for 15 mM at room temperature. Then, the tissues were permeated in situ and blocked with 5% FBS and 0.25% Triton X100 in PBS for 1 hour. Next, the AngioChip cardiac tissues were incubated in primary antibody, sarcomeric α-actinin (Mouse, 1:200 dilution, Sigma) overnight at 4° C., followed by incubation with corresponding secondary antibodies, Alexa 488 conjugated anti-mouse IgG (1:200 dilution, Sigma) and F-actin (Phalloidin 660 conjugated, Sigma) for 1 hour. The cardiac tissues were imaged with Olympus FV5-PSU confocal microscope. The AngioChip hepatic tissues were first labeled with CFDA and then fixed as described above and stained with F-Actin (Phalloidin 660 conjugated, Sigma) for 1 hour. To visualize the vasculature, endothelialized AngioChip scaffolds were fixed in 4% PFA and blocked in 5% FBS for 1 hour. Then, the scaffolds were incubated in primary antibody, CD31 (Mouse, 1:200 dilution, Sigma), followed by incubation with secondary antibody; Alexa 647 conjugated anti-mouse IgG (1:200 dilution, Sigma). Live and dead staining was performed with carboxyfluorescein diacetate (CFDA, 1:1000 dilution, Invitrogen) and propidium iodide (PI, Invitrogen) in PBS at 37° C. for 30 min. To visualize the cross-section of the cardiac tissue with live and dead staining, the tissues were sliced in half transversely and rotated manually to show the cross-section. To visualize both endothelial cells and parenchymal cells, cultivated tissues were fixed in 10% formalin for 3 days at 4° C., paraffin embedded, and sectioned into 4 μm slices for histology at the Pathology Research Program Laboratory of Toronto University Health Network. Histology sections show the tissue cross-section in the transverse direction and were stained with Hematoxylin and Eosin (H&E), Masson's Trichrome stain, CD31, or albumin.

Urea Assay.

The AngioChip hepatic tissues were incubated with 1 mL hepatocytes media, containing 10 mM ammonium bicarbonate, in the main wells and perfused with 1 mL endothelial cell media, containing 10 mM ammonium bicarbonate, from the inlet wells. After each 24 hr incubation, the media from the main wells and the outlet wells were collected. The media were briefly centrifuged (300×g for 5 min) to remove any cells and frozen at −20° C. Urea was detected using QuantiChrom Urea assay kit (BioAssay Systems) as per manufactures instructions. The media were typically used undiluted for detection.

Liver Drug Test.

On day 3 of culture, terfenadine (10 μM, Sigma) in hepatocye culture media was placed in the inlet wells and perfused through the endothelialized hepatic tissue at 0.7 μL/min (0.62 dynes/cm$^2$, Re, 0.01) for 24 hr. After 24 hr incubation, the media in the inlet wells, middle wells, and outlet wells were collected and analyzed for the concentration of fexofenadine with Liquid Chromatography-Mass Spectrometry (LC-MS) and correlated to a standard curve. DMSO was used to dissolve the drugs initially. The final concentration of DMSO in the media was always less than 0.1%.

Functional Characterization of Engineered Cardiac Tissue.

To stimulate the AngioChip cardiac tissue and measure their electrical excitability parameters, two carbon electrodes spaced 1 cm apart were placed within each main well on the opposite sides of the tissue in parallel. The electrodes were connected to an external electric stimulator (Grass s88x) with platinum wires. Using monophasic pulses of 2 ms duration and frequency of 1 pulse per second, the excitation threshold (minimum voltage at which synchronous contractions of 75% of the tissue in the field of view can be observed) was first determined. Then the maximum capture rate (maximum beating frequency) was determined at 200% of the determined excitation threshold voltage. The amplitude of the tissue contraction was determined from the change of width in the engineered tissue between contractions. To access the progress of tissue remodeling, a brightfield image of the cardiac tissue was taken daily in the first 5 days after cell seeding. The width of the tissue across the center short edge was measured from the images using Image J.

Optical Mapping.

Activation maps were generated using a custom-made program written in IDL (Exelis, McLean Va., USA), using fluorescent imaging. Calcium dye Fluo-4 was used and was excited using a Short Arc Mercury light source (X-Cite Exacte, Lumen Dynamics, Mississauga ON, Canada), bandpass filtered at 482 nm and the emission was measured through a 488 nm long-pass filter (Semrock Corp, Rochester N.Y., USA) installed in a fluorescence macro-zoom microscope system (MVX-10, Olympus Corporation Tokyo, Japan) with optical magnification ranging between 1.6 and 2.5×. The fluorescence was recorded using a high-speed CMOS camera (Micam-L, Scimedia USA, Costa Mea Calif., USA) at 200 frames per second. The 1 cm$^2$ sensor had 100×100 pixels, giving a resolution from 40 to 60 microns per pixel.

Lactose Dehydrogenase (LDH) Assay.

The AngioChip cardiac tissues were cultured with cardiomyocyte media with or without media perfusion through the built-in network at 0.7 µL/min (0.62 dynes/cm$^2$, Re: 0.01). From the middle wells where the tissues resided, 1 mL of cardiomyocyte media were collected and replaced with new media every day for 6 days. The collected media were analyzed for lactose dehydrogenase (LDH) concentration with a LDH toxicity assay kit (Cayman Chemical) as per manufacturers instructions and correlated to a standard curve.

Cardiac Drug Test.

On day 7 of culture, the spontaneous contractions of the cardiac tissues were recorded as bright-field videos. Then, epinephrine (10 µM, Sigma) or digoxin (10 µM, Sigma) in cardiac culture media were placed in the inlet wells and perfused at 0.7 µL/min (0.62 dynes/cm$^2$, Re: 0.01) through the endothelialized cardiac tissue for 30 min. After 30 min incubation, the spontaneous contractions of the cardiac tissues were recorded again as bright-field videos. The frequency of contraction was analyzed from the recorded videos with image J. DMSO was used to dissolve the drugs. The final concentration of DMSO in the culture media was diluted to less than 0.1% (v/v).

Rat Femoral Vessel Surgery.

All procedures below were performed at the Department of Comparative Medicine Animal Facility, University of Toronto under a protocol approved by the Committee on Animal Care. AngioChip scaffolds cultured with Lewis neonatal rat cardiomyocytes on day 7 were used for the implantation experiments. AngioChip scaffolds were not endothelialized for in vivo experiments. First, adult male Lewis rats (150-250 g) from Charles River were anesthetized with 1-3% isoflurane at flow rate of 1 L/min Analgesic was administered (5 mg/kg ketoprofen, SQ) and both hindlimbs were prepared for surgery. For the surgical procedure, a dissection microscope was used to obtain an enlarged view of the hindlimb region. Skin was shaved and incisions were made on the left leg, approximately 2 cm long starting from the knee to the medial thigh. Then, subcutaneous fat tissue and the underlying neurovascular bundle were revealed. The femoral artery and vein were dissected and separated from the nerve. For artery bypass configuration, a segment of the femoral artery (approximately 1.5 cm in length) was fully exposed and ligated for the insertion of the AngioChip cardiac tissue. Two ends of artery were clamped with a microsurgical approximating clamp to stop blood flow temporary during the surgery. One 25 gauge cuff (polyimide tube) was inserted into each end of the artery and secured with 7-0 sutures. Biodegradable surgical cuff can also be used in future application. The inlet and outlet of the AngioChip cardiac tissue were then inserted into the cuffs and sealed with tissue glue (Cyanoacrylate). Clamps were then removed and blood perfusion was established. For artery-to-vein configuration, a segment (approximately 5 mm in length) of the femoral artery and femoral vein was fully exposed and ligated for the insertion of the AngioChip cardiac tissue. Two ends of artery and vein were clamped with a microsurgical approximating clamp to stop blood flow temporary during the surgery. One 25 gauge cuff (polyimide tube) was inserted into each top end of the artery and vein and secured with 7-0 sutures. The bottom ends of the artery and vein were sealed with 7-0 sutures. The inlet and outlet of the AngioChip cardiac tissue were then inserted into the cuffs and sealed with tissue glue (Cyanoacrylate). Clamps were then removed and blood perfusion was re-established. Lastly, another cardiac tissue patch was implanted to the right leg subcutaneously in a similar manner but without anastomoses to serve as a control. For post-operative pain management, rats received ketoprofen (5 mg/kg, subcutaneous injection daily) for 2 days. At 1-week time point the animals were humanely euthanized and the tissue implants were isolated for histology sectioning.

Statistical Analysis.

Significant differences between experimental groups were determined using independent two-tailed Students' t-test. In FIG. 59j, paired one-tailed Students' t-test was used because the fexofenadine concentration in outlet wells was expected to only increase and cannot be lower than inlet well control that contains no fexofenadine. In addition to Students' test, in FIG. 59i statistics was also done using three-way ANOVA in Sigma Plot. Normality test (Shapiro-Wilk) and pairwise multiple comparison procedures (Holm-Sidak method) were used. $P<0.05$ was considered significant for all statistic tests.

Example Applications

The example devices disclosed herein in the Examples may be suitable for cultivation and generation of various tissue structures. The disclosed devices may be designed to provide an in vitro platform that mimics or reproduces native tissue architecture found in vivo, to enable cells to mature and function in the way they normally would in vivo.

In various examples, the disclosed devices may be suitable for culture of various tissues, including muscle cells such as cardiomyocytes, skeletal muscle cells, smooth muscle cells as well as excitable tissues such as neurons and cells that may require rich vasculature such as hepatocytes, among others.

In various examples, the disclosed devices may be suitable for various applications, including drug-testing in vitro, for building a human-on-a-chip with several different compartments as well as for direct anastomosis and implantation into an animal or a human patient, among other applications.

> The embodiments of the present disclosure described above are intended to be examples only. The present disclosure may be embodied in other specific forms. Alterations, modifications and variations to the disclosure may be made without departing from the intended scope of the present disclosure. While the systems, devices and processes disclosed and shown herein may comprise a specific number of elements/components, the systems, devices and assemblies could be modified to include additional or fewer of such elements/components. For example, while any of the elements/components disclosed may be referenced as being singular, the embodiments disclosed herein could be modified to include a plurality of such elements/components. Selected features from one or more of the above-described embodiments may be combined to create alternative embodiments not explicitly described. All values and sub-ranges within disclosed ranges are also disclosed. The subject matter described herein intends to cover and embrace all suitable changes in technology. All references mentioned are hereby incorporated by reference in their entirety.

Example 5: Angiotube

Introduction

In this example, we propose AngioTube plate, which is a 96 well-plate embedded with a perfusable micro-tubes named Angiotube. The embedded Angiotube can be rapidly endothelialized overnight to form a blood vessel mimics. Around the Angio-tube, various cells, such as cardiomyocytes, hepatocytes, smooth muscle, and podocytes, etc., can be assembled to form a functional 3-D tissue. This simple configuration can be universally applied to incorporate a 3-D vascular interface to various types of tissues. The Angiotube has thin channel wall (25-50 um) with patterned 10 um micro-holes for the exchange of small and large biomolecules as well as allows the migration of cells, such as monocytes, across the vascular interface. Therefore, intercellular interaction across vessel wall, vessel permeability, and chemotaxis can all be studied.

Additional exterior features can also be incorporated onto the Angiotube, such as a cantilever structure that allow the measurement of passive tension and active contraction of the parenchymal tissue. This feature is important in examine the constriction and relaxation of the smooth muscle tissue as well as the active contraction of cardiac muscle tissue. This type of readout provides valuable tissue-level response to external stimuli and can be performed continuously on-line without destruction of the tissue.

Lastly, since the Angiotube is embedded within a 96-well plate connecting through multiple well, different types of tissue can be cultured around the same Angiotube within different wells. Through the same Angiotube, multiple tissue units become automatically linked together allowing user to easily probe inter-organ level interactions recapitulating integrated human physiology in vitro. For instance, many drugs get converted and processed by the liver into multiple forms before they are delivered to other vital organs. So a drug could be nontoxic in its original form during the initial screening, but become toxic in animal or human trials. Therefore, integrating a liver tissue unit with other organ units could potentially reveal inter-organ level toxicity in the early screening stage.

Preliminary Results

The AngioTube multi-well perfusable system comprising an array of chambers, wherein each chamber contains one or more wells for seeding and growing 3D tissue strands around a permeable/perfusable tube positioned within the wells (FIG. 75). Each chamber may also contain at least two opposing elements for anchoring the tissue stand and whose movements may be discerned and measured during contraction/relaxation cycles of the 3D tissue strands (FIG. 75). The chambers may also be configured with electrodes for stimulating cardiac tissues.

Angiotube can be perfused from the inlet well to the outlet well by tilting the plate in an angle and hence generate a pressure head differences between the inlet and outlet well. FIG. 76 demonstrates the results of passive perfusion of an AngioTube multi-well perfusable bioreactor as measured by flow rate (μl/min) or shear stress (dynes/cm$^2$) as a function of the tilt height of the bioreactor. PBS was perfused the angiotube.

To shows a time course of the development of a 3D tissue strand in a single chamber of an AngioTube bioreactor, rat cardiomyocytes was casted over the AngioTube in collagen/Matrigel matrix (FIG. 77). The first image in the series shows the point at which the cells are first seeded into the bioreactor chamber. As time progresses, the cells grow and begin to cluster towards the two flexible cantilever elements in the chamber, while maintaining a tissue connection between the flexible elements. The particular embodiment shown in the photographs is an embodiment only and other configurations are contemplated by the invention. For example, the flexible cantilever elements may be formed having a different shape and/or length (e.g., curved, rounded, nonlinear, flat, round, bent, thickness) and attached to the permeable tubular element at a different angle or orientation such that measurement and/or detection of cantilever displacement can be detected. The chamber may also contain electrodes for stimulating cardiac cells. The bar at the right demonstrates the degree of cantilever displacement that can be observed during the formation of the 3D tissue strand.

Light microscopy image of a tissue strand shows the tissue wrapping around the cantilevel (FIG. 78, left image). To show the morphology of the 3-D tissue strand formed around the AngioTube the tissue was stained with sarcomere-α-actinin and F-actin (FIG. 78) to show the distribution and morphology and orientation of cells of the tissue strand.

To demonstrate the cantilever can be used to detect the active contraction of the cardiac tissue strand, we measured the cantilever displacement (as measured by pixels) after 5 days and after 10 days of growth post-seeding (FIG. 79). We saw an increase in the degree of bending of the cantilever. This trend indicates the maturation of the tissue strand over time.

Conclusion

The Angiotube plate is a versatile platform that utilizes a universal configuration to create various types of tissues. The configuration is simple, but yet it could recapitulate complex cellular interaction across the built-in vascular interface in a 3-D environment. Mostly importantly, the setup is naturally adapted for scaling to a multi-organ configuration. The Angiotube plate in a conventional 96 well-plate format is also readily adapted for the existing industrial infrastructure in high-throughput drug toxicity screening, such as robotic liquid dispenser and multi-well plate reader.

Example 6: BIOWIRE (Human Stem Cell-Derived Cardiac Model of Chronic Drug Exposure In Vitro)

Animal model systems have been instrumental in providing important insights into the molecular basis of disease. While such information has been successfully applied to the study of human disease, this translation would be significantly strengthened by the availability of models based on human cells. This would be particularly important for cardiovascular disease, as the physiology of the human cardiomyocyte differs significantly from rodents. Here, we have utilized a 3-dimensional model of human myocardium through tissue engineering and human embryonic stem cell-derived cardiomyocytes (hESC-CMs) to question whether hESC-CMs can respond to chronic treatment with isoproterenol, endothelin-1 or angiotensin II and undergo changes compatible with chronic drug exposure. We show that hESC-CM treated with either isoproterenol, endothelin-1 or angiotensin II display disrupted myofibril alignment, increased cell size, and significantly reduced force of contraction. Isoproterenol-treated hESC-CM tissues display an induction of brain natriuretic peptide (BNP) and atrial natriuretic factor (ANF) gene expression, the current gold standard biomarker for human heart failure. BNP can also be found in the conditioned media of cells treated with both Isoproterenol and Endothelin-1. This demonstrates that hESC-CM can respond to appropriate environmental stress signals and undergo changes compatible with in vivo chronic drug exposure.

Introduction

Animal models are commonly used for modeling heart diseases and testing new drugs' safety and efficacy. Mice are the most used animal model because of the relative availability and the possibility to precisely manipulate the genome [1]. However, there are significant differences between mouse and human cardiac physiology. For instance, the mouse heart rate is 10 times faster than the human. Contractile proteins, such as α- and β-myosin heavy chain, also have differential expression in mice and humans. In addition, repolarization of mouse cardiomyocytes is driven primarily by $I_{to}$, $I_{K,slow1}$, $I_{K,slow2}$, $I_{SS}$ ion channels, while in human cardiomyocytes it is primarily driven by $I_{kr}$ and $I_{ks}$ [1-3]. This can result in different responses to drugs and therefore hinder their effective use as a drug screening model.

Human drug screening models available rely on tumor-derived cell lines or patient's samples that can be genetically unstable and/or lack the specificity of the cardiac cells. The majority of cardiac toxicity/arrhythmia studies so far have relied on heterologous expression systems in which single ion channel genes are expressed in non-cardiac cells. These models have several limitations since they cannot replicate most characteristics of cardiomyocytes and therefore are not ideal for generating in vitro models of human tissues.

The generation of human embryonic and induced pluripotent stem cells (hESC and iPSC, respectively) and the possibility to differentiate bona fide cardiomyocytes from them [4-6] represent an exceptional opportunity for creating in vitro models of healthy [7, 8] and diseased human cardiac tissues [9, 10]. Therefore, hESC and iPSC-derived cardiomyocytes (CMs) hold the potential for the development of platforms for pre-clinical drug screening and optimization for clinical use [7, 11]. These technologies can be used to triage drugs that might display toxicity for human cardiac cells that are often not toxic in animal models.

Human models of diseased cardiomyocytes have relied on the use of cell lines with specific mutations that replicate the disease characteristics in vitro. Recently, human iPSC-derived CMs have been used to model cardiac arrhythmias such as long QT syndrome [12-14]. This rare genetic disorder causes the heart muscle to take longer to repolarize and results in arrhythmias that can lead to sudden death. Using cardiomyocytes from iPSC lines derived from long QT syndrome patients, authors demonstrated that the CMs generated displayed the disease's electrophysiological signature and established a powerful system for studying mechanisms of pathogenesis and therapeutic drug testing. A library of human iPSC-CMs from patients with various hereditary cardiac disorders was also used to model differences in cardiac drug toxicity susceptibility for patients of different genetic backgrounds and highlights the importance of utilizing human cells for pre-clinical drug screening [15]. However, due to the high prevalence of non-genetic cardiomyopathies, developing non-genetic disease models from healthy hESC-CMs would be of great benefit as they would have enormous potential for use as in vitro screening platforms for new therapeutic agents' efficacy.

Cardiomyopathies can be a result of myocardial infarction, genetic mutations, and chronic drug exposure, among others. Isoproterenol, angiotensin II and endothelin-1 are molecules that have been successfully used to reproduce cardiomyopathies in animal models. Therefore, they are suitable candidates for use as a tool to interrogate the potential application of human stem cell-derived CMs as a tool for in vitro screening of side effects compatible with cardiomyopathy due to chronic drug exposure.

To evaluate the potential of hESC-CMs to serve as a cardiac tissue model suitable for the study of chronic drug application, we generated 3-dimensional cardiac tissues from hESC-CMs and interrogated their response to chronic exposure to isoproterenol, endothelin-1 or angiotensin II. After treatment with these agents, human tissues display hallmarks of pathological hypertrophy including disrupted sarcomere organization, induction of the fetal gene program (upregulation of brain natriuretic peptide (BNP) and atrial natriuretic factor (ANF)), secretion of BNP, increase in cell size and significantly decreased force of contraction. This indicates that hESC-CMs can respond to chronic drug exposure in a manner compatible with in vivo models and might be useful in pre-clinical application for chronic drug exposure.

Materials and Methods

Human Embryonic Stem Cell Maintenance and Differentiation.

We have used cardiomyocytes derived from Hes2 hESC line that was maintained as described [5, 16]. Embryoid bodies (EBs) were differentiated to the cardiovascular lineage as previously [5, 16]. In brief, EBs were generated by culture in StemPro-34 (Invitrogen) media containing BMP4 (1 ng/ml). On day 1, EBs were harvested and suspended in induction medium (StemPro-34, basic fibroblast growth factor (bFGF; 2.5 ng/ml), activin A (6 ng/ml) and BMP4 (10 ng/ml)). On day 4, the EBs were harvested from the induction medium and re-cultured in StemPro-34 supplemented with vascular endothelial growth factor (VEGF; 10 ng/ml) and DKK1 (150 ng/ml). On day 8, the medium was changed again and the EBs were cultured in StemPro-34 containing VEGF (20 ng/ml) and bFGF (10 ng/ml) for the duration of the experiment. Cultures were maintained in hypoxic environment (5% $CO_2$, 5% $O_2$) for the first 12 days and then transferred into 5% $CO_2$ for the remainder of the culture period. EBs were dissociated at day 20 (EBd20) for seeding in biowires.

Biowire Generation:

Day 20 EBs were incubated in collagenase type I (1 mg/ml; Worthington) and DNAse (1 mg/ml, CalBiochem) in Hank's Balanced Salt Solution (NaCl, 136 mM; $NaHCO_3$, 4.16 mM; $Na_3PO_4$, 0.34 mM; KCl, 5.36 mM; $KH_2PO_4$, 0.44 mM; dextrose, 5.55 mM; HEPES, 5 mM) for 2 hr at 37° C. EBs were centrifuged (800 r.p.m., 5 min), incubated with trypsin (0.25%, Gibco) for 5 min at 37° C. and pipetted gently to dissociate the cells. After dissociation, cells were centrifuged (1,000 r.p.m., 5 min), counted and seeded at $0.5 \times 10^6$ cells/wire of 0.5 cm in length. This ratio was maintained for generation of longer biowires. Cells were seeded in Collagen Type I gels (4 μl/0.5 cm wire length; 2.1 mg/ml of rat tail collagen type I; BD Biosciences) in 24.9 mM Glucose, 23.81 mM $NaHCO_3$, 14.34 mM NaOH, 10 mM HEPES, in 1×M199 media+10% of growth factor reduced Matrigel (BD Biosciences) by pipetting the cell suspension into the main channel of the PDMS template. After seeding, cells were kept in culture for 7 days to allow collagen matrix remodeling and assembly around the suture as described [8].

After preculture for 7 days, biowires were randomly transferred to 6-well plates and cultured in StemPro-34 media in the absence or presence of Isoproterenol (100 nM), Angiotensin II (200 nM [17]) or Endothelin-1 (150 nM) (Sigma) for 7 days. This protocol was chosen to replicate the chronic treatment of mice as described [18]. For single-cell analysis, biowires were digested with collagenase type I (1 mg/ml; Sigma) and DNAse (1 mg/ml, CalBiochem) in Hank's Balanced Salt Solution (NaCl, 136 mM; $NaHCO_3$, 4.16 mM; $Na_3PO_4$, 0.34 mM; KCl, 5.36 mM; $KH_2PO_4$, 0.44 mM; dextrose, 5.55 mM; HEPES, 5 mM) for 4 hr at 37° C., centrifuged (800 r.p.m., 5 min), incubated with trypsin (0.25%, Gibco) for 5 min at 37° C. and pipetted gently to dissociate the cells. Isolated single cells were seeded on Matrigel-coated glass cover slips before cell area and calcium transient measurements were performed.

Alternatively, to measure the force generated by the 3D engineered cardiac tissues, a bioreactor consisting of a PDMS tissue chamber capable of housing 8 micotissues was employed. Each engineered cardiac tissue consisted of 1.5× $10^6$ cells obtained from the dissociation of EBs, suspended in 25 μL of collagen I hydrogel (3.0 mg/mL) as previously described [19]. Briefly, each well of the PDMS chamber had two posts which served as anchoring points for each cardiac tissue during gel compaction. Furthermore, by tracking a post's deflection, the force of contraction a cardiac tissue generated was determined Cardiac tissues underwent 7 days of pre-culture followed by 7 days of treatment with endothelin-1, angiotensin II or isoproterenol. After the treatment, the contractile force of each cardiac tissue was determined by video recording, one at a time, the top surface of a post for each cardiac tissue while being paced at 0.5 or 1 Hz using CellSens software (Olympus). Each video was then exported as a series of Tiff images and opened in ImageJ. Using the ImageJ plugin SpotTracker [20], the distance the post moved was determined. Using the method of superposition for a cantilever beam-partial uniform deflection, a point force was calculated and then normalized to the tissues cross sectional area (assumed circular) to determine the cardiac force per area.

Assessments.

The progression of tissue assembly was assessed at various levels: ultrastructural (sarcomere structure), cellular (cell size and shape, proliferation, distribution of cardiac proteins: actin, troponin T and α-actinin), molecular (gene expression levels), and functional (force of contraction, conduction velocity, $Ca^{2+}$ handling).

Immunostaining and Fluorescence Microscopy.

Immunostaining was performed using the following antibodies: mouse anti-cTNT (1:100, Thermo Scientific; MS-295-P1), mouse anti-α-actinin (1:200, Abcam, ab9465), anti-mouse-Alexa Fluor 488 (1:400, Invitrogen, A21202), anti-rabbit-TRITC (1:400, Invitrogen, 81-6114). DAPI was used to counterstain nuclei Phalloidin Alexa Fluor 660 (1:1000, Invitrogen, A22285) was used to detect actin fibers. The stained cells were visualized using a fluorescence microscope (Leica CTR6000) and images captured using the Leica Application Suite software. For confocal microscopy cells were visualized using a fluorescence confocal microscope (Zeiss LSM-510).

Transmission Electron Microscopy (TEM).

Tissue was fixed with 4% Paraformaldehyde, 1% Glutaraldehyde in 0.1 M PBS for at least 1 hr and washed 3 times with PBS pH 7.2. Post-fixation was done with 1% Osmium Tetraoxide in 0.1 M PBS, pH 7.2 for 1 hr and dehydrated using ethanol series from 25 to 100%. Tissue was infiltrated using Epon resin and polymerized in plastic dishes at 40° C. for 48 hr. Tissue was stained with Uranyl Acetate and Lead Citrate after sectioning. Imaging was performed at Hitachi H-7000 transmission electron microscope.

Optical Mapping.

Biowires were incubated with a voltage sensitive dye (Di-4-ANEPPS 5 μM, Invitrogen) for 20 min at 37° C. in warm Tyrode's solution (NaCl 118 mM, KCl, 4.7 mM, $CaCl_2$ 1.25 mM, $MgSO_4$ 0.6 mM, $KH_2PO_4$ 1.2 mM, $NaHCO_3$ 25 mM, glucose 6 mM; oxygenated by bubbling carbogen 95% $O_2$, 5% $CO_2$ for at least 20 minutes shortly before use). Dye fluorescence was recorded on a MVX-10 Olympus fluorescence microscope equipped with a high-speed CMOS camera (Ultima-L, Scimedia) [21, 22]. The 1-cm sensor had 100×100 pixel resolution and the spatial resolution varied between 50 to 100 μm/pixel. Imaging was performed at 200 frames/s. The fluorescence was excited using a mercury arc source (X-Cite Exacte) with green filter (Olympus U-MWIG2 filter cube). The constructs were electrically point-stimulated using a bipolar electrode made of two fine wires (AWG#32) inserted in a stainless steel needle, which was mounted on a micromanipulator (World Precision Instruments). The plate containing the biowires was placed on a heated plate (MATS-U55S, Olympus) and temperature was regulated at 38° C. Data analysis was performed using BrainVision software (Scimedia).

Calcium Transient Measurements.

Biowires were dissociated through incubation with collagenase type I (1 mg/ml; Worthington) and DNAse (1 mg/ml, CalBiochem) in Hank's Balanced Salt Solution (NaCl, 136 mM; $NaHCO_3$, 4.16 mM; $Na_3PO_4$, 0.34 mM; KCl, 5.36 mM; $KH_2PO_4$, 0.44 mM; dextrose, 5.55 mM; HEPES, 5 mM) for 2 hr at 37° C. Then, biowires were centrifuged (800 r.p.m., 5 min), incubated with trypsin (0.25%, Gibco) for 5 min at 37° C. and pipetted gently to dissociate the cells. The dissociated cardiomyocytes were plated onto growth factor free Matrigel (diluted 1:60 in RPMI media)-coated 25-mm microscope glass coverslips overnight. Cells were then incubated with 5 μM of Rhod-3 AM calcium imaging dye (Invitrogen) in culture media for 2 hours at 37° C. Subsequently, cardiomyocytes were washed twice with dye-free medium and placed back into the incubator for 30 min. A laser scanning confocal microscope (Zeiss LSM 510) was used to measure the fluorescence intensity. The coverslips containing the Rhod-3 AM-loaded cardiomyocytes were moved onto a special chamber and tightly secured. Approximately 1.8-1.9 ml of culture medium was added into the chamber, which was placed on a temperature controlled-plate (37° C.) on the microscope. Changes in Rhod-3 AM fluorescence intensity, which indicates transient fluctuation of cytosolic calcium concentration, were recorded in frame and line scan model. The images and fluorescence data were acquired through Zeiss software. The fluorescence data were analyzed with Origin 8.5 software. Fluorescence signals (F) were normalized to baseline fluorescence after loading fluo-4 AM. The rising phase of the signals was fitted by linear model while the decaying phase of the signals was fitted by ExpDecay with Offset model.

ELISA.

Quantification of soluble BNP from the conditioned media was performed using commercially available ELISA kits.

Quantitative RT-PCR.

RT-PCR was performed as previously described [23]. Total RNA was prepared with the High Pure RNA Isolation Kit (Roche) and treated with RNase-free DNase (Roche). RNA was reverse transcribed into cDNA using random hexamers and Oligo (dT) with SuperScript VILO (Invitrogen). RT-qPCR was performed on a LightCycler 480 (Roche) using LightCycler 480 SYBR Green I Master (Roche). Expression levels were normalized to the housekeeping genes TATA box binding protein (TBP) or Glyceraldehyde 3-phosphate dehydrogenase (GAPDH).

Statistical Analysis.

Statistical analysis was performed using SigmaPlot 12.0. Statistics was done using two-way ANOVA. Normality test (Komogorov-Smirnov) was followed by an equal variance test. If normality test failed, a Kruskal-Wallis 1 way ANOVA on Ranks was performed. $P<0.05$ was considered significant for all statistical tests.

Results

The architecture of the heart is highly sophisticated. To replicate some of its characteristics in vitro we have utilized 3-dimensional, self-assembled cardiac tissue mimics such as biowires, as previously described [8] in our in vitro assays. Human ESC-derived CMs obtained from the dissociation of embryoid bodies were seeded in collagen type I gels. After 1 week in culture; which allowed for matrix remodeling and gel compaction [8], as depicted in FIG. 82A, biowires were chronically exposed to different compounds by treatment with either isoproterenol (ISO, 100 nM), endothelin-1 (Et-1, 150 nM [17, 24], or angiotensin II (AngII, 200 nM) for one week. This protocol was chosen to replicate the chronic treatment responsible for cardiac toxicity and consequent cardiac hypertrophy in vivo [18]. We then assessed if changes in the human ESC-derived CMs were consistent with changes described in vivo by analyzing sarcomere structure, expression of the fetal gene program, secretion of brain natriuretic peptide (BNP) and troponin, changes in cell size and force of contraction.

Analysis of α-actinin, actin, cardiac troponin T and con-nexin 43 by confocal microscopy revealed that chronic treatment with ISO caused substantial disruption of sarcomere structure (FIG. 82B) in comparison with non-treated biowire controls. Treatment with Et-1 and AngII also led to a disruption in the organized myofibril striation pattern, as shown through α-actinin staining, although to a lesser extent than ISO (FIG. 82B). Transmission electron microscopy analysis (FIG. 82C) confirmed the disruptive effect of these molecules in the human CM contractile apparatus, as illustrated by the significant absence of distinct Z-disks and the lack of a defined sarcomere structure in hESC-CMs treated with ISO, Et-1 and AngII compared to untreated control.

Chronic drug exposure with adverse cardiac effects can lead to the induction of the fetal gene program, specifically BNP and atrial natriuretic factor (ANF) Analysis of the expression of the fetal gene program in our samples showed that while treatment with ISO significantly induced ANF and BNP gene expression compared to untreated control (FIG. 84), no changes in gene expression were detected with treatment with AngII and Et-1. Interestingly, analysis of the conditioned medium of treated cells at early and late time-points, indicated a 2.5-fold and 5-fold increase in the secretion of BNP in ISO and Et-1 conditions, respectively already at day 2 post-treatment. After media changes, levels of BNP in the media were analyzed at days 2 and 7. Despite conditioning for only 24 h (as compared to the day 2 condition where BNP was measured in media conditioned for 48 h), it was still possible to detect a 70% and 7-fold increase in ISO and Et-1-treated conditions, respectively at day 7. Analysis of the conditioned media from the AngII condition was not possible due to cross-reactivity between BNP and AngII in the ELISA.

Changes in cell size were analyzed by dissociation of biowires at the end of treatment as in [8]. Single cells were then seeded at low density on Matrigel-coated wells as described in the Material and Methods section, and area measurements were performed after staining with the CM marker cardiac troponin T. There was a tendency to an increase in cell size in the treated conditions. A 100% increase in cell size was observed in cells treated with ET-1, while cells treated with ISO and AngII displayed an increase in size of 35 and 38%, respectively.

Next, we evaluated the force of contraction of 3D human cardiac tissues in each condition. Since the presence of the suture in the biowires does not allow for force measurements, we have used a platform previously developed and validated by us using rat neonatal cardiomyocytes [19] in which deflectable posts are used to calculate the force of contraction of 3D cardiac tissues. There was a significant decrease in the force of contraction of hESC-derived CMs 3D tissues in all conditions (FIG. 86) when compared to untreated controls. This is compatible with the disruption of the contractile machinery organization observed in FIG. 87. Assessment of cell viability in 3D tissues using live/dead staining revealed no differences between ISO and non-treated controls (FIG. 87). Conduction velocity, assessed upon point stimulation at the end of cultivation was also the same between ISO and non-treated controls (FIG. 87). Moreover, analysis of calcium transients from single cells isolated from the biowires at the end of cultivation showed that both ISO-treated and non-treated cells displayed similar characteristics.

References for Example 6

Each of the following references are incorporated herein by reference.
1. Rajamohan, D., et al., *Current status of drug screening and disease modelling in human pluripotent stem cells.* BioEssays: news and reviews in molecular, cellular and developmental biology, 2013. 35(3): p. 281-98.
2. Miklas, J. W., S. S. Nunes, and M. Radisic, *Engineering Cardiac Tissues from Pluripotent Stem Cells for Drug Screening and Studies of Cell Maturation.* Israel Journal of Chemistry, 2013. 53(9-10): p. 680-694.
3. Davis, R. P., et al., *Pluripotent stem cell models of cardiac disease and their implication for drug discovery and development.* Trends in molecular medicine, 2011. 17(9): p. 475-84.
4. Kehat, I., et al., *Human embryonic stem cells can differentiate into myocytes with structural and functional properties of cardiomyocytes.* J Clin Invest, 2001. 108(3): p. 407-14.
5. Yang, L., et al., *Human cardiovascular progenitor cells develop from a KDR+ embryonic-stem-cell-derived population.* Nature, 2008. 453(7194): p. 524-8.
6. Zhang, J., et al., *Functional cardiomyocytes derived from human induced pluripotent stem cells.* Circ Res, 2009. 104(4): p. e30-41.
7. Navarrete, E. G., et al., *Screening drug-induced arrhythmia events using human induced pluripotent stem cell-derived cardiomyocytes and low-impedance microelectrode arrays.* Circulation, 2013. 128(11 Suppl 1): p. S3-13.
8. Nunes, S. S., et al., *Biowire: a platform for maturation of human pluripotent stem cell-derived cardiomyocytes.* Nature methods, 2013. 10(8): p. 781-7.
9. Carvajal-Vergara, X., et al., *Patient-specific induced pluripotent stem-cell-derived models of LEOPARD syndrome.* Nature, 2010. 465(7299): p. 808-12.
10. Sun, N., et al., *Patient-specific induced pluripotent stem cells as a model for familial dilated cardiomyopathy.* Sci Transl Med, 2012. 4(130): p. 130ra47.
11. Schaaf, S., et al., *Human engineered heart tissue as a versatile tool in basic research and preclinical toxicology.* PloS one, 2011. 6(10): p. e26397.
12. Itzhaki, I., et al., *Modelling the long QT syndrome with induced pluripotent stem cells.* Nature, 2011. 471(7337): p. 225-9.
13. Moretti, A., et al., *Patient-specific induced pluripotent stem-cell models for long-QT syndrome.* The New England journal of medicine, 2010. 363(15): p. 1397-409.
14. Yazawa, M., et al., *Using induced pluripotent stem cells to investigate cardiac phenotypes in Timothy syndrome.* Nature, 2011. 471(7337): p. 230-4.

15. Liang, P., et al., *Drug screening using a library of human induced pluripotent stem cell-derived cardiomyocytes reveals disease-specific patterns of cardiotoxicity.* Circulation, 2013. 127(16): p. 1677-91.
16. Kattman, S. J., et al., *Stage-specific optimization of activin/nodal and BMP signaling promotes cardiac differentiation of mouse and human pluripotent stem cell lines.* Cell stem cell, 2011. 8(2): p. 228-40.
17. Gray, M. O., et al., *Angiotensin II stimulates cardiac myocyte hypertrophy via paracrine release of TGF-beta 1 and endothelin-1 from fibroblasts.* Cardiovascular research, 1998. 40(2): p. 352-63.
18. Antos, C. L., et al., *Activated glycogen synthase-3 beta suppresses cardiac hypertrophy in vivo.* Proceedings of the National Academy of Sciences of the United States of America, 2002. 99(2): p. 907-12.
19. Miklas, J. W., et al., *Bioreactor for modulation of cardiac microtissue phenotype by combined static stretch and electrical stimulation.* Biofabrication, 2014. 6(2): p. 024113.
20. Sage, D., et al., *Automatic tracking of individual fluorescence particles: Application to the study of chromosome dynamics.* IEEE Transactions on Image Processing, 2005. 14(9): p. 1372-1383.
21. Nanthakumar, K., et al., *Optical mapping of Langendorff-perfused human hearts: establishing a model for the study of ventricular fibrillation in humans.* Am J Physiol Heart Circ Physiol, 2007. 293(1): p. H875-80.
22. Witkowski, F. X., et al., *Voltage-sensitive dye recordings of electrophysiological activation in a Langendorff-perfused mouse heart.* Can J Cardiol, 1997. 13(11): p. 1077-82.
23. Dubois, N.C., et al., *SIRPA is a specific cell-surface marker for isolating cardiomyocytes derived from human pluripotent stem cells.* Nat Biotechnol, 2011. 29(11): p. 1011-8.
24. Iwanaga, Y., et al., *Cardiac endothelin-1 plays a critical role in the functional deterioration of left ventricles during the transition from compensatory hypertrophy to congestive heart failure in salt-sensitive hypertensive rats.* Circulation, 1998. 98(19): p. 2065-73.
25. Barker, D. J., et al., *Fetal origins of adult disease: strength of effects and biological basis.* International journal of epidemiology, 2002. 31(6): p. 1235-9.
26. Luo, Z. C., et al., *Tracing the origins of "fetal origins" of adult diseases: programming by oxidative stress?* Medical hypotheses, 2006. 66(1): p. 38-44.
27. Barker, D. J., *The fetal origins of coronary heart disease.* European heart journal, 1997. 18(6): p. 883-4.

REFERENCES CITED IN SPECIFICATION

Each of the following references are incorporated herein by reference.
1 Kehat, I. et al. Human embryonic stem cells can differentiate into myocytes with structural and functional properties of cardiomyocytes. *J Clin Invest* 108, 407-414, doi:10.1172/JCI12131 (2001).
2 Yang, L. et al. Human cardiovascular progenitor cells develop from a KDR+ embryonic-stem-cell-derived population. *Nature* 453, 524-528, doi:nature06894 [pii] 10.1038/nature06894 (2008).
3 Zhang, J. et al. Functional cardiomyocytes derived from human induced pluripotent stem cells. *Circ Res* 104, e30-41, doi:CIRCRESAHA.108.192237 [pii] 10.1161/CIRCRESAHA.108.192237 (2009).
4 Kaltman, S. J. et al. Stage-specific optimization of activin/nodal and BMP signaling promotes cardiac differentiation of mouse and human pluripotent stem cell lines. *Cell Stem Cell* 8, 228-240, doi:S1934-5909(10)00703-4 [pii] 10.1016/j.stem.2010.12.008 (2011).
5 Carvajal-Vergara, X. et al. Patient-specific induced pluripotent stem-cell-derived models of LEOPARD syndrome. *Nature* 465, 808-812, doi:nature09005 [pii] 10.1038/nature09005 (2010).
6 Laflamme, M. A. & Murry, C. E. Heart regeneration. *Nature* 473, 326-335, doi:nature10147 [pii] 10.1038/nature10147 (2011).
7 Snir, M. et al. Assessment of the ultrastructural and proliferative properties of human embryonic stem cell-derived cardiomyocytes. *Am J Physiol Heart Circ Physiol* 285, H2355-2363, doi:10.1152/ajpheart.00020.2003 285/6/H2355 [pii] (2003).
8 McDevitt, T. C., Laflamme, M. A. & Murry, C. E. Proliferation of cardiomyocytes derived from human embryonic stem cells is mediated via the IGF/PI 3-kinase/Akt signaling pathway. *J Mol Cell Cardiol* 39, 865-873, doi:S0022-2828(05)00287-7 [pii] 10.1016/j.yjmcc.2005.09.007 (2005).
9 Mummery, C. et al. Differentiation of human embryonic stem cells to cardiomyocytes: role of coculture with visceral endoderm-like cells. *Circulation* 107, 2733-2740, doi:10.1161/01.CIR.0000068356.38592.68 01.CIR.0000068356.38592.68 [pii] (2003).
10 Dolnikov, K. et al. Functional properties of human embryonic stem cell-derived cardiomyocytes: intracellular Ca2+ handling and the role of sarcoplasmic reticulum in the contraction. *Stem Cells* 24, 236-245, doi:2005-0036 [pii] 10.1634/stemcells.2005-0036 (2006).
11 Doss, M. X. et al. Maximum diastolic potential of human induced pluripotent stem cell-derived cardiomyocytes depends critically on I(Kr). *PLoS One* 7, e40288, doi:10.1371/journal.pone.0040288 PONE-D-12-03570 [pii] (2012).
12 Liu, J., Fu, J. D., Siu, C. W. & Li, R. A. Functional sarcoplasmic reticulum for calcium handling of human embryonic stem cell-derived cardiomyocytes: insights for driven maturation. *Stem Cells* 25, 3038-3044, doi:2007-0549 [pii] 10.1634/stemcells.2007-0549 (2007).
13 Satin, J. et al. Calcium handling in human embryonic stem cell-derived cardiomyocytes. *Stem Cells* 26, 1961-1972, doi:2007-0591 [pii] 10.1634/stemcells.2007-0591 (2008).
14 Tulloch, N. L. et al. Growth of engineered human myocardium with mechanical loading and vascular coculture. *Circ Res* 109, 47-59, doi:CIRCRESAHA.110.237206 [pii] 10.1161/CIRCRESAHA.110.237206 (2011).
15 Caspi, O. et al. Tissue engineering of vascularized cardiac muscle from human embryonic stem cells. *Circ Res* 100, 263-272, doi:01.RES.0000257776.05673.ff [pii] 10.1161/01.RES.0000257776.05673.ff (2007).
16 Chien, K. R., Knowlton, K. U., Zhu, H. & Chien, S. Regulation of cardiac gene expression during myocardial growth and hypertrophy: molecular studies of an adaptive physiologic response. *FASEB J* 5, 3037-3046 (1991).
17 Frank, D. et al. Gene expression pattern in biomechanically stretched cardiomyocytes: evidence for a stretch-specific gene program. *Hypertension* 51, 309-318, doi:HYPERTENSIONAHA.107.098046 [pii] 10.1161/HYPERTENSIONAHA.107.098046 (2008).

18 Kuwahara, K. et al. NRSF regulates the fetal cardiac gene program and maintains normal cardiac structure and function. *EMBO J* 22, 6310-6321, doi:10.1093/emboj/cdg601 (2003).

19 Nuccitelli, R. Endogenous ionic currents and DC electric fields in multicellular animal tissues. *Bioelectromagnetics* Suppl 1, 147-204 (1992).

20 Henderson, D. J. & Chaudhry, B. Getting to the heart of planar cell polarity signaling. *Birth Defects Res A Clin Mol Teratol* 91, 460-467, doi:10.1002/bdra.20792 (2011).

21 Zhao, M., Forrester, J. & McCaig, C. A small, physiological electric field orients cell division. *Proceedings of the National Academy of Sciences of the United States of America* 96, 4942-4948 (1999).

22 Radisic, M. et al. Functional assembly of engineered myocardium by electrical stimulation of cardiac myocytes cultured on scaffolds. *Proc Natl Acad Sci USA* 101, 18129-18134, doi:0407817101 [pii] 10.1073/pnas.0407817101 (2004).

23 Berger, H. J. et al. Continual electric field stimulation preserves contractile function of adult ventricular myocytes in primary culture. *Am J Physiol* 266, H341-349 (1994).

24 Derby, B. Printing and Prototyping of Tissues and Scaffolds. *Science* 338, 921-926, doi:10.1126/science.1226340 (2012).

25 Miller, J. S. et al. Rapid casting of patterned vascular networks for perfusable engineered three-dimensional tissues. *Nature Materials* advance on, 768-774, doi:10.1038/nmat3357 (2012).

26 Ye, X. et al. A biodegradable microvessel scaffold as a framework to enable vascular support of engineered tissues. *Biomaterials* (2013).

27 Tran, R. T. et al. Synthesis and characterization of a biodegradable elastomer featuring a dual crosslinking mechanism. *Soft Matter* 6 (2010).

28 Lundy, S. D., Zhu, W. Z., Regnier, M. & Laflamme, M. Structural and Functional Maturation of Cardiomyocytes Derived From Human Pluripotent Stem Cells. *Stem Cells Dev*, doi:10.1089/scd.2012.0490 (2013).

29 Nanthakumar, K. et al. Optical mapping of Langendorff-perfused human hearts: establishing a model for the study of ventricular fibrillation in humans. *Am J Physiol Heart Circ Physiol* 293, H875-880, doi:01415.2006 [pii] 10.1152/ajpheart.01415.2006 (2007).

30 Witkowski, F. X., Clark, R. B., Larsen, T. S., Melnikov, A. & Giles, W. R. Voltage-sensitive dye recordings of electrophysiological activation in a Langendorff-perfused mouse heart. *Can J Cardiol* 13, 1077-1082 (1997).

31 Snyders, D. J. & Chaudhary, A. High affinity open channel block by dofetilide of HERG expressed in a human cell line. *Mol Pharmacol* 49, 949-955 (1996).

32 Dubois, N. C. et al. SIRPA is a specific cell-surface marker for isolating cardiomyocytes derived from human pluripotent stem cells. *Nat Biotechnol* 29, 1011-1018, doi:nbt.2005 [pii] 10.1038/nbt.2005 (2011).

33 Borg, T. K. et al. Specialization at the Z line of cardiac myocytes. *Cardiovasc Res* 46, 277-285, doi:50008-6363(99)00433-2 [pii] (2000).

34 Bird, S. D. et al. The human adult cardiomyocyte phenotype. *Cardiovasc Res* 58, 423-434, doi:S0008636303002530 [pii] (2003).

35 Frey, N. & Olson, E. N. Cardiac hypertrophy: the good, the bad, and the ugly. *Annu Rev Physiol* 65, 45-79, doi:10.1146/annurev.physiol.65.092101.142243 092101.142243 [pii] (2003).

36 Wang, J., Huang, Y. & Ning, Q. Review on regulation of inwardly rectifying potassium channels. *Crit Rev Eukaryot Gene Expr* 21, 303-311, doi:5879f5f63658cafa, 596f2027362b5865 [pii] (2011).

37 De Weer, P., Gadsby, D. C. & Rakowski, R. F. Voltage dependence of the Na—K pump. *Annu Rev Physiol* 50, 225-241, doi:10.1146/annurev.ph.50.030188.001301 (1988).

38 Sakai, R., Hagiwara, N., Matsuda, N., Kassanuki, H. & Hosoda, S. Sodium—potassium pump current in rabbit sino-atrial node cells. *J Physiol* 490 (Pt 1), 51-62 (1996).

39 Polak, S. & Fijorek, K. Inter-individual variability in the pre-clinical drug cardiotoxic safety assessment—analysis of the age-cardiomyocytes electric capacitance dependence. *Journal of cardiovascular translational research* 5, 321-332, doi: 10.1007/s12265-012-9357-8 (2012).

40 Feng, J., Li, G. R., Fermini, B. & Nattel, S. Properties of sodium and potassium currents of cultured adult human atrial myocytes. *The American journal of physiology* 270, H1676-1686 (1996).

41 Satin, J. et al. Mechanism of spontaneous excitability in human embryonic stem cell derived cardiomyocytes. *J Physiol* 559, 479-496, doi:10.1113/jphysiol.2004.068213 (2004).

42 Zhu, W. Z., Santana, L. F. & Laflamme, M. A. Local control of excitation-contraction coupling in human embryonic stem cell-derived cardiomyocytes. *PloS one* 4, e5407, doi:10.1371/journal.pone.0005407 (2009).

43 Patterson, M. et al. Defining the nature of human pluripotent stem cell progeny. *Cell Res* 22, 178-193, doi: cr2011133 [pii] 10.1038/cr.2011.133 (2012).

44 D. Arduini. *Fetal Cardiac Function*. 43-49 (Parthenon Publishing Group, 1995).

45 Lieu, D. K. et al. Absence of transverse tubules contributes to non-uniform Ca(2+) wavefronts in mouse and human embryonic stem cell-derived cardiomyocytes. *Stem Cells Dev* 18, 1493-1500, doi:10.1089/scd.2009.0052 (2009).

46 Baharvand, H., Azarnia, M., Parivar, K. & Ashtiani, S. K. The effect of extracellular matrix on embryonic stem cell-derived cardiomyocytes. *J Mol Cell Cardiol* 38, 495-503, doi:S0022-2828(04)00409-2 [pii] 10.1016/j.yjmcc.2004.12.011 (2005).

47 Schaaf, S. et al. Human engineered heart tissue as a versatile tool in basic research and preclinical toxicology. *PLoS One* 6, e26397, doi:10.1371/journal.pone.0026397 PONE-D-11-08333 [pii] (2011).

48 Chattergoon, N. N. et al. Thyroid hormone drives fetal cardiomyocyte maturation. *FASEB J* 26, 397-408, doi: fj.10-179895 [pii] 10.1096/fj.10-179895 (2012).

49 McMullen, J. R. et al. The insulin-like growth factor 1 receptor induces physiological heart growth via the phosphoinositide 3-kinase (p110alpha) pathway. *J Biol Chem* 279, 4782-4793, doi:10.1074/jbc.M310405200 M310405200 [pii] (2004).

50 Seif-Naraghi, S. B. et al. Safety and efficacy of an injectable extracellular matrix hydrogel for treating myocardial infarction. *Science translational medicine* 5, 173ra125, doi:10.1126/scitranslmed.3005503 (2013).

51 Rodriguez, A. G., Han, S. J., Regnier, M. & Sniadecki, N. J. Substrate stiffness increases twitch power of neonatal cardiomyocytes in correlation with changes in myofibril structure and intracellular calcium. *Biophys J* 101, 2455-2464, doi:S0006-3495(11)01193-3 [pii] 10.1016/j.bpj.2011.09.057 (2011).

52 Hazeltine, L. B. et al. Effects of substrate mechanics on contractility of cardiomyocytes generated from human pluripotent stem cells. *Int J Cell Biol* 2012, 508294, doi:10.1155/2012/508294 (2012).
53 Blazeski, A. et al. Electrophysiological and contractile function of cardiomyocytes derived from human embryonic stem cells. *Prog Biophys Mol Biol* 110, 178-195, doi:50079-6107(12)00065-X [pii] 10.1016/j.pbiomolbio.2012.07.012 (2012).
54 Wiedeman, M. P. Dimensions of blood vessels from distributing artery to collecting vein. *Circ Res* 12, 375-378 (1963).
55 Legant, W. R. et al. Microfabricated tissue gauges to measure and manipulate forces from 3D microtissues. *Proc Natl Acad Sci USA* 106, 10097-10102, doi: 0900174106 [pii] 10.1073/pnas.0900174106 (2009).
56 Caspi, O. et al. In vitro electrophysiological drug testing using human embryonic stem cell derived cardiomyocytes. *Stem Cells Dev* 18, 161-172, doi:10.1089/scd.2007.0280 (2009).
57 Ionescu-Zanetti, C. et al. Mammalian electrophysiology on a microfluidic platform. *Proc Natl Acad Sci USA* 102, 9112-9117, doi:0503418102 [pii] 10.1073/pnas.0503418102 (2005).
58 Zimmermann, W. H. et al. Engineered heart tissue grafts improve systolic and diastolic function in infarcted rat hearts. *Nat Med* 12, 452-458, doi:nm1394 [pii] 10.1038/nm1394 (2006).
59 Piccini, J. P. et al. Current challenges in the evaluation of cardiac safety during drug development: translational medicine meets the Critical Path Initiative. *Am Heart J* 158, 317-326, doi:S0002-8703(09)00449-9 [pii] 10.1016/j.ahj.2009.06.007 (2009).
60 Boudou, T. et al. A microfabricated platform to measure and manipulate the mechanics of engineered cardiac microtissues. *Tissue Eng Part A* 18, 910-919, doi: 10.1089/ten.TEA.2011.0341 (2012).
61 Agarwal, A., Goss, J. A., Cho, A., McCain, M. L. & Parker, K. K. Microfluidic heart on a chip for higher throughput pharmacological studies. *Lab chip* 13, 3599-3608, doi:10.1039/c3lc50350j (2013).
62 Ragheb, A. O. et al. Coated implantable medical device. U.S. Pat. No. 7,410,665, (2008).
63 Simmons, A., Padsalgikar, A. D., Ferris, L. M. & Poole-Warren, L. A. Biostability and biological performance of a PDMS-based polyurethane for controlled drug release. *Biomaterials* 29, 2987-2995, doi:S0142-9612(08)00238-X [pii] 10.1016/j.biomaterials.2008.04.007 (2008).
64 Wu, Z., Jiang, Y., Kim, T & Lee, K. Effects of surface coating on the controlled release of vitamin B1 from mesoporous silica tablets. *J Control Release* 119, 215-221, doi:S0168-3659(07)00126-5 [pii] 10.1016/j.jconrel.2007.03.001 (2007).
65 Chen, C. H., Doan, P. D., Chitre, Y. & Helland, J. R. Method of molding silicone elastomer drug carrier in an endocardial. U.S. Pat. No. 7,363,091 (2008).
66 Vandenburgh, H. et al. Drug-screening platform based on the contractility of tissue-engineered muscle. *Muscle Nerve* 37, 438-447, doi:10.1002/mus.20931 (2008).
67 Hansen, A. et al. Development of a drug screening platform based on engineered heart tissue. *Circ Res* 107, 35-44, doi:CIRCRESAHA.109.211458 [pii] 10.1161/CIRCRESAHA.109.211458 (2010).
68 Grosberg, A. et al. Muscle on a chip: in vitro contractility assays for smooth and striated muscle. *J Pharmacol Toxicol Methods* 65, 126-135, doi:S1056-8719(12)00041-X [pii] 10.1016/j.vascn.2012.04.001 (2012).
69 Tran, R. T. et al. Synthesis and characterization of a biodegradable elastomer featuring a dual crosslinking mechanism. *Soft Matter* 6, 2449-2461, doi:10.1039/C001605E (2010).
70 Eder, A., AHansen, A. & Eschenhagen, T. in *Toxicity and Drug Testing* (ed Prof. Bill Acree) Ch. 4, 71-89 (InTech Europe, 2012).
71 Serrao, G. W. et al. Myocyte-depleted engineered cardiac tissues support therapeutic potential of mesenchymal stem cells. *Tissue Eng Part A* 18, 1322-1333, doi:10.1089/ten.TEA.2011.0278 (2012).
72 Goldberg, L. I., Bloodwell, R. D., Braunwald, E. & Morrow, A. G. The direct effects of norepinephrine, epinephrine, and methoxamine on myocardial contractile force in man. *Circulation* 22, 1125-1132 (1960).
73 Fleisch, J. H. & Titus, E. The prevention of isoproterenol desensitization and isoproterenol reversal. *J Pharmacol Exp Ther* 181, 425-433 (1972).
74 Nunes, S. S., Song, H., Chiang, C. K. & Radisic, M. Stem cell-based cardiac tissue engineering. *J Cardiovasc Transl Res* 4, 592-602, doi:10.1007/s12265-011-9307-x (2011).
75 Xu, C. et al. Feeder-free growth of undifferentiated human embryonic stem cells. *Nature biotechnology* 19, 971-974, doi:10.1038/nbt1001-971 (2001).
76 Lian, X. et al. Robust cardiomyocyte differentiation from human pluripotent stem cells via temporal modulation of canonical Wnt signaling. *Proceedings of the National Academy of Sciences of the United States of America* 109, E1848-1857, doi:10.1073/pnas.1200250109 (2012).
77 Engelmayr, G. C. et al. Accordion-like honeycombs for tissue engineering of cardiac anisotropy. *Nature Materials* 7, 1003-1010, doi:10.1038/nmat2316 (2008).
78 Hoshi, R. A. Nanoporous Biodegradable Elastomers. *Advanced Materials* 21, 188-192 (2009).

The invention claimed is:
1. A bioreactor comprising:
a device having a well configured for growing a tissue from cells seeded therein, wherein the well has a bottom; and
at least two elastic sensing elements disposed across the well such that there is a gap between the sensing elements and the bottom of the well, wherein the sensing elements are configured to: (a) permit attachment of the tissue formed therebetween, thereby suspending the tissue above the bottom of the well, and (b) deform in response to the contractile force exerted on the sensing elements by the tissue, thereby simulating a physiological environment that is native to the tissue and/or permitting measurement of the contractile force.
2. The bioreactor of claim 1, comprising 2 to 25 sensing elements per well.
3. The bioreactor of claim 1, wherein the bioreactor is a multi-well plate comprising 6 wells, 12 wells, 24 wells, 96 wells, 384 wells, or 1536 wells.
4. The bioreactor of claim 1, wherein the sensing elements comprise a natural materials selected from the group consisting of collagen and collagen derivatives, animal intestines, cellulose and cellulose derivatives, proteoglycans, heparin sulfate, chondroitin sulfate, keratin sulfates, hyaluronic acid, elastin, fibronectin, laminin, fibrin, chitosan, alginate, matrigel, and combinations thereof.
5. The bioreactor of claim 1, wherein the sensing elements comprise a polymer selected from the group consisting of synthetic and biologic, and wherein the polymer is degradable or nondegradable.
6. The bioreactor of claim 5, wherein the polymer is at least one of polylactic acid, poly(lactic-co-glycolic) acid, poly(caprolactone), polyglycolide, polylactide, polyhydroxobutyrate, polyhydroxyalcanoic acid, chitosan, hyaluronic acid, a hydrogels, poly(2-hydroxyethyl-methacrylate), poly(ethylene glycol), poly(L-lactide) (PLA), poly(dimethysiloxane) (PDMS), poly(methylmethacrylate) (PMMA), poly(glycerol sebacate), poly(octamethylene maleate (anhydride) citrate) (POMaC), POMaC without citric acid, poly(ε-caprolactone), polyurethane, silk, a nanofabricated material, a co-polymer, a blended polymer, or a combination thereof.

7. The bioreactor of claim 6, wherein the polymer is POMaC.

8. The bioreactor of claim 1, wherein the sensing elements comprise a polymer which is doped with a nanostructure.

9. The bioreactor of claim 1, wherein the sensing elements comprise at least one of an intestinal material, monocryl, polyglycolide, prolene, polyglactin, polydioxanone, polypropylene, nylon, polyester, or a combination thereof.

10. The bioreactor of claim 1, further comprising a cell seeded in the well.

11. The bioreactor of claim 10, wherein the cell seeded in the well is at least one of a cardiomyocyte, a skeletal muscle cell, a hepatocyte, a renal cell, a chondrocyte, a skin cell, a contractile cell, a blood cell, an immune system cell, a germ cell, a neural cell, an epithelial cell, a hormone secreting cell, a bone marrow cell, a stem cell, a tumor cell, a smooth muscle cell, an endothelial cell, a fibroblast, an adipose derived stem cell, a mesenchymal stem cell, a progenitor cell, or combinations thereof.

12. The bioreactor of claim 10, wherein the cell seeded in the well is a cardiomyocyte.

13. The bioreactor of claim 1, further comprising a tissue formed therein.

14. The bioreactor of claim 1, wherein the well is configured to have a longitudinal axis.

15. The bioreactor of claim 14, wherein the sensing elements have an orientation that is perpendicular, parallel, or diagonal relative to the longitudinal axis of the well.

16. The bioreactor of claim 1, further comprising electrode configured to create an electrical current across the well of the bioreactor.

17. The bioreactor of claim 1, wherein the sensing elements comprise a polymer whose mechanical properties are tunable during a polymerization reaction.

18. The bioreactor of claim 1, wherein the sensing elements are porous, thereby permitting delivery of nutrients and growth factors to the tissue.

19. The bioreactor of claim 1, wherein the sensing elements have an elasticity from about 20 kPa to 0.5 MPa.

20. The bioreactor of claim 1, wherein the sensing elements are polymer wires.

21. The bioreactor of claim 1, wherein the cells are seeded in a hydrogel that comprises polyvinyl alcohol, sodium polyacrylate, an acrylate polymer, agarose, methylcellulose, or hyaluronan.

22. A method for measuring the effect of a test agent on the contractile force of a tissue using the bioreactor of claim 1, comprising:
 (a) measuring a first contractile force of the tissue in the bioreactor of claim 1 before exposure to the test agent;
 (b) contacting the tissue with the test agent under conditions sufficient for the test agent to affect the contractile force;
 (c) measuring a second contractile force of the tissue after exposure to the test agent;
 (d) determining whether the test agent affects the contractile force by comparing the first contractile force of (a) with the second contractile force of (c),
 wherein measuring the first or second contractile force comprises measuring the amount of movement imposed by the tissue on the sensing elements from a first position to a second position.

23. The method of claim 22, wherein the test agent is selected from the group consisting of a small molecule, an antibody, an ion, a protein, a peptide, a lipid, DNA, RNA, a virus, bacteria, a microparticle, a nanoparticle, a therapeutic agent, and a toxin.

24. A method for evaluating the safety of a test agent on a tissue, comprising:
 (a) contacting the tissue of the bioreactor of claim 1 with the test agent;
 (b) measuring the effect on one or more physiological parameters indicative of safety;
 (c) comparing the physiological parameters in (b) to the same physiological parameters measured from a control bioreactor not exposed to the test agent,
 wherein a statistically significant change in the physiological parameters in (b) as compared to the same physiological parameters measured from the control bioreactor indicates that the test agent lacks safety.

25. A method for fabricating the bioreactor of claim 1 for cultivation of a tissue, comprising the steps of:
 (a) microfabricating a surface comprising a well configured for growing a tissue from cells seeded therein; and
 (b) affixing at least two sensing elements to each well, wherein the sensing elements are configured to become encapsulated by the tissue once formed in the well.

26. A method comprising:
 (a) growing an implantable tissue in the bioreactor of claim 1; and
 (b) providing the implantable tissue for use in treating a damaged and/or diseased tissue.

\* \* \* \* \*